US008722859B2

(12) United States Patent
Miller et al.

(10) Patent No.: US 8,722,859 B2
(45) Date of Patent: May 13, 2014

(54) MULTIVALENT ANTIBODIES AND USES THEREFOR

(75) Inventors: Kathy L. Miller, San Francisco, CA (US); Leonard G. Presta, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/470,189

(22) Filed: May 11, 2012

(65) Prior Publication Data

US 2012/0238728 A1 Sep. 20, 2012

Related U.S. Application Data

(63) Continuation of application No. 11/535,031, filed on Sep. 25, 2006, now abandoned, which is a continuation of application No. 11/218,821, filed on Sep. 2, 2005, now abandoned, which is a continuation of application No. 09/813,341, filed on Mar. 20, 2001, now abandoned.

(60) Provisional application No. 60/195,819, filed on Apr. 11, 2000.

(51) Int. Cl.
*C07K 16/00* (2006.01)

(52) U.S. Cl.
USPC ............................................. 530/387.3

(58) Field of Classification Search
USPC ............................................. 530/387.3
See application file for complete search history.

(56) References Cited

U.S. PATENT DOCUMENTS

| 4,816,567 A | 3/1989 | Cabilly et al. |
| 4,968,603 A | 11/1990 | Slamon et al. |
| 5,183,884 A | 2/1993 | Kraus et al. |
| 5,434,340 A | 7/1995 | Krimpenfort et al. |
| 5,480,968 A | 1/1996 | Kraus et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,591,699 A | 1/1997 | Hodge |
| 5,591,828 A | 1/1997 | Bosslet et al. |
| 5,595,721 A | 1/1997 | Kaminski et al. |
| 5,641,869 A | 6/1997 | Vandlen et al. |
| 5,641,870 A | 6/1997 | Rinderknecht et al. |
| 5,677,171 A | 10/1997 | Hudziak et al. |
| 5,736,137 A | 4/1998 | Anderson et al. |
| 5,783,186 A | 7/1998 | Arakawa et al. |
| 5,821,337 A | 10/1998 | Carter et al. |
| 5,824,311 A | 10/1998 | Greene et al. |
| 5,874,409 A | 2/1999 | Victoria et al. |
| 5,959,083 A | 9/1999 | Bosslet et al. |
| 5,989,830 A | 11/1999 | Davis et al. |
| 6,027,725 A | 2/2000 | Whitlow et al. |
| 6,066,719 A | 5/2000 | Zapata |
| 6,214,984 B1 | 4/2001 | Zapata |
| 6,239,259 B1 | 5/2001 | Davis et al. |
| 6,268,411 B1 | 7/2001 | Schneck et al. |
| 6,368,596 B1 | 4/2002 | Ghetie et al. |
| 6,476,198 B1 | 11/2002 | Kang |
| 6,515,110 B1 | 2/2003 | Whitlow et al. |
| 6,670,453 B2 | 12/2003 | Frenken et al. |
| 6,824,780 B1 | 11/2004 | Devaux et al. |
| 2002/0002271 A1 | 1/2002 | Rinderknecht et al. |
| 2006/0025576 A1 | 2/2006 | Miller et al. |
| 2006/0263367 A1 | 11/2006 | Fey et al. |
| 2013/0149308 A1* | 6/2013 | Campagne ............... 424/136.1 |

FOREIGN PATENT DOCUMENTS

| EP | 0307247 A2 | 3/1989 |
| EP | 0417563 A2 | 3/1991 |
| EP | 0517024 A2 | 12/1992 |
| EP | 0 599 274 A1 | 6/1994 |
| EP | 0628078 A1 | 12/1994 |
| EP | 0870827 A2 | 10/1998 |
| WO | WO 90/14357 A1 | 11/1990 |
| WO | WO 91/05264 A1 | 4/1991 |
| WO | WO 91/19515 A1 | 12/1991 |
| WO | WO 92/22583 A2 | 12/1992 |
| WO | WO 94/00136 A1 | 1/1994 |
| WO | WO 94/13804 A1 | 6/1994 |
| WO | WO 94/15642 A1 | 7/1994 |
| WO | WO 94/22478 A1 | 10/1994 |
| WO | WO 95/09917 A1 | 4/1995 |
| WO | WO 96/33206 A1 | 10/1996 |
| WO | WO 97/01633 A1 | 1/1997 |
| WO | WO 97/14719 A1 | 4/1997 |
| WO | WO 97/25428 A1 | 7/1997 |
| WO | WO 98/17797 A1 | 4/1998 |
| WO | WO 98/18921 A1 | 5/1998 |
| WO | WO 98/28426 A2 | 7/1998 |
| WO | WO 98/32856 A1 | 7/1998 |
| WO | WO 98/35986 A1 | 8/1998 |

(Continued)

OTHER PUBLICATIONS 1.132 Declaration of Dr. Carter filed in the U.S. Appl. No. 11/218,821 on Aug. 11, 2011; pp. 1-4.
Alderson et al., "Regulation of apoptosis and T cell activation by Fas-specific mAB," International Immunology 6:1799-1806 (1994).
Alt et al., "Novel tetravalent and tetravalent and bispecific IgG-like antibody molecules combining single-chain diabodies with the immunoglobulin γ1 Fc or CH3 region ," FEBS Letters 454(1-2) :90-94 (Jul. 2, 1999).
Amakawa et al., "The Hodgkin Disease Antigen CD30 is Crucial for Antigen-Induced Death of Developing T Cells," Symposium on Programmed Cell Death (Abstract No. 10), Cold Spring Harbor Laboratory (1995).

(Continued)

*Primary Examiner* — Lynn Bristol
(74) *Attorney, Agent, or Firm* — Jones Day

(57) ABSTRACT

The present application describes engineered antibodies, with three or more functional antigen binding sites, and uses, such as therapeutic applications, for such engineered antibodies.

4 Claims, 88 Drawing Sheets

(56) References Cited

FOREIGN PATENT DOCUMENTS

| | | |
|---|---|---|
| WO | WO 98/39361 A1 | 9/1998 |
| WO | WO 98/41629 A2 | 9/1998 |
| WO | WO 98/43089 A1 | 10/1998 |
| WO | WO 98/46643 A1 | 10/1998 |
| WO | WO 98/46751 A1 | 10/1998 |
| WO | WO 98/51793 A1 | 11/1998 |
| WO | WO 98/58965 A2 | 12/1998 |
| WO | WO 99/02567 A2 | 1/1999 |
| WO | WO 99/02653 A1 | 1/1999 |
| WO | WO 99/04001 A1 | 1/1999 |
| WO | WO 99/07738 A2 | 2/1999 |
| WO | WO 99/09165 A1 | 2/1999 |
| WO | WO 99/11791 A2 | 3/1999 |
| WO | WO 99/23221 A2 | 5/1999 |
| WO | WO 99/33980 A2 | 7/1999 |
| WO | WO 99/37684 A1 | 7/1999 |
| WO | WO 99/37791 A1 | 7/1999 |
| WO | WO 99/57150 A2 | 11/1999 |
| WO | WO 99/60846 A1 | 12/1999 |
| WO | WO 99/64461 A2 | 12/1999 |
| WO | WO 00/06605 A2 | 2/2000 |
| WO | WO 02/08293 A2 | 1/2002 |
| WO | WO 2004/003019 A2 | 1/2004 |

OTHER PUBLICATIONS

Anderson et al., "Expression of Human B Cell-Associated Antigens on Leukemias and Lymphomas: A Model of Human B Cell Differentiation," Blood 63(6) :1424-1433 (1984).

Armitage et al., "Molecular and Biological Characterization of a Murine Ligand for CD40," Nature 357 (6373) :80-82 (1992).

Arteaga et al., "p185c-erbB-2 Signaling Enhances Cisplatin-induced Cytotoxicity in Human Breast Carcinoma Cells: Association Between an Oncogenic Receptor Tyrosine Kinase and Drug-induced DNA Repair," Cancer Research 54(14) :3758-3765 (Jul. 15, 1994).

Ashkenazi and Dixit, "Death Receptors: Signaling and Modulation," Science, 281(5381) ,1305-1308 (1998).

Bacus et al., "Differentiation of Cultured Human Breast Cancer Cells (AU-565 and MCP-7) Associated with Loss of Cell Surface HER-2/neu Antigen," Molecular Carcinogenesis, 3(6) :350-362 (1990).

Bacus et al., "Tumor-inhibitory Monoclonal Antibodies to the HER-2/Neu Receptor Induce Differentiation of Human Breast Cancer Cells," Cancer Research 52 (9) :2580-2589 (May 1, 1992).

Baldwin, A., "The NF-KB and IKB Proteins: New Discoveries and Insights," Ann. Rev. Immunol. 14:649-683 (1996).

Banner et al. "Crystal Structure of the Soluble Human 55 kd TNF Receptor-Human TNFp Complex: Implications for TNP Receptor Activation," Cell, 73:431-445 (1993).

Baselga and Mendelsohn, "Receptor Blockade With Monoclonal Antibodies as Anti-Cancer Therapy," Phamac. Ther., 64: 127-154 (1994).

Behr et al., "Targeting of Liver Metastases of Colorectal Cancer with IgG F(ab')2, and Fab' Anti-Carcinoembryonic Antigen Antibodies Labeled with 99mTc: The Role of Metabolism and Kinetics," Cancer REsaerch, Supppl. 55:507-511 (2002).

Baselga et al., "Phase II Study of Weekly Intravenous Recombinant Humanized Anti-p185$^{HER2}$ Monoclonal Antibody in Patients With HER2/neu-Overexpressing Metastatic Breast Cancer," J. Clin. Oncol., 14 (3): 737-744 (Mar. 1996).

Beckman et al., "Antibody constructs in cancer therapy: protein engineering strategies to improve exposure in solid tumors," Can. 109:70-179 (2007).

Bindon et al., "Human monoclonal IgG isotypes differ in complement activation function at the level of C4 as well as Clq," Journal of Experimental Medicine 168(1) :127-142 (Jul. 1988).

Bodmer et al., "TRAMP, A Novel Apoptosis-Mediating Receptor with Sequence Homology to Tumor Necrosis Factor Receptor 1 and Fas(Apo-I/CD95)." Immunity, 6:79-88 (1997).

Boerner et al., "Production of Antigen-Specific Human Monoclonal Antibodies from In Vitro-Primed Human Splenocytes ," The Journal of Immunology, 147(1):86-95 (Jul. 1991).

Borrebaeck et al., "Human monoclonal antibodies produced by primary in vitro immunization of peripheral blood lymphocytes," Proc. Natl. Acad. Sci. USA, 85(11):3995-3999 (Jun. 1988).

Boulianne et al., "Production of functional chimaeric mouse/human antibody," Nature 312:643-646 (Dec. 13, 1984).

Brockhaus et al., "Identification of Two Types of Tumor Necrosis Factor Receptors on Human Cell Lines by Monoclonal Antibodies," Proc. Natl. Acad. Sci. USA 87:3127-3131 (1990).

Brojatsch et al., "CAR1, A TNFR-Related Protein, Is a Cellular Receptor for Cytopathic Avian Leukosis-Sarcoma Viruses and Mediates Apoptosis," Cell. 87:845-855 (1996).

Brown et al., "Anti-Tac-H, a humanized antibody to the interleukin 2 receptor, prolongs primate cardiac allograft survival," Proc. Natl. Acad. Sci. USA 88,2663-2667 (Apr. 1991).

Browning et al. "Lymphotoxin β, a Novel Member of the TNF Family that Forms a Heteromeric Complex with Lymphotoxin on the Cell Surface," Cell 72: 847-856 (1993).

Bruggemann et al., Comparison of the effector functions of human immunoglobulins using a matched set of chimeric antibodies, Journal of Experimental Medicine 166:1351-1361 (1987).

Caron et al., "Engineering Humanized Dimeric Forms of IgG are More Effective Antibodies," Journal of Experimental Medicine 176:1191-1195 (Oct. 1992).

Carraway and Cantley, "A New Acquaintance for ErbB3 and ErbB4: A Role for Receptor Heterodimerization in Growth Signaling," Cell 78: 5-8 (Jul. 15, 1994).

Carraway et al., "Neurogulin-2, A New Ligand of ErbB3/ErbB4-Receptor Tyrosine Kinases," Nature 387:512-516 (May 1997).

Casset et al., "A peptide mimetic of an anti-CD4 monoclonal antibody by rational design," BBRC 307:198-205 (2003).

Cespedes et al., "Mouse models in oncogenesis and cancer therapy," Clin. Trans. Oncol. 8(5):318-329 (2006).

Chang et al., "Ligands for ErbB-Family Receptors Encoded by a Neuregulin-Like Gene," Nature 387:509-512 (May 29, 1997).

Chen et al., "Selection and analysis of an optimized anti-VEGF antibody: crystal structure of an affinity-matured Fab in complex with antigen," J. Mol. Bio. 293(4):865-881 (1999).

Chicheportiche et al., "TWEAK, A New Secreted Ligand in the Tumor Necrosis Factor Family that Weakly Induces Apoptosis," Journal of Biological Chemistry 272(51) :32401-32410 (1997).

Chinnaiyan et al., "Signal Transduction by DR3, A Death Domain-Containing Receptor Related to TNFR-1 and CD95," Science. 274: 990-992 (1996).

Chothia et al., "Domain Association in Immunoglobulin Molecules. The Packing of Vriable Domains," Journal of Molecular Biology 186:651-663 (1985).

Co et al., "Humanized antibodies for antiviral therapy," Proc. Natl. Acad. Sci. USA 88:2869-2873 (Apr. 1991).

Coloma and Morrison, "Design and production of novel tetravalent bispecific antigbodies," Nature Biotechnology 15(2) :159-163 (Feb. 1997).

D'Souza and Taylor-Papadimitriou, "Overexpression of ERBB2 in Human Mamary Epithelial Cells Signals Inhibition of Transcription of the E-Cadherin Gene, " Proc. Natl. Acad. Sci. USA 91 (15): 7202-7206 (Jul. 19, 1994).

Daugherty et al. "Polymerase chain reaction facitlitates the cloning CDR-grafting and rapid expression of a murine monoclonal antibody directed against the CD1B component of leukocyte integrins," Nucleic Acids Research, 19(9):2471-2476 (May 11, 1991).

Dealtry et al., "DNA Fragmentation and Cytotoxicity Cause by Tumor Necrosis Factor is Enhanced by Interferon-γ," European Journal of Immunology, 17:689-693 (1987).

Degli-Esposti et al., "Cloning and Characterization of TRAIL-R3, a Novel Member of the Emerging TRAIL Receptor Family," Journal of Experimental Medicine 186(7):1165-1170 (1997).

Degli-Esposti et al., "The Novel Receptor TRAIL-R4 Induces NF-KB and Protects against TRAIL-mediated Apoptosis, yet Retains an Incomplete Death Domain," Immunity 7:813-820 (1997).

Demidem et al., "Chimeric Anti—CD20 (IDEC-C2B8) Monoclonal Antibody Sensitizes a dB Cell Lymphma Cell Line to Cell Killing by Cytotoxic Drugs," Cancer Biotherapy & Radiopharmaceuticals 12(3) :177-186 (1997).

Dennis, "Cancer: Off by a Whisker," Nature 442:739-741 (2006).

(56) References Cited

OTHER PUBLICATIONS

DePascalis et al., "Grafting of 'abbreviated' complementarity-determining regions containing specificity-determining residues essential for ligand contact to engineer a less immunogenic humanized monoclonal antibody," J. Immunol. 169(6):3076-3084 (2002).
Drebin et al., "Down-Modulation of an Oncogene Protein Product and Reversion of the Transformed Phenotype by Monoclonal Antibodies," Cell 41(3):695-706 (Jul. 1985).
Drebin et al., "Monoclonal Antibodies Reactive With Diesinct Domains of the neu Oncogene-Encoded p185 Molecule Exert Synergistic Anti-Tumor Effects In Vivo," Oncogene 2:273-277 (198S).
Duchosal et al., "Immunization of hu-PBL-SCID mice and the rescue of human monoclonal Fab fragments through combinatorial libraries," Nature 355 (6357) :258-262 (Jan. 16, 1992).
Earp et al., "Heterodimerization and Functional Interaction Between EGF Receptor Family Members: A New signaling Paradigm With Implicatons for Breast Cancer Research," Breast Cancer Res and Treatment, 35:115-132 (1995).
Einfeld et al., "Molecular Cloning of the Human B Cell CD20 Receptor Predicts a Hydrophobic Protein with Multiple Transmembrane Domains," EMBO Journal 7(3) ,711-717 (1988).
Emery et al., "Osteoprotegerin is a Receptor for the Cytotoxin Ligand TRAIL, " J. Bio. Chem. 273 (23):14363-14367 (1998).
Fendly et al., "Characterization of Murine Monoclonal Antibodies Reactive to Either the Human Epidermal Growth Factor Receptor or HER2/neu Gene Product," Cancer Research 50:1550-1558 (Mar. 1, 1990).
Fujimori et al., "A modeling analysis of monoclonal antibody percolation through tumors: a binding-site barrier," J. Nucl. Med. 31(7):1191-1198 (1990).
Garrard and Henner, "Selection of an anti-IGF-1 Fab from a Fab phage library created by mutageneisis of multiple CDR loops," Gene 128 (1):103-109 (Jun. 15, 1993).
Ghetie et al., "Homodimerizaton of tumor-reactive monoclonal antibodies markedly increases their ability to induce growth arrest or apoptosis of tumor cells," Proc. Natl. Acad. Sci. USA 94 (14):7509-7514, (Jul. 8, 1997).
Goldstein, P., "Cell Death: TRAIL and its Receptors," Curr. Biol. 7:R750-R753 (1997).
Goodwin et al., "Molecular Cloning and Expression of the Type 1 and Type 2 Murine Receptors for Tumor Necrosis Factor," Mol. Cell. Bio. 11;3020-3026 (1991).
Gorman et al., "Reshaping a therapeutic CD4 antibody," Proc. Natl. Acad. Sci, USA 88(10):4181-4185 (May 15, 1991.
Graham et al., "Characteristics of a Human Cell Line Transformed by DNA from Human Adenvirus Type 5," J. Gen. Virol. 36:59-72 (1977).
Gram et al. "In vitro selection and affinity maturation of antibodies from a naïve combinatorial immunoglobulin library," Proc. Natl. Acad. Sci. USA 89(B) :3576-3580 (Apr. 15, 1992).
Gras et al. "BCMAp: An Integral Membrane Protein in the Golgi Apparatus of Human Mature B Lymphocytes," Int. Immunology. 7:1093-1106 (1995).
Greenwood et al., "Engineering multiple domain forms of the therapeutic antibody CAMPATH-1H: effects on Complement lysis," Therapeutic Immunology 1 (5) :247-255 (Oct. 1994).
Griffiths et al., "Human anti-self antibodies with high specificity from phage display libraries," The EMBO Journal, 12,725-734 (1993).
Groenen et al., "Structure-Function Relationships for the EGF/TGF-α Familyh of Mitogens," Growth Factors, 11:235-257 (1994).
Gruss and Dower, "Tumor Necrosis Factor Ligand Superfamily: Involvement in the Pathology of Malignant Lymphomas," Blood, 85:3378-3404 (1995).
Hahne et al., "APRIL, A New Ligand of the Tumor Necrosis Factor Family Stimulates Tumor Cell Growth," Journal of Experimental Medicine 188(6) :1185-1190 (1998).
Hale et al., "Demonstration of In Vitro and In Vivo Efficacy of Two Biologically Active Human Soluble TNF Receptors Expressed in *E. coli.*, " Cell. Biochem. (abstract only, suppl. 15F; p. 424) pp. 113 (1991).

Hanasaki et al., "Binding of Human Plasma Sialoglycoproteins by the B Cell-Specific Lectin CD22: Selective Recognition of Immunoglobin M and Haptoglobin," Database Biosis (Accession No. PREV199598267581) (XPOO2177287), J. Biol. Chem. Mar. 31, 1995; 270(13):7533-42.
Hancock et al., "A Monoclonal Antibody Against the c-erbB-2 Protein Enhances the Cytotoxicity of cis-Diamminedichloroplatinum Against Human Breast and ovarian Tumor Cell Lines," Cancer Research 51:4575-4580 (Sep. 1, 1991).
Harwerth et al., "Monoclonal Antibodies Against the Extracellular Domain of the erbB-2 erbB-2 Receptor Function as Partial Ligand Agonists," Journal of Biological Chemistry 267(21):15160-15167 (Jul. 25, 1992).
Hohmann et al., "Two different cell types have different major receptors for human tumor necrosis factor (TNFα)," Journal of Biological Chemistry 264(25) :14927-14934 (1989).
Holm et al., "Functional mapping and single chain construction of the anti-cytokeratin 8 monoclonal antibody TS1," Mol. Immunol. 44(6):1075-1084 (2007).
Holmes et al., "Identification of Heregulin, A Specific Activator of $p185^{erbB2}$," Science, 256:1205-12010 (May 22, 1992).
Hoogenboom and Winter, "By-Passing Immunisation: Human Antibodies from Synthetic Repertoires of Germline $V_H$ Gene Segments Rearragned in Vitro," J. Mol. Biol. 227:381-388 (1992).
Hudziak et al., "$p185^{HER2}$ Monoclonal Antibody Has Antiproliferative Effiects In Vitro and Sensitizes Human Breast Tumor Cells to Tumor Necrosis Factor," Molecular & Cellular Biology 9(3) :1165-1172 (Mar. 1989).
Hymowitz et al., "Triggering Cell Death: The Crystal Structure of Apo2L/TRAIL in a Complex with Death Receptor 5," Molecular Cell 4(4) :563-571 (1999).
Itoh et al., "The Polypeptide Encoded by the cDNA for Human Cell Surface Antigen Fas Can Mediate Apoptosi, "Cell, 66:233-243 (1991).
Jaffers et al., "Monoclonal Antibody Therapy, Anti-Idiotypic and Non-Anti-Idiotypic Antibodies to OKT3 Arising Despite Intense Immunosuppressionl," Transplantation , 41(5) :572-578 (May 1986).
Johnson et al., "Expression and Structure of Human NGF Receptor," Cell 47:545-554 (1986).
Jones et al., "Replacing the Complementarity—Determining Regions in a Human Antibody with Those From a Mouse, " Nature 321:522-525 (May 29, 1986).
Junghans et al., "Anti-Tac-H, a Humanized Antibody to the Interleukin 2 Receptor with New Features for Immunotherapy in Malignant and. Immune Disorders," Cancer Research 50(5):1495-1502 (Mar. 1990).
Kabat et al., "Introduction," Sequences of Proteins of Immunological Interest, US Dept. of Health and Human Services, NIH, 5th edition, Bethesda, MD vol. 1:xiii-xcvi (1991).
Kasprzyk et al., "Therapy of an Animal Model of Human Gastric Cancer Using a Combination of Anti-erbB-2 Monoclonal Antibodies, " Cancer Research 52(10):2771-2776 (May 15, 1992).
Kiesel et al., "Removal of Cells From a Malignant B-cell Line From Bone Marrow with Immunomagnetic Beads and with Complement and Immunoglobulin Switch Variant Mediated Cytolysis," Leukemia Research 11(12):1119-1125 (1987).
Kitson et al., "A Dearh-Domain-Containing Receptor that Mediates Apoptosis," Nature 384: 372-375 (1996).
Klapper et al., "A Subclass of Tumor-Inhibitory Monoclonal Antibodies to ErbB-2/HER2 Blocks Crosstalk With Growth Factor Receptors," Oncogene 14:2099-2109 (1997).
Kohno et al., "A Second Tumor Necrosis Factor Receptor Gene Product Can Shed a Naturally Occurring Tumor Necrosis Factor Inhibitor," Proc. Natl. Acad. Sci. USA 87:8331-8335 91990).
Koopman et al., "Annexin V for Flow Cytometric Detection of Phosphatidylserine Expression on B Cells Undergoing Apoptosis," Blood 84:1415-1420 (1994).
Kotts et al., "Differential Growth Inhibition of Human Carcinoma Cells Exposed to Monoclonal Antibodies Directed against the Extracellular Domain of the HER2/ERBB2 Protooncogene," In Vitro (Abstract #176) 26(3):59A (1990).
Krammer et al., "Regulation of Apoptosis in the Immune System," Curr. Op. Immunol. 6:279-289 (1994).

(56) References Cited

OTHER PUBLICATIONS

Kraus et al., "Isolation and Characterization of ERBB3, a Third Member of the ERBB Epidermal Browth Factor Receptor Family: Evidence for Overexpression in a Subset of Human Mammary Tumors," Proc. Natl. Acad. Sci. USA 86:9193-9197 (1989).
Kumar et al., "Regulation of Phosphorylation of the c-erbB-2HER2 Gene Product by a Monoclonal Antibody and Serum Groth Factor(s) in Human Mammary Carcinoa Cells," Molecular & cellular Biology 11(2): 979-986 (1991).
Kumar et al., "Molecular cloning and expression of the Fabs of human autoantibodies in *Escherichia coli*. Determination of the heavy or light chain contribution to the anti-DNA/-cardiolipin activity of the Fab," J. Biol. Chem. 275(45):35129-35136 (2000).
Laabi et al., "A New Gene, BCM, on Chromosome 16 is Fused to the Inerleukin 2 gene by a t(4;16) (q26;p13) Translocation in a Malignant T Cell Lymphoma," EMBO Journal 11:3897-3904 (1992).
Laabi et al., "The BCMA Gene, Preferentially Expressed During B Lymphoid Maturation is Bidirectionally Transcribed," Nucleic Acids Research 22:1147-1154 (1994).
Lee et al., "Transforming Growth Factor α: Expression, Regulation, and Biological Activities," Pharmacological Reviews 47(10: 51-85 (1995).
Lemke, G., "Neuregulins in Development," Molecular and Cellular Neurosciences 7: 247-262 (1996).
Levi et al., "The Influence of Heregulins on Human Schawnn Cell Proliferation," J. Neuroscience 15(2): 1329-1340 (1995).
Lewis et al., "Cloning and Expression of cDNAs for Two Distinct Murine Tumor Necrosis Factor Receptors Demonstrate One Receptor is Species Specific," Proc. Natl. Acad. Sci. USA 88:2830-2834 (1991).
Lewis et al., "Differential Responses of Human Tumor Cell Lines to Anti-p185$^{HER2}$ Monoclonal Antibodies," Cancer Immunol. Immunother. 37:255-263 (1993).
Lewis et al., "Growth Regulation of Human Breast and Ovarian Tumor Cells by Heregulin: Evidence for the Requirement of ErbB2 as a Critical Component in Mediate Heregulin Responsiveness," Cancer research 56:1457-1465 (1996).
Li et al., "Pancreatic Cancer," Lancet 363:1049-1057 (2004).
Loetscher et al., "Molecular Cloning and Expression of the Human 55 kd Tumor Necrosis Factor Receptor," Cell 561:351-359 (1990).
Lotz et al., "The Nerve Growth Factor/Tumor Necrosis Factor Receptor Family," J. Leukocyte Biol. 60:1-7 (1996)Lov.
Love et al., "Recombinant antibodies possessing novel effector functions," Methods in Enzymology 178:515-527 (1989).
MacCallum et al., "Antibody-antigen interactions: contact analysis and binding site topography," J. Mol. Biol. 262(5):732-745 (1996).
MacFarlane et al., "Mice Transgenic for BAFF Develop Lymphocytic Disorders Along with Autoimmune Manifestations," Journal of Experimental Medicine 190:1697-1710 (1999).
Mackay et al., "Mice Transgenic for BAFF Develop Lymphocytic Disorders Along with Autoimmune Manifestations," Journal of Experimental Medicine 190:1697-1710 (1999).
Madry et al., "The Characterization of Murine BCMA Gene Defines it as a New Member of the Tumor Necrosis Factor Receptor Superfamily," Int. Immunology 10:1693-1702 (1998).
Maier et al., "Requirements for the Internalization of a Murine Monoclonal Antibody Directed Against the HER-2/neu Gene Product c-erbB-2," Cancer Research 51(19):5361-5369 (1991).
Mallet et al., "Characterization of the MRC OX40 Antigen of Activated CD4 Positive T Lymphocytes—A molecule Related to Nerve Growth Factor Receptor," EMBO Journal 9(4):1063-1068 (1990).
Maloney et al., "The Anti-Tumor Effect of Monoclonal Anti-CD20 Antibody (mAb) Therapy Includes Direct Anti-Proliferative Activity and Induction of Apoptosis in CD20 Positive Non-Hodgkin's Lymphoma (NHL) Cell Lines," Blood (Abstract #2535) 88(10):637(a) (1996).
Marks et al., "By-Passing Immunization: Human Antibodies from V-gene Libraries Displayed on Phage," J Mol. Biol. 222:581-597 (1991).

Marks et al., "By-Passing Immunization: Building High Affinity Human Antibodies by Chain Shuffling," Bio/Technology 10:779783 (1992).
Marsters et al., "A Novel Receptor for Apo2L/TRAIL Contains a Truncated Death Domain," Current Biology 7:1003-1006 (1997).
Marsters et al., "Activation of Apoptosis by Apo-2 Ligand is Independent of FADD but Blocked by CrmA," Current Biology 6(6):750-752 (1996).
Marsters et al., "Apo-3, A New Member of the Tumor Necrosis Factor Receptor Family, Contains a Death Domain and Activates Apoptosis and NF-κB," Curr. Biol 6(12):1669-1676 (1996).
Marsters et al., "Herpesvirus Entry Mediator, A Member of the Tumor Necrosis Factor Receptor (TNFR) Family, Interacts with Members of the TNFR-Associated Factor Family and Activates the Transcription Factors NF-κB and AP-1," J. Bio. Chem. 272(22):14029-14032 (1997).
Masui et al., "Growth Inhibition of Human Tumor Cells in Athymic Mice by Anti-Epidermal Growth Factor Receptor Monoclonal Antibodies," Cancer Research 44(3):1002-1007 (1984).
McKenzie et al., "Generation and Characterization of Monoclonal Antibdoeis Specific for the Human neu Oncogene Product, p. 185," Oncogene 4:543-548 (1989).
Miknoyoczki et al., Clin. Cancer REsaerch 5:2205-2212 (1999).
Miller et al., "Monoclonal antibody therapeutic trials in seven patients with T-cell lymphoma," Blood 62:988-995 (1983).
Mongkolsapaya et al., "Cutting Edge: Lymphocyte Inhibitor of TRAIL (TNF-Related Apoptosis-Inducing Ligand): A New Receptor Protecting Lymphocytes From the Death Ligand TRAIL," J. Immunol. 160(1):3-6 (1998).
Montgomery et al., "Herpes Simplex Virus-1 Entry into Cells Mediated by a Novel Member of the TNF/NGF Receptor Family," Cell 87(3):427-436 (1996).
Moore et al., "BLyS: Member of the Tumor Necrosis Factor Family and B Lymphocyte Stimulator," Science 285(5425): 260-263 (1999).
Morrison et al., "Chimeric Human Antibody Molecules: Mouse Antigen-Binding Domains with Human Constant Region Domains," Proc. Natl. Acad. Sci. USA 81:6851-6855 (1984).
Morrissey et al., "Axon Induced Mitogenesis of Human Schwann Cells Involves Heregulin and p185erbB2," Proc. Natl. Acad. Sci. USA 92:1431-1435 (1995).
Mukhopadhyay et al., "Identification and Characterization of a Novel Cytokin, THANK, a TNF Homologue That Activates Apoptosis, Nuclear Factor-κB and c-Jun NH2-Terminal Kinase," J. Bio. Chem. 274:15978-15981 (1999).
Myers et al., "Biological Effects of Monoclonal Antireceptor Antibodies Reactive with neu Oncogene Product, p185neu," Methods in Enzymology 198:277-290 (1991).
Nadler et al., "B4, a human B lymphocyte-associated antigen expressed on normal, mitogen-activated, and malignant B lymphocytes," J. Immunol. 132(1):244-250 (1983).
Nadler et al., "Diagnosis and treatment of human leukemias and lymphomas utilizing monoclonal antibdoies," Progress in Hematology, Brown, E., Grune & Stratton, Inc. vol. XII:187-225 (1981)).
Nadler, L., "B CellLeukemia Panel Workshop: Summary and Comments (Chap. 1)," Leukocyte Typing II, Reinherz et al., Springer Verlag vol. 2:3-37 and Appendix (1986).
Nagata and Golstein, "The Fas Death Factor," Science 267:1449-1456 (1995).
Nagata, S., "Apoptosis by Death Cell Factor," Cell 88:355-365 (1997).
Neuberger et al., "A hapten-specific chimaeric IgE antibody with human physiological effector function," Nature 314:268-270 (1985).
Nocentini et al., "A New Member of the Tumor Necrosis Factor/Nerve Growth Factor Receptor Family Inhibits T Cell Receptor-Induced Apoptosis," Proc. Natl. Acad. Sci. 94(12):6216-6221 (1997).
Nophar et al., "Soluble Forms of Tumor Necrosis Factor Receptors (TNF-Rs). The cDNA for the Type I TNF-R, Cloned Using Amino Acid Sequence Data of its Soluble Form, Encodes Both the Cell Surface and Soluble Form of the Receptor," EMBO Journal 9:3269-3278 (1990).
Novotny et al, "Structural invariants of antigen binding: comparison of immunoglobulin VL-VH and VL-VL domain dimers," Proc. Natl. Acad. Sci. USA 82(14):4592-4596 (1985).

(56) References Cited

OTHER PUBLICATIONS

Pan et al., "An Antagonist Decoy Receptor and a Death-Domain Containing Receptor for TRAIL," Science 277:815-818 (1997).
Pan et al., "The Receptor for the Cytotoxic Ligand TRAIL," Science 276: 111-113 (1997).
Pan et al., "TRUNDD, A New Member of the Trail Receptor Family That Antagonizes TRAIL Signalling," FEBS Letters 424(1-2):41-45 (1998).
Paprocka et al., "The activity of two immunotoxins composed of monoclonal antibody MoAb-16 and A-chaing of ricin (MoAb-16-RTA) or A-chain of mistletoe lectin I (MoAB-16-MLIA)," Arch. Immunol. Ther. Exp. 40(3-4):223-7 (1992).
Peipp et al., "Bispecific Antibodies Targeting Cancer Cells," Mediation and Modulation of Antibody Function 507-511 (2002.
Pietras et al., "Antibody to HER-2/neu Receptor Blocks DNA Repair After Cisplatin in Human Breast and Ovarian Cancer Cells," Oncogene 9:1829-1838 (1994).
Pitti et al., "Genomic Amplification of a Decoy Receptor for Fas Ligand in Lung and Colon Cancer," Nature 396(6712):699-703 (1998).
Pitti et al., "Induction of Apoptosis by Apo-2 Ligand, a New Member of the Tumor Necrosis Factor Cytokine Family," Journal of Biological Chemistry 271:12687-12690 (1996).
Plowman et al., "Heregulin Induces Tyrosine Phoshorylation of HER4/p180erbB4," Nature (Letters to Nature) 366:473-475 (1993).
Plowman et al., "Ligand-Specific Activation of HER4/p180erbB4, a Fourth Member of the Epidermal Growth Factor Receptor Family," Proc. Natl. Acad. Sci. USA 90:1746-1750 (1993).
Pluckthun and Pack, "New Protein Engineering Approaches to Multivalent and Bispecific Antibody Fragments," Imuunotechnology 3:83-105 (1997).
Queen et al., "A humanized antibody that binds to the interleukin 2 receptor," Proc. Natl. Acad. Sci. USA 86(24): 10029-10033 (1989).
Radaev et al., "Recognition of IgG by Fcγ Receptor," The Journal of Biological Chemistry 276(10):16478-16483 (2001).
Radeke et al., "Gene Transfer and Molecular Cloning of the Rat Nerve Growth Factor Receptor," Nature 325:593-597 (1987).
Reff et al., "Depletion of B Cells In Vivo by a Chimeric Mouse Human Monoclonal Antibody to CD20," Blood 83(2): 435-445 (1994).
Renshaw et al., "Humoral Immune Responses in CD40 Ligand-deficient Mice," Journal of Experimental Medicine 180:1889-1900 (1994).
Riechmann et al., "Reshaping Human Antibodies for Therapy," Nature 332:323-327 (1988).
Rudnick et al., Can. Biother. Radiopharm. 24: 155-162 (2009).
Santos et al., "Generation and characterization of a single gene-encoded single-chain-tetravalent antitumor antibody," Clinical Cancer Research 5(10 Suppl):3118s-3123s (1998).
Sarup et al., "Characterization of an Anti-P185HER2 Monoclonal Antibody that Stimulates Receptor Function and Inhibits Tumor Cell Growth," Growth Regulation 1:72-82 (1991).
Schaefer et al., "γ-Heregulin: A Novel Heregulin Isoform That is an Autocrine Growth Factor for the Human Breast Cancer Cell Line, MDA-MB-175," Oncogene 15:1385-1394 (1997).
Schall et al., "Molecular Cloning and Expression of a Receptor for Human Tumor Necrosis Factor," Cell 61:361-370 (1990).
Schmid et al., "DNA Fragmentation: Manifestation of Target Cell Destruct. Mediated by Cytotoxic T-cell Lines, Lymphotoxin-Secreting Helper T-cell Clones, and Cell-Free Lymphotoxin-Containing Supernatant," Proc. Natl. Acad. Sci. USA 83:1881-1885 (1986).
Schneider et al., "BAFF, A Novel Ligand of the Tumor Necrosis Factor Family, Stimulates Cell Growth," Journal of Experimental Medicine 189:1747-1756 (1999).
Schneider et al., "Characterization of Two Receptors for TRAIL," FEBS Letters 416:329-334 (1997).
Schroff et al., "Human anti-murine immunoglobulin responses in patients receiving monoclonal antibody therapy," Cancer Research 45:879-885 (1985).
Scott et al., "p185HER2 Signal Transduction in Breast Cancer Cells," Journal of Biological Chemistry 266(22):14300-14305(1991).
Screaton et al., "LARD: A New Lymphoid-Specific Death Domain Containing Receptor Regulated by Alternative Pre-mRNA Splicing," PRoc. Natl. Acad. Sci. 94:4615-4619 (1997).
Screaton et al., "TRICK2, A New Alternatively Spliced Receptor that Transduces the Cytotoxic Signal From TRAIL," Current Biology 7:693-696 (1997).
Shawver et al., "Ligand-Life Effects Induced by Anti-c-erbB-2 Antibodies Do Not Correlate with and Are Not Required for Growth Inhibition of Human Carcinoma Cells," Cancer Research 54(5):1367-1373 (1994).
Shepard et al., "Monoclonal Antibody Therapy of Human Cancer: Taking the HER2 Protooncogene to the Clinic," J. Clin. Immunol. 11(3):117-127 (1991).
Sheridan et al., "Control of TRAIL-Induced Apoptosis by a Family of Signaling and Decoy Receptors," Science 277:818-821 (1997).
Shopes, "A Geneticlaly Engineered Human IgG Mutant with Enhanced Cytolytic Activity," Journal of Immunology 148(9): 2918-2922 (1992).
Shu et al., "Secretion of a single-gene-encoded immunoglobulin from myeloma cells," Proc Natl. Acad. Sci. USA 90:7995-7999 (1993).
Shu et al., "TALL-1 is a Novel Mmeber of the TNF Family that is Down-Regulated by Mitogens," J. Leukocyte Biol. 65:680-683 (1999).
Shuford et al., "Effect of light chain V region duplication on IgG oligomerization and in vivo efficacy," Science 252(5006):724-727 (1991).
Sias et al., "ELISA for Quantitation of the Extracellular Domain of p185HER2 in Biological Fluids," Journal of Immunological Methods 132(1):73-80 (1990).
Simonet et al., "Osteoprotegerin: A Novel Secreted Protein Involved in the Regulation of Bone Density," Cell 89:309-319 (1997).
Slamon et al., "Human Breast Cancer: Correlation of Relapse and Survival with Amplification of the HeER-2/neu Oncogene," Science 235: 177-182 (1987).
Sliwkowski et al., "Coexpression of erbB2 and erbB3 Proteins Reconstitutes a High Affinity Receptor for Heregulin," Journal of Biological Chemistry 269(20):14661-14665 (1994).
Smith and Morrison, "Recombinant polymeric IgG: an approach to engineering more potent antibodies," Bio/Technology 12(7):683-688 (1994).
Smith et al., "A Receptor for Tumor Necrosis Factor Denies an Unusual Family of Cellular and Viral Proteins," Science 48: 1019-1023 (1990).
Smith-Gill et al., "Contributions of immunoglobulin heavy and light chains to antibody specificity for lysozyme and two haptens," J. Immunol. 139(12):4135-4144 (1987).
Smith et al., "T2 Open Reading Frame From the Shope Fibroma Virus Encodes a Soluble Form of the TNF Receptor," Biochem & Biophys. Res. Comm. 176:335-342 (1991).
Song et al., "Light chain of natural antibody plays a dominant role in protein antigen binding," Biochem. Biophys. Res. Comm. 268(2):390-394 (2000).
Stamenkovic et al., "A B-Lymphocyte Activation Molecule Related to the Nerve Browth Factor Receptor and Induced by Cytokines in Carcinomas," EMBO Journal 8(5):1403-1410 (1989).
Stancovski et al, "Mechanistic Aspects of the Opposing Effects of Monoclonal Antibodies tot the ERBB2 Receptor on Tumor Growth," Proc. Natl, Acad, Sci. USA 88(19):8691-8695 (1991).
Stevensons et al., "A Chimeric Antibody With Dual Fc Regions (bisFABFc) Prepared by Manipulations at the IgG Hinge," Anti-Cancer Drug Design 3(4):219-230 (1989).
Tagliabue et al., "Selection of Monoclonal Antibodies Which Induce Internalization and Phosphorylation of p185HER2 and Growth Inhibition of Cells With HER2/NEU Gene Amplification," International Journal of Cancer 47(6):993-937 (1991).
Talmadge et al., "Murine models to evaluate novel and conventional therapeutic strategies for cancer," Am. J. Pathol. 170(3):793-804 (2007).

(56) References Cited

OTHER PUBLICATIONS

Tedder et al., "The B Cell Surgace Molecule B1 is Functionally Linked with B Cell Activation and Differentiation," The Journal of Immunology 135(2):973-979 (1985).

Tedder et al., "The CD20 Surface Molecule of B Lymphocytes Functions as a Calcium Channel," J. Cell. Biochem. (Abstract #M 023) 14D:195 (1990).

Tewari and Dixit, "Recent Advances in Tumor Necrosis Factor and CD40 Signaling," Curr. OP. Genet. Develop. 6:39-44 (1996).

Thurber et al., "Antibody tumor penetration: transport opposed by systemic and antigen-mediated clearance," Adv. Drug Deliv. Rev. 60:1421-1434 (2008).

Tutt et al., "Trispecific F(ab')3 derivatives that use cooperative signaling via the TCR/CD3 complex and CD2 to activates and redirect resting cytotoxic T cells," J. Immunol. 147(1):60-69 (1991).

Upton et al., "Myxoma Virus Expresses a Secreted Protein with Homology to the Tumor Necrosis Factor Receptor Gene Family that Contributes to Viral Virulence," Virology 184:370-382 (1991).

Urlaub and Chasin, "Isolation of Chinese Hamster Cell Mutante Deficient in Diydrofolate Reductase Activity," Proc. Natl. Acad. Sci. USA 77(7):4216 (1980).

Vajdos et al., "Comprehensive functional maps of the antigen-binding site of an anti-ErbB2 antibody obtained with shotgun scanning mutagenesis," J. Mol. Biol. 320(2):415-428 (2002).

Valentine et al., "Phosphorylation of the CD20 Phosphoprotein in Resting B Lymphocytes," J. Bio. Chem. 264(19):11282-11287 (1989).

Vassilev et al., "Antibodies to the CD5 molecule in normal human immunoglobulins for therapeutic use (intravenous immunoglobulins, IVIg)" Clin. Exp. Immuno. 92:369-372 (1993).

Verhoeyen et al., "Reshaping Human Antibodies: Grafting an Antilysozyme Activity," Science 239:1534-1536 (1988).

Verma et al., "Rel/NFκB/IκB Family: Intimate Tales of Association and Dissociation," Genes Develop. 9:2723:2735 (1995).

Vietta and Uhr, "Monoclonal Antibodies as Agonists: An Expanded Role for Their Use in Cancer Therapy," Cancer Research 54(2):5301-5309 (1994).

Von Bulow and Bram, "NF-AT Activation Induced by a CAML-Interacting Member of the Tumor Necrosis Factor Receptor Superfamily," Science 278:138-141 (1997).

Voskoglou-Nomikos, "Clinical predictive value of the in vitro cell line, human xenograft, and mouse allograft preclinical cancer models," Clin. Can. Res. 9(11):4227-4239 (2003).

Walczak et al., "TRAIL-R2: A Novel Apoptosis-Mediating Receptor for TRAIL," EMBO Journal 16(17): 5386-5397 (1997).

Ward et al., "Binding activities of a repertoire of single immunoglobulin variable domains secreted from *Escherichia coli*," Nature 341(6242):544-546 (1989).

Wiley et al., "Identification and Characterization of a New Member of the TNF Family that Induces Apoptosis," Immunity 3:673-682 (1995).

Winter et al., "Making antibodies by phage display technology," Annual Review of Immunology 12:433-455 (1994).

Wolff et al., "Monoclonal antibody homodimers: enhanced antitumor activity in nude mice," Cancer Research 53(11):2560-2565 (1993).

Wu et al., "Apoptosis Induced by an Anti-Epidermal Growth Factor Receptor Monoclonal Antibody in a Human Colorectal Carcinoma Cell Line and Its Delay by Insulin," Journal of Clinical Investigation 95(4):1897-1905 (1995).

Wu et al., "Killer/DR5 is a DNA Damage-Inducible p53 Regulated Death Receptor Gene," Nature Genetics 17:141-143 (1997).

Wu et al., "Humanization of a murine monoclonal antibody by simultaneous optimization of framework and CDR residues," J. Mol. Biol. 294(1):151-162 (1999).

Xu et al., "Antibody-Induced Growth Inhibition is Mediated Through Immunochemically and Functionally Distinct Epitopes on the Extracellular Domain of the c-erbB-2 (HER-2/neu) Gene Product p185," International Journal of Cancer 53(3): 401-408 (1993).

Yokota et al., "Rapid Tumor Penetration of a Single-Chain Fv and Comparison with Other Immunoglobulin Forms," Cancer Research 52:3402-3408 (1992).

Yonehara et al., "A Cell-Killing Monoclonal Antibody (Anti-Fas) to a Cell Surface Antigen CO-Downregulated with the Receptor of Tumor Necrosis Factor," Journal of Experimental Medicine 169:1747-1756 (1989).

Yonehara et al., "Involvement of Apoptosis Antigen Fas in Clonal Deletion of Human Thymocytes," International Immunology 6(1): 1849-1856 (1994).

Zapata et al., "Engineering linear F9ab')2 fragments for efficient production in *Escherichia coli* and enhanced antiproliferative activity," Protein Eng. 8:1057-62 (1995).

Zhang et al., "Neuregulin-3 (NRG3): A novel neural tissue-enriched protein that binds and activates ErbB4," Proc. Natl. Acad. Sci. USA 94: 95629567 (1997).

Zheng et al., "Induction of Apoptosis in Mature T Cells by Tumor Necrosis Factor," Nature 377:248-351 (1995).

Carter, Paul J,, "Declaration of Dr. Paul J. Carter Under 37 C.F.R. 1.132," United States Patent and Trademark Office, U.S. Appl. No. 11/218,821, pp. 1-18, (Aug. 11, 2011).

Chan, Conrad En Zuo, et al., "Optimized Expression of Full-Length IgG1 Antibody in a Common *E. coli* Strain," PLoS One, vol. 5, No. 4, e10261, pp. 1-8, (Apr. 2010).

Better, Marc, et al., "Potent anti-CD5 ricin A chain immunoconjugates from bacterially produced Fab' and F(ab')2," Proc. Natl. Acad. Sci. vol. 90, pp. 457-461, (Jan. 1993).

Hoogenboom, Hennie R., "Mix and match: Building manifold binding sites," Nature Biotechnology, 15:125-126 (1997).

* cited by examiner

```
          230       240       250       260       270
humIgG1   PAPELLGGPSVFLFPPKPKDTLMISRTPEVTCVVVDVSHEDPEVKFNWYV
humIgG2   PAP-PVAGPSVFLFPPKPKDTLMISRTPEVTCVVVDVSHEDPEVQFNWYV
humIgG3   PAPELLGGPSVFLFPPKPKDTLMISRTPEVTCVVVDVSHEDPEVQFKWYV
humIgG4   PAPEFLGGPSVFLFPPKPKDTLMISRTPEVTCVVVDVSQEDPEVQFNWYV
murIgG1   ---TVPEVSSVFIFPPKPKDVLTITLTPKVTCVVVDISKDDPEVQFSWFV
murIgG2A  PAPNLLGGPSVFIFPPKIKDVLMISLSPIVTCVVVDVSEDDPDVQISWFV
murIgG2B  PAPNLEGGPSVFIFPPNIKDVLMISLTPKVTCVVVDVSEDDPDVQISWFV
murIgG3   PPGNILGGPSVFIFPPKPKDALMISLTPKVTCVVVDVSEDDPDVHVSWFV 280       290       300       310       320
humIgG1   DGVEVHNAKTKPREEQYNSTYRVVSVLTVLHQDWLNGKEYKCKVSNKALP
humIgG2   DGVEVHNAKTKPREEQFNSTFRVVSVLTVVHQDWLNGKEYKCKVSNKGLP
humIgG3   DGVEVHNAKTKPREEQFNSTFRVVSVLTVLHQDWLNGKEYKCKVSNKALP
humIgG4   DGVEVHNAKTKPREEQFNSTYRVVSVLTVLHQDWLNGKEYKCKVSNKGLP
murIgG1   DDVEVHTAQTQPREEQFNSTFRSVSELPIMHQDCLNGKEFKCRVNSAAFP
murIgG2A  NNVEVHTAQTQTHREDYNSTLRVVSALPIQHQDWMSGKEFKCKVNNKDLP
murIgG2B  NNVEVHTAQTQTHREDYNSTIRVVSHLPIQHQDWMSGKEFKCKVNNKDLP
murIgG3   DNKEVHTAWTQPREAQYNSTFRVVSALPIQHQDWMRGKEFKCKVNNKALP 330       340       350       360       370
humIgG1   APIEKTISKAKGQPREPQVYTLPPSREEMTKNQVSLTCLVKGFYPSDIAV
                              D L
humIgG2   APIEKTISKTKGQPREPQVYTLPPSREEMTKNQVSLTCLVKGFYPSDIAV
humIgG3   APIEKTISKTKGQPREPQVYTLPPSREEMTKNQVSLTCLVKGFYPSDIAV
humIgG4   SSIEKTISKAKGQPREPQVYTLPPSQEEMTKNQVSLTCLVKGFYPSDIAV
murIgG1   APIEKTISKTKGRPKAPQVYTIPPPKEQMAKDKVSLTCMITDFFPEDITV
murIgG2A  APIERTISKPKGSVRAPQVYVLPPPEEEMTKKQVTLTCMVTDFMPEDIYV
murIgG2B  SPIERTISKPKGLVRAPQVYTLPPPAEQLSRKDVSLTCLVVGFNPGDISV
murIgG3   APIERTISKPKGRAQTPQVYTIPPPREQMSKKKVSLTCLVTNFFSEAISV 380       390       400       410       420
humIgG1   EWESNGQPENNYKTTPPVLDSDGSFFLYSKLTVDKSRWQQGNVFSCSVMH
humIgG2   EWESNGQPENNYKTTPPMLDSDGSFFLYSKLTVDKSRWQQGNVFSCSVMH
humIgG3   EWESSGQPENNYNTTPPMLDSDGSFFLYSKLTVDKSRWQQGNIFSCSVMH
humIgG4   EWZSNGQPENNYKTTPPVLDSDGSFFLYSKLTVDKSRWQEGNVFSCSVMH
murIgG1   EWQWNGQPAENYKNTQPIMDTDGSYFVYSKLNVQKSNWEAGNTFTCSVLH
murIgG2A  EWTNNGKTELNYKNTEPVLDSDGSYFMYSKLRVEKKNWVERNSYSCSVVH
murIgG2B  EWTSNGHTEENYKDTAPVLDSDGSYFIYSKLNMKTSKWEKTDSFSCNVRH
murIgG3   EWERNGELEQDYKNTPPILDSDGTYFLYSKLTVDTDSWLQGEIFTCSVVH 430       440
humIgG1   EALHNHYTQKSLSLSPGK
humIgG2   EALHNHYTQKSLSLSPGK
humIgG3   EALHNRFTQKSLSLSPGK
humIgG4   EALHNHYTQKSLSLSLGK
murIgG1   EGLHNHHTEKSLSHSPGK
murIgG2A  EGLHNHHTTKSFSRTPGK
murIgG2B  EGLKNYYLKKTISRSPGK
murIgG3   EALHNHHTQKNLSRSPGK
```

*FIG. 3*

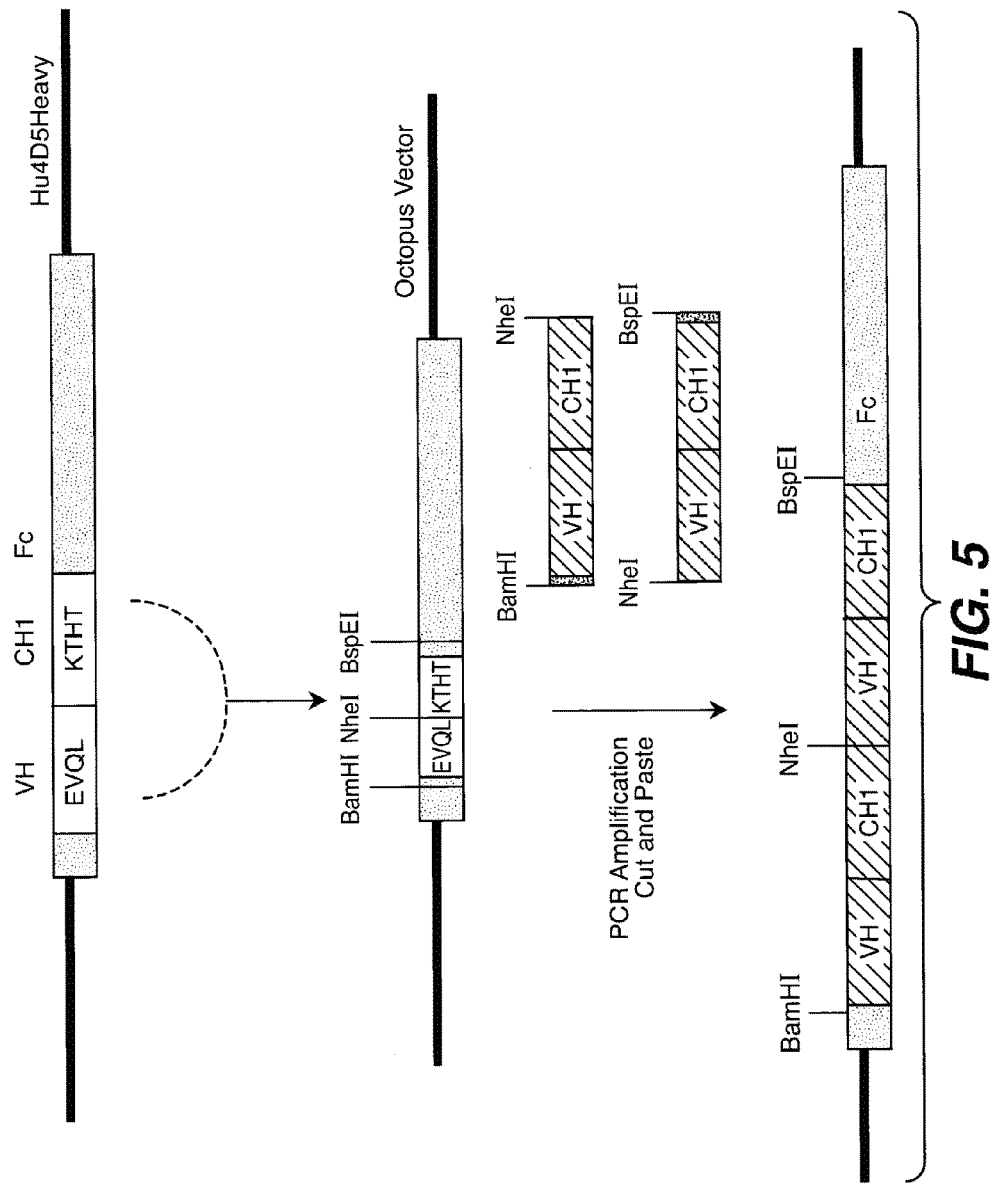

OctHER2 - 5hr

16E2 Octopus (anti-DR5) - 2 Day

Log10 Concentration

| Panel/Cell Line | Time Zero | Ctrl | 0.0 | 0.5 | 1.0 | 1.5 | 2.0 |
|---|---|---|---|---|---|---|---|
| Leukemia | | | | | | | |
| CCRF-CEM | 0.081 | 0.557 | 0.526 | 0.491 | 0.457 | 0.299 | 0.125 |
| HL-60(TB) | 0.487 | 1.935 | 1.821 | 1.827 | 1.486 | 0.843 | 0.561 |
| K-562 | 0.238 | 1.548 | 1.548 | 1.525 | 1.473 | 1.494 | 1.458 |
| MOLT-4 | 0.215 | 1.046 | 0.976 | 0.908 | 0.890 | 0.888 | 0.874 |
| RPMI-8226 | 0.335 | 1.302 | 1.067 | 1.009 | 0.947 | 0.937 | 0.959 |
| SR | 0.279 | 1.868 | 0.965 | 0.807 | 0.681 | 0.600 | 0.537 |
| Non-Small Cell Lung Cancer | | | | | | | |
| A549/ATCC | 0.212 | 1.132 | 1.155 | 1.091 | 1.061 | 1.094 | 1.096 |
| EKVX | 0.561 | 1.345 | 1.247 | 1.256 | 1.237 | 1.142 | 1.181 |
| HOP-62 | 0.363 | 1.082 | 1.147 | 1.156 | 1.191 | 1.182 | 1.158 |
| HOP-92 | 0.630 | 0.958 | 0.717 | 0.617 | 0.541 | 0.551 | 0.564 |
| NCI-H226 | 0.269 | 0.702 | 0.660 | 0.588 | 0.531 | 0.541 | 0.539 |
| NCI-H23 | 0.602 | 1.657 | 1.581 | 1.525 | 1.463 | 1.512 | 1.540 |
| NCI-H322M | 0.488 | 1.265 | 1.222 | 1.265 | 1.256 | 1.276 | 0.211 |
| NCI-H460 | 0.362 | 1.677 | 0.416 | 0.305 | 0.244 | 0.256 | 0.237 |
| NCI-H522 | 0.374 | 0.954 | 0.868 | 0.830 | 0.804 | 0.828 | 0.839 |
| Colon Cancer | | | | | | | |
| COLO 205 | 0.145 | 0.829 | 0.003 | -0.002 | -0.008 | 0.004 | 0.009 |
| HCC-2998 | 0.334 | 0.797 | 0.511 | 0.353 | 0.246 | 0.250 | 0.252 |
| HCT-116 | 0.385 | 2.058 | 1.341 | 1.051 | 1.008 | 0.926 | 0.904 |
| HCT-15 | 0.205 | 1.218 | 0.324 | 0.204 | 0.146 | 0.154 | 0.169 |
| HT29 | 0.322 | 1.464 | 1.547 | 1.523 | 1.566 | 1.553 | 1.485 |
| KM12 | 0.240 | 1.281 | 1.243 | 1.218 | 1.224 | 1.096 | 1.097 |
| SW-620 | 0.134 | 0.961 | 0.713 | 0.721 | 0.678 | 0.645 | 0.594 |
| CNS Cancer | | | | | | | |
| SF-268 | 0.360 | 1.045 | 1.005 | 1.008 | 0.992 | 1.013 | 0.970 |
| SF-295 | 0.512 | 1.311 | 0.344 | 0.313 | 0.312 | 0.313 | 0.282 |
| SF-539 | 0.220 | 1.153 | 0.860 | 0.750 | 0.673 | 0.674 | 0.657 |

*FIG. 20A-1*

16E2 Octopus (anti-DR5) - 2 Day

Log10 Concentration

| Panel/Cell Line | Percent Growth | | | | | GI50 | TGI | LC50 |
|---|---|---|---|---|---|---|---|---|
| | 0.0 | 0.5 | 1.0 | 1.5 | 2.0 | | | |
| Leukemia | | | | | | | | |
| CCRF-CEM | 94 | 86 | 79 | 46 | 9 | 2.74E+01 | >1.00E+02 | >1.00E+02 |
| HL-60(TB) | 92 | 93 | 69 | 25 | 5 | 1.64E+01 | >1.00E+02 | >1.00E+02 |
| K-562 | 100 | 98 | 94 | 96 | 93 | >1.00E+02 | >1.00E+02 | >1.00E+02 |
| MOLT-4 | 92 | 83 | 81 | 81 | 79 | >1.00E+02 | >1.00E+02 | >1.00E+02 |
| RPMI-8226 | 76 | 70 | 63 | 62 | 65 | >1.00E+02 | >1.00E+02 | >1.00E+02 |
| SR | 43 | 33 | 25 | 20 | 16 | <1.00E+00 | >1.00E+02 | >1.00E+02 |
| Non-Small Cell Lung Cancer | | | | | | | | |
| A549/ATCC | 102 | 95 | 92 | 96 | 96 | >1.00E+02 | >1.00E+02 | >1.00E+02 |
| EKVX | 87 | 89 | 86 | 74 | 79 | >1.00E+02 | >1.00E+02 | >1.00E+02 |
| HOP-62 | 109 | 110 | 115 | 114 | 111 | >1.00E+02 | >1.00E+02 | >1.00E+02 |
| HOP-92 | 26 | -2 | -14 | -13 | -10 | <1.00E+00 | 2.92E+00 | >1.00E+02 |
| NCI-H226 | 90 | 74 | 61 | 63 | 62 | >1.00E+02 | >1.00E+02 | >1.00E+02 |
| NCI-H23 | 93 | 88 | 82 | 86 | 89 | >1.00E+02 | >1.00E+02 | >1.00E+02 |
| NCI-H322M | 94 | 100 | 99 | 101 | 93 | >1.00E+02 | >1.00E+02 | >1.00E+02 |
| NCI-H460 | 4 | -16 | -33 | -29 | -35 | <1.00E+00 | 1.27E+00 | >1.00E+02 |
| NCI-H522 | 85 | 79 | 74 | 78 | 80 | >1.00E+02 | >1.00E+02 | >1.00E+02 |
| Colon Cancer | | | | | | | | |
| COLO 205 | -98 | -100 | -100 | -98 | -94 | <1.00E+00 | <1.00E+00 | <1.00E+00 |
| HCC-2998 | 38 | 4 | -26 | -25 | -25 | <1.00E+00 | 3.70E+00 | >1.00E+02 |
| HCT-116 | 57 | 40 | 37 | 32 | 31 | 1.61E+00 | >1.00E+02 | >1.00E+02 |
| HCT-15 | 12 | 0 | -29 | -25 | -18 | <1.00E+00 | 3.03E+00 | >1.00E+02 |
| HT29 | 107 | 105 | 109 | 108 | 102 | >1.00E+02 | >1.00E+02 | >1.00E+02 |
| KM12 | 96 | 94 | 95 | 82 | 82 | >1.00E+02 | >1.00E+02 | >1.00E+02 |
| SW-620 | 70 | 71 | 66 | 62 | 56 | >1.00E+02 | >1.00E+02 | >1.00E+02 |
| CNS Cancer | | | | | | | | |
| SF-268 | 94 | 94 | 92 | 95 | 89 | >1.00E+02 | >1.00E+02 | >1.00E+02 |
| SF-295 | -33 | -39 | -39 | -39 | -45 | <1.00E+00 | <1.00E+00 | >1.00E+02 |
| SF-539 | 69 | 57 | 49 | 49 | 47 | 8.14E+00 | >1.00E+02 | >1.00E+02 |

FIG. 20A-2

16E2 Octopus (anti-DR5) - 2 Day
Log10 Concentration

| Panel/Cell Line | Time Zero | Ctrl | 0.0 | 0.5 | 1.0 | 1.5 | 2.0 |
|---|---|---|---|---|---|---|---|
| CNS Cancer | | | | | | | |
| SNB-19 | 0.316 | 1.123 | 1.139 | 1.143 | 1.121 | 1.136 | 1.157 |
| SNB-75 | 0.326 | 0.637 | 0.651 | 0.640 | 0.596 | 0.623 | 0.628 |
| U251 | 0.197 | 0.981 | 0.766 | 0.718 | 0.642 | 0.620 | 0.636 |
| Melanoma | | | | | | | |
| LOX IMVI | 0.349 | 1.703 | 1.589 | 1.510 | 1.366 | 1.321 | 1.299 |
| MALME-3M | 0.350 | 0.732 | 0.643 | 0.600 | 0.555 | 0.557 | 0.553 |
| M14 | 0.320 | 1.246 | 0.982 | 0.783 | 0.716 | 0.689 | 0.703 |
| SK-MEL-2 | 0.592 | 0.982 | 0.758 | 0.712 | 0.639 | 0.618 | 0.622 |
| SK-MEL-28 | 0.345 | 1.033 | 0.853 | 0.835 | 0.768 | 0.729 | 0.668 |
| SK-MEL-5 | 0.346 | 2.111 | 1.937 | 1.893 | 1.770 | 1.869 | 1.721 |
| UACC-257 | 0.612 | 1.307 | 1.211 | 1.133 | 1.062 | 1.053 | 0.976 |
| UACC-62 | 0.597 | 1.806 | 1.509 | 1.318 | 1.166 | 1.038 | 1.024 |
| Ovarian Cancer | | | | | | | |
| IGROV1 | 0.209 | 0.934 | 0.927 | 0.876 | 0.915 | 0.905 | 0.893 |
| OVCAR-3 | 0.434 | 1.295 | 0.566 | 0.526 | 0.460 | 0.439 | 0.431 |
| OVCAR-4 | 0.359 | 1.495 | 1.464 | 1.453 | 1.442 | 1.404 | 1.361 |
| OVCAR-5 | 1.107 | 1.829 | 1.539 | 1.355 | 1.318 | 1.181 | 1.253 |
| OVCAR-8 | 0.238 | 0.890 | 0.903 | 0.875 | 0.881 | 0.923 | 0.882 |
| SK-OV-3 | 0.450 | 1.051 | 1.051 | 1.061 | 1.034 | 1.068 | 1.075 |
| Renal Cancer | | | | | | | |
| 786-0 | 0.453 | 1.495 | 1.504 | 1.506 | 1.492 | 1.491 | 1.512 |
| A498 | 0.757 | 1.482 | 1.150 | 0.968 | 0.743 | 0.690 | 0.726 |
| ACHN | 0.360 | 1.644 | 1.336 | 1.290 | 0.931 | 0.904 | 0.899 |
| CAKI-1 | 0.292 | 1.410 | 1.326 | 1.213 | 1.151 | 1.071 | 1.062 |
| RXF 393 | 0.546 | 1.151 | 1.107 | 1.203 | 1.149 | 1.156 | 1.157 |
| SN12C | 0.511 | 1.145 | 0.962 | 0.839 | 0.755 | 0.730 | 0.788 |
| TK-10 | 0.539 | 1.127 | 1.116 | 1.095 | 1.021 | 1.028 | 0.999 |
| DO-31 | 0.580 | 1.330 | 1.391 | 1.351 | 1.319 | 1.301 | 1.294 |

*FIG. 20A-3*

16E2 Octopus (anti-DR5) - 2 Day

Log10 Concentration

| Panel/Cell Line | Percent Growth | | | | | GI50 | TGI | LC50 |
|---|---|---|---|---|---|---|---|---|
| | 0.0 | 0.5 | 1.0 | 1.5 | 2.0 | | | |
| CNS Cancer | | | | | | | | |
| SNB-19 | 102 | 102 | 100 | 102 | 104 | >1.00E+02 | >1.00E+02 | >1.00E+02 |
| SNB-75 | 104 | 101 | 87 | 96 | 97 | >1.00E+02 | >1.00E+02 | >1.00E+02 |
| U251 | 73 | 66 | 57 | 54 | 56 | >1.00E+02 | >1.00E+02 | >1.00E+02 |
| Melanoma | | | | | | | | |
| LOX IMVI | 92 | 86 | 75 | 72 | 70 | >1.00E+02 | >1.00E+02 | >1.00E+02 |
| MALME-3M | 77 | 65 | 53 | 54 | 53 | >1.00E+02 | >1.00E+02 | >1.00E+02 |
| M14 | 72 | 50 | 43 | 40 | 41 | 3.16E+00 | >1.00E+02 | >1.00E+02 |
| SK-MEL-2 | 43 | 31 | 12 | 7 | 8 | <1.00E+00 | >1.00E+02 | >1.00E+02 |
| SK-MEL-28 | 74 | 71 | 61 | 56 | 47 | 6.76E+01 | >1.00E+02 | >1.00E+02 |
| SK-MEL-5 | 90 | 88 | 81 | 86 | 78 | >1.00E+02 | >1.00E+02 | >1.00E+02 |
| UACC-257 | 86 | 75 | 65 | 63 | 52 | >1.00E+02 | >1.00E+02 | >1.00E+02 |
| UACC-62 | 75 | 60 | 47 | 36 | 35 | 7.66E+00 | >1.00E+02 | >1.00E+02 |
| Ovarian Cancer | | | | | | | | |
| IGROV1 | 99 | 92 | 97 | 96 | 94 | >1.00E+02 | >1.00E+02 | >1.00E+02 |
| OVCAR-3 | 15 | 11 | 3 | 1 | -1 | <1.00E+00 | 5.19E+01 | >1.00E+02 |
| OVCAR-4 | 97 | 96 | 95 | 92 | 88 | >1.00E+02 | >1.00E+02 | >1.00E+02 |
| OVCAR-5 | 60 | 34 | 29 | 10 | 20 | 1.56E+00 | >1.00E+02 | >1.00E+02 |
| OVCAR-8 | 102 | 98 | 99 | 105 | 99 | >1.00E+02 | >1.00E+02 | >1.00E+02 |
| SK-OV-3 | 100 | 102 | 97 | 103 | 104 | >1.00E+02 | >1.00E+02 | >1.00E+02 |
| Renal Cancer | | | | | | | | |
| 786-0 | 101 | 101 | 100 | 100 | 102 | >1.00E+02 | >1.00E+02 | >1.00E+02 |
| A498 | 54 | 29 | -2 | -9 | -4 | 1.21E+00 | 9.33E+00 | >1.00E+02 |
| ACHN | 76 | 72 | 44 | 42 | 42 | 7.98E+00 | >1.00E+02 | >1.00E+02 |
| CAKI-1 | 92 | 82 | 77 | 70 | 69 | >1.00E+02 | >1.00E+02 | >1.00E+02 |
| RXF 393 | 93 | 109 | 100 | 101 | 101 | >1.00E+02 | >1.00E+02 | >1.00E+02 |
| SN12C | 71 | 52 | 39 | 34 | 44 | 3.70E+00 | >1.00E+02 | >1.00E+02 |
| TK-10 | 98 | 95 | 82 | 83 | 78 | >1.00E+02 | >1.00E+02 | >1.00E+02 |
| DO-31 | 108 | 103 | 99 | 96 | 95 | >1.00E+02 | >1.00E+02 | >1.00E+02 |

*FIG. 20A-4*

16E2 Octopus (anti-DR5) - 2 Day

Log10 Concentration

| Panel/Cell Line | Time Zero | Ctrl | 0.0 | 0.5 | 1.0 | 1.5 | 2.0 |
|---|---|---|---|---|---|---|---|
| Prostate Cancer | | | | | | | |
| PC-3 | 0.332 | 0.865 | 0.653 | 0.628 | 0.546 | 0.545 | 0.552 |
| DU-145 | 0.336 | 1.268 | 1.174 | 1.189 | 1.130 | 1.125 | 1.112 |
| Breast Cancer | | | | | | | |
| MCF7 | 0.361 | 1.913 | 1.881 | 1.935 | 1.827 | 1.950 | 2.020 |
| NCI/ADR-RES | 0.331 | 0.988 | 0.958 | 0.976 | 0.977 | 0.992 | 0.996 |
| MDA-MB-231/ATCC | 0.590 | 0.974 | 0.998 | 0.958 | 0.883 | 0.895 | 0.887 |
| HS 578T | 0.579 | 1.268 | 1.146 | 1.028 | 0.976 | 0.977 | 1.018 |
| MDA-MB-435 | 0.261 | 1.249 | 1.055 | 0.972 | 0.858 | 0.843 | 0.783 |
| MDA-N | 0.217 | 0.971 | 0.910 | 0.895 | 0.782 | 0.795 | 0.766 |
| BT-549 | 0.570 | 1.446 | 1.237 | 0.989 | 0.820 | 0.773 | 0.728 |
| T-47D | 0.382 | 1.004 | 0.963 | 0.993 | 1.010 | 1.013 | 1.026 |

Mean Optical Densities

*FIG. 20A-5*

16E2 Octopus (anti-DR5) - 2 Day

Log10 Concentration

| Panel/Cell Line | Percent Growth | | | | | GI50 | TGI | LC50 |
|---|---|---|---|---|---|---|---|---|
| | 0.0 | 0.5 | 1.0 | 1.5 | 2.0 | | | |
| Prostate Cancer | | | | | | | | |
| PC-3 | 60 | 55 | 40 | 40 | 41 | 4.75E+00 | >1.00E+02 | >1.00E+02 |
| DU-145 | 90 | 91 | 85 | 85 | 83 | >1.00E+02 | >1.00E+02 | >1.00E+02 |
| Breast Cancer | | | | | | | | |
| MCF7 | 98 | 101 | 94 | 102 | 107 | >1.00E+02 | >1.00E+02 | >1.00E+02 |
| NCI/ADR-RES | 95 | 98 | 98 | 101 | 101 | >1.00E+02 | >1.00E+02 | >1.00E+02 |
| MDA-MB-231/ATCC | 106 | 96 | 76 | 79 | 77 | >1.00E+02 | >1.00E+02 | >1.00E+02 |
| HS 578T | 82 | 65 | 58 | 58 | 64 | >1.00E+02 | >1.00E+02 | >1.00E+02 |
| MDA-MB-435 | 80 | 72 | 60 | 59 | 53 | >1.00E+02 | >1.00E+02 | >1.00E+02 |
| MDA-N | 92 | 90 | 75 | 77 | 73 | >1.00E+02 | >1.00E+02 | >1.00E+02 |
| BT-549 | 76 | 48 | 29 | 23 | 18 | 2.90E+00 | >1.00E+02 | >1.00E+02 |
| T-47D | 93 | 98 | 101 | 101 | 103 | >1.00E+02 | >1.00E+02 | >1.00E+02 |

*FIG. 20A-6*

APO2L - 2 Day

Log10 Concentration

| Panel/Cell Line | Time Zero | Ctrl | 0.0 | 0.5 | 1.0 | 1.5 | 2.0 |
|---|---|---|---|---|---|---|---|
| Leukemia | | | | | | | |
| CCRF-CEM | 0.081 | 0.576 | 0.400 | 0.510 | 0.443 | 0.447 | 0.476 |
| HL-60(TB) | 0.487 | 1.926 | 1.660 | 1.118 | 1.074 | 0.881 | 0.857 |
| K-562 | 0.238 | 1.596 | 1.629 | 1.557 | 1.416 | 1.371 | 1.349 |
| MOLT-4 | 0.215 | 1.126 | 1.132 | 1.131 | 1.136 | 1.136 | 1.167 |
| RPMI-8226 | 0.335 | 1.284 | 0.599 | 0.427 | 0.348 | 0.359 | 0.345 |
| SR | 0.279 | 1.820 | 1.578 | 1.475 | 1.417 | 1.428 | 1.460 |
| Non-Small Cell Lung Cancer | | | | | | | |
| A549/ATCC | 0.212 | 1.164 | 1.177 | 1.173 | 1.086 | 1.052 | 1.068 |
| EKVX | 0.561 | 1.328 | 1.325 | 1.337 | 1.228 | 1.275 | 1.266 |
| HOP-62 | 0.363 | 1.260 | 1.241 | 1.174 | 1.106 | 1.202 | 1.136 |
| HOP-92 | 0.630 | 1.002 | 0.843 | 0.788 | 0.755 | 0.753 | 0.766 |
| NCI-H226 | 0.269 | 0.642 | 0.651 | 0.691 | 0.677 | 0.665 | 0.663 |
| NCI-H23 | 0.602 | 1.620 | 1.597 | 1.636 | 1.626 | 1.641 | 1.670 |
| NCI-H322M | 0.488 | 1.265 | 1.138 | 1.054 | 0.821 | 0.808 | 0.779 |
| NCI-H460 | 0.362 | 1.562 | 0.342 | 0.228 | 0.171 | 0.140 | 0.124 |
| NCI-H522 | 0.374 | 0.760 | 0.722 | 0.705 | 0.691 | 0.674 | 0.657 |
| Colon Cancer | | | | | | | |
| COLO 205 | 0.145 | 0.814 | 0.029 | 0.025 | 0.015 | 0.021 | 0.021 |
| HCC-2998 | 0.334 | 0.742 | 0.538 | 0.354 | 0.291 | 0.260 | 0.235 |
| HCT-116 | 0.385 | 1.855 | 0.726 | 0.483 | 0.389 | 0.348 | 0.349 |
| HCT-15 | 0.205 | 1.183 | 0.279 | 0.211 | 0.144 | 0.128 | 0.125 |
| HT29 | 0.322 | 1.477 | 1.515 | 1.485 | 1.404 | 1.462 | 1.446 |
| KM12 | 0.240 | 1.440 | 1.235 | 1.190 | 0.922 | 0.865 | 0.799 |
| SW-620 | 0.134 | 0.962 | 0.849 | 0.744 | 0.674 | 0.632 | 0.607 |
| CNS Cancer | | | | | | | |
| SF-268 | 0.360 | 0.874 | 0.891 | 0.873 | 0.886 | 0.901 | 0.898 |
| SF-295 | 0.512 | 1.273 | 0.862 | 0.728 | 0.636 | 0.670 | 0.603 |
| SF-539 | 0.220 | 1.040 | 1.006 | 0.820 | 0.632 | 0.528 | 0.574 |

Mean Optical Densities

*FIG. 20B-1*

APO2L - 2 Day

Log10 Concentration

| Panel/Cell Line | Percent Growth | | | | | | GI50 | TGI | LC50 |
|---|---|---|---|---|---|---|---|---|---|
| | 0.0 | 0.5 | 1.0 | 1.5 | 2.0 | | | | |
| Leukemia | | | | | | | | | |
| CCRF-CEM | 64 | 87 | 73 | 74 | 80 | | >1.00E+02 | >1.00E+02 | >1.00E+02 |
| HL-60(TB) | 82 | 44 | 41 | 27 | 26 | | 2.63E+00 | >1.00E+02 | >1.00E+02 |
| K-562 | 102 | 97 | 87 | 83 | 82 | | >1.00E+02 | >1.00E+02 | >1.00E+02 |
| MOLT-4 | 101 | 101 | 101 | 101 | 104 | | >1.00E+02 | >1.00E+02 | >1.00E+02 |
| RPMI-8226 | 28 | 10 | 1 | 2 | 1 | | <1.00E+00 | >1.00E+02 | >1.00E+02 |
| SR | 84 | 78 | 74 | 75 | 77 | | >1.00E+02 | >1.00E+02 | >1.00E+02 |
| Non-Small Cell Lung Cancer | | | | | | | | | |
| A549/ATCC | 101 | 101 | 92 | 88 | 90 | | >1.00E+02 | >1.00E+02 | >1.00E+02 |
| EKVX | 100 | 101 | 87 | 93 | 92 | | >1.00E+02 | >1.00E+02 | >1.00E+02 |
| HOP-62 | 98 | 90 | 83 | 94 | 86 | | >1.00E+02 | >1.00E+02 | >1.00E+02 |
| HOP-92 | 57 | 43 | 33 | 33 | 37 | | 1.77E+00 | >1.00E+02 | >1.00E+02 |
| NCI-H226 | 102 | 113 | 109 | 106 | 106 | | >1.00E+02 | >1.00E+02 | >1.00E+02 |
| NCI-H23 | 98 | 102 | 101 | 102 | 105 | | >1.00E+02 | >1.00E+02 | >1.00E+02 |
| NCI-H322M | 84 | 73 | 43 | 41 | 37 | | 7.61E+00 | >1.00E+02 | >1.00E+02 |
| NCI-H460 | -6 | -37 | -53 | -61 | -66 | | <1.00E+00 | <1.00E+00 | 8.18E+00 |
| NCI-H522 | 90 | 86 | 82 | 78 | 73 | | >1.00V+02 | >1.00E+02 | >1.00E+02 |
| Colon Cancer | | | | | | | | | |
| COLO 205 | -80 | -83 | -90 | -86 | -86 | | <1.00E+00 | <1.00E+00 | <1.00E+00 |
| HCC-2998 | 50 | 5 | -13 | -22 | -30 | | <1.00E+00 | 4.34E+00 | >1.00E+02 |
| HCT-116 | 23 | 7 | 0 | -10 | -9 | | <1.00E+00 | 1.03E+01 | >1.00E+02 |
| HCT-15 | 8 | 1 | -30 | -38 | -39 | | <1.00E+00 | 3.24E+00 | >1.00E+02 |
| HT29 | 103 | 101 | 94 | 99 | 97 | | >1.00E+02 | >1.00E+02 | >1.00E+02 |
| KM12 | 83 | 79 | 57 | 52 | 47 | | 4.89E+01 | >1.00E+02 | >1.00E+02 |
| SW-620 | 86 | 74 | 65 | 60 | 57 | | >1.00E+02 | >1.00E+02 | >1.00E+02 |
| CNS Cancer | | | | | | | | | |
| SF-268 | 103 | 100 | 102 | 105 | 105 | | >1.00E+02 | >1.00E+02 | >1.00E+02 |
| SF-295 | 46 | 28 | 16 | 21 | 12 | | <1.00E+00 | >1.00E+02 | >1.00E+02 |
| SF-539 | 96 | 73 | 50 | 38 | 43 | | 1.02E+01 | >1.00E+02 | >1.00E+02 |

*FIG. 20B-2*

APO2L - 2 Day

Log10 Concentration

Mean Optical Densities

| Panel/Cell Line | Time Zero | Ctrl | 0.0 | 0.5 | 1.0 | 1.5 | 2.0 |
|---|---|---|---|---|---|---|---|
| CNS Cancer | | | | | | | |
| SNB-19 | 0.316 | 1.144 | 1.164 | 1.172 | 1.151 | 1.194 | 1.191 |
| SNB-75 | 0.326 | 0.663 | 0.623 | 0.637 | 0.618 | 0.634 | 0.589 |
| U251 | 0.197 | 0.980 | 0.913 | 0.909 | 0.814 | 0.833 | 0.876 |
| Melanoma | | | | | | | |
| LOX IMVI | 0.349 | 1.657 | 1.606 | 1.494 | 1.415 | 1.380 | 1.464 |
| MALME-3M | 0.350 | 0.690 | 0.710 | 0.701 | 0.663 | 0.671 | 0.647 |
| M14 | 0.320 | 1.267 | 1.213 | 1.130 | 1.167 | 1.124 | 1.104 |
| SK-MEL-2 | 0.592 | 1.003 | 0.879 | 0.929 | 0.920 | 0.905 | 0.954 |
| SK-MEL-28 | 0.345 | 1.061 | 1.051 | 1.028 | 0.986 | 0.991 | 0.930 |
| SK-MEL-5 | 0.346 | 2.127 | 2.076 | 2.082 | 2.081 | 2.217 | 2.042 |
| UACC-257 | 0.612 | 1.245 | 1.289 | 1.256 | 1.199 | 1.189 | 1.113 |
| UACC-62 | 0.597 | 2.056 | 1.844 | 1.677 | 1.650 | 1.675 | 1.582 |
| Ovarian Cancer | | | | | | | |
| IGROV1 | 0.209 | 0.916 | 0.947 | 0.982 | 0.912 | 0.960 | 0.973 |
| OVCAR-3 | 0.434 | 1.456 | 0.983 | 0.787 | 0.765 | 0.658 | 0.651 |
| OVCAR-4 | 0.359 | 1.518 | 1.472 | 1.477 | 1.274 | 1.310 | 1.180 |
| OVCAR-5 | 1.107 | 1.815 | 1.700 | 1.618 | 1.446 | 1.452 | 1.493 |
| OVCAR-8 | 0.238 | 0.927 | 0.928 | 0.938 | 0.896 | 0.930 | 0.950 |
| SK-OV-3 | 0.450 | 1.167 | 1.126 | 1.123 | 1.077 | 1.162 | 1.175 |
| Renal Cancer | | | | | | | |
| 786-0 | 0.453 | 1.424 | 1.386 | 1.400 | 1.434 | 1.446 | 1.489 |
| A498 | 0.757 | 1.493 | 1.293 | 0.950 | 0.768 | 0.606 | 0.616 |
| ACHN | 0.360 | 1.548 | 1.526 | 1.590 | 1.327 | 1.363 | 1.318 |
| CAKI-1 | 0.292 | 1.503 | 1.439 | 1.477 | 1.266 | 1.371 | 1.210 |
| RXF 393 | 0.546 | 1.208 | 1.172 | 1.170 | 1.087 | 1.086 | 1.058 |
| SN12C | 0.511 | 1.155 | 1.055 | 1.072 | 1.050 | 1.080 | 1.064 |
| TK-10 | 0.539 | 1.080 | 1.060 | 0.975 | 0.939 | 0.839 | 0.756 |
| DO-31 | 0.580 | 1.342 | 1.334 | 1.361 | 1.391 | 1.387 | 1.439 |

*FIG. 20B-3*

APO2L - 2 Day

Log10 Concentration

| Panel/Cell Line | Percent Growth | | | | | GI50 | TGI | LC50 |
|---|---|---|---|---|---|---|---|---|
| | 0.0 | 0.5 | 1.0 | 1.5 | 2.0 | | | |
| CNS Cancer | | | | | | | | |
| SNB-19 | 102 | 103 | 101 | 106 | 106 | >1.00E+02 | >1.00E+02 | >1.00E+02 |
| SNB-75 | 88 | 92 | 87 | 91 | 78 | >1.00E+02 | >1.00E+02 | >1.00E+02 |
| U251 | 91 | 91 | 79 | 81 | 87 | >1.00E+02 | >1.00E+02 | >1.00E+02 |
| Melanoma | | | | | | | | |
| LOX IMVI | 96 | 88 | 81 | 79 | 85 | >1.00E+02 | >1+00E+02 | >1.00E+02 |
| MALME-3M | 106 | 103 | 92 | 94 | 87 | >1.00E+02 | >1+00E+02 | >1.00E+02 |
| M14 | 94 | 85 | 89 | 85 | 83 | >1.00E+02 | >1+00E+02 | >1.00E+02 |
| SK-MEL-2 | 70 | 82 | 80 | 76 | 88 | >1.00E+02 | >1+00E+02 | >1.00E+02 |
| SK-MEL-28 | 99 | 95 | 89 | 90 | 82 | >1.00E+02 | >1+00E+02 | >1.00E+02 |
| SK-MEL-5 | 97 | 98 | 97 | 105 | 95 | >1.00E+02 | >1+00E+02 | >1.00E+02 |
| UACC-257 | 107 | 102 | 93 | 91 | 79 | >1.00E+02 | >1+00E+02 | >1.00E+02 |
| UACC-62 | 85 | 74 | 72 | 74 | 68 | >1.00E+02 | >1+00E+02 | >1.00E+02 |
| Ovarian Cancer | | | | | | | | |
| IGROV1 | 104 | 109 | 99 | 106 | 108 | >1.00E+02 | >1+00E+02 | >1.00E+02 |
| OVCAR-3 | 54 | 34 | 32 | 22 | 21 | 1.25E+00 | >1+00E+02 | >1.00E+02 |
| OVCAR-4 | 96 | 96 | 79 | 82 | 71 | >1.00E+02 | >1+00E+02 | >1.00E+02 |
| OVCAR-5 | 84 | 72 | 48 | 49 | 54 | | >1+00E+02 | >1.00E+02 |
| OVCAR-8 | 100 | 102 | 95 | 100 | 103 | >1.00E+02 | >1+00E+02 | >1.00E+02 |
| SK-OV-3 | 94 | 94 | 87 | 99 | 101 | >1.00E+02 | >1+00E+02 | >1.00E+02 |
| Renal Cancer | | | | | | | | |
| 786-0 | 96 | 98 | 101 | 102 | 107 | >1.00E+02 | >1+00E+02 | >1.00E+02 |
| A498 | 73 | 26 | 1 | -20 | -19 | 1.76E+00 | 1+09E+01 | >1.00E+02 |
| ACHN | 98 | 104 | 81 | 84 | 81 | >1.00E+02 | >1+00E+02 | >1.00E+02 |
| CAKI-1 | 95 | 98 | 80 | 89 | 76 | >1.00E+02 | >1+00E+02 | >1.00E+02 |
| RXF 393 | 95 | 94 | 82 | 82 | 77 | >1.00E+02 | >1+00E+02 | >1.00E+02 |
| SN12C | 85 | 87 | 84 | 88 | 86 | >1.00E+02 | >1+00E+02 | >1.00E+02 |
| TK-10 | 96 | 81 | 74 | 56 | 40 | 4.77E+01 | >1+00E+02 | >1.00E+02 |
| DO-31 | 99 | 102 | 106 | 106 | 113 | >1.00E+02 | >1+00E+02 | >1.00E+02 |

FIG. 20B-4

APO2L - 2 Day
Log10 Concentration

| Panel/Cell Line | Time Zero | Ctrl | 0.0 | Mean Optical Densities 0.5 | 1.0 | 1.5 | 2.0 |
|---|---|---|---|---|---|---|---|
| Prostate Cancer | | | | | | | |
| PC-3 | 0.332 | 0.886 | 0.758 | 0.746 | 0.700 | 0.684 | 0.692 |
| DU-145 | 0.336 | 1.314 | 1.249 | 1.215 | 1.052 | 0.842 | 0.766 |
| Breast Cancer | | | | | | | |
| MCF7 | 0.361 | 2.217 | 1.918 | 1.618 | 1.333 | 1.279 | 1.180 |
| NCI/ADR-RES | 0.331 | 0.947 | 0.987 | 1.016 | 0.975 | 0.985 | 0.981 |
| MDA-MB-231/ATCC | 0.590 | 0.986 | 0.985 | 0.988 | 0.958 | 0.924 | 1.020 |
| HS 578T | 0.579 | 1.049 | 1.074 | 1.055 | 1.045 | 1.047 | 1.077 |
| MDA-MB-435 | 0.261 | 1.392 | 1.295 | 1.274 | 1.027 | 1.055 | 0.954 |
| MDA-N | 0.217 | 0.929 | 0.859 | 0.897 | 0.806 | 0.806 | 0.807 |
| BT-549 | 0.570 | 1.415 | 1.383 | 1.377 | 1.294 | 1.297 | 1.256 |
| T-47D | 0.382 | 1.044 | 1.014 | 1.025 | 1.000 | 1.054 | 0.955 |

*FIG. 20B-5*

APO2L - 2 Day

| Panel/Cell Line | Percent Growth Log10 Concentration | | | | | GI50 | TGI | LC50 |
|---|---|---|---|---|---|---|---|---|
| | 0.0 | 0.5 | 1.0 | 1.5 | 2.0 | | | |
| Prostate Cancer | | | | | | | | |
| PC-3 | 77 | 75 | 66 | 64 | 65 | >1.00E+02 | >1.00E+02 | >1.00E+02 |
| DU-145 | 93 | 90 | 73 | 52 | 44 | 4.07E+01 | >1.00E+02 | >1.00E+02 |
| Breast Cancer | | | | | | | | |
| MCF7 | 84 | 68 | 52 | 49 | 44 | 2.57E+01 | >1.00E+02 | >1.00E+02 |
| NCI/ADR-RES | 106 | 111 | 104 | 106 | 105 | >1.00E+02 | >1.00E+02 | >1.00E+02 |
| MDA-MB-231/ATCC | 100 | 100 | 93 | 84 | 109 | >1.00E+02 | >1.00E+02 | >1.00E+02 |
| HS 578T | 105 | 101 | 99 | 100 | 106 | >1.00E+02 | >1.00E+02 | >1.00E+02 |
| MDA-MB-435 | 91 | 90 | 68 | 70 | 61 | >1.00E+02 | >1.00E+02 | >1.00E+02 |
| MDA-N | 90 | 96 | 83 | 83 | 83 | >1.00E+02 | >1.00E+02 | >1.00E+02 |
| BT-549 | 96 | 96 | 86 | 86 | 81 | >1.00E+02 | >1.00E+02 | >1.00E+02 |
| T-47D | 95 | 97 | 93 | 101 | 87 | >1.00E+02 | >1.00E+02 | >1.00E+02 |

*FIG. 20B-6*

16E2 Octopus (anti-DR5) - 6 Day
Log10 Concentration

Mean Optical Densities

| Panel/Cell Line | Time Zero | Ctrl | 0.0 | 0.5 | 1.0 | 1.5 | 2.0 |
|---|---|---|---|---|---|---|---|
| Leukemia | | | | | | | |
| CCRF-CEM | 0.004 | 0.731 | 0.832 | 0.730 | 0.789 | 0.720 | 0.103 |
| HL-60(TB) | 0.068 | 2.840 | 2.914 | 2.950 | 2.924 | 2.813 | 2.039 |
| K-562 | 0.046 | 2.941 | 2.912 | 2.718 | 2.776 | 2.799 | 2.688 |
| MOLT-4 | 0.009 | 0.981 | 0.450 | 0.287 | 0.266 | 0.282 | 0.196 |
| RPMI-8226 | 0.061 | 1.637 | 0.904 | 0.725 | 0.604 | 0.584 | 0.618 |
| SR | 0.031 | 2.631 | 0.642 | 0.261 | 0.136 | 0.091 | 0.110 |
| Non-Small Cell Lung Cancer | | | | | | | |
| A549/ATCC | 0.021 | 2.721 | 2.734 | 2.443 | 2.524 | 2.458 | 2.314 |
| EKVX | 0.057 | 1.201 | 0.939 | 0.896 | 0.773 | 0.683 | 0.581 |
| HOP-62 | 0.059 | 0.922 | 0.750 | 0.767 | 0.683 | 0.595 | 0.541 |
| HOP-92 | 0.110 | 0.792 | 0.642 | 0.573 | 0.577 | 0.525 | 0.512 |
| NCI-H23 | 0.103 | 1.191 | 1.103 | 1.027 | 1.069 | 1.034 | 1.057 |
| NCI-H322M | 0.038 | 1.051 | 0.841 | 0.716 | 0.858 | 0.965 | 0.826 |
| NCI-H460 | 0.050 | 2.780 | 1.042 | 0.668 | 0.399 | 0.459 | 0.387 |
| NCI-H522 | 0.064 | 0.648 | 0.481 | 0.406 | 0.386 | 0.409 | 0.307 |
| Colon Cancer | | | | | | | |
| COLO 205 | 0.001 | 1.430 | -0.014 | -0.033 | -0.014 | -0.014 | -0.013 |
| HCC-2998 | 0.031 | 0.974 | 0.296 | 0.096 | 0.067 | 0.047 | 0.036 |
| HCT-116 | 0.068 | 2.951 | 2.404 | 2.329 | 2.028 | 1.901 | 1.691 |
| HCT-15 | 0.020 | 2.056 | 0.435 | 0.168 | 0.100 | 0.096 | 0.107 |
| HT29 | 0.052 | 2.528 | 2.445 | 2.325 | 2.293 | 2.387 | 2.210 |
| KM12 | 0.010 | 0.708 | 0.390 | 0.334 | 0.486 | 0.290 | 0.283 |
| SW-620 | 0.010 | 2.141 | 1.392 | 1.302 | 1.282 | 1.145 | 0.966 |
| CNS Cancer | | | | | | | |
| SF-268 | 0.041 | 1.069 | 1.017 | 0.969 | 0.993 | 0.980 | 0.958 |
| SF-295 | 0.054 | 1.614 | 0.031 | 0.019 | 0.018 | 0.023 | 0.023 |
| SF-539 | 0.030 | 1.468 | 0.875 | 0.672 | 0.624 | 0.646 | 0.572 |

*FIG. 21A-1*

16E2 Octopus (anti-DR5) - 6 Day

| Panel/Cell Line | Percent Growth Log10 Concentration | | | | | GI50 | TGI | LC50 |
|---|---|---|---|---|---|---|---|---|
| | 0.0 | 0.5 | 1.0 | 1.5 | 2.0 | | | |
| Leukemia | | | | | | | | |
| CCRF-CEM | 114 | 100 | 108 | 98 | 14 | 6.11E+01 | >1.00E+02 | >1.00E+02 |
| HL-60(TB) | 103 | 104 | 103 | 99 | 71 | >1.00E+02 | >1.00E+02 | >1.00E+02 |
| K-562 | 99 | 92 | 94 | 95 | 91 | >1.00E+02 | >1.00E+02 | >1.00E+02 |
| MOLT-4 | 45 | 29 | 26 | 28 | 19 | >1.00E+02 | >1.00E+02 | >1.00E+02 |
| RPMI-8226 | 53 | 42 | 34 | 33 | 35 | <1.00E+00 | >1.00E+02 | >1.00E+02 |
| SR | 24 | 9 | 4 | 2 | 3 | 1.43E+00 | >1.00E+02 | >1.00E+02 |
| | | | | | | <1.00E+00 | >1.00E+02 | >1.00E+02 |
| Non-Small Cell Lung Cancer | | | | | | | | |
| A549/ATCC | 100 | 90 | 93 | 90 | 85 | >1.00E+02 | >1.00E+02 | >1.00E+02 |
| EKVX | 77 | 73 | 63 | 55 | 46 | 5.80E+01 | >1.00E+02 | >1.00E+02 |
| HOP-62 | 80 | 82 | 72 | 62 | 56 | >1.00E+02 | >1.00E+02 | >1.00E+02 |
| HOP-92 | 78 | 68 | 68 | 61 | 59 | >1.00E+02 | >1.00E+02 | >1.00E+02 |
| NCI-H23 | 92 | 85 | 89 | 86 | 88 | >1.00E+02 | >1.00E+02 | >1.00E+02 |
| NCI-H322M | 79 | 67 | 81 | 92 | 78 | >1.00E+02 | >1.00E+02 | >1.00E+02 |
| NCI-H460 | 36 | 23 | 13 | 15 | 12 | <1.00E+00 | >1.00E+02 | >1.00E+02 |
| NCI-H522 | 71 | 59 | 55 | 59 | 42 | 5.77E+01 | >1.00E+02 | >1.00E+02 |
| Colon Cancer | | | | | | | | |
| COLO 205 | -100 | -100 | -100 | -100 | -100 | <1.00E+00 | <1.00E+00 | <1.00E+00 |
| HCC-2998 | 28 | 7 | 4 | 2 | 1 | <1.00E+00 | >1.00E+02 | >1.00E+02 |
| HCT-116 | 81 | 78 | 68 | 64 | 56 | >1.00E+02 | >1.00E+02 | >1.00E+02 |
| HCT-15 | 20 | 7 | 4 | 4 | 4 | <1.00E+00 | >1.00E+02 | >1.00E+02 |
| HT29 | 97 | 92 | 91 | 94 | 87 | >1.00E+02 | >1.00E+02 | >1.00E+02 |
| KM12 | 54 | 46 | 68 | 40 | 39 | >1.00E+02 | >1.00E+02 | >1.00E+02 |
| SW-620 | 65 | 61 | 60 | 53 | 45 | 4.95E+01 | >1.00E+02 | >1.00E+02 |
| CNS Cancer | | | | | | | | |
| SF-268 | 95 | 90 | 93 | 91 | 89 | >1.00E+02 | >1.00E+02 | >1.00E+02 |
| SF-295 | -43 | -66 | -67 | -57 | -57 | <1.00E+00 | <1.00E+00 | 1.45E+00 |
| SF-539 | 59 | 45 | 41 | 43 | 38 | 2.05E+00 | >1.00E+02 | >1.00E+02 |

*FIG. 21A-2*

16E2 Octopus (anti-DR5) - 6 Day

Log10 Concentration

| Panel/Cell Line | Time Zero | Ctrl | 0.0 | 0.5 | 1.0 | 1.5 | 2.0 |
|---|---|---|---|---|---|---|---|
| CNS Cancer | | | | | | | |
| SNB-19 | 0.016 | 1.813 | 1.594 | 1.598 | 1.544 | 1.794 | 1.822 |
| SNB-75 | 0.063 | 0.524 | 0.534 | 0.477 | 0.485 | 0.541 | 0.530 |
| U251 | 0.012 | 1.561 | 0.188 | 0.163 | 0.116 | 0.166 | 0.147 |
| Melanoma | | | | | | | |
| LOX IMVI | 0.037 | 3.073 | 2.094 | 1.635 | 1.272 | 1.229 | 1.274 |
| M14 | 0.035 | 1.838 | 1.147 | 0.745 | 0.628 | 0.585 | 0.652 |
| SK-MEL-2 | 0.083 | 0.498 | 0.209 | 0.160 | 0.166 | 0.151 | 0.153 |
| SK-MEL-28 | 0.045 | 1.316 | 0.703 | 0.668 | 0.603 | 0.524 | 0.478 |
| SK-MEL-5 | 0.095 | 1.885 | 1.902 | 1.947 | 1.880 | 1.916 | 1.895 |
| UACC-257 | 0.070 | 0.841 | 0.504 | 0.447 | 0.420 | 0.393 | 0.376 |
| UACC-62 | 0.121 | 1.601 | 1.119 | 0.932 | 0.781 | 0.764 | 0.810 |
| Ovarian Cancer | | | | | | | |
| IGROV1 | 0.018 | 1.567 | 1.476 | 1.603 | 1.622 | 1.529 | 1.510 |
| OVCAR-3 | 0.086 | 1.285 | 0.039 | 0.041 | 0.039 | 0.040 | 0.033 |
| OVCAR-4 | 0.071 | 1.563 | 1.304 | 1.287 | 1.028 | 0.998 | 0.854 |
| OVCAR-5 | 0.101 | 1.606 | 1.390 | 1.053 | 1.046 | 0.873 | 0.837 |
| OVCAR-8 | 0.020 | 1.565 | 1.634 | 1.571 | 1.587 | 1.630 | 1.570 |
| SK-OV-3 | 0.056 | 0.811 | 0.817 | 0.812 | 0.813 | 0.759 | 0.769 |
| Renal Cancer | | | | | | | |
| 786-0 | 0.073 | 1.715 | 1.716 | 1.715 | 1.726 | 1.731 | 1.686 |
| A498 | 0.087 | 1.058 | 0.996 | 0.877 | 0.737 | 0.692 | 0.716 |
| ACHN | 0.041 | 1.970 | 1.331 | 0.307 | 0.016 | 0.020 | 0.020 |
| CAKI-1 | 0.033 | 1.215 | 0.797 | 0.758 | 0.492 | 0.535 | 0.512 |
| RXF 393 | 0.101 | 0.973 | 0.496 | 0.086 | 0.043 | 0.029 | 0.028 |
| SN12C | 0.054 | 1.263 | 0.669 | 0.504 | 0.358 | 0.315 | 0.249 |
| TK-10 | 0.057 | 1.064 | 1.000 | 0.925 | 0.811 | 0.666 | 0.568 |
| UO-31 | 0.095 | 1.457 | 1.201 | 0.838 | 0.701 | 0.476 | 0.418 |

Mean Optical Densities

*FIG. 21A-3*

16E2 Octopus (anti-DR5) - 6 Day

| Panel/Cell Line | Percent Growth Log10 Concentration | | | | | | GI50 | TGI | LC50 |
|---|---|---|---|---|---|---|---|---|---|
| | 0.0 | 0.5 | 1.0 | 1.5 | 2.0 | | | | |
| CNS Cancer | | | | | | | | | |
| SNB-19 | 88 | 88 | 85 | 99 | 100 | | >1.00E+02 | >1.00E+02 | >1.00E+02 |
| SNB-75 | 102 | 90 | 91 | 104 | 101 | | >1.00E+02 | >1.00E+02 | >1.00E+02 |
| U251 | 11 | 10 | 7 | 10 | 9 | | <1.00E+00 | >1.00E+02 | >1.00E+02 |
| Melanoma | | | | | | | | | |
| LOX IMVI | 68 | 53 | 41 | 39 | 41 | | 4.08E+00 | >1.00E+02 | >1.00E+02 |
| M14 | 62 | 39 | 33 | 31 | 34 | | 1.83E+00 | >1.00E+02 | >1.00E+02 |
| SK-MEL-2 | 30 | 19 | 20 | 16 | 17 | | <1.00E+00 | >1.00E+02 | >1.00E+02 |
| SK-MEL-28 | 52 | 49 | 44 | 38 | 34 | | 2.11E+00 | >1.00E+02 | >1.00E+02 |
| SK-MEL-5 | 101 | 103 | 100 | 102 | 101 | | >1.00E+02 | >1.00E+02 | >1.00E+02 |
| UACC-257 | 56 | 49 | 45 | 42 | 40 | | 2.64E+00 | >1.00E+02 | >1.00E+02 |
| UACC-62 | 67 | 55 | 45 | 43 | 47 | | 5.44E+00 | >1.00E+02 | >1.00E+02 |
| Ovarian Cancer | | | | | | | | | |
| IGROV1 | 94 | 102 | 104 | 98 | 96 | | >1.00E+02 | >1.00E+02 | >1.00E+02 |
| OVCAR-3 | -55 | -52 | -55 | -53 | -62 | | <1.00E+00 | <1.00E+00 | <1.00E+00 |
| OVCAR-4 | 83 | 81 | 64 | 62 | 52 | | >1.00E+02 | >1.00E+02 | >1.00E+02 |
| OVCAR-5 | 86 | 63 | 63 | 51 | 49 | | 5.85E+01 | >1.00E+02 | >1.00E+02 |
| OVCAR-8 | 104 | 100 | 101 | 104 | 100 | | >1.00E+02 | >1.00E+02 | >1.00E+02 |
| SK-OV-3 | 101 | 100 | 100 | 93 | 94 | | >1.00E+02 | >1.00E+02 | >1.00E+02 |
| Renal Cancer | | | | | | | | | |
| 786-0 | 100 | 100 | 101 | 101 | 98 | | >1.00E+02 | >1.00E+02 | >1.00E+02 |
| A498 | 94 | 81 | 67 | 62 | 65 | | >1.00E+02 | >1.00E+02 | >1.00E+02 |
| ACHN | 67 | 14 | -61 | -51 | -51 | | 1.44E+00 | 3.92E+00 | 8.46E+00 |
| CAKI-1 | 65 | 61 | 39 | 42 | 41 | | 5.66E+00 | >1.00E+02 | >1.00E+02 |
| RXF 393 | 45 | -15 | -58 | -71 | -72 | | <1.00E+00 | 2.37E+00 | 8.08E+00 |
| SN12C | 51 | 37 | 25 | 22 | 16 | | 1.08E+00 | >1.00E+02 | >1.00E+02 |
| TK-10 | 94 | 86 | 75 | 60 | 51 | | >1.00E+02 | >1.00E+02 | >1.00E+02 |
| UO-31 | 81 | 55 | 44 | 28 | 24 | | 5.32E+00 | >1.00E+02 | >1.00E+02 |

*FIG. 21A-4*

16E2 Octopus (anti-DR5) - 6 Day

Log10 Concentration

| Panel/Cell Line | Time Zero | Ctrl | 0.0 | 0.5 | 1.0 | 1.5 | 2.0 |
|---|---|---|---|---|---|---|---|
| Prostate Cancer | | | | | | | |
| PC-3 | 0.030 | 0.879 | 0.520 | 0.379 | 0.334 | 0.315 | 0.333 |
| DU-145 | 0.057 | 1.962 | 1.887 | 1.790 | 1.717 | 1.662 | 1.654 |
| Breast Cancer | | | | | | | |
| MCF7 | 0.060 | 2.908 | 2.856 | 2.870 | 2.865 | 2.833 | 2.843 |
| NCI/ADR-RES | 0.045 | 1.087 | 1.064 | 1.054 | 1.157 | 1.130 | 1.088 |
| MDA-MB-231/ATCC | 0.042 | 0.819 | 0.674 | 0.577 | 0.538 | 0.488 | 0.575 |
| HS 578T | 0.055 | 0.759 | 0.470 | 0.322 | 0.261 | 0.260 | 0.201 |
| MDA-MB-435 | 0.041 | 2.284 | 1.227 | 0.955 | 0.806 | 0.819 | 0.723 |
| MDA-N | 0.010 | 0.861 | 0.490 | 0.457 | 0.355 | 0.322 | 0.313 |
| BT-549 | 0.100 | 1.316 | 0.995 | 0.521 | 0.364 | 0.319 | 0.251 |
| T-47D | 0.049 | 0.626 | 0.613 | 0.564 | 0.528 | 0.526 | 0.613 |

Mean Optical Densities

*FIG. 21A-5*

16E2 Octopus (anti-DR5) - 6 Day

| Panel/Cell Line | Percent Growth | | | | | GI50 | TGI | LC50 |
|---|---|---|---|---|---|---|---|---|
| | | Log10 Concentration | | | | | | |
| | 0.0 | 0.5 | 1.0 | 1.5 | 2.0 | | | |
| Prostate Cancer | | | | | | | | |
| PC-3 | 58 | 41 | 36 | 34 | 36 | 1.70E+00 | >1.00E+02 | >1.00E+02 |
| DU-145 | 96 | 91 | 87 | 84 | 84 | >1.00E+02 | >1.00E+02 | >1.00E+02 |
| Breast Cancer | | | | | | | | |
| MCF7 | 98 | 99 | 98 | 97 | 98 | >1.00E+02 | >1.00E+02 | >1.00E+02 |
| NCI/ADR-RES | 98 | 97 | 107 | 104 | 100 | >1.00E+02 | >1.00E+02 | >1.00E+02 |
| MDA-MB-231/ATCC | 81 | 69 | 64 | 57 | 69 | >1.00E+02 | >1.00E+02 | >1.00E+02 |
| HS 578T | 59 | 38 | 29 | 29 | 21 | 1.64E+00 | >1.00E+02 | >1.00E+02 |
| MDA-MB-435 | 53 | 41 | 34 | 35 | 30 | 1.32E+00 | >1.00E+02 | >1.00E+02 |
| MDA-N | 56 | 53 | 40 | 37 | 36 | 4.04E+00 | >1.00E+02 | >1.00E+02 |
| BT-549 | 74 | 35 | 22 | 18 | 12 | 2.01E+00 | >1.00E+02 | >1.00E+02 |
| T-47D | 98 | 89 | 83 | 83 | 98 | >1.00E+02 | >1.00E+02 | >1.00E+02 |

*FIG. 21A-6*

APO2L - 6 Day

| Panel/Cell Line | Time Zero | Ctrl | \multicolumn{5}{c}{Mean Optical Densities — Log10 Concentration} | | | | |
|---|---|---|---|---|---|---|---|
| | | | 0.0 | 0.5 | 1.0 | 1.5 | 2.0 |
| Leukemia | | | | | | | |
| CCRF-CEM | 0.004 | 0.842 | 0.753 | 0.453 | 0.365 | 0.574 | 0.569 |
| HL-60(TB) | 0.068 | 2.822 | 0.712 | 0.317 | 0.202 | 0.116 | 0.080 |
| K-562 | 0.046 | 2.792 | 2.962 | 3.017 | 2.920 | 2.716 | 2.626 |
| MOLT-4 | 0.009 | 1.040 | 0.929 | 0.928 | 0.965 | 0.999 | 0.797 |
| RPMI-8226 | 0.061 | 1.661 | 0.072 | 0.038 | 0.041 | 0.025 | 0.022 |
| SR | 0.031 | 2.591 | 2.540 | 2.234 | 1.915 | 1.822 | 1.708 |
| Non-Small Cell Lung Cancer | | | | | | | |
| A549/ATCC | 0.021 | 2.037 | 2.071 | 2.070 | 2.029 | 2.045 | 2.038 |
| EKVX | 0.057 | 1.052 | 1.070 | 1.039 | 1.078 | 1.000 | 0.962 |
| HOP-62 | 0.059 | 0.891 | 0.854 | 0.854 | 0.787 | 0.725 | 0.662 |
| HOP-92 | 0.110 | 0.906 | 0.750 | 0.698 | 0.700 | 0.705 | 0.723 |
| NCI-H23 | 0.103 | 1.184 | 1.180 | 1.147 | 1.122 | 1.185 | 1.163 |
| NCI-H322M | 0.038 | 0.976 | 0.824 | 0.606 | 0.488 | 0.436 | 0.346 |
| NCI-H460 | 0.050 | 2.857 | 0.536 | 0.239 | 0.153 | 0.063 | 0.048 |
| NCI-H522 | 0.064 | 0.461 | 0.354 | 0.344 | 0.336 | 0.263 | 0.238 |
| Colon Cancer | | | | | | | |
| COLO 205 | 0.001 | 1.396 | -0.005 | -0.007 | 0.006 | 0.002 | 0.014 |
| HCC-2998 | 0.031 | 1.083 | 0.682 | 0.274 | 0.305 | 0.202 | 0.189 |
| HCT-116 | 0.068 | 3.014 | 2.272 | 1.606 | 1.249 | 0.953 | 0.821 |
| HCT-15 | 0.020 | 2.169 | 0.196 | 0.054 | 0.039 | 0.018 | 0.030 |
| HT29 | 0.052 | 1.968 | 1.970 | 1.962 | 2.035 | 2.034 | 2.063 |
| KM12 | 0.010 | 0.633 | 0.249 | 0.218 | 0.113 | 0.052 | 0.052 |
| SW-620 | 0.010 | 2.236 | 1.477 | 1.220 | 1.040 | 0.943 | 0.608 |
| CNS Cancer | | | | | | | |
| SF-268 | 0.041 | 0.893 | 0.891 | 0.914 | 0.906 | 0.852 | 0.927 |
| SF-295 | 0.054 | 1.659 | 1.054 | 0.706 | 0.634 | 0.557 | 0.529 |
| SF-539 | 0.030 | 1.513 | 1.411 | 1.046 | 1.113 | 1.034 | 0.689 |

FIG. 21B-1

APO2L - 6 Day

| Panel/Cell Line | 0.0 | 0.5 | 1.0 | 1.5 | 2.0 | GI50 | TGI | LC50 |
|---|---|---|---|---|---|---|---|---|
| Leukemia | | | | | | | | |
| CCRF-CEM | 89 | 54 | 43 | 68 | 67 | . | >1.00E+02 | >1.00E+02 |
| HL-60(TB) | 23 | 9 | 5 | 2 | 0 | <1.00E+00 | >1.00E+02 | >1.00E+02 |
| K-562 | 106 | 108 | 105 | 97 | 94 | >1.00E+02 | >1.00E+02 | >1.00E+02 |
| MOLT-4 | 89 | 89 | 93 | 96 | 76 | >1.00E+02 | >1.00E+02 | >1.00E+02 |
| RPMI-8226 | 1 | -39 | -34 | -59 | -65 | <1.00E+00 | 1.02E+00 | 2.10E+01 |
| SR | 98 | 86 | 74 | 70 | 65 | >1.00E+02 | >1.00E+02 | >1.00E+02 |
| Non-Small Cell Lung Cancer | | | | | | | | |
| A549/ATCC | 102 | 102 | 100 | 100 | 100 | >1.00E+02 | >1.00E+02 | >1.00E+02 |
| EKVX | 102 | 99 | 103 | 95 | 91 | >1.00E+02 | >1.00E+02 | >1.00E+02 |
| HOP-62 | 96 | 95 | 87 | 80 | 72 | >1.00E+02 | >1.00E+02 | >1.00E+02 |
| HOP-92 | 80 | 74 | 74 | 75 | 77 | >1.00E+02 | >1.00E+02 | >1.00E+02 |
| NCI-H23 | 100 | 97 | 94 | 100 | 98 | >1.00E+02 | >1.00E+02 | >1.00E+02 |
| NCI-H322M | 84 | 60 | 48 | 42 | 33 | 8.30E+00 | >1.00E+02 | >1.00E+02 |
| NCI-H460 | 17 | 7 | 4 | 0 | -4 | <1.00E+00 | 3.57E+01 | >1.00E+02 |
| NCI-H522 | 73 | 70 | 68 | 50 | 44 | 3.22E+01 | >1.00E+02 | >1.00E+02 |
| Colon Cancer | | | | | | | | |
| COLO 205 | -100 | -100 | 0 | 0 | 1 | <1.00E+00 | . | . |
| HCC-2998 | 62 | 23 | 26 | 16 | 15 | 1.43E+00 | >1.00E+02 | >1.00E+02 |
| HCT-116 | 75 | 52 | 40 | 30 | 26 | 3.91E+00 | >1.00E+02 | >1.00E+02 |
| HCT-15 | 8 | 2 | 1 | -10 | 0 | <1.00E+00 | . | . |
| HT29 | 100 | 100 | 103 | 103 | 105 | >1.00E+02 | >1.00E+02 | >1.00E+02 |
| KM12 | 38 | 33 | 20 | 7 | 7 | <1.00E+00 | >1.00E+02 | >1.00E+02 |
| SW-620 | 66 | 54 | 46 | 42 | 27 | 5.89E+00 | >1.00E+02 | >1.00E+02 |
| CNS Cancer | | | | | | | | |
| SF-268 | 100 | 103 | 102 | 95 | 104 | >1.00E+02 | >1.00E+02 | >1.00E+02 |
| SF-295 | 62 | 41 | 36 | 31 | 30 | 1.92E+00 | >1.00E+02 | >1.00E+02 |
| SF-539 | 93 | 68 | 73 | 68 | 44 | 7.59E+01 | >1.00E+02 | >1.00E+02 |

Percent Growth — Log10 Concentration

FIG. 21B-2

APO2L - 6 Day

Log10 Concentration

| Panel/Cell Line | Time zero | Ctrl | 0.0 | 0.5 | 1.0 | 1.5 | 2.0 |
|---|---|---|---|---|---|---|---|
| CNS Cancer | | | | | | | |
| SNB-19 | 0.016 | 1.579 | 1.639 | 1.558 | 1.586 | 1.650 | 1.563 |
| SNB-75 | 0.063 | 0.524 | 0.484 | 0.529 | 0.497 | 0.531 | 0.531 |
| U251 | 0.012 | 1.537 | 0.360 | 0.314 | 0.358 | 0.332 | 0.353 |
| Melanoma | | | | | | | |
| LOX IMVI | 0.037 | 3.184 | 2.701 | 2.366 | 2.418 | 2.050 | 2.276 |
| M14 | 0.035 | 1.827 | 1.721 | 1.740 | 1.634 | 1.636 | 1.551 |
| SK-MEL-2 | 0.083 | 0.504 | 0.366 | 0.344 | 0.393 | 0.383 | 0.391 |
| SK-MEL-28 | 0.045 | 1.350 | 1.130 | 1.163 | 1.105 | 1.015 | 0.843 |
| SK-MEL-5 | 0.095 | 1.718 | 1.748 | 1.792 | 1.711 | 1.824 | 2.003 |
| UACC-257 | 0.070 | 0.830 | 0.756 | 0.716 | 0.744 | 0.692 | 0.664 |
| UACC-62 | 0.121 | 1.729 | 1.649 | 1.630 | 1.410 | 1.396 | 1.459 |
| Ovarian Cancer | | | | | | | |
| IGROV1 | 0.018 | 1.901 | 1.898 | 1.794 | 1.820 | 1.801 | 1.734 |
| OVCAR-3 | 0.086 | 1.293 | 0.097 | 0.073 | 0.049 | 0.032 | 0.037 |
| OVCAR-4 | 0.071 | 1.553 | 1.364 | 1.289 | 1.245 | 1.060 | 1.102 |
| OVCAR-5 | 0.101 | 1.436 | 1.357 | 1.269 | 1.246 | 1.206 | 1.149 |
| OVCAR-8 | 0.020 | 1.641 | 1.540 | 1.606 | 1.595 | 1.634 | 1.608 |
| SK-OV-3 | 0.056 | 0.848 | 0.834 | 0.807 | 0.853 | 0.821 | 0.834 |
| Renal Cancer | | | | | | | |
| 786-0 | 0.073 | 1.816 | 1.818 | 1.830 | 1.853 | 1.816 | 1.834 |
| A498 | 0.087 | 1.108 | 1.080 | 1.046 | 1.034 | 0.988 | 0.969 |
| ACHN | 0.041 | 2.105 | 2.060 | 2.051 | 1.993 | 1.958 | 1.867 |
| CAKI-1 | 0.033 | 1.080 | 1.108 | 0.941 | 1.017 | 1.031 | 0.959 |
| RXF 393 | 0.101 | 0.982 | 0.589 | 0.322 | 0.362 | 0.450 | 0.262 |
| SN12C | 0.054 | 1.352 | 1.354 | 1.353 | 1.319 | 1.346 | 1.257 |
| TK-10 | 0.057 | 1.226 | 1.159 | 1.058 | 1.042 | 0.939 | 0.802 |
| UO-31 | 0.095 | 1.523 | 1.434 | 1.395 | 1.377 | 1.343 | 1.340 |

*FIG. 21B-3*

APO2L - 6 Day

| Panel/Cell Line | Percent Growth Log10 Concentration | | | | | | GI50 | TGI | LC50 |
|---|---|---|---|---|---|---|---|---|---|
| | 0.0 | 0.5 | 1.0 | 1.5 | 2.0 | | | | |
| CNS Cancer | | | | | | | | | |
| SNB-19 | 104 | 99 | 100 | 105 | 99 | | >1.00E+02 | >1.00E+02 | >1.00E+02 |
| SNB-75 | 91 | 101 | 94 | 102 | 102 | | >1.00E+02 | >1.00E+02 | >1.00E+02 |
| U251 | 23 | 20 | 23 | 21 | 22 | | <1.00E+00 | >1.00E+02 | >1.00E+02 |
| Melanoma | | | | | | | | | |
| LOX IMVI | 85 | 74 | 76 | 64 | 71 | | >1.00E+02 | >1.00E+02 | >1.00E+02 |
| M14 | 94 | 95 | 89 | 89 | 85 | | >1.00E+02 | >1.00E+02 | >1.00E+02 |
| SK-MEL-2 | 67 | 62 | 73 | 71 | 73 | | >1.00E+02 | >1.00E+02 | >1.00E+02 |
| SK-MEL-28 | 83 | 86 | 81 | 74 | 61 | | >1.00E+02 | >1.00E+02 | >1.00E+02 |
| SK-MEL-5 | 102 | 105 | 100 | 107 | 118 | | >1.00E+02 | >1.00E+02 | >1.00E+02 |
| UACC-257 | 90 | 85 | 89 | 82 | 78 | | >1.00E+02 | >1.00E+02 | >1.00E+02 |
| UACC-62 | 95 | 94 | 80 | 79 | 83 | | >1.00E+02 | >1.00E+02 | >1.00E+02 |
| Ovarian Cancer | | | | | | | | | |
| IGROV1 | 100 | 94 | 96 | 95 | 91 | | >1.00E+02 | >1.00E+02 | >1.00E+02 |
| OVCAR-3 | 1 | -16 | -43 | -63 | -57 | | <1.00E+00 | 1.07E+00 | 1.50E+01 |
| OVCAR-4 | 87 | 82 | 79 | 67 | 70 | | >1.00E+02 | >1.00E+02 | >1.00E+02 |
| OVCAR-5 | 94 | 87 | 86 | 83 | 78 | | >1.00E+02 | >1.00E+02 | >1.00E+02 |
| OVCAR-8 | 94 | 98 | 97 | 100 | 98 | | >1.00E+02 | >1.00E+02 | >1.00E+02 |
| SK-OV-3 | 98 | 95 | 101 | 97 | 98 | | >1.00E+02 | >1.00E+02 | >1.00E+02 |
| Renal Cancer | | | | | | | | | |
| 786-0 | 100 | 101 | 102 | 100 | 101 | | >1.00E+02 | >1.00E+02 | >1.00E+02 |
| A498 | 97 | 94 | 93 | 88 | 86 | | >1.00E+02 | >1.00E+02 | >1.00E+02 |
| ACHN | 98 | 97 | 95 | 93 | 88 | | >1.00E+02 | >1.00E+02 | >1.00E+02 |
| CAKI-1 | 103 | 87 | 94 | 95 | 88 | | >1.00E+02 | >1.00E+02 | >1.00E+02 |
| RXF 393 | 55 | 25 | 30 | 40 | 18 | | 1.23E+00 | >1.00E+02 | >1.00E+02 |
| SN12C | 100 | 100 | 97 | 100 | 93 | | >1.00E+02 | >1.00E+02 | >1.00E+02 |
| TK-10 | 94 | 86 | 84 | 75 | 64 | | >1.00E+02 | >1.00E+02 | >1.00E+02 |
| UO-31 | 94 | 91 | 90 | 87 | 87 | | >1.00E+02 | >1.00E+02 | >1.00E+02 |

FIG. 21B-4

APO2L - 6 Day

Log10 Concentration

| Panel/Cell Line | Time Zero | Ctrl | 0.0 | Mean Optical Densities 0.5 | 1.0 | 1.5 | 2.0 |
|---|---|---|---|---|---|---|---|
| Prostate Cancer | | | | | | | |
| PC-3 | 0.030 | 0.817 | 0.520 | 0.467 | 0.384 | 0.426 | 0.342 |
| DU-145 | 0.057 | 1.911 | 1.810 | 1.744 | 1.693 | 1.359 | 1.024 |
| Breast Cancer | | | | | | | |
| MCF7 | 0.060 | 3.104 | 2.284 | 2.012 | 1.444 | 0.809 | 0.770 |
| NCI/ADR-RES | 0.045 | 1.013 | 1.037 | 1.036 | 1.017 | 1.007 | 0.974 |
| MDA-MB-231/ATCC | 0.042 | 0.873 | 0.774 | 0.755 | 0.805 | 0.750 | 0.720 |
| HS 578T | 0.055 | 0.491 | 0.512 | 0.511 | 0.508 | 0.518 | 0.515 |
| MDA-MB-435 | 0.041 | 2.083 | 2.007 | 1.758 | 1.719 | 1.519 | 1.387 |
| MDA-N | 0.010 | 0.984 | 0.809 | 0.738 | 0.803 | 0.677 | 0.571 |
| BT-549 | 0.100 | 1.296 | 1.457 | 1.398 | 1.377 | 1.432 | 1.346 |
| T-47D | 0.049 | 0.567 | 0.582 | 0.568 | 0.595 | 0.566 | 0.490 |

*FIG. 21B-5*

APO2L - 6 Day

Log10 Concentration

| Panel/Cell Line | Percent Growth | | | | | | GI50 | TGI | LC50 |
|---|---|---|---|---|---|---|---|---|---|
| | 0.0 | 0.5 | 1.0 | 1.5 | 2.0 | | | | |
| Prostate Cancer | | | | | | | | | |
| PC-3 | 62 | 56 | 45 | 50 | 40 | | | >1.00E+02 | >1.00E+02 |
| DU-145 | 95 | 91 | 88 | 70 | 52 | | >1.00E+02 | >1.00E+02 | >1.00E+02 |
| Breast Cancer | | | | | | | | | |
| MCF7 | 73 | 64 | 45 | 25 | 23 | | 7.57E+00 | >1.00E+02 | >1.00E+02 |
| NCI/ADR-RES | 102 | 102 | 100 | 99 | 96 | | >1.00E+02 | >1.00E+02 | >1.00E+02 |
| MDA-MB-231/ATCC | 88 | 86 | 92 | 85 | 82 | | >1.00E+02 | >1.00E+02 | >1.00E+02 |
| HS 578T | 105 | 105 | 104 | 106 | 106 | | >1.00E+02 | >1.00E+02 | >1.00E+02 |
| MDA-MB-435 | 96 | 84 | 82 | 72 | 66 | | >1.00E+02 | >1.00E+02 | >1.00E+02 |
| MDA-N | 82 | 75 | 81 | 68 | 58 | | >1.00E+02 | >1.00E+02 | >1.00E+02 |
| BT-549 | 113 | 109 | 107 | 111 | 104 | | >1.00E+02 | >1.00E+02 | >1.00E+02 |
| T-47D | 103 | 100 | 105 | 100 | 85 | | >1.00E+02 | >1.00E+02 | >1.00E+02 |

FIG. 21B-6

Representative Plot of n = 6 Cytostasis Assays; Crystal Violet

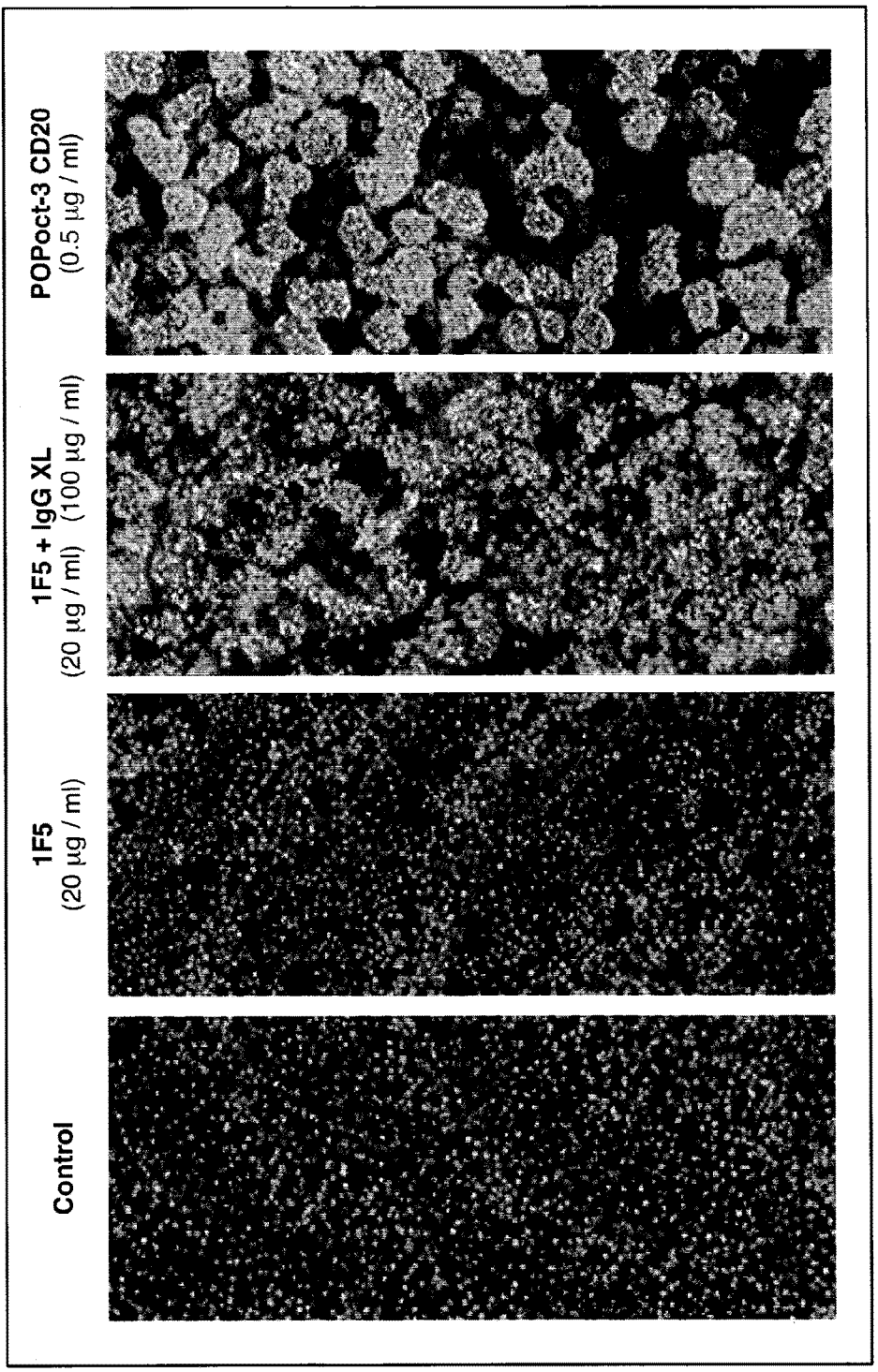

MULTIVALENT ANTIBODIES AND USES THEREFOR

CROSS REFERENCE TO RELATED APPLICATIONS

This application is a continuation application claiming priority to application Ser. No. 11/535,031, filed Sep. 25, 2006, abandoned, which is a continuation application claiming priority to application Ser. No. 11/218,821, filed Sep. 2, 2005, abandoned, which is a continuation application claiming priority to application Ser. No. 09/813,341, filed Mar. 20, 2001, abandoned, which claims priority under 35 U.S.C. §119(e) to provisional application No.60/195,819, filed Apr. 11, 2000, the entire contents of each of which are hereby incorporated by reference.

BACKGROUND OF THE INVENTION

1. Field of the Invention

The present invention concerns engineered antibodies, with three or more functional antigen binding sites, and uses, such as therapeutic uses, for such engineered antibodies.

2. Description of Related Art

Structure of Naturally Occurring Antibodies

Naturally occurring antibodies (immunoglobulins) comprise two heavy chains linked together by disulfide bonds and two light chains, one light chain being linked to each of the heavy chains by disulfide bonds. Each heavy chain has at one end a variable domain (VH) followed by a number of constant domains (three or four constant domains, CH1, CH2, CH3 and CH4, depending on the antibody class). Each light chain has a variable domain (VL) at one end and a constant domain (CL) at its other end; the constant domain of the light chain is aligned with the first constant domain of the heavy chain, and the light chain variable domain is aligned with the variable domain of the heavy chain. See FIG. 1 herein. Particular amino acid residues are believed to form an interface between the light and heavy chain variable domains, see e.g. Chothia et al., *J. Mol. Biol.* 186:651-663 (1985); and Novotny and Haber, *Proc. Natl. Acad. Sci. USA* 82:4592-4596 (1985).

The constant domains are not involved directly in binding the antibody to an antigen, but are involved in various effector functions, such as participation of the antibody in antibody-dependent cell-mediated cytotoxicity (ADCC) and complement dependent cytotoxicity (CDC). The variable domains of each pair of light and heavy chains are involved directly in binding the antibody to the antigen. The variable domains of naturally occurring light and heavy chains have the same general structure; each comprising four framework regions (FRs), whose sequences are somewhat conserved, connected by three complementarity determining regions (CDRs) (see Kabat et al., *Sequences of Proteins of Immunological Interest*, National Institutes of Health, Bethesda, Md., (1991)). The four FRs largely adopt a beta-sheet conformation and the CDRs form loops connecting, and in some cases forming part of, the beta-sheet structure. The CDRs in each chain are held in close proximity by the FRs and, with the CDRs from the other chain, contribute to the formation of the antigen binding site.

FIGS. 2A-E herein depict the structures of the five major naturally occurring immunoglobulin isotypes. IgG, IgD and IgE immunoglobulins possess only two antigen binding sites. IgA and IgM, on the other hand, are capable of forming polymeric structures with higher valencies.

IgM is secreted by plasma cells as a pentamer in which five monomer units are held together by disulfide bonds linking their carboxyl-terminal (C:4/C:4) domains and C:3/C:3 domains. The five monomer subunits are arranged with their Fc regions in the center of the pentamer and the 10 antigen-binding sites on the periphery of the molecule. Each pentamer contains an additional Fc-linked polypeptide called the J (joining) chain, which is disulfide-bonded to the carboxyl-terminal cysteine residue of 2 of the 10: chains. The J chain appears to be required for polymerization of the monomers to form pentameric IgM; it is added just before secretion of the pentamer. An IgM molecule can bind 10 small hapten molecules; however, because of steric hindrance, only 5 molecules of larger antigens can be bound simultaneously. The increased valency of pentameric IgM increases its capacity to bind such multi-dimensional antigens as viral particles and red blood cells (RBCS).

IgA exists primarily as a monomer, although polymeric forms such as dimers, trimers, and even tetramers are sometimes seen. The IgA of external secretions consists of a dimer or tetramer, a J-chain polypeptide, and a polypeptide chain called secretory component.

Antibodies for Clinical Uses

Widespread use has been made of monoclonal antibodies, particularly those derived from rodents including mice, however they are frequently antigenic in human clinical use. For example, a major limitation in the clinical use of rodent monoclonal antibodies is an anti-globulin response during therapy (Miller et al., *Blood* 62:988-995 (1983); and Schroff, R. W. et al., *Cancer Res.* 45:879-885 (1985)).

The art has attempted to overcome this problem by constructing "chimeric" antibodies in which an animal antigen binding variable domain is coupled to a human constant domain (Cabilly et al., U.S. Pat. No. 4,816,567; Morrison et al., *Proc. Natl. Acad. Sci. USA* 81:6851-6855 (1984); Boulianne et al., *Nature* 312:643-646 (1984); and Neuberger et al., *Nature* 314:268-270 (1985)). The isotype of the human constant domain may be selected to tailor the chimeric antibody for participation in ADCC and CDC (see e.g. BrOggemann et al., *J. Exp. Med.* 166:1351-1361 (1987); Riechmann et al., *Nature* 332:323-327 (1988); Love et al., *Methods in Enzymology* 178:515-527 (1989); and Bindon et al., *J. Exp. Med.* 168:127-142 (1988)). In the typical embodiment, such chimeric antibodies contain about one third rodent (or other non-human species) sequence and thus are capable of eliciting a significant anti-globulin response in humans. For example, in the case of the murine anti-CD3 antibody, OKT3, much of the resulting anti-globulin response is directed against the variable region rather than the constant region (Jailers et al., *Transplantation* 41:572-578 (1986)).

In a further effort to resolve the antigen binding functions of antibodies and to minimize the use of heterologous sequences in human antibodies, Winter and colleagues (Jones et al., *Nature* 321:522-525 (1986); Riechmann et al., *Nature* 332:323-327 (1988); and Verhoeyen et al., *Science* 239:1534-1536 (1988)) have substituted rodent CDRs or CDR sequences for the corresponding segments of a human antibody.

The therapeutic promise of this approach is supported by the clinical efficacy of a humanized antibody specific for the CAMPATH-1 antigen with two non-Hodgkin lymphoma patients, one of whom had previously developed an anti-globulin response to the parental rat antibody (Riechmann et al., *Nature* 332:323-327 (1988); and Hale et al., *Lancet* 2:1394-1399 (1988)).

In some cases, substituting CDRs from rodent antibodies for the human CDRs in human frameworks is sufficient to transfer high antigen binding affinity (Jones et al., *Nature* 321:522-525 (1986); Verhoeyen et al., *Science* 239:1534-1536 (1988)), whereas in other cases it has been necessary to additionally replace one (Riechmann et al., *Nature* 332:323-327 (1988)) or several (Queen et al., *Proc. Natl. Acad. Sci. USA* 86:10029-10033 (1989)) framework residues. See also Co et al., *Proc. Natl. Acad. Sci. USA* 88:2869-2873 (1991); U.S. Pat. No. 5,821,337 (Carter et al.); and U.S. Pat. No. 5,530,101 (Queen et al.). Additional references relating to humanization of antibodies include Gorman et al., *Proc. Natl. Acad. Sci. USA* 88:4181-4185 (1991); Daugherty et al., *Nucleic Acids Research* 19(9):2471-2476 (1991); Brown et al., *Proc. Natl. Acad. Sci. USA* 88:2663-2667 (1991); and Junghans et al., *Cancer Research* 50:1495-1502 (1990).

Instead of a chimeric/humanized antibody, one may treat a patient with a human antibody in order to avoid human antibodies raised against a murine antibody (known as the "HAMA response"). Several technologies are available for generating human antibodies.

Human antibodies may be selected using phage display technology. Phage display has been adapted to select human antibodies from an unimmunized donor (Marks et al. *J. Mol. Biol.* 222:581-597 (1991)). According to this approach, PCR is used to amplify variable domain genes from mRNA prepared from human peripheral blood lymphocytes (PBLs). Primers are used such that DNA from both IgG and IgM heavy chains and both 6 and 8 chains is amplified. These genes are then randomly combined and expressed as single chain Fv (scFv) fused to the gene III coat protein of M13 phage. Human antibodies against an antigen of interest may then be identified by rounds of growth and selection by binding to that antigen (e.g. to the immobilized antigen). See Griffiths et al. *EMBO J.* 12:725-734 (1993).

"Synthetic" phage-antibody repertoires have also been built from cloned human VH-gene segments. A repertoire ($2\times10^7$ clones) was first constructed using a short H3 loop of five or eight random residues with each of 49 segments, and combined with a fixed light chain (Hoogenboom et al. *J. Mol. Biol.* 227:381-388 (1992)). By adding a range of H3 loops of different lengths, up to 12 residues, a single library was created from which a range of more than 20 binding specificities could be selected (Winter et al. *Ann. Rev. Immuno.* 12:433-55 (1994)). Other synthetic libraries have been built from the framework of a single antibody by randomizing CDRs of the human antibody (Garrard and Henner Gene 128:103-109 (1993)). Antibodies derived from such synthetic phage-antibody repertoires are also considered to be "human" antibodies herein.

The affinity of low affinity "primary" phage-antibodies may be improved by using phage display technology. One approach is to use a chain-shuffling strategy in which the VH domain is held constant and then recombined with the original library of VL genes and tighter binders selected by binding to immobilized antigen. This cycle is repeated by fixing the new VL domain and recombining with the original VH library (Marks et al. *Bio/Technology* 10:779-783 (1992)). Alternatively, point mutations in the primary antibody may be introduced using error-prone PCR and higher affinity binders selected by using phage display. Gram et al. *PNAS (USA)* 89: 3576-3580 (1992).

One may also produce human antibodies by immunizing mice which have been genetically engineered to express human antibodies. Severe combined immune deficient (SCID) mice lack the ability to produce their own immunoglobulins due to a defect in the recombinase gene. Several groups have reconstituted a functional humoral immune system in these mice by transfer of human peripheral blood lymphocytes (PBLs). These hu-PBL-SCID mice can be used to raise human antibodies upon immunization with antigen. Duchosal et al. *Nature* 355:258-262 (1992). Using another approach, the heavy- and light-chain genes within mice are turned off and then yeast artificial chromosomes (YACs) engineered with large DNA sequences containing human heavy- and light-chain genes are introduced into the mice. Such "XenoMice" are able to produce human antibodies upon immunization with an antigen of interest. See U.S. Pat. Nos. 5,434,340; 5,591,699; 5,569,825; 5,545,806; and 5,545,807.

Human monoclonal antibodies may also be generated by immortalizing a human B lymphocyte producing an antibody of interest. The ethical issues surrounding immunizing humans in order to generate activated human B lymphocytes can be avoided by immunizing human lymphocytes in vitro. Both human PBLs (Borrebaeck et al. *Proc. Natl. Acad. Sci. USA* 85:3995-4000 (1988)) and human splenocytes (Boerner et al. *J. Immunol.* 147, 86-95 (1991)) have been successfully immunized in vitro. Improvements in human hybridoma technology have been achieved by using a mouse-human heterohybrid as the fusion partner (Boerner et al.).

Antibody Variants

Antibodies have been modified in order to increase their antigen-binding valency. For instance, Ghetie et al. homodimerized tumor-reactive monoclonal antibodies (anti-CD19, anti-CD20, anti-CD21, anti-CD22 and anti-HER2 antibodies) by chemically introducing a thioether bond between a pair of IgGs using two heterobifunctional crosslinkers. Ghetie et al. *PNAS (USA)* 94:7509-7514 (1997); and WO 99/02567. Wolff et al. *Cancer Research* 53: 2560-2565 (1993) also chemically linked an IgG monoclonal antibody (CHiBR96) using heterobifunctional cross-linkers to generate a monoclonal antibody homodimer with enhanced anti-tumor activity in nude mice.

Shopes et al. replaced a serine residue near the carboxyl terminus of a human IgG1 heavy chain ($Ser^{444}$) with a cysteine. The introduced intermolecular disulfide bonds between $Cys^{444}$ residues linked pairs of immunoglobulins "tail-to-tail" to form covalent dimers $(H_2L_2)_2$. The anti-dansyl dimers were said to be more efficient than monomeric human IgG1 at antibody-dependent complement-mediated cytolysis of hapten-bearing erythrocytes. Shopes, B. *J. Immunol.* 148(9): 2918-2922 (1992); and WO 91/19515. This approach, involving introduction of cysteine residues, has also been used to generate a homodimeric form of the CAMPATH-1H antibody. The homodimeric CAMPATH-1H antibody exhibited improved lysis using target cells expressing antigen at low density, but no improvement in lysis was observed using cells expressing antigen at high density. Greenwood et al. *Ther. Immunol.* 1:247-255 (1994). See, also, Caron et al. *J. Exp. Med.* 176:1191-1195 (1992), concerning an engineered anti-CD33 antibody with a serine to cysteine substitution at position 444 of the heavy chain allowing interchain disulfide bond formation at the COOH terminus of the IgG. The homodimeric IgG was said to have similar avidity to the parent IgG, but apparently showed an improved ability to internalize and retain radioisotope in target leukemia cells, and was more potent at complement-mediated leukemia cell killing and antibody-dependent cellular cytotoxicity using human effectors.

Coloma and Morrison *Nature Biotech.* 15: 159-163 (1997) describe a tetravalent bispecific antibody which was engineered by fusing DNA encoding a single chain anti-dansyl antibody Fv (scFv) after the C terminus (CH3-scFv) or after the hinge (Hinge-scFv) of an IgG3 anti-dansyl antibody. See, also, WO95/09917. Smith and Morrison engineered three versions of mu-like IgG3 by engineering either (1) Cys414 of an IgM heavy chain or (2) Cys575 of an IgM heavy chain, or both (1) and (2), into the IgG3 heavy chain gene. All three mutant constructs were expressed by Sp2/0 cells and assembled into polymers containing up to six $H_2L_2$ subunits. The thus-produced 'IgM-like' polymers of IgG were considered to possess both the Fc gamma receptor binding properties of IgG and the more potent complement activity of IgM. See, Smith and Morrison *Bio/Technology* 12:683-688 (1994).

Shuford and colleagues isolated a human IgG1 anti-group B streptococci antibody oligomer from a transfected myeloma cell line. Shuford et al. *Science* 252:724-727 (1991). Immunochemical analysis and DNA sequencing indicated that the cell line produced both a normal kappa light chain and a 37 kD V-V-C variant light chain (L37). Contransfection of vectors encoding the heavy chain and L37 resulted in the production of oligomeric IgG.

U.S. Pat. No. 5,641,870 (Rinderknecht et al.) describes a bivalent, linear F(ab')$_2$ fragment comprising tandem repeats of a heavy chain fragment (VH-CH1-VH-CH1) cosecreted with a light chain. The C-terminus of CH1 was joined directed to the N-terminus of VH without any extraneous linking protein sequences.

Other publications on antibody variants include WO 00/06605; U.S. Pat. Nos. 5,591,828; 5,959,083; 6,027,725; WO98/58965; WO94/13804; Tutt et al. *J. Immunol.* 147:60-69 (1991); WO99/37791; U.S. Pat. No. 5,989,830; WO94/15642; EP 628,078B1; WO97/14719; Stevenson et al. *Anti-Cancer Drug Design* 3:219-230 (1989).

ErbB Receptor Tyrosine Kinases

The ErbB receptor tyrosine kinases are important mediators of cell growth, differentiation and survival. The receptor family includes at least four distinct members including Epidermal Growth Factor Receptor (EGFR or ErbB1), HER2 (ErbB2 or p185$^{neu}$), HER3 (ErbB3) and HER4 (ErbB4 or tyro2).

EGFR, encoded by the erbB1 gene, has been causally implicated in human malignancy. In particular, increased expression of EGFR has been observed in breast, bladder, lung, head, neck and stomach cancer, as well as glioblastomas. Increased EGFR receptor expression is often associated with increased production of the EGFR ligand, Transforming Growth Factor alpha (TGF-alpha), by the same tumor cells resulting in receptor activation by an autocrine stimulatory pathway. Baselga and Mendelsohn *Pharmac. Ther.* 64:127-154 (1994). Monoclonal antibodies directed against the EGFR or its ligands, TGF-alpha and EGF, have been evaluated as therapeutic agents in the treatment of such malignancies. See, e.g., Baselga and Mendelsohn., supra; Masui et al. *Cancer Research* 44:1002-1007 (1984); and Wu et al. *J. Clin. Invest.* 95:1897-1905 (1995).

The second member of the ErbB family, p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science*, 235:177-182 (1987); Slamon et al., *Science*, 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder.

Antibodies directed against the rat p185$^{neu}$ and human HER2 protein products have been described. Drebin and colleagues have raised antibodies against the rat neu gene product, p185$^{neu}$. See, for example, Drebin et al., *Cell* 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of p185$^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165-1172 (1989) describe the generation of a panel of anti-HER2 antibodies which were characterized using the human breast tumor cell line SKBR3. Relative cell proliferation of the SKBR3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-alpha. See, also, U.S. Pat. No. 5,677,171, issued Oct. 14, 1997. The anti-HER2 antibodies discussed in Hudziak et al. were further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2): 979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

A recombinant humanized IgG1 version of the murine anti-HER2 antibody 4D5 (rhuMAb HER2 or HERCEPTIN®; commercially available from Genentech, Inc., South San Francisco) is clinically active in patients with HER2-overexpressing metastatic breast cancers that have received extensive prior anti-cancer therapy (Baselga et al., *J. Clin. Oncol.* 14:737-744 (1996)). HERCEPTIN® received marketing approval from the Food and Drug Administration Sep. 25, 1998 for the treatment of patients with metastatic breast cancer whose tumors overexpress the HER2 protein.

Other anti-HER2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS (USA)* 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373 (1994); Arteaga et al. *Cancer Res.* 54:3758-3765 (1994); Harwerth et al. *J. Biol. Chem.* 267:15160-15167 (1992); U.S. Pat. No. 5,783,186; Klepper et al. *Oncogene* 14:2099-2109 (1997); WO 98/17797; and U.S. Pat. No. 5,783,186. Homology screening has resulted in the identification of two other ErbB receptor family members; HER3 (U.S. Pat. Nos. 5,183,884 and 5,480,968 as well as Kraus et al. *PNAS (USA)* 86:9193-9197 (1989)) and HER4 (EP Pat Appln No 599,274; Plowman et al., *Proc. Natl. Acad. Sci. USA*, 90:1746-1750 (1993); and Plowman et al., *Nature*, 366:473-475 (1993)). Both of these receptors display increased expression on at least some breast cancer cell lines.

The ErbB receptors are generally found in various combinations in cells and heterodimerization is thought to increase the diversity of cellular responses to a variety of ErbB ligands (Earp et al. *Breast Cancer Research and Treatment* 35: 115-132 (1995)). EGFR is bound by six different ligands; Epidermal Growth Factor (EGF), Transforming Growth Factor alpha (TGF-alpha), amphiregulin, Heparin Binding Epidermal Growth Factor (HB-EGF), betacellulin and epiregulin (Groenen et al. *Growth Factors* 11:235-257 (1994)). A family of heregulin proteins resulting from alternative splicing of a single gene are ligands for HER3 and HER4. The heregulin family includes alpha, beta and gamma heregulins (Holmes et al., *Science*, 256:1205-1210 (1992); U.S. Pat. No. 5,641,869; and Schaefer et al. *Oncogene* 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. *Growth Factors* 11:235-257 (1994); Lemke, G. *Molec. & Cell. Neurosci.* 7:247-262 (1996) and Lee et al. *Pharm. Rev.* 47:51-85 (1995). Recently, two additional ErbB ligands were identified; neuregulin-2 (NRG-2) which is reported to bind either HER3 or HER4 (Chang et al. *Nature* 387 509-512 (1997); and Carraway et al *Nature* 387:512-516 (1997)) and neuregulin-3 which binds HER4 (Zhang et al. *PNAS (USA)* 94(18):9562-7 (1997)). HB-EGF, betacellulin and epiregulin also bind to HER4.

While EGF and TGF-alpha do not bind HER2, EGF stimulates EGFR and HER2 to form a heterodimer, which activates EGFR and results in transphosphorylation of HER2 in the heterodimer. Dimerization and/or transphosphorylation appears to activate the HER2 tyrosine kinase. See Earp et al., supra. Likewise, when HER3 is co-expressed with HER2, an active signaling complex is formed and antibodies directed against HER2 are capable of disrupting this complex (Sliwkowski et al., *J. Biol. Chem.*, 269(20):14661-14665 (1994)). Additionally, the affinity of HER3 for heregulin (HRG) is increased to a higher affinity state when co-expressed with HER2. See also, Levi et al., *Journal of Neuroscience* 15: 1329-1340 (1995); Morrissey et al., *Proc. Natl. Acad. Sci. USA* 92: 1431-1435 (1995); and Lewis et al., *Cancer Res.*, 56:1457-1465 (1996) with respect to the HER2-HER3 protein complex. HER4, like HER3, forms an active signaling complex with HER2 (Carraway and Cantley, *Cell* 78:5-8 (1994)).

TNF Receptor Superfamily

Various molecules, such as Tumor Necrosis Factor-alpha ("TNF-alpha"), Tumor Necrosis Factor-beta ("TNF-beta"), Lymphotoxin-alpha ("LT-alpha"), CD30 ligand, CD27 ligand, CD40 ligand, OX-40 ligand, 4-1 BB ligand, Apo-1 ligand (also referred to as Fas ligand or CD95 ligand), Apo-2 ligand (also referred to as TRAIL), Apo-3 ligand (also referred to as TWEAK), osteoprotegerin (OPG), APRIL, RANK ligand (also referred to as TRANCE), and TALL-1 (also referred to as BlyS, BAFF or THANK) have been identified as members of the Tumor Necrosis Factor ("TNF") family of cytokines (See, e.g., Gruss and Dower, Blood, 85:3378-3404 (1995); Pitti et al., *J. Biol. Chem.*, 271:12687-12690 (1996); Wiley et al., *Immunity*, 3:673-682 (1995); Browning et al., *Cell*, 72:847-856 (1993); Armitage et al. *Nature*, 357:80-82 (1992); WO 97/01633 published Jan. 16, 1997; WO 97/25428 published Jul. 17, 1997; Marsters et al., *Curr. Biol.*, 8:525-528 (1998); Simonet et al., *Cell*, 89:309-319 (1997); Chicheportiche et al., *Biol. Chem.*, 272:32401-32410 (1997); Hahne et al., *J. Exp. Med.*, 188:1185-1190 (1998); WO98/28426 published Jul. 2, 1998; WO98/46751 published Oct. 22, 1998; WO/98/18921 published May 7, 1998; Moore et al., *Science*, 285:260-263 (1999); Shu et al., *J. Leukocyte Biol.*, 65:680 (1999); Schneider et al., *J. Exp. Med.*, 189:1747-1756 (1999); and Mukhopadhyay et al., *J. Biol. Chem.*, 274:15978-15981 (1999)). Among these molecules, TNF-alpha, TNF-beta, CD30 ligand, 4-1BB ligand, Apo-1 ligand, Apo-2 ligand (Apo2L/TRAIL) and Apo-3 ligand (TWEAK) have been reported to be involved in apoptotic cell death. Both TNF-alpha and TNF-beta have been reported to induce apoptotic death in susceptible tumor cells (Schmid et al., *Proc. Natl. Acad. Sci.*, 83:1881 (1986); Dealtry et al., *Eur. J. Immunol.*, 17:689 (1987)).

Various molecules in the TNF family also have purported role(s) in the function or development of the immune system (Gruss et al., *Blood*, 85:3378 (1995)). Zheng et al. have reported that TNF-alpha is involved in post-stimulation apoptosis of CD8-positive T cells (Zheng et al., *Nature*, 377:348-351 (1995)). Other investigators have reported that CD30 ligand may be involved in deletion of self-reactive T cells in the thymus (Amakawa et al., *Cold Spring Harbor Laboratory Symposium on Programmed Cell Death*, Abstr. No. 10, (1995)). CD40 ligand activates many functions of B cells, including proliferation, immunoglobulin secretion, and survival (Renshaw et al., *J. Exp. Med.*, 180:1889 (1994)). Another recently identified TNF family cytokine, TALL-1 (BlyS), has been reported, under certain conditions, to induce B cell proliferation and immunoglobulin secretion. (Moore et al., supra; Schneider et al., supra; Mackay et al., *J. Exp. Med.*, 190:1697 (1999)).

Mutations in the mouse Fas/Apo-1 receptor or ligand genes (called lpr and gld, respectively) have been associated with some autoimmune disorders, indicating that Apo-1 ligand may play a role in regulating the clonal deletion of self-reactive lymphocytes in the periphery (Krammer et al., *Curr. Op. Immunol.*, 6:279-289 (1994); Nagata et al., *Science*, 267: 1449-1456 (1995)). Apo-1 ligand is also reported to induce post-stimulation apoptosis in CD4-positive T lymphocytes and in B lymphocytes, and may be involved in the elimination of activated lymphocytes when their function is no longer needed (Krammer et al., supra; Nagata et al., supra). Agonist mouse monoclonal antibodies specifically binding to the Apo-1 receptor have been reported to exhibit cell killing activity that is comparable to or similar to that of TNF-alpha (Yonehara et al., *J. Exp. Med.*, 169:1747-1756 (1989)).

Induction of various cellular responses mediated by such TNF family cytokines is believed to be initiated by their binding to specific cell receptors. Previously, two distinct TNF receptors of approximately 55-kDa (TNFR1) and 75-kDa (TNFR2) were identified (Hohmann et al., *J. Biol. Chem.*, 264:14927-14934 (1989); Brockhaus et al., *Proc. Natl. Acad. Sci.*, 87:3127-3131 (1990); EP 417,563, published Mar. 20, 1991; Loetscher et al., *Cell*, 61:351 (1990); Schall et al., *Cell*, 61:361 (1990); Smith et al., *Science*, 248: 1019-1023 (1990); Lewis et al., *Proc. Natl. Acad. Sci.*, 88:2830-2834 (1991); Goodwin et al., *Mol. Cell. Biol.*, 11:3020-3026 (1991)). Those TNFRs were found to share the typical structure of cell surface receptors including extracellular, transmembrane and intracellular regions. The extracellular portions of both receptors were found naturally also as soluble TNF-binding proteins (Nophar et al., *EMBO J.*, 9:3269 (1990); and Kohno et al., *Proc. Natl. Acad. Sci. U.S.A.,* 87:8331 (1990); Hale et al., *J. Cell. Biochem.* Supplement 15F, 1991, p. 113 (P424)).

The extracellular portion of type 1 and type 2 TNFRs (TNFR1 and TNFR2) contains a repetitive amino acid sequence pattern of four cysteine-rich domains (CRDs) designated 1 through 4, starting from the $NH_2$-terminus. (Schall et al., supra; Loetscher et al., supra; Smith et al., supra; Nophar et al., supra; Kohno et al., supra; Banner et al., *Cell,* 73:431-435 (1993)). A similar repetitive pattern of CRDs exists in several other cell-surface proteins, including the p75 nerve growth factor receptor (NGFR) (Johnson et al., *Cell,* 47:545 (1986); Radeke et al., *Nature,* 325:593 (1987)), the B cell antigen CD40 (Stamenkovic et al., *EMBO J.,* 8:1403 (1989)), the T cell antigen OX40 (Mallet et al., *EMBO J.,* 9:1063 (1990)) and the Fas antigen (Yonehara et al., supra and Itoh et al., *Cell,* 66:233-243 (1991)). CRDs are also found in the soluble TNFR (sTNFR)-like T2 proteins of the Shope and myxoma poxviruses (Upton et al., *Virology,* 160:20-30 (1987); Smith et al., *Biochem. Biophys. Res. Commun.,* 176: 335 (1991); Upton et al., *Virology,* 184:370 (1991)). Optimal alignment of these sequences indicates that the positions of the cysteine residues are well conserved. These receptors are sometimes collectively referred to as members of the TNF/NGF receptor superfamily.

The TNF family ligands identified to date, with the exception of Lymphotoxin-alpha, are type II transmembrane proteins, whose C-terminus is extracellular. In contrast, most receptors in the TNF receptor (TNFR) family identified to date are type I transmembrane proteins. In both the TNF ligand and receptor families, however, homology identified between family members has been found mainly in the extracellular domain ("ECD"). Several of the TNF family cytokines, including TNF-alpha, Apo-1 ligand and CD40 ligand, are cleaved proteolytically at the cell surface; the resulting protein in each case typically forms a homotrimeric molecule that functions as a soluble cytokine. TNF receptor family proteins are also usually cleaved proteolytically to release soluble receptor ECDs that can function as inhibitors of the cognate cytokines.

More recently, other members of the TNFR family have been identified. In von Bulow et al., *Science,* 278:138-141 (1997), investigators describe a plasma membrane receptor referred to as Transmembrane Activator and CAML-Interactor or "TACI". The TACI receptor is reported to contain a cysteine-rich motif characteristic of the TNFR family. In an in vitro assay, cross linking of TACI on the surface of transfected Jurkat cells with TACI-specific antibodies led to activation of NF-KB (see also, WO 98/39361 published Sep. 11, 1998).

Laabi et al., *EMBO J.,* 11:3897-3904 (1992) reported identifying a new gene called "BCM" whose expression was found to coincide with B cell terminal maturation. The open reading frame of the BCM normal cDNA predicted a 184 amino acid long polypeptide with a single transmembrane domain. These investigators later termed this gene "BCMA." (Laabi et al., *Nucleic Acids Res.,* 22:1147-1154 (1994)). BCMA mRNA expression was reported to be absent in human malignant B cell lines which represent the pro-B lymphocyte stage, and thus, is believed to be linked to the stage of differentiation of lymphocytes (Gras et al., *Int. Immunology,* 7:1093-1106 (1995)). In Madry et al., *Int. Immunology,* 10:1693-1702 (1998), the cloning of murine BCMA cDNA was described. The murine BCMA cDNA is reported to encode a 185 amino acid long polypeptide having 62% identity to the human BCMA polypeptide. Alignment of the murine and human BCMA protein sequences revealed a conserved motif of six cysteines in the N-terminal region, suggesting that the BCMA protein belongs to the TNFR superfamily (Madry et al., supra).

In Marsters et al., *Curr. Biol.,* 6:750 (1996), investigators describe a full length native sequence human polypeptide, called Apo-3, which exhibits similarity to the TNFR family in its extracellular cysteine-rich repeats and resembles TNFR1 and CD95 in that it contains a cytoplasmic death domain sequence (see also Marsters et al., *Curr. Biol.,* 6:1669 (1996)). Apo-3 has also been referred to by other investigators as DR3, wsl-1, TRAMP, and LARD (Chinnaiyan et al., *Science,* 274: 990 (1996); Kitson et al., *Nature,* 384:372 (1996); Bodmer et al., *Immunity,* 6:79 (1997); Screaton et al., *Proc. Natl. Acad. Sci.,* 94:4615-4619 (1997)).

Pan et al. have disclosed another TNF receptor family member referred to as "DR4" (Pan et al., *Science,* 276:111-113 (1997); see also WO98/32856 published Jul. 30, 1998). The DR4 was reported to contain a cytoplasmic death domain capable of engaging the cell suicide apparatus. Pan et al. disclose that DR4 is believed to be a receptor for the ligand known as Apo2L/TRAIL.

In Sheridan et al., *Science,* 277:818-821 (1997) and Pan et al., *Science,* 277:815-818 (1997), another molecule believed to be a receptor for Apo2L/TRAIL is described (see also, WO98/51793 published Nov. 19, 1998; and WO98/41629 published Sep. 24, 1998). That molecule is referred to as DR5 (it has also been alternatively referred to as Apo-2; TRAIL-R, TR6, Tango-63, hAPO8, TRICK2 or KILLER (Screaton et al., *Curr. Biol.,* 7:693-696 (1997); Walczak et al., *EMBO J.,* 16:5386-5397 (1997); Wu et al., *Nature Genetics,* 17:141-143 (1997); WO98/35986 published Aug. 20, 1998; EP870, 827 published Oct. 14, 1998; WO98/46643 published Oct. 22, 1998; WO99/02653 published Jan. 21, 1999; WO99/09165 published Feb. 25, 1999; and WO99/11791 published Mar. 11, 1999). Like DR4, DR5 is reported to contain a cytoplasmic death domain and be capable of signaling apoptosis. The crystal structure of the complex formed between Apo2L/TRAIL and DR5 is described in Hymowitz et al., *Molecular Cell,* 4:563-571 (1999).

Yet another death domain-containing receptor, DR6, was recently identified (Pan et al., *FEBS Letters,* 431:351-356 (1998)). Aside from containing four putative extracellular cysteine rich domains and a cytoplasmic death domain, DR6 is believed to contain a putative leucine-zipper sequence that overlaps with a proline-rich motif in the cytoplasmic region. The proline-rich motif resembles sequences that bind to src-homology-3 domains, which are found in many intracellular signal-transducing molecules.

A further group of recently identified receptors are referred to as "decoy receptors," which are believed to function as inhibitors, rather than transducers of signaling. This group includes DcR1 (also referred to as TRID, LIT or TRAIL-R3) (Pan et al., *Science,* 276:111-113 (1997); Sheridan et al., *Science,* 277:818-821 (1997); MacFarlane et al., *J. Biol. Chem.,* 272:25417-25420 (1997); Schneider et al., *FEBS Letters,* 416:329-334 (1997); Degli-Esposti et al., *J. Exp. Med.,* 186:1165-1170 (1997); and Mongkolsapaya et al., *J. Immunol.,* 160:3-6 (1998)) and DcR2 (also called TRUNDD or TRAIL-R4) (Marsters et al., *Curr. Biol.,* 7:1003-1006 (1997); Pan et al., *FEBS Letters,* 424:41-45 (1998); Degli-Esposti et al., *Immunity,* 7:813-820 (1997)), both cell surface molecules, as well as OPG (Simonet et al., supra; Emery et al., infra) and DcR3 (Pitti et al., *Nature,* 396:699-703 (1998)), both of which are secreted, soluble proteins.

Additional newly identified members of the TNFR family include CAR1, HVEM, GITR, ZTNFR-5, NTR-1, and TNFL1 (Brojatsch et al., *Cell,* 87:845-855 (1996); Montgomery et al., *Cell*, 87:427-436 (1996); Marsters et al., *J. Biol. Chem.*, 272:14029-14032 (1997); Nocentini et al., *Proc. Natl. Acad. Sci. USA* 94:6216-6221 (1997); Emery et al., *J. Biol. Chem.*, 273:14363-14367 (1998); WO99/04001 published Jan. 28, 1999; WO99/07738 published Feb. 18, 1999; WO99/33980 published Jul. 8, 1999).

As reviewed recently by Tewari et al., TNFR1, TNFR2 and CD40 modulate the expression of proinflammatory and costimulatory cytokines, cytokine receptors, and cell adhesion molecules through activation of the transcription factor, NF-6B (Tewari et al., *Curr. Op. Genet. Develop.*, 6:39-44 (1996)). NF-6B is the prototype of a family of dimeric transcription factors whose subunits contain conserved Rel regions (Verma et al., *Genes Develop.*, 9:2723-2735 (1995); Baldwin, Ann. Rev. Immunol., 14:649-683 (1996)). In its latent form, NF-6B is complexed with members of the I-6B inhibitor family; upon inactivation of the I-6B in response to certain stimuli, released NF-6B translocates to the nucleus where it binds to specific DNA sequences and activates gene transcription. As described above, the TNFR members identified to date either include or lack an intracellular death domain region. Some TNFR molecules lacking a death domain, such as TNFR2, CD40, HVEM, and GITR, are capable of modulating NF-6B activity. (see, e.g., Lotz et al., *J. Leukocyte Biol.*, 60:1-7 (1996)).

For a review of the TNF family of cytokines and their receptors, see Ashkenazi and Dixit, *Science*, 281:1305-1308 (1998); Golstein, *Curr. Biol.*, 7:750-753 (1997); Gruss and Dower, supra, and Nagata, *Cell*, 88:355-365 (1997).

B Cell Surface Antigens

Lymphocytes are one of many types of white blood cells produced in the bone marrow during the process of hematopoiesis. There are two major populations of lymphocytes: B lymphocytes (B cells) and T lymphocytes (T cells). The lymphocytes of particular interest herein are B cells.

B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called "plasma cells". Memory B cells have a longer life span and continue to express membrane-bound antibody with the same specificity as the original parent cell. Plasma cells do not produce membrane-bound antibody but instead produce the antibody in a form that can be secreted. Secreted antibodies are the major effector molecule of humoral immunity.

The CD20 antigen (also called human B-lymphocyte-restricted differentiation antigen, Bp35) is a hydrophobic transmembrane protein with a molecular weight of approximately 35 kD located on pre-B and mature B lymphocytes (Valentine et al. *J. Biol. Chem.* 264(19):11282-11287 (1989); and Einfeld et al. *EMBO J.* 7(3):711-717 (1988)). The antigen is also expressed on greater than 90% of B cell non-Hodgkin's lymphomas (NHL) (Anderson et al. *Blood* 63(6):1424-1433 (1984)), but is not found on hematopoietic stem cells, pro-B cells, normal plasma cells or other normal tissues (Tedder et al. *J. Immunol.* 135(2):973-979 (1985)). CD20 regulates an early step(s) in the activation process for cell cycle initiation and differentiation (Tedder et al., supra) and possibly functions as a calcium ion channel (Tedder et al. *J. Cell. Biochem.* 14D:195 (1990)).

Given the expression of CD20 in B cell lymphomas, this antigen can serve as a candidate for "targeting" of such lymphomas. In essence, such targeting can be generalized as follows: antibodies specific to the CD20 surface antigen of B cells are administered to a patient. These anti-CD20 antibodies specifically bind to the CD20 antigen of (ostensibly) both normal and malignant B cells; the antibody bound to the CD20 surface antigen may lead to the destruction and depletion of neoplastic B cells. Additionally, chemical agents or radioactive labels having the potential to destroy the tumor can be conjugated to the anti-CD20 antibody such that the agent is specifically "delivered" to the neoplastic B cells. Irrespective of the approach, a primary goal is to destroy the tumor; the specific approach can be determined by the particular anti-CD20 antibody which is utilized and, thus, the available approaches to targeting the CD20 antigen can vary considerably.

CD19 is another antigen that is expressed on the surface of cells of the B lineage. Like CD20, CD19 is found on cells throughout differentiation of the lineage from the stem cell stage up to a point just prior to terminal differentiation into plasma cells (Nadler, L. *Lymphocyte Typing II* 2: 3-37 and Appendix, Renling et al. eds. (1986) by Springer Verlag). Unlike CD20 however, antibody binding to CD19 causes internalization of the CD19 antigen. CD19 antigen is identified by the HD237-CD19 antibody (also called the "B4" antibody) (Kiesel et al. *Leukemia Research* 11(12):1119 (1987)), among others. The CD19 antigen is present on 4-8% of peripheral blood mononuclear cells and on greater than 90% of B cells isolated from peripheral blood, spleen, lymph node or tonsil. CD19 is not detected on peripheral blood T cells, monocytes or granulocytes. Virtually all non-T cell acute lymphoblastic leukemias (ALL), B cell chronic lymphocytic leukemias (CLL) and B cell lymphomas express CD19 detectable by the antibody B4 (Nadler et al. *J. Immunol.* 131:244 (1983); and Nadler et al. in *Progress in Hematology* Vol. XII pp. 187-225. Brown, E. ed. (1981) by Grune & Stratton, Inc).

Additional antibodies which recognize differentiation stage-specific antigens expressed by cells of the B cell lineage have been identified. Among these are the B2 antibody directed against the CD21 antigen; B3 antibody directed against the CD22 antigen; and the J5 antibody directed against the CD10 antigen (also called CALLA). See U.S. Pat. No. 5,595,721 issued Jan. 21, 1997 (Kaminski et al.).

The rituximab (RITUXAN®) antibody is a genetically engineered chimeric murine/human monoclonal antibody directed against the CD20 antigen. Rituximab is the antibody called "C2B8" in U.S. Pat. No. 5,736,137 issued Apr. 7, 1998 (Anderson et al.). RITUXAN® is indicated for the treatment of patients with relapsed or refractory low-grade or follicular, CD20 positive, B cell non-Hodgkin's lymphoma. In vitro mechanism of action studies have demonstrated that RITUXAN® binds human complement and lyses lymphoid B cell lines through CDC (Reff et al. *Blood* 83(2):435-445 (1994)). Additionally, it has significant activity in assays for ADCC. More recently, RITUXAN® has been shown to have anti-proliferative effects in tritiated thymidine incorporation assays and to induce apoptosis directly, while other anti-CD19 and CD20 antibodies do not (Maloney et al. *Blood* 88(10):637a (1996)). Synergy between RITUXAN® and chemotherapies and toxins has also been observed experimentally. In particular, RITUXAN® sensitizes drug-resistant human B cell lymphoma cell lines to the cytotoxic effects of doxorubicin, CDDP, VP-16, diphtheria toxin and ricin (Demidem et al. *Cancer Biotherapy & Radiopharmaceuticals* 12(3):177-186 (1997)). In vivo preclinical studies have shown that RITUXAN® depletes B cells from the peripheral blood, lymph nodes, and bone marrow of cynomolgus monkeys, presumably through complement and cell-mediated processes (Reff et al. *Blood* 83(2):435-445 (1994)).

SUMMARY OF THE INVENTION

The present invention provides multivalent antibodies (e.g. tetravalent antibodies) with three or more antigen binding sites, which can be readily produced by recombinant expression of nucleic acid encoding the polypeptide chains of the antibody. In one embodiment, the multivalent antibody comprises a dimerization domain and three or more antigen binding sites. The preferred dimerization domain comprises (or consists of) an Fc region or a hinge region. In one embodiment, the invention provides an isolated antibody comprising a dimerization domain and three or more antigen binding sites amino-terminal thereto. The invention further provides an isolated antibody comprising an Fc region and three or more antigen binding sites amino-terminal to the Fc region. The preferred multivalent antibody herein comprises (or consists of) three to about eight, but preferably four, antigen binding sites (which are generally all "functional", as hereindefined). In one embodiment, the multivalent antibody comprises five or more (e.g. up to about eight) antigen binding sites. The multivalent antibody herein is preferably not a native sequence IgA or IgM, and may lack an Fc region or have only one Fc region.

In the preferred embodiment, the multivalent antibody comprises at least one polypeptide chain (and preferably two polypeptide chains), wherein the polypeptide chain(s) comprise two or more variable domains. For instance, the polypeptide chain(s) may comprise VD1-$(X1)_n$-VD2-$(X2)_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; VH-CH1-VH-CH1-Fc region chain; VL-CL-flexible linker-VL-CL-Fc region chain; or VL-CL-VL-CL-Fc region chain. Where the polypeptide chain (or polypeptide chains) comprise Fd-flexible linker-Fd, the flexible linker may comprise a peptide such as gly-ser, gly-ser-gly-ser (SEQ ID NO:10), ala-ser, or gly-gly-gly-ser (SEQ ID NO:11).

The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

The multivalent antibodies herein have properties which are desirable, among other things, from a therapeutic standpoint. For instance, the multivalent antibody may (1) be internalized (and/or catabolized) faster than a bivalent antibody by a cell expressing an antigen to which the antibodies bind; (2) be an agonist antibody; and/or (3) induce cell death and/or apoptosis of a cell expressing an antigen which the multivalent antibody is capable of binding to. The "parent antibody" which provides at least one antigen binding specificity of the multivalent antibody may be one which is internalized (and/or catabolized) by a cell expressing an antigen to which the antibody binds; and/or may be an agonist, cell-death-inducing, and/or apoptosis-inducing antibody, and the multivalent form of the antibody as described herein may display improvement(s) in one or more of these properties. Moreover, the parent antibody may lack any one or more of these properties, but may be endowed with them when constructed as a multivalent antibody as hereindescribed.

The three or more antigen binding sites of the multivalent antibodies herein may all bind the same antigen; or may bind two or more (e.g. from two to about three) different antigens.

The multivalent antibody may bind (1) a cell surface protein expressed (or overexpressed) by tumor cells, e.g. Epidermal Growth Factor Receptor (EGFR), HER2 receptor, HER3 receptor, HER4 receptor, or DcR3; (2) a receptor in the Tumor Necrosis Factor (TNF) receptor superfamily (e.g. an Apo2L receptor, such as DR4, DR5, DcR1 or DcR2); and/or (3) a B cell surface antigen (such as CD19, CD20, CD22 or CD40). In the preferred embodiment of the invention, all of the functional antigen binding sites of the multivalent antibody bind the same antigen as listed above (e.g. all four antigen binding sites of a tetravalent antibody bind either (1), (2) or (3)).

The invention also provides immunoconjugates comprising the multivalent antibody conjugated with a cytotoxic agent. The cytotoxic agent here may be one which is active in killing cells once internalized.

The invention additionally pertains to a polypeptide chain comprising VD1-$(X1)_n$-VD2-$(X2)_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain may comprise VH-CH1-flexible linker-VH-CH1-Fc region chain; VH-CH1-VH-CH1-Fc region chain; VL-CL-flexible linker-VL-CL-Fc region chain; or VL-CL-VL-CL-Fc region chain. In another embodiment, the polypeptide chain comprises VH-CH1-flexible linker-VH-CH1-dimerization domain; VH-CH1-VH-CH1-dimerization domain; VL-CL-flexible linker-VL-CL-dimerization domain; or VL-CL-VL-CL-dimerization domain. For instance, the polypeptide chain may comprise VH-CH1-flexible linker-VH-CH1-hinge region; VH-CH1-VH-CH1-hinge region. The invention additionally provides an antibody comprising one or more (preferably two) of such polypeptide chains. The antibody preferably further comprises at least two (and preferably four) light chain or heavy chain variable domain polypeptides, e.g., where the light chain variable domain polypeptides comprise VL-CL and the heavy chain variable domain polypeptides comprise VH-CH1.

The invention further provides a polypeptide chain comprising three or more heavy chain or light chain variable domains, wherein each of the variable domains is able to combine with three or more light chain or heavy chain variable domain polypeptides to form three or more antigen binding sites, each directed against the same antigen. The invention also provides an isolated antibody comprising the polypeptide chain. In the preferred embodiment, where the polypeptide chain comprises three or more heavy chain variable domains, the antibody preferably further comprises three or more light chain variable domain polypeptides which can combine with the heavy chain variable domains to form the three or more antigen binding sites. Examples of such antibodies are shown in FIG. 23 D (with three antigen binding sites) and FIG. 23E (with four antigen binding sites). In addition, the invention provides a polypeptide chain comprising the formula: (a) VL-CL-flexible linker-VL-CL-flexible linker-VL-CL; (b) VH-CH1-flexible linker-VH-CH1-flexible linker-VH-CH1; (c) $(VL-CL)_n$, wherein n is three or more; or (d) $(VH-CH1)_n$, wherein n is three or more.

The invention further provides: isolated nucleic acid encoding the multivalent antibody or polypeptide chain; a vector comprising nucleic acid encoding the multimeric antibody or polypeptide chain, optionally, operably linked to control sequences recognized by a host cell transformed with the vector; a host cell comprising (e.g. transformed with) nucleic acid encoding the multimeric antibody or polypeptide chain; a method for producing the multivalent antibody or polypeptide chain comprising culturing the host cell so that the nucleic acid is expressed and, optionally, recovering the multivalent antibody or polypeptide chain from the host cell culture (e.g. from the host cell culture medium). Nucleic acids encoding (1) the heavy chain variable domains and (2) the light chain variable domains of the multivalent antibody are preferably co-expressed by a host cell transformed with both (1) and (2). Nucleic acids (1) and (2) may be present in the same, or different, vectors.

Diagnostic and therapeutic uses for the multivalent antibodies disclosed herein are contemplated. In one diagnostic application, the invention provides a method for determining the presence of an antigen of interest comprising exposing a sample suspected of containing the antigen to the multivalent antibody and determining binding of the multivalent antibody to the sample. Both in vitro and in vivo diagnostic methods are provided.

In one therapeutic application, the invention provides a method of treating a mammal suffering from, or predisposed to, a disease or disorder, comprising administering to the mammal a therapeutically effective amount of a multivalent antibody as disclosed herein, or of a composition comprising the multivalent antibody and a pharmaceutically acceptable carrier. The disorder to be treated herein may be cancer, in which case the method may further comprise administering a therapeutically effective amount of a cytotoxic agent to the mammal. The present invention further relates to a method of inducing apoptosis of a cancer cell comprising exposing the cell to a multivalent antibody as described herein, wherein the multivalent antibody binds a receptor in the Tumor Necrosis Factor (TNF) receptor superfamily. The method may involve killing a B cell by exposing the B cell to a multivalent antibody that binds a B cell surface antigen. Moreover, the method may relate to killing a cell which expresses (or overexpresses) an ErbB receptor comprising exposing the cell to an antibody that binds the ErbB receptor.

BRIEF DESCRIPTION OF THE DRAWINGS

In FIG. 4A, the four antigen binding Fabs are numbered (1 and 2 for each arm of the tetravalent antibody) and X represents a dimerization domain. In FIG. 4B, the dimerization domain of the tetravalent antibody is an Fc region.

FIGS. 11A-F show subcellular localization of $^{125}$I-OctHER2 in SKBR3 cells. Autoradiographic silver grains were observed associated with the villi of the apical cell membrane (FIG. 11A), in close proximity with a forming coated pit (FIG. 11B, arrow), with smooth cytosolic vesicles (FIGS. 11C and D) and endosomes (FIGS. 11E and F). Bars=0.25:M. FIGS. 11G-I show internalization at time 0 hours (FIG. 11G) and 5 hours (FIGS. 11H and 11I).

FIGS. 20A-B present a quantitative summary of the 2 day in vitro results from the National Cancer Institute Developmental Therapeutics Program comparing the anti-DR516E2 Octopus (FIG. 20A) to Apo2L/TRAIL (FIG. 20B) analyzing growth inhibition (GI50), stasis (TGI), and toxicity (LC50).

FIGS. 21A-B present a quantitative summary of the 6 day in vitro results from the National Cancer Institute Developmental Therapeutics Program comparing the anti-DR516E2 Octopus (FIG. 21A) to Apo2L/TRAIL (FIG. 21B) analyzing growth inhibition (GI50), stasis (TGI), and toxicity (LC50).

FIG. 34 depicts homotypic cell adhesion in WIL2S cells induced by IFS anti-CD20 antibody, IgG cross-linked IFS antibody and POPoct-3 CD20.

DETAILED DESCRIPTION OF THE PREFERRED EMBODIMENTS

I. Definitions

Figure 1:
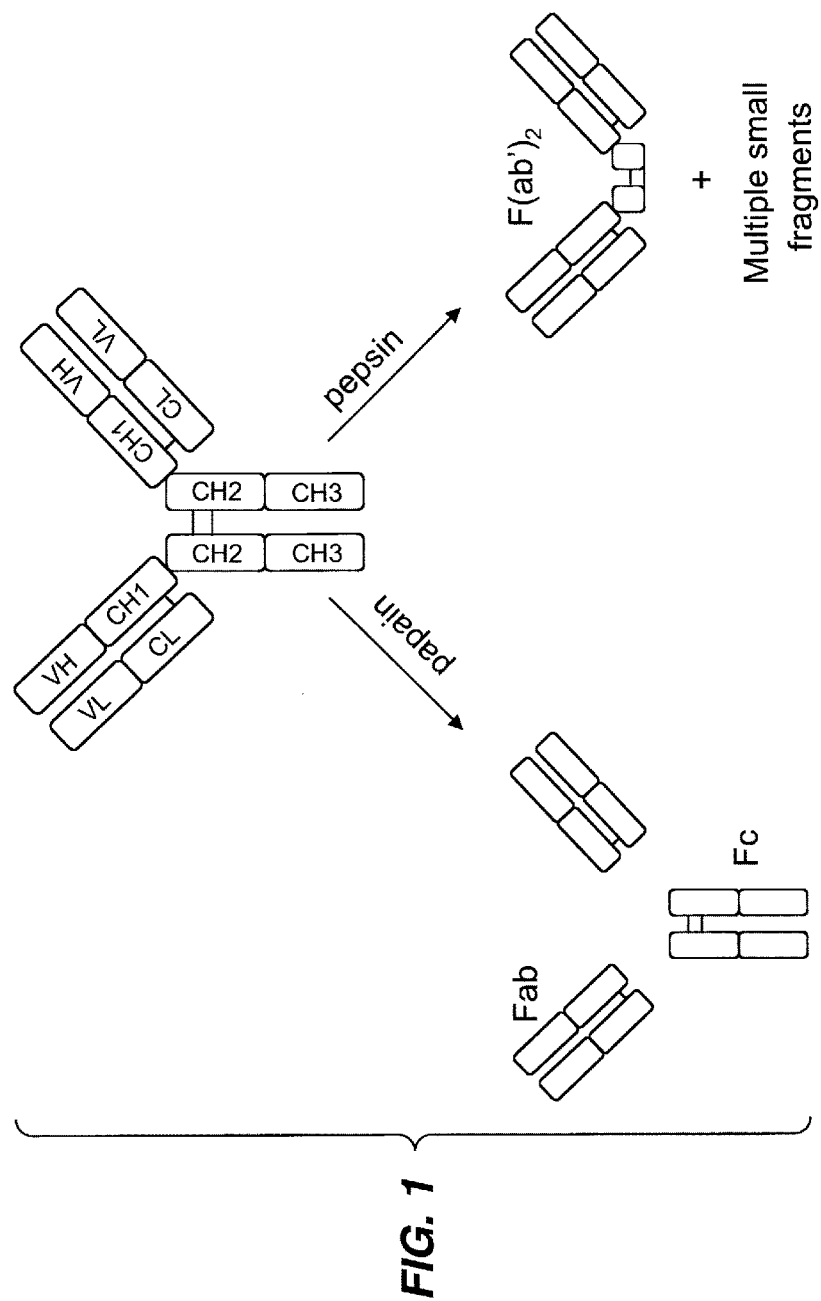
FIG. 1 is a schematic representation of a native IgG and digestion thereof with (1) papain to generate two Fab fragments and an Fc region or (2) pepsin to generate a F(ab')$_2$ fragment and multiple small fragments. Disulfide bonds are represented by lines between CH1 and CL domains and the two CH2 domains. V is variable domain; C is constant domain; L stands for light chain and H stands for heavy chain.
Figures 2A, 2B, 2C:
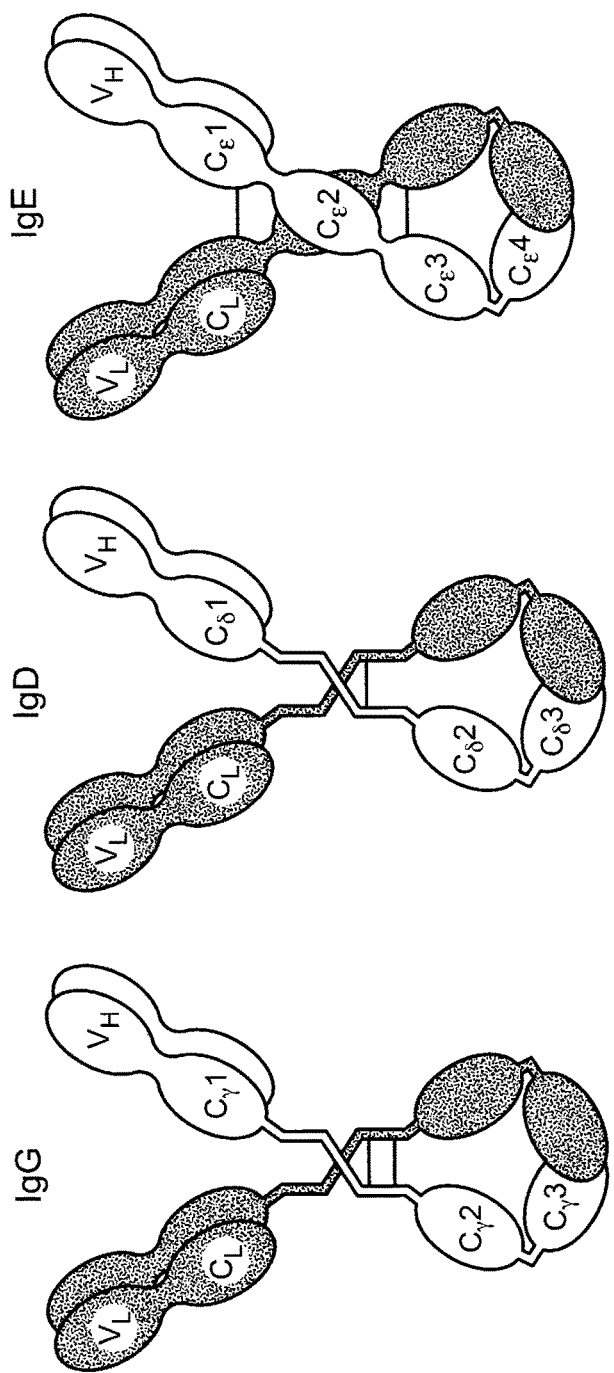
FIGS. 2A-E depict the structures of the five major naturally occurring immunoglobulin isotypes; IgG (FIG. 2A), IgD (FIG. 2B), IgE (FIG. 2C), IgA dimer (FIG. 2D), and IgM pentamer (FIG. 2E).
Figure 2E:
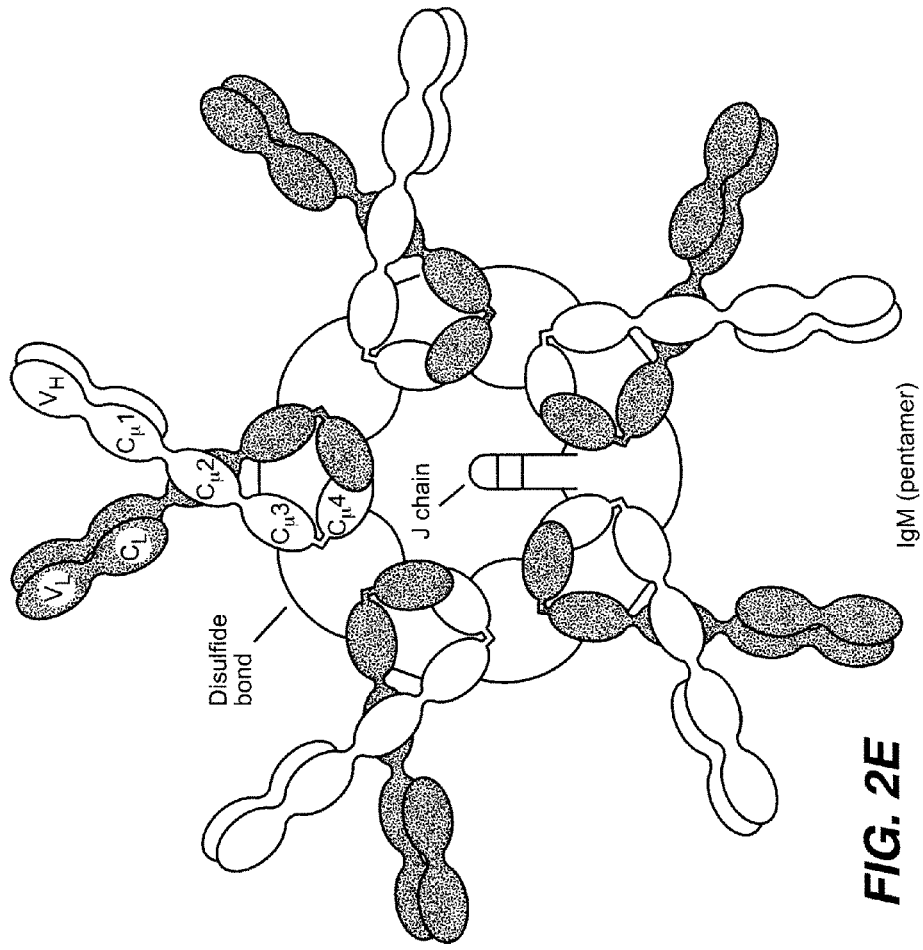
Figure 2D:
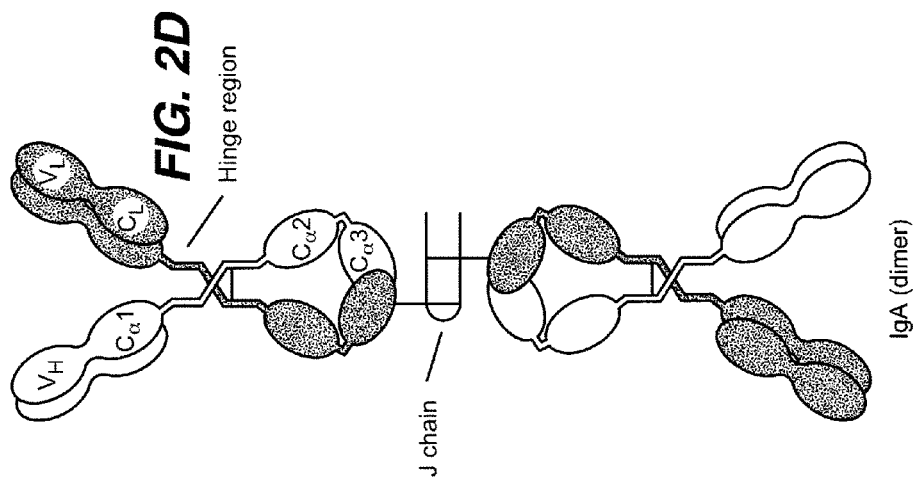
Figure 4A:
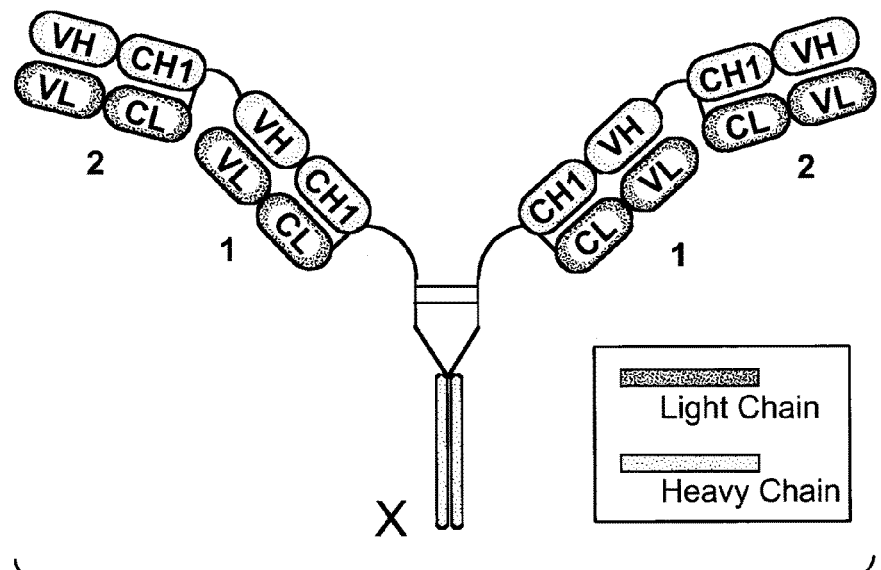
FIGS. 4A-B depict schematically tetravalent antibodies according to the present invention.
Figure 4B:
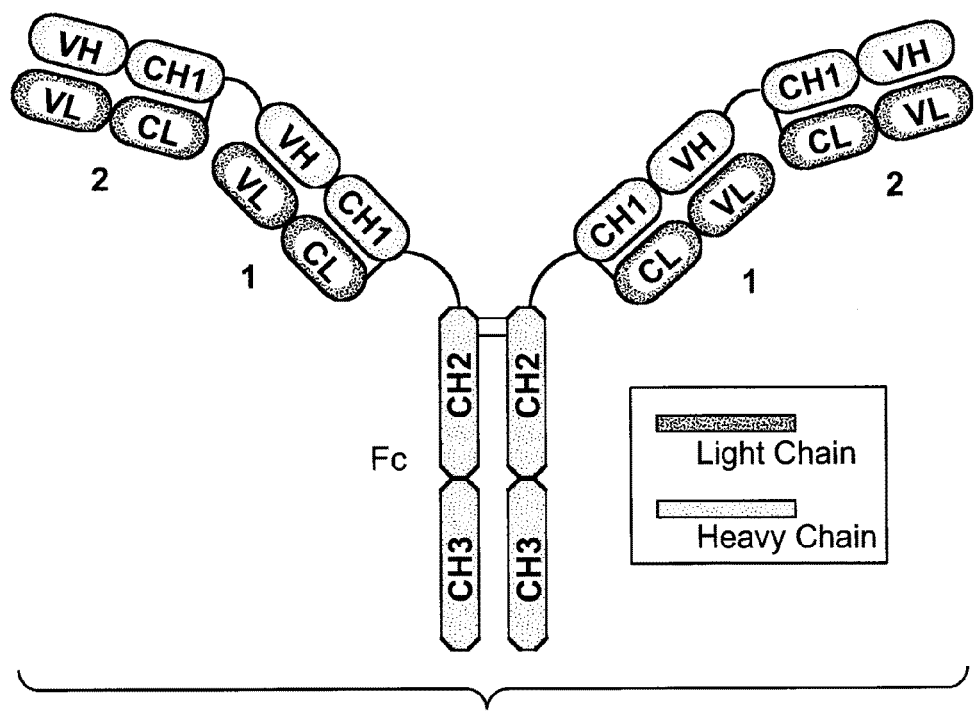

Throughout the present specification and claims, the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991), expressly incorporated herein by reference. The "EU index as in Kabat" refers to the residue numbering of the human IgG1 EU antibody.

An "ErbB receptor" is a receptor protein tyrosine kinase which belongs to the ErbB receptor family and includes EGFR, HER2, ErbB3 and ErbB4 receptors as well as TEGFR (U.S. Pat. No. 5,708,156) and other members of this family to be identified in the future. The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a native sequence ErbB receptor or an amino acid sequence variant thereof. Preferably the ErbB receptor is native sequence human ErbB receptor.

By "ErbB ligand" is meant a polypeptide which binds to and/or activates an ErbB receptor. The ErbB ligand of particular interest herein is a native sequence human ErbB ligand such as Epidermal Growth Factor (EGF) (Savage et al., *J. Biol. Chem.* 247:7612-7621 (1972)); Transforming Growth Factor alpha (TGF-alpha) (Marquardt et al., *Science* 223: 1079-1082 (1984)); amphiregulin also known as schwanoma or keratinocyte autocrine growth factor (Shoyab et al. *Science* 243:1074-1076 (1989); Kimura et al. *Nature* 348:257-260

(1990); and Cook et al. *Mol. Cell. Biol.* 11:2547-2557 (1991)); betacellulin (Shing et al., *Science* 259:1604-1607 (1993); and Sasada et al. *Biochem. Biophys. Res. Commun.* 190:1173 (1993)); heparin-binding epidermal growth factor (HB-EGF) (Higashiyama et al., *Science* 251:936-939 (1991)); epiregulin (Toyoda et al., *J. Biol. Chem.* 270:7495-7500 (1995); and Komurasaki et al. *Oncogene* 15:2841-2848 (1997)), a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); or cripto (CR-1) (Kannan et al. *J. Biol. Chem.* 272(6):3330-3335 (1997)). ErbB ligands which bind EGFR include EGF, TGF-alpha, amphiregulin, betacellulin, HB-EGF and epiregulin. ErbB ligands which bind HER3 include heregulins. ErbB ligands capable of binding HER4 include betacellulin, epiregulin, HB-EGF, NRG-2, NRG-3 and heregulins.

"Heregulin" (HRG) when used herein refers to a polypeptide comprising an amino acid sequence encoded by the heregulin gene product as disclosed in U.S. Pat. No. 5,641,869 or Marchionni et al., *Nature,* 362:312-318 (1993), and biologically active variants of such polypeptides. Examples of heregulins include heregulin-alpha heregulin-beta1, heregulin-beta2 and heregulin-beta3 (Holmes et al., *Science,* 256:1205-1210 (1992); and U.S. Pat. No. 5,641,869); neu differentiation factor (NDF) (Peles et al. *Cell* 69: 205-216 (1992)); acetylcholine receptor-inducing activity (ARIA) (Falls et al. *Cell* 72:801-815 (1993)); glial growth factors (GGFs) (Marchionni et al., *Nature,* 362:312-318 (1993)); sensory and motor neuron derived factor (SMDF) (Ho et al. *J. Biol. Chem.* 270:14523-14532 (1995)); gamma-heregulin (Schaefer et al. *Oncogene* 15:1385-1394 (1997)). An example of a biologically active fragment/amino acid sequence variant of a native sequence HRG polypeptide, is an EGF-like domain fragment (e.g. HRGbeta1$_{177-244}$).

An "ErbB hetero-oligomer" herein is a noncovalently associated oligomer comprising at least two different ErbB receptors. Such complexes may form when a cell expressing two or more ErbB receptors is exposed to an ErbB ligand and can be isolated by immunoprecipitation and analyzed by SDS-PAGE as described in Sliwkowski et al., *J. Biol. Chem.,* 269(20):14661-14665 (1994), for example. Examples of such ErbB hetero-oligomers include EGFR-HER2, HER2-HER3 and HER3-HER4 complexes. Moreover, the ErbB hetero-oligomer may comprise two or more HER2 receptors combined with a different ErbB receptor, such as HER3, HER4 or EGFR. Other proteins, such as a cytokine receptor subunit (e.g. gp130), may be included in the hetero-oligomer.

The terms "ErbB1", "epidermal growth factor receptor" and "EGFR" are used interchangeably herein and refer to native sequence EGFR as disclosed, for example, in Carpenter et al. *Ann. Rev. Biochem.* 56:881-914 (1987), including variants thereof (e.g. a deletion mutant EGFR as in Humphrey et al. *PNAS (USA)* 87:4207-4211 (1990)). erbB1 refers to the gene encoding the EGFR protein product. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225) and reshaped human 225 (H225) (see, WO 96/40210, Imclone Systems Inc.).

The expressions "ErbB2" and "HER2" are used interchangeably herein and refer to native sequence human HER2 protein described, for example, in Semba et al., *PNAS (USA)* 82:6497-6501 (1985) and Yamamoto et al. *Nature* 319:230-234 (1986) (Genebank accession number X03363), and variants thereof. The term erbB2 refers to the gene encoding human HER2 and neu refers to the gene encoding rat p185$^{neu}$. Preferred HER2 is native sequence human HER2. Examples of antibodies which bind HER2 include MAbs 4D5 (ATCC CRL 10463), 2C4 (ATCC HB-12697), 7F3 (ATCC HB-12216), and 7C2 (ATCC HB 12215) (see, U.S. Pat. No. 5,772,997; WO98/77797; and U.S. Pat. No. 5,840,525, expressly incorporated herein by reference). Humanized anti-HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as described in Table 3 of U.S. Pat. No. 5,821,337 expressly incorporated herein by reference; humanized 520C9 (WO93/21319). Human anti-HER2 antibodies are described in U.S. Pat. No. 5,772,997 issued Jun. 30, 1998 and WO 97/00271 published Jan. 3, 1997.

"ErbB3" and "HER3" refer to the receptor polypeptide as disclosed, for example, in U.S. Pat. Nos. 5,183,884 and 5,480,968 as well as Kraus et al. *PNAS (USA)* 86:9193-9197 (1989), including variants thereof. Examples of antibodies which bind HER3 are described in U.S. Pat. No. 5,968,511 (Akita and Sliwkowski), e.g. the 8B8 antibody (ATCC HB 12070) or a humanized variant thereof.

The terms "ErbB4" and "HER4" herein refer to the receptor polypeptide as disclosed, for example, in EP Pat Appln No 599,274; Plowman et al., *Proc. Natl. Acad. Sci. USA,* 90:1746-1750 (1993); and Plowman et al., *Nature,* 366:473-475 (1993), including variants thereof such as the HER4 isoforms disclosed in WO 99/19488.

A "B cell surface marker" herein is an antigen expressed on the surface of a B cell which can be targeted with an antibody which binds thereto. Exemplary B cell surface markers include the CD10, CD19, CD20, CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CD85 and CD86 leukocyte surface markers. The B cell surface marker of particular interest is preferentially expressed on B cells compared to other non-B cell tissues of a mammal and may be expressed on both precursor B cells and mature B cells. In one embodiment, the marker is one, like CD20 or CD19, which is found on B cells throughout differentiation of the lineage from the stem cell stage up to a point just prior to terminal differentiation into plasma cells. The preferred B cell surface markers herein are CD19, CD20, CD22 and CD40.

The "CD20" antigen is an about 35 kDa, non-glycosylated phosphoprotein found on the surface of greater than 90% of B cells from peripheral blood or lymphoid organs. CD20 is expressed during early pre-B cell development and remains until plasma cell differentiation. CD20 is present on both normal B cells as well as malignant B cells. Other names for CD20 in the literature include "B-lymphocyte-restricted antigen" and "Bp35". The CD20 antigen is described in Clark et al. *PNAS (USA)* 82:1766 (1985), for example. Examples of antibodies which bind the CD20 antigen include: "C2B8" which is now called "rituximab" ("RITUXAN®") (U.S. Pat. No. 5,736,137, expressly incorporated herein by reference); the yttrium-[90]-labeled 2B8 murine antibody designated "Y2B8" (U.S. Pat. No. 5,736,137, expressly incorporated herein by reference); murine IgG2a "B1" optionally labeled with $^{131}$I to generate the "$^{131}$I-B1" antibody (BEXXAR™) (U.S. Pat. No. 5,595,721, expressly incorporated herein by reference); murine monoclonal antibody "1F5" (Press et al. *Blood* 69(2):584-591 (1987)); "chimeric 2H7" antibody (U.S. Pat. No. 5,677,180, expressly incorporated herein by reference); and monoclonal antibodies L27, G28-2, 93-1B3, B-C1 or NU-B2 available from the International Leukocyte Typing Workshop (Valentine et al., In: *Leukocyte Typing* III (McMichael, Ed., p. 440, Oxford University Press (1987)).

The "CD19" antigen refers to the about 90 kDa antigen identified, for example, by the HD237-CD19 or B4 antibody (Kiesel et al. *Leukemia Research II,* 12: 1119 (1987)). Like CD20, CD19 is found on cells throughout differentiation of the lineage from the stem cell stage up to a point just prior to terminal differentiation into plasma cells. Binding of an antibody to CD19 may cause internalization of the CD19 antigen. Examples of antibodies which bind the CD19 antigen include the anti-CD19 antibodies in Hekman et al. *Cancer Immunol. Immunother.* 32:364-372 (1991) and Vlasveld et al. *Cancer Immunol. Immunother.* 40:37-47 (1995); and the B4 antibody in Kiesel et al. *Leukemia Research II,* 12: 1119 (1987).

The "CD22" antigen has a molecular weight of about 140,000 kD. CD22 is expressed in the cytoplasm of early pre-B and progenitor cells, appears on the surface of only mature B cells and on the majority of non-Hodgkin's lymphoma (NHL) cells, and is then lost during terminal differentiation prior to the plasma cell stage from both the surface and cytoplasm. An example of an anti-CD22 antibody is the LL2 antibody described in Juweid et al. *Cancer Research* 55:5899-5907 (1995), including chimeric/humanized variants thereof.

The "CD40" antigen is a cell surface phosphorylated glycoprotein that is expressed on a variety of cell types, including B cells, B cell malignancies, follicular dendritic cells, basal epithelial cells and carcinomas. CD40 binds CD40 ligand (CD40L). Aside from being a B cell surface antigen, CD40 is also a member of the TNF receptor superfamily. Examples of antibodies that bind CD40 include those which (1) block CD40/CD40L interaction and have anti-neoplastic properties (Armitage et al., U.S. Pat. No. 5,674,492); (2) antagonize signaling through CD40 (deBoer et al., U.S. Pat. No. 5,677,165); (3) deliver a stimulatory signal through CD40 but do not increase the interaction between CD40 and CD40L, e.g., G28-5 (Ledbetter et al., U.S. Pat. No. 5,182,368); (4) increase the interaction between CD40 and CD40L, e.g., CD40.4 (5C3) (PharMingen, San Diego, Calif.) and S2C6 (deposited with the American Type Culture Collection (ATCC), Manassass, Va. on May 25, 1999 under accession number PTA-110).

The "tumor necrosis factor receptor superfamily" or "TNF receptor superfamily" herein refers to receptor polypeptides bound by cytokines in the TNF family. Generally, these receptors are Type I transmembrane receptors with one or more cysteine rich repeat sequences in their extracellular domain. The TNF receptor superfamily may be further subdivided into (1) death receptors; (2) decoy receptors; and (3) signaling receptors that lack death domains. The "death receptors" contain in their cytoplasmic or intracellular region a "death domain", i.e., a region or sequence which acts to transduce signals in the cell which can result in apoptosis or in induction of certain genes. The "decoy receptors" lack a functional death domain and are incapable of transducing signals which result in apoptosis. Examples of cytokines in the TNF gene family include Tumor Necrosis Factor-alpha (TNF-alpha), Tumor Necrosis Factor-beta (TNF-beta or lymphotoxin), CD30 ligand, CD27 ligand, CD40 ligand, OX-40 ligand, 4-1BB ligand, Apo-1 ligand (also referred to as Fas ligand or CD95 ligand), Apo-2 ligand (also referred to as TRAIL), Apo-3 ligand (also referred to as TWEAK), osteoprotegerin (OPG), APRIL, RANK ligand (also referred to as TRANCE), and TALL-1 (also referred to as BlyS, BAFF or THANK). Examples of receptors in the TNF receptor superfamily include: type 1 Tumor Necrosis Factor Receptor (TNFR1), type 2 Tumor Necrosis Factor Receptor (TNFR2), p75 Nerve Growth Factor receptor (NGFR), the B cell surface antigen CD40, the T cell antigen OX-40, Apo-1 receptor (also called Fas or CD95), Apo-3 receptor (also called DR3, swl-1, TRAMP and LARD), the receptor called "Transmembrane Activator and CAML-Interactor" or "TACI", BCMA protein, DR4, DR5 (alternatively referred to as Apo-2; TRAIL-R2, TR6, Tango-63, hAPO8, TRICK2 or KILLER), DR6, DcR1 (also referred to as TRID, LIT or TRAIL-R3), DcR2 (also called TRAIL-R4 or TRUNDD), OPG, DcR3 (also called TR6 or M68), CAR1, HVEM (also called ATAR or TR2), GITR, ZTNFR-5, NTR-1, TNFL1, CD30, Lymphotoxin beta receptor (LTBr), 4-1 BB receptor and TR9 (EP988, 371A1).

The terms "Apo-2 ligand" or "Apo2L" refer to the Apo2L polypeptides disclosed in WO97/25428, published 17 Jul. 1997 and expressly incorporated herein by reference. For purposes of the present application, these terms also refer to the polypeptides referred to as TRAIL disclosed in WO97/01633, published 16 Jan., 1997 and U.S. Pat. No. 5,763,223, issued Jun. 9, 1998 and expressly incorporated herein by reference.

An "Apo2L receptor" is a polypeptide to which Apo2L can specifically bind. The term "Apo2L receptor" when used herein encompasses native sequence Apo2L receptors and variants thereof. These terms encompass Apo2L receptor from a variety of mammals, including humans. The Apo2L receptor may be isolated from a variety of sources, such as from human tissue types or from another source, or prepared by recombinant or synthetic methods. Examples of "native sequence" Apo2L receptors include Apo-2 polypeptide or DR5 (WO98/51793, expressly incorporated herein by reference), native sequence DR4 as described in Pan et al. *Science* 276:111-113 (1997); native sequence decoy receptor 1 or DcR1 as in Sheridan et al., *Science* 277:818-821 (1997); and native sequence decoy receptor 2 or DcR2 as in Marsters et al. *Curr. Biol.* 7:1003-1006 (1997); native sequence osteoprotegerin (see Simonet et al. *Cell* 89:309-319 (1997); and Emery et al. *J. Interferon and Cytokine Research* 18(5): A47 Abstract 2.17 (1998)). Examples of anti-DR5 antibodies include 3F11.39.7 (ATCC HB-12456), 3H3.14.5 (ATCC HB-12534), 3D5.1.10 (HB-12536) and 3H1.18.10 (HB-12535), 16E2 and 20E6 (see WO 98/51793, expressly incorporated herein by reference). Examples of anti-DR4 antibodies include 4E7.24.3 (ATCC HB-12454) and 4H6.17.8 (ATCC HB-12455) (see, WO 99/37684, expressly incorporated herein by reference).

Native sequence "DcR3" is described in WO99/14330, expressly incorporated herein by reference. That patent publication describes the following mAbs directed against DcR3: 4C4.1.4 (ATCC HB-12573); 5C4.14.7 (ATCC HB-12574); 1105.2.8 (ATCC HB-12572); 8D3.1.5 (ATCC HB-12571); and 4B7.1.1 (ATCC HB-12575).

A "native sequence" polypeptide comprises a polypeptide having the same amino acid sequence as a polypeptide derived from nature. Thus, a native sequence polypeptide can have the amino acid sequence of naturally-occurring polypeptide from any mammal. Such native sequence polypeptide can be isolated from nature or can be produced by recombinant or synthetic means. The term "native sequence" polypeptide specifically encompasses naturally-occurring truncated or secreted forms of the polypeptide (e.g., an extracellular domain sequence), naturally-occurring variant forms (e.g., alternatively spliced forms) and naturally-occurring allelic variants of the polypeptide.

A polypeptide "variant" means a biologically active polypeptide having at least about 80% amino acid sequence identity with the native sequence polypeptide. Such variants include, for instance, polypeptides wherein one or more amino acid residues are added, or deleted, at the N- or C-terminus of the polypeptide. Ordinarily, a variant will have at least about 80% amino acid sequence identity, more preferably at least about 90% amino acid sequence identity, and even more preferably at least about 95% amino acid sequence identity with the native sequence polypeptide.

"Apoptosis" refers to programmed cell death. Physiological events often indicative of the occurrence of apoptosis include: fragmentation of DNA, cell shrinkage, dilation of endoplasmic reticulum, cell fragmentation, and/or formation of membrane vesicles (called apoptotic bodies). Various methods are available for evaluating the cellular events associated with apoptosis. For example, phosphatidyl serine (PS) translocation can be measured by annexin V binding; DNA fragmentation can be evaluated through DNA laddering or propidium-iodine staining; and nuclear/chromatin condensation along with DNA fragmentation can be evaluated by any increase in hypodiploid cells.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments (see below) so long as they exhibit the desired biological activity.

Unless indicated otherwise, the expression "multivalent antibody" is used throughout this specification to denote an antibody comprising three or more antigen binding sites. The multivalent antibody is preferably engineered to have the three or more antigen binding sites and is generally not a native sequence IgM or IgA antibody.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 341, 544-546 (1989)) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) or Marks et al., J. Mol. Biol. 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. Nature Biotechnology 14:309-314 (1996): Sheets et al. PNAS (USA) 95:6157-6162 (1998)); Hoogenboom and Winter, J. Mol. Biol., 227:381 (1991); Marks et al., J. Mol. Biol., 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., *Bio/Technology* 10: 779-783 (1992); Lonberg et al., *Nature* 368: 856-859 (1994); Morrison, *Nature* 368:812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody-dependent cell-mediated cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1 (including non-A and A allotypes), IgG2, IgG3, IgG4, IgA, and IgA2. The heavy-chain constant domains that correspond to the different classes of antibodies are called ∀, *, γ, (and μ, respectively. The subunit structures and three-dimensional configurations of different classes of immunoglobulins are well known.

The light chains of antibodies from any vertebrate species can be assigned to one of two clearly distinct types, called kappa (6) and lambda (8), based on the amino acid sequences of their constant domains.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain.

By "Fc region chain" herein is meant one of the two polypeptide chains of an Fc region.

The "CH2 domain" of a human IgG Fc region (also referred to as "Cγ2" domain) usually extends from an amino acid residue at about position 231 to an amino acid residue at about position 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985). The CH2 domain herein may be a native sequence CH2 domain or variant CH2 domain.

The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protroberance" in one chain thereof and a corresponding introduced "cavity" in the other chain thereof; see U.S. Pat. No. 5,821,333, expressly incorporated herein by reference). Such variant CH3 domains may be used to make multispecific (e.g. bispecific) antibodies as herein described.

"Hinge region" is generally defined as stretching from about Glu216, or about Cys226, to about Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions. The hinge region herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

Figures 1, 18A:
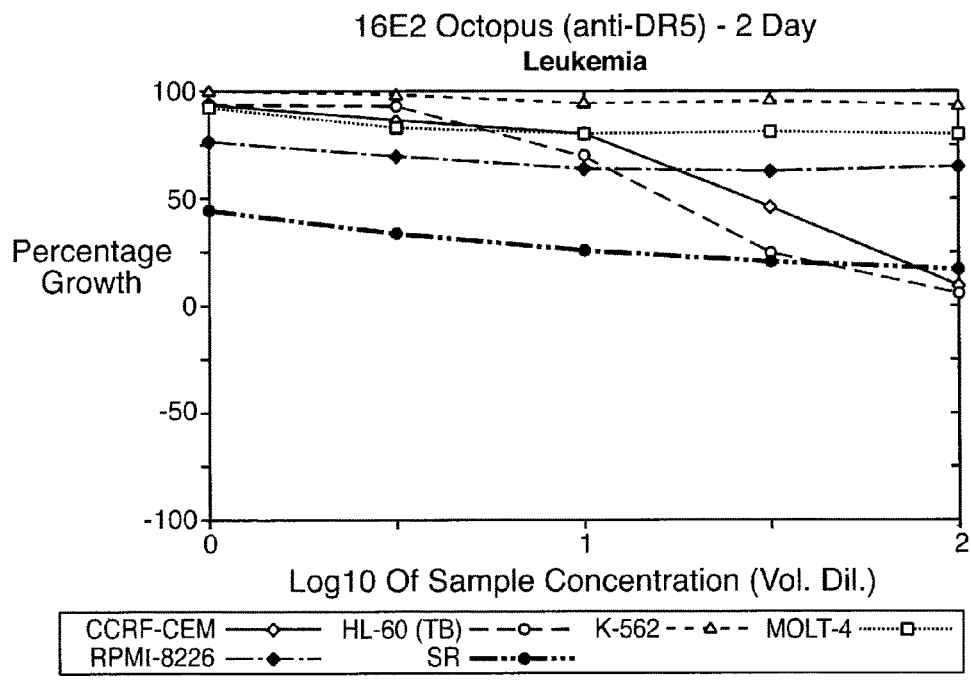
FIGS. 18A-C depict dose response curves that show the effect of the anti-DR516E2 Octopus (upper graphs) compared to Apo2L/TRAIL (lower graphs) on the growth of leukemia, non-small cell lung cancer, colon cancer, central nervous system (CNS) cancer, melanoma, ovarian cancer, renal cancer, prostate cancer and breast cancer human tumor cell lines at 2 days. Results are from the National Cancer Institute Developmental Therapeutics Program. All samples were tested at 5 concentrations, starting at 1% of the stock solution (16E2 Octopus stock 0.2 mg/ml) and 4×0.5 log dilutions.
Figures 2, 18A:
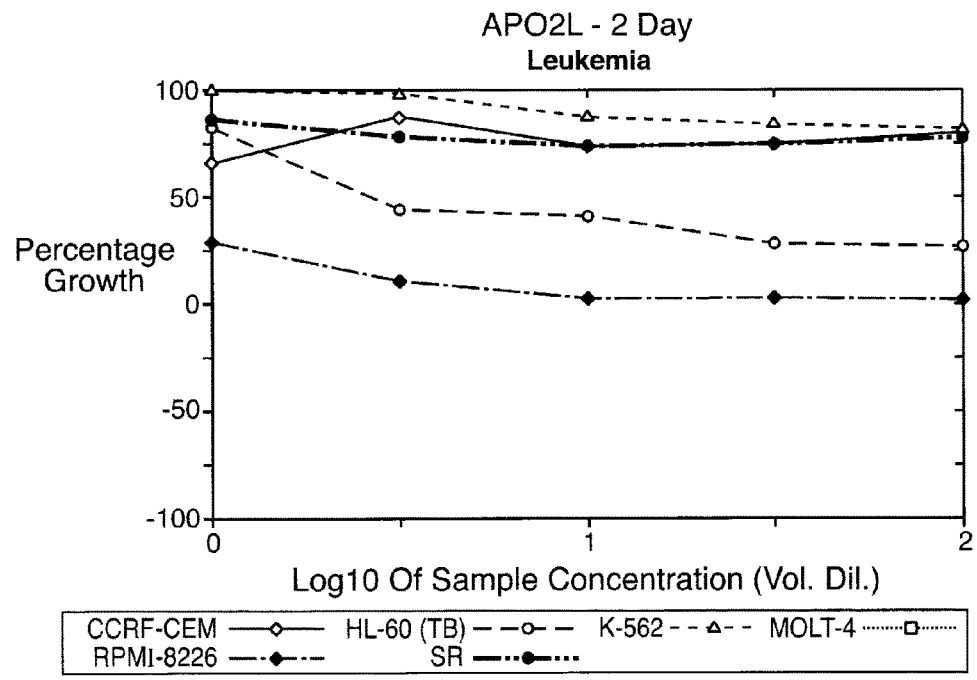
Figures 3, 18A:
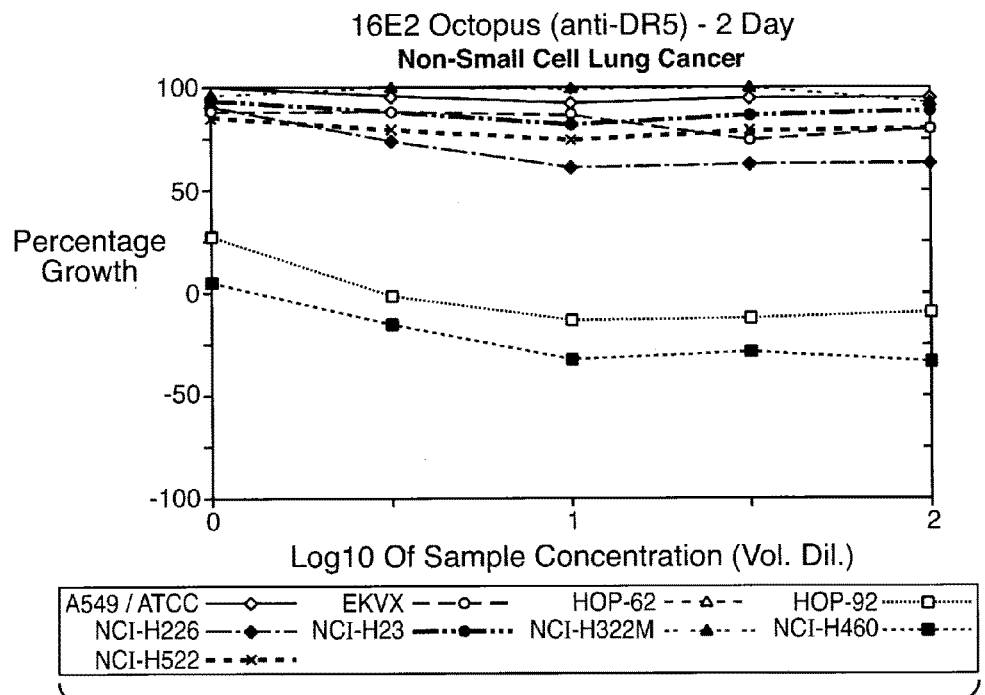
FIG. 3 depicts alignments of native sequence IgG Fc regions. Native sequence human IgG Fc region sequences, humIgG1 (non-A and A allotypes) (SEQ ID NOs: 1 and 2, respectively), humIgG2 (SEQ ID NO:3), humIgG3 (SEQ ID NO:4) and humIgG4 (SEQ ID NO:5), are shown. The human IgG1 sequence is the non-A allotype, and differences between this sequence and the A allotype (at positions 356 and 358; EU numbering system) are shown below the human IgG1 sequence. Native sequence murine IgG Fc region sequences, murIgG1 (SEQ ID NO:6), murIgG2A (SEQ ID NO:7), murIgG2B (SEQ ID NO:8) and murIgG3 (SEQ ID NO:9), are also shown.

A "native sequence Fc region" comprises an amino acid sequence identical to the amino acid sequence of an Fc region found in nature. FIG. 3 provides amino acid sequences of native sequence human and murine IgG Fc regions.

A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express Fc(RIII only, whereas monocytes express Fc(R1, Fc(RII and Fc(RIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least Fc(RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" and "FcR" are used to describe a receptor that binds to the Fc region of an antibody. The preferred FcR is a native sequence human FcR. Moreover, a preferred FcR is one which binds an IgG antibody (a gamma receptor) and includes receptors of the Fc(R1, Fc(RII, and Fc(RIII subclasses, including allelic variants and alternatively spliced forms of these receptors. Fc(RII receptors include Fc(RIIA (an "activating receptor") and Fc(RIIB (an "inhibiting receptor"), which have similar amino acid sequences that differ primarily in the cytoplasmic domains thereof. Activating receptor Fc(RIIA contains an immunoreceptor tyrosine-based activation motif (ITAM) in its cytoplasmic domain. Inhibiting receptor Fc(RIIB contains an immunoreceptor tyrosine-based inhibition motif (ITIM) in its cytoplasmic domain (reviewed in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976); and Kim et al., *J. Immunol.* 24:249 (1994)).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci*, USA 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

A "polypeptide chain" is a polypeptide wherein each of the domains thereof is joined to other domain(s) by peptide bond(s), as opposed to non-covalent interactions or disulfide bonds.

A "flexible linker" herein refers to a peptide comprising two or more amino acid residues joined by peptide bond(s), and provides more rotational freedom for two polypeptides (such as two Fd regions) linked thereby. Such rotational freedom allows two or more antigen binding sites joined by the flexible linker to each access target antigen(s) more efficiently. Examples of suitable flexible linker peptide sequences include gly-ser, gly-ser-gly-ser (SEQ ID NO:10), ala-ser, and gly-gly-gly-ser (SEQ ID NO:11). Preferably the flexible linker comprises 2 to about 10 amino acid residues, and most preferably four or less residues.

A "dimerization domain" is formed by the association of at least two amino acid residues (generally cysteine residues) or of at least two peptides or polypeptides (which may have the same, or different, amino acid sequences). The peptides or polypeptides may interact with each other through covalent and/or non-covalent association(s). Examples of dimerization domains herein include an Fc region; a hinge region; a CH3 domain; a CH4 domain; a CH1-CL pair; an "interface" with an engineered "knob" and/or "protruberance" as described in U.S. Pat. No. 5,821,333, expressly incorporated herein by reference; a leucine zipper (e.g. a jun/fos leucine zipper, see Kostelney et al., *J. Immunol.*, 148: 1547-1553 (1992); or a yeast GCN4 leucine zipper); an isoleucine zipper; a receptor dimer pair (e.g., interleukin-8 receptor (IL-8R); and integrin heterodimers such as LFA-1 and GPIIIb/IIIa), or the dimerization region(s) thereof; dimeric ligand polypeptides (e.g. nerve growth factor (NGF), neurotrophin-3 (NT-3), interleukin-8 (IL-8), vascular endothelial growth factor (VEGF), and brain-derived neurotrophic factor (BDNF); see Arakawa et al. *J. Biol. Chem.* 269(45): 27833-27839 (1994) and Radziejewski et al. *Biochem.* 32(48): 1350 (1993)), or the dimerization region(s) thereof; a pair of cysteine residues able to form a disulfide bond; a pair of peptides or polypeptides, each comprising at least one cysteine residue (e.g. from about one, two or three to about ten cysteine residues) such that disulfide bond(s) can form between the peptides or polypeptides (hereinafter "a synthetic hinge"); and antibody variable domains. The most preferred dimerization domain herein is an Fc region or a hinge region.

"Naturally occurring amino acid residues" (i.e. amino acid residues encoded by the genetic code) may be selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. *Meth. Enzym.* 202:301-336 (1991). To generate such non-naturally occurring amino acid residues, the procedures of Noren et al. *Science* 244:182 (1989) and Ellman et al., supra, can be used. Briefly, these procedures involve chemically activating a suppressor tRNA with a non-naturally occurring amino acid residue followed by in vitro transcription and translation of the RNA.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For the multimeric antibodies herein, the number of functional antigen binding sites can be evaluated using ultracentrifugation analysis as described in Example 2 below. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

By "ligand activation of a receptor" is meant signal transduction (e.g. for a tyrosine kinase receptor, that caused by an intracellular kinase domain of a tyrosine kinase receptor phosphorylating tyrosine residues in the receptor or a substrate polypeptide) mediated by ligand binding to the receptor (or a receptor complex comprising the receptor of interest). In the case of an ErbB receptor, generally, this will involve binding of an ErbB ligand to an ErbB hetero-oligomer which activates a kinase domain of one or more of the ErbB receptors in the hetero-oligomer and thereby results in phosphorylation of tyrosine residues in one or more of the ErbB receptors and/or phosphorylation of tyrosine residues in additional substrate polypeptides(s).

An antibody which "blocks" ligand activation of an receptor is one which reduces or prevents such activation as hereinabove defined. Such blocking can occur by any means, e.g. by interfering with: ligand binding to the receptor, receptor complex formation, tyrosine kinase activity of a tyrosine kinase receptor in a receptor complex and/or phosphorylation of tyrosine kinase residue(s) in or by the receptor. Examples of antibodies which block ligand activation of an ErbB receptor include monoclonal antibodies 2C4 and 7F3 (which block HRG activation of HER2/HER3 and HER2/HER4 hetero-oligomers; and EGF, TGF-beta or amphiregulin activation of an EGFR/HER2 hetero-oligomer); and L26, L96 and L288 antibodies (Klapper et al. *Oncogene* 14:2099-2109 (1997)), which block EGF and NDF binding to T47D cells which express EGFR, HER2, HER3 and HER4.

An antibody having a "biological characteristic" of a designated antibody is one which possesses one or more of the biological characteristics of that antibody which distinguish it from other antibodies that bind to the same antigen.

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

Examples of "growth inhibitory" anti-HER2 antibodies are those which bind to HER2 and inhibit the growth of cancer cells overexpressing HER2. Preferred growth inhibitory anti-HER2 antibodies inhibit growth of SKBR3 breast tumor cells in cell culture by greater than 20%, and preferably greater than 50% (e.g. from about 50% to about 100%) at an antibody concentration of about 0.5 to 30 µg/ml, where the growth inhibition is determined six days after exposure of the SKBR3 cells to the antibody (see U.S. Pat. No. 5,677,171 issued Oct. 14, 1997).

An antibody which "induces cell death" is one which causes a viable cell to become nonviable. The cell is generally one which expresses the antigen to which the antibody binds, especially where the cell overexpresses the antigen. Preferably, the cell is a cancer cell, e.g. a breast, ovarian, stomach, endometrial, salivary gland, lung, kidney, colon, thyroid, pancreatic or bladder cell. In vitro, the cell may be a SKBR3, BT474, Calu 3, MDA-MB-453, MDA-MB-361 or SKOV3 cell. Cell death in vitro may be determined in the absence of complement and immune effector cells to distinguish cell death induced by antibody dependent cell-mediated cytotoxicity (ADCC) or complement dependent cytotoxicity (CDC). Thus, the assay for cell death may be performed using heat inactivated serum (i.e. in the absence of complement) and in the absence of immune effector cells. To determine whether the antibody is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is one which expresses the antigen to which the antibody binds and may be one which overexpresses the antigen. The cell may be a tumor cell, e.g. a breast, ovarian, stomach, endometrial, salivary gland, lung, kidney, colon, thyroid, pancreatic or bladder cell. In vitro, the cell may be a SKBR3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering as disclosed in the example herein; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using cells expressing the antigen to which the antibody binds.

Examples of antibodies which induce apoptosis include the anti-HER2 monoclonal antibodies 7F3 (ATCC HB-12216), and 7C2 (ATCC HB 12215), including humanized and/or affinity matured variants thereof; the anti-DR5 antibodies 3F11.39.7 (ATCC HB-12456); 3H3.14.5 (ATCC HB-12534); 3D5.1.10 (ATCC HB-12536); and 3H3.14.5 (ATCC HB-12534), including humanized and/or affinity matured variants thereof; the human anti-DR5 receptor antibodies 16E2 and 20E6, including affinity matured variants thereof (WO98/51793, expressly incorporated herein by reference); the anti-DR4 antibodies 4E7.24.3 (ATCC HB-12454); 4H6.17.8 (ATCC HB-12455); 1H5.25.9 (ATCC HB-12695); 4G7.18.8 (ATCC PTA-99); and 5G11.17.1 (ATCC HB-12694), including humanized and/or affinity matured variants thereof.

In order to screen for antibodies which bind to an epitope on an antigen bound by an antibody of interest, a routine cross-blocking assay such as that described in *Antibodies, A Laboratory Manual*, Cold Spring Harbor Laboratory, Ed Harlow and David Lane (1988), can be performed.

An "agonist antibody" is an antibody which binds to and activates a receptor. Generally, the receptor activation capability of the agonist antibody will be at least qualitatively similar (and may be essentially quantitatively similar) to a native agonist ligand of the receptor. An example of an agonist antibody is one which binds to a receptor in the TNF receptor superfamily and induces apoptosis of cells expressing the TNF receptor. Assays for determining induction of apoptosis are described in WO98/51793 and WO99/37684, both of which are expressly incorporated herein by reference.

A "disorder" is any condition that would benefit from treatment with the antibody. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the time to disease progression (TTP) and/or determining the response rates (RR).

"Treatment" refers to both therapeutic treatment and prophylactic or preventative measures. Those in need of treatment include those already with the disorder as well as those in which the disorder is to be prevented.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

An "autoimmune disease" herein is a non-malignant disease or disorder arising from and directed against an individual's own tissues. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc.

By "foreign antigen" is meant a molecule or molecules which is/are not endogenous or native to a mammal which is exposed to it. The foreign antigen may elicit an immune response, e.g. a humoral and/or T cell mediated response in the mammal. Generally, the foreign antigen will provoke the production of antibodies thereagainst. Examples of foreign antigens contemplated herein include immunogenic therapeutic agents, e.g. proteins such as antibodies, particularly antibodies comprising non-human amino acid residues (e.g. rodent, chimeric/humanized, and primatized antibodies); toxins (optionally conjugated to a targeting molecule such as an antibody, wherein the targeting molecule may also be immunogenic); gene therapy viral vectors, such as retroviruses and adenoviruses; grafts; infectious agents (e.g. bacteria and virus); alloantigens (i.e. an antigen that occurs in some, but not in other members of the same species) such as differences in blood types, human lymphocyte antigens (HLA), platelet antigens, antigens expressed on transplanted organs, blood components, pregnancy (Rh), and hemophilic factors (e.g. Factor VIII and Factor IX).

By "blocking an immune response" to a foreign antigen is meant reducing or preventing at least one immune-mediated response resulting from exposure to a foreign antigen. For example, one may dampen a humoral response to the foreign antigen, i.e., by preventing or reducing the production of antibodies directed against the antigen in the mammal. Alternatively, or additionally, one may suppress idiotype; "pacify" the removal of cells coated with alloantibody; and/or affect alloantigen presentation through depletion of antigen-presenting cells.

The term "graft" as used herein refers to biological material derived from a donor for transplantation into a recipient. Grafts include such diverse material as, for example, isolated cells such as islet cells; tissue such as the amniotic membrane of a newborn, bone marrow, hematopoietic precursor cells, and ocular tissue, such as corneal tissue; and organs such as skin, heart, liver, spleen, pancreas, thyroid lobe, lung, kidney, tubular organs (e.g., intestine, blood vessels, or esophagus), etc. The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. Preferably the graft is bone marrow or an organ such as heart and the donor of the graft and the host are matched for HLA class II antigens.

The term "mammalian host" as used herein refers to any compatible transplant recipient. By "compatible" is meant a mammalian host that will accept the donated graft. Preferably, the host is human. If both the donor of the graft and the host are human, they are preferably matched for HLA class II antigens so as to improve histocompatibility.

The term "donor" as used herein refers to the mammalian species, dead or alive, from which the graft is derived. Preferably, the donor is human. Human donors are preferably volunteer blood-related donors that are normal on physical examination and of the same major ABO blood group, because crossing major blood group barriers possibly prejudices survival of the allograft. It is, however, possible to transplant, for example, a kidney of a type O donor into an A, B or AB recipient.

The term "transplant" and variations thereof refers to the insertion of a graft into a host, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, such as a baboon heart transplanted into a human recipient host, and including animals from phylogenically widely separated species, for example, a pig heart valve, or animal beta islet cells or neuronal cells transplanted into a human host.

The expression "desensitizing a mammal awaiting transplantation" refers to reducing or abolishing allergic sensitivity or reactivity to a transplant, prior to administration of the transplant to the mammal. This may be achieved by any mechanism, such as a reduction in anti-donor antibodies in the desensitized mammal, e.g. where such anti-donor antibodies are directed against human lymphocyte antigen (HLA).

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin ($_1^I$ and calicheamicin $2^I_1$, see, e.g., *Agnew Chem. Intl. Ed. Engl.* 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethyl-hydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

An "angiogenic factor" is a growth factor which stimulates the development of blood vessels. The preferred angiogenic factor herein is Vascular Endothelial Growth Factor (VEGF).

The word "label" when used herein refers to a detectable compound or composition which is conjugated directly or indirectly to the polypeptide. The label may be itself be detectable (e.g., radioisotope labels or fluorescent labels) or, in the case of an enzymatic label, may catalyze chemical alteration of a substrate compound or composition which is detectable.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

II. Modes for Carrying Out the Invention

A. Multivalent Antibodies

The invention herein relates to a method for making a multivalent antibody. Various techniques for generating the "parent" or "starting" antibody from which the variable domain(s) of the multivalent antibody may be derived will be described later in this application.

The multivalent antibody of particular interest herein is one which comprises at least three (and preferably four, or more, e.g. four or five to about eight) antigen binding sites. Generally, all of the antigen binding sites are "functional" as defined hereinabove. Preferably, the multivalent antibody does not exist in nature and is not a native sequence IgM or IgA antibody. The multivalent antibody herein is preferably not produced in vitro by chemically cross-linking a pair antibodies (e.g. as in Ghetie et al. (1997), supra or Wolff et al. (1993), supra). The present application also provides multivalent antibodies which do not require introduced cysteine residue(s) in a parent antibody in order to make the multivalent antibody via disulfide bond(s) between a pair of Fc regions (e.g. as in Shopes et al. (1992), supra or Caron et al. (1992), supra).

In one embodiment, the multivalent antibody comprises a first polypeptide chain comprising at least two heavy chain (or light chain) variable domains and a second polypeptide chain comprising at least two heavy chain (or light chain) variable domains. Preferably, the first polypeptide chain comprises two heavy chain variable domains and the second polypeptide chain also comprises two heavy chain variable domains, which can be combined with corresponding light chain variable domains (at least two for each polypeptide chain) to generate four (or more) antigen binding sites.

In one preferred embodiment of the invention, the multivalent antibody comprises a dimerization domain which combines (1) two (or more) antigen binding sites with (2) one, two (or more) antigen binding sites. Various dimerization domains are contemplated herein, but the preferred dimerization domain is an Fc region or a hinge region. Where the multivalent antibody comprises an Fc region (e.g. a native sequence or variant Fc region), the Fc region is preferably "functional" as defined hereinabove and thus is capable of performing one or more antibody effector functions, such as ADCC or CDC. Preferably, the multivalent antibody has only one Fc region or lacks an Fc region.

Where the multivalent antibody comprises an Fc region, preferably, the three or more antigen binding sites are provided amino terminal to the Fc region (rather than at the carboxy terminus of the Fc region as in Coloma and Morrison, (1997) supra). This may be achieved by providing a first polypeptide chain represented by the formula VD1-X1-VD2-X2-Fc, wherein (1) VD1 is a first heavy or light chain variable domain (preferably a heavy chain variable domain), (2) VD2 is a second heavy or light chain variable domain (preferably a heavy chain variable domain), (3) Fc comprises one chain of an Fc region, and (4) X1 and X2 represent an optional intervening amino acid or polypeptide. Preferably X1 and X2 comprise, or consist of, a CH1 domain (where VD1 or VD2 is a heavy chain variable domain) or a CL domain (where VD1 or VD2 is a light chain variable domain). Optionally, X1 further comprises a flexible linker which is generally C-terminal to VD1 (or C-terminal to CH1 or CL, if present). The flexible linker may comprise a peptide such as gly-ser, gly-ser-gly-ser (SEQ ID NO:10), ala-ser or gly-gly-gly-ser (SEQ ID NO:11).

The multivalent antibody of particular interest herein comprises three or more (e.g. four or five to about eight) Fab polypeptides, each capable of binding antigen. The Fab fragments are preferably provided amino terminal to the Fc region (where the multivalent antibody has an Fc region). For instance, two or more Fd fragments may be fused to the amino terminus of one chain of an Fc region. The polypeptide chain thus engineered may be combined with (1) another polypeptide chain formed by two or more Fd fragments fused to the amino terminus of the other chain of the Fc region, as well as (2) complementary VL domains (e.g. four or more VL domains which each, optionally, are fused to a CL domain). Optionally, the antibody comprises a flexible linker between the two or more Fd fragments. The multivalent antibody may, for example, comprise a pair of polypeptide chains with the formula (1) VH-CH1-flexible linker-VH-CH1-Fc chain, or (2) VH-CH1-VH-CH1-Fc chain (i.e. where there is no flexible linker between the two Fd fragments).

The three or more functional antigen binding sites of the multivalent antibody herein are each preferably formed by a heavy and light chain variable domain. Thus, where two or more heavy chain variable domains are fused together (optionally with intervening amino acid residue(s) as noted above), two or more complementary light chain variable domain-containing polypeptides are combined with the heavy chain variable domains (for instance by co-expressing the fusion protein and the light chain variable domain polypeptide(s) in the same host cell). Preferably, the antibody comprises four, or five, or more (e.g. up to about eight) light chain variable domain polypeptides, which each, optionally, comprise a CL domain.

In one embodiment herein, the antibody with three or more more (e.g. three to about ten, but preferably three or four) antigen binding sites may comprise a polypeptide chain comprising three or more (e.g. three to about ten, but preferably three or four) heavy chain or light chain variable domains, wherein each of the variable domains is combined with, or associated with, three or more (e.g. three to about ten, but preferably three or four) light chain or heavy chain variable domain polypeptides in such a way as to form the antigen binding sites. Thus, where the polypeptide chain comprises three or more heavy chain variable domains, it is combined or associated with three or more corresponding light chain variable domain polypeptides (e.g. with VL-CL polypeptides). Alternatively, where the polypeptide chain comprises three or more light chain variable domains, it is combined or associated with three or more corresponding heavy chain variable domain polypeptides (e.g. with VH-CH1 polypeptides). Preferably each of the three or more antigen binding sites is directed against the same antigen. Examples of antigens bound by such antibodies include (1) a receptor in the Tumor Necrosis Factor (TNF) receptor superfamily (such receptors may be 'trimeric receptors', hence the antibody need only include only three antigen binding sites as desired) such as DR4 and DR5; (2) a B cell surface antigen such as CD20; (3) an ErbB receptor exemplified by the HER2 receptor; or (4) a cell surface protein expressed by tumor cells. For instance, the polypeptide chain may comprise three (or four) heavy chain variable domains which are able to combine with three (or four) light chain variable domain polypeptides (preferably VL-CL polypeptides) to generate three (or four) antigen binding sites directed against the same antigen. Such antibodies are exemplified by those depicted in FIG. 23D (with three antigen binding sites) and FIG. 23E (with four antigen binding sites). The multivalent antibody may also comprise a polypeptide chain comprising the formula: (a) VL-CL-flexible linker-VL-CL-flexible linker-VL-CL; In this embodiment, the polypeptide may comprise three to about eight VL-CL polypeptides joined by flexible linkers. (b) VH-CH1-flexible linker-VH-CH1-flexible linker-VH-CH1; In this embodiment, the polypeptide may comprise three to about eight VH-CH1 polypeptides joined by flexible linkers. (c) $(VL-CL)_n$, wherein n is three or more more (e.g. three to about eight, but preferably three or four); or (d) $(VH-CH1)_n$, wherein n is three or more more (e.g. three to about eight, but preferably three or four). Preferably, the polypeptide chain comprises the formula: (a) VH-CH1-flexible linker-VH-CH1-flexible linker-VH-CH1; (b) VH-CH1-flexible linker-VH-CH1-flexible linker-VH-CH1-flexible linker-VH-CH1; or (c) $(VH-CH1)_n$, wherein n is three or four.

The multivalent antibodies herein have desirable properties particularly for in vivo therapy and diagnosis. For instance, the multivalent antibody may be internalized and catabolized by a cell expressing an antigen, to which the antibody binds, faster than a bivalent antibody. Thus, the invention provides an immunoconjugate comprising the multivalent antibody conjugated with a cytotoxic agent (e.g. one which is active in killing cells once internalized). Various cytotoxic agents for generating an immunoconjugate are described herein, but the preferred cytotoxic agent is a radioactive isotope, a maytansinoid or a calecheamicin.

The multivalent antibody, and/or a parent antibody from which at least one of the multivalent antibody's antigen binding specificities is derived, may have certain properties. For instance, the multivalent antibody and/or parent antibody may (1) be an agonist antibody (e.g. where an antigen bound by the antibody is a receptor in the TNF receptor family or a B cell surface antigen); (2) induce apoptosis (for instance, where an antigen bound by the antibody is an ErbB receptor or a receptor in the TNF receptor superfamily); (3) bind a cell surface protein (such as a B cell surface antigen or an ErbB receptor) expressed on tumor cells; (4) bind a cell surface protein (e.g. Epidermal Growth Factor Receptor (EGFR), HER2 receptor, ErbB3 receptor, ErbB4 receptor, or DcR3 receptor) overexpressed by tumor cells; and/or (5) be a growth inhibitory antibody.

The multivalent antibody herein may have specificity for only one antigen, or more than one antigens (e.g. from two to about three antigens). In one embodiment, the three or more functional antigen binding sites of the multivalent antibody may all bind the same antigen (preferably the same epitope on that antigen, in which case the multivalent antibody would be considered to be "monospecific"). This application also provides "multispecific" antibodies. Thus, the three or more functional antigen binding sites may bind two or more (e.g. from two to about three) different antigens or epitopes.

The present application shows that a multivalent antibody directed against a receptor antigen can be engineered which, surprisingly, has agonistic and/or apoptosis-inducing capability which is quantitatively similar to that of the native ligand. By "quantitatively similar" here is meant that the multivalent antibody has an activity in an assay which determines agonistic and/or apoptosis-inducing activity, within about ten fold, and preferably within about five fold of the agonistic and/or apoptosis-inducing activity of the native ligand. In this embodiment, the antibody with agonistic and/or apoptosis-inducing activity may be one with specificity for a receptor in the TNF receptor superfamily, e.g. an Apo2L receptor such as DR4, DR5, DcR1 and DcR2 (preferably DR4 or DR5), in which case the activity of the antibody in an apoptosis assay such as those described in Example 3 below is within about ten fold, e.g. within about five fold, of the activity of Apo2L in that assay.

The multivalent antibody herein may, in one embodiment of the invention, bind a B cell surface antigen. Preferred B cell surface antigens include CD19, CD20, CD22 and CD40, and most preferably CD20.

Various applications for the multivalent antibodies herein are contemplated and described in more detail below. Where the multivalent antibody possesses one or more functional Fc regions, it is anticipated to have the ability to mediate effector functions (such as ADCC and CDC) and have a longer half-life than multivalent antibodies lacking an Fc region. Such multivalent antibodies may be used where killing of cells, such as tumor or cancer cells, is desired. Other forms of the multivalent antibodies herein which lack a Fc region may be desirable where a shorter half-life is desired (e.g. for treating cardiovascular or inflammatory diseases or disorders, or where the antibody is conjugated with a cytotoxic agent); where internalization of the antibody is desired (e.g. for therapy with an immunoconjugate comprising the antibody and a cytotoxic agent); for improved penetration of a solid tumor; where expression of the multivalent antibody in a non-mammalian host cell (e.g. a prokaryotic host cell such as an E. coli host cell) is desired; for therapy of nononcological diseases or disorders; and/or to avoid the 'first dose affect' observed upon administration of certain antibodies possessing effector function(s) to patients. Such forms of the antibody may comprise a multivalent antibody including a dimerization domain, wherein the dimerization domain comprises an antibody hinge region fused to a leucine zipper domain (the leucine zipper domain facilitates association of the polypeptides which form the dimerization domain, but may be subsequently proteolytically removed prior to administration to a patient) (see FIG. 23C); a multivalent antibody with three antigen binding sites such as that shown in FIG. 23D; or a multivalent antibody with four antigen binding sites such as that depicted in FIG. 23E.

B. Antigen Binding Specificity

The multivalent antibody herein is directed against, or binds specifically to, one or more target antigen(s). Preferably, at least one of the antigens bound by the multivalent antibody is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20 and CD25 (Tac subunit of the IL-2 receptor); erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 or VCAM; a tumor associated antigen such as HER2, HER3 or HER4 receptor; and fragments of any of the above-listed polypeptides.

Preferred molecular targets for antibodies encompassed by the present invention include leukocyte surface markers or CD proteins such as CD1a-c, CD2, CD2R, CD3, CD4, CD5, CD6, CD7, CD8, CD9, CD10, CD11a, CD11b, CD11c, CDw12, CD13, CD14, CD15, CD15s, CD16, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, C41, CD42a-d, CD43, CD44, CD44R, CD45, CD45A, CD45B, CD450, CD46-CD48, CD49a-f, CD50, CD51, CD52, CD53-CD59, CDw60, CD61, CD62E, CD62L, CD62P, CD63, CD64, CDw65, CD66a-e, CD68-CD74, CDw75, CDw76, CD77, CDw78, CD79a-b, CD8O-CD83, CDw84, CD85-CD89, CDw90, CD91, CDw92, CD93-CD98, CD99, CD99R, CD100, CDw101, CD102-CD106, CD107a-b, CDw108, CDw109, CD115, CDw116, CD117, CD119, CD120a-b, CD121a-b, CD122, CDw124, CD126-CD129, and CD130; members of the ErbB receptor family such as the EGF receptor, HER2 receptor, HER3 receptor or HER4 receptor; prostate specific antigen(s); cell adhesion molecules such as IIb/IIIa, LFA-1, Mac1, p150.95, VLA-4, ICAM-1, VCAM, α4/β7 integrin, and αv/β3 integrin including either α or β subunits thereof (e.g. anti-CD11a, anti-CD18 or anti-CD11b antibodies); growth factors such as VEGF; tissue factor (TF); alpha interferon (∀-IFN); an interleukin, such as IL-8; IgE; blood group antigens; flk2/flt3 receptor; obesity (OB) receptor; c-mpl receptor; CTLA-4; protein C etc.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

Preferred target antigens for the multivalent antibodies herein include (1) ErbB receptors, including EGFR, HER2, HER3 and HER4; (2) receptors in the TNF receptor superfamily, e.g. Apo2L receptors, such as DR4, DR5, DcR1 and DcR2; (3) B cell surface antigens, especially CD19, CD20, CD22 and CD40; (4) antigens expressed by tumor cells; (5)

antigens overexpressed by tumor cells (e.g. ErbB receptors; DcR3 receptors); (6) receptors activated by multimeric (e.g. dimeric or trimeric) ligands (e.g. receptors in the TNF receptor superfamily; VEGF receptors, etc.). In one embodiment, three or more (e.g. four to about eight) of the antigen binding sites of the multivalent antibody may all be directed against the same antigenic determinant or epitope on one of the above antigens.

The present application also provides multispecific antibodies, i.e., antibodies that have binding specificities for at least two different epitopes or antigenic determinants. Multispecific antibodies (e.g. bispecific antibodies; BsAbs) have significant potential in a wide range of clinical applications as targeting agents for in vitro and in vivo immunodiagnosis and therapy, and for diagnostic immunoassays.

Bispecific antibodies have been very useful in probing the functional properties of cell surface molecules and in defining the ability of the different Fc receptors to mediate cytotoxicity (Fanger et al., *Crit. Rev. Immunol.* 12:101-124 (1992)). Nolan et al., *Biochem. Biophys. Acta.* 1040:1-11 (1990) describe other diagnostic applications for BsAbs. In particular, BsAbs can be constructed to immobilize enzymes for use in enzyme immunoassays. To achieve this, one arm of the BsAb can be designed to bind to a specific epitope on the enzyme so that binding does not cause enzyme inhibition, the other arm of the BsAb binds to the immobilizing matrix ensuring a high enzyme density at the desired site. Examples of such diagnostic BsAbs include the rabbit anti-IgG/anti-ferritin BsAb described by Hammerling et al., *J. Exp. Med.* 128:1461-1473 (1968) which was used to locate surface antigens. BsAbs having binding specificities for Horse Radish Peroxidase (HRP) as well as a hormone have also been developed. Another potential immunochemical application for BsAbs involves their use in two-site immunoassays. For example, two BsAbs are produced binding to two separate epitopes on the analyte protein—one BsAb binds the complex to an insoluble matrix, the other binds an indicator enzyme (see Nolan et al., supra).

Multispecific antibodies can also be used for in vitro or in vivo immunodiagnosis of various diseases such as cancer (Songsivilai et al., *Clin. Exp. Immunol.* 79:315 (1990)). To facilitate this diagnostic use of the BsAb, one arm of the BsAb can bind a tumor associated antigen and the other arm can bind a detectable marker such as a chelator which tightly binds a radionuclide. Using this approach, Le Doussal et al. made a BsAb useful for radioimmunodetection of colorectal and thryoid carcinomas which had one arm which bound a carcinoembryonic antigen (CEA) and another arm which bound diethylenetriaminepentacetic acid (DPTA). See Le Doussal et al., *Int. J. Cancer Suppl.* 7:58-62 (1992) and Le Doussal et al., *J. Nucl. Med.* 34:1662-1671 (1993). Stickney et al. similarly describe a strategy for detecting colorectal cancers expressing CEA using radioimmunodetection. These investigators describe a BsAb which binds CEA as well as hydroxyethylthiourea-benzyl-EDTA (EOTUBE). See Stickney et al., *Cancer Res.* 51:6650-6655 (1991).

Multispecific antibodies can also be used for human therapy in redirected cytotoxicity by providing one arm which binds a target (e.g. pathogen or tumor cell) and another arm which binds a cytotoxic trigger molecule, such as the T-cell receptor or an Fc gamma receptor. Accordingly, multispecific antibodies can be used to direct a patient's cellular immune defense mechanisms specifically to the tumor cell or infectious agent. Using this strategy, it has been demonstrated that bispecific antibodies which bind to the Fc gamma RIII (i.e. CD16) can mediate tumor cell killing by natural killer (NK) cell/large granular lymphocyte (LGL) cells in vitro and are effective in preventing tumor growth in vivo. Segal et al., *Chem. Immunol.* 47:179 (1989) and Segal et al., *Biologic Therapy of Cancer* 2(4) DeVita et al. eds. J.B. Lippincott, Philadelphia (1992) p. 1. Similarly, a bispecific antibody having one arm which binds Fc gamma RIII and another which binds to the HER2 receptor has been developed for therapy of ovarian and breast tumors that overexpress the HER2 antigen. (Hseih-Ma et al. *Cancer Research* 52:6832-6839 (1992) and Weiner et al. *Cancer Research* 53:94-100 (1993)). Bispecific antibodies can also mediate killing by T cells. Normally, the bispecific antibodies link the CD3 complex on T cells to a tumor-associated antigen. A fully humanized F(ab')$_2$ BsAb consisting of anti-CD3 linked to anti-p185$^{HER2}$ has been used to target T cells to kill tumor cells overexpressing the HER2 receptor. Shalaby et al., *J. Exp. Med.* 175(1):217 (1992). Bispecific antibodies have been tested in several early phase clinical trials with encouraging results. In one trial, 12 patients with lung, ovarian or breast cancer were treated with infusions of activated T-lymphocytes targeted with an anti-CD3/anti-tumor (MOC31) bispecific antibody. deLeij et al. *Bispecific Antibodies and Targeted Cellular Cytotoxicity*, Romet-Lemonne, Fanger and Segal Eds., Lienhart (1991) p. 249. The targeted cells induced considerable local lysis of tumor cells, a mild inflammatory reaction, but no toxic side effects or anti-mouse antibody responses. In a very preliminary trial of an anti-CD3/anti-CD19 bispecific antibody in a patient with B cell malignancy, significant reduction in peripheral tumor cell counts was also achieved. Clark et al. *Bispecific Antibodies and Targeted Cellular Cytotoxicity*, Romet-Lemonne, Fanger and Segal Eds., Lienhart (1991) p. 243. See also Kroesen et al., *Cancer Immunol. Immunother.* 37:400-407 (1993), Kroesen et al., *Br. J. Cancer* 70:652-661 (1994) and Weiner et al., *J. Immunol.* 152:2385 (1994) concerning therapeutic applications for multispecific antibodies.

Multispecific antibodies may also be used as fibrinolytic agents or vaccine adjuvants. Furthermore, these antibodies may be used in the treatment of infectious diseases (e.g. for targeting of effector cells to virally infected cells such as HIV or influenza virus or protozoa such as *Toxoplasma gondii*), used to deliver immunotoxins to tumor cells, or target immune complexes to cell surface receptors (see Fanger et al., supra).

Various multispecific antibodies are contemplated herein. For instance, the multispecific antibody may bind two or more different epitopes on an antigen of interest. Alternatively, the multispecfic antibody may have specificity for (1) an antigen expressed by a target cell (e.g. where the target cell is a tumor cell) and (2) a triggering molecule on a leukocyte, such as a T-cell receptor molecule (e.g. CD2 or CD3), or Fc receptors for IgG (Fc gamma R), such as Fc gamma R1 (CD64), Fc gamma RII (CD32) and Fc gamma RIII (CD16) so as to focus cellular defense mechanisms to the antigen-expressing cell. Multispecific antibodies may also be used to localize cytotoxic agents to cells which express the target antigen. These antibodies possess an target antigen-binding arm and an arm which binds the cytotoxic agent (e.g. saporin, interferon-alpha, vinca alkaloid, ricin A chain, methotrexate or radioactive isotope hapten).

WO 96/16673 describes a bispecific anti-HER2/anti-Fc gamma RIII antibody and U.S. Pat. No. 5,837,234 discloses a bispecific anti-HER2/anti-Fc gamma RI antibody. A bispecific anti-HER2/Fc alpha antibody is shown in WO98/02463. U.S. Pat. No. 5,821,337 teaches a bispecific anti-HER2/anti-CD3 antibody.

C. Preparation of the Parent Antibody

In order to generate the multivalent antibody, a "parent" or "starting" antibody with variable domains directed against an antigen may be prepared using various methodologies for making antibodies, such as those described hereinbelow. The sequences of the variable domains of the starting or parent antibody may be used in the design of the multivalent antibody herein.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with 1/5 to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Plückthun, Immunol. Revs., 130: 151-188 (1992). Recombinant expression of antibodies is described in more detail below.

In a further embodiment, monoclonal antibodies or antibody fragments can be isolated from antibody phage libraries generated using the techniques described in McCafferty et al., Nature, 348:552-554 (1990). Clackson et al., Nature, 352: 624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl. Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Human Antibodies

Human monoclonal antibodies may be made via an adaptation of the hybridoma method first described by Kohler and Milstein by using human B lymphocytes as the fusion partner. Human B lymphocytes producing an antibody of interest may, for example, be isolated from a human individual, after obtaining informed consent. For instance, the individual may be producing antibodies against an autoantigen as occurs with certain disorders such as systemic lupus erythematosus (Shoenfeld et al. *J. Clin. Invest.* 70:205 (1982)), immune-mediated thrombocytopenic purpura (ITP) (Nugent et al. *Blood* 70(1):16-22 (1987)), or cancer. Alternatively, or additionally, lymphocytes may be immunized in vitro. For instance, one may expose isolated human periperal blood lymphocytes in vitro to a lysomotrophic agent (e.g. L-leucine-β-methyl ester, L-glutamic acid dimethly ester or L-leucyl-L-leucine-O-methyl ester) (U.S. Pat. No. 5,567,610, Borrebaeck et al.); and/or T-cell depleted human peripheral blood lymphocytes may be treated in vitro with adjuvants such as 8-mercaptoguanosine and cytokines (U.S. Pat. No. 5,229,275, Goroff et al.).

The B lymphocytes recovered from the subject or immunized in vitro, are then generally immortalized in order to generate a human monoclonal antibody. Techniques for immortalizing the B lymphocyte include, but are not limited to: (a) fusion of the human B lymphocyte with human, murine myelomas or mouse-human heteromyeloma cells; (b) viral transformation (e.g. with an Epstein-Barr virus; see Nugent et al., supra, for example); (c) fusion with a lymphoblastoid cell line; or (d) fusion with lymphoma cells.

Lymphocytes may be fused with myeloma cells using a suitable fusing agent, such as polyethylene glycol, to form a hybridoma cell (Goding, *Monoclonal Antibodies: Principles and Practice*, pp. 59-103 (Academic Press, 1986)). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Suitable human myeloma and mouse-human heteromyeloma cell lines have been described (Kozbor, *J. Immunol.,* 133:3001 (1984); Brodeur et al., *Monoclonal Antibody Production Techniques and Applications*, pp. 51-63 (Marcel Dekker, Inc., New York, 1987)). Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. The monoclonal antibodies secreted by the subclones are suitably separated from the culture medium, ascites fluid, or serum by conventional immunoglobulin purification procedures such as, for example, protein A chromatography, gel electrophoresis, dialysis, or affinity chromatography.

Human antibodies may also be generated using a non-human host, such as a mouse, which is capable of producing human antibodies. As noted above, transgenic mice are now available that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); U.S. Pat. No. 5,591,669; U.S. Pat. No. 5,589,369; and U.S. Pat. No. 5,545,807. Human antibodies may also be prepared using SCID-hu mice (Duchosal et al. *Nature* 355:258-262 (1992)).

In another embodiment, the human antibody may be selected from a human antibody phage display library. The preparation of libraries of antibodies or fragments thereof is well known in the art and any of the known methods may be used to construct a family of transformation vectors which may be introduced into host cells. Libraries of antibody light and heavy chains in phage (Huse et al., *Science,* 246:1275 (1989)) or of fusion proteins in phage or phagemid can be prepared according to known procedures. See, for example, Vaughan et al., *Nature Biotechnology* 14:309-314 (1996); Barbas et al., *Proc. Natl. Acad. Sci., USA,* 88:7978-7982 (1991); Marks et al., *J. Mol. Biol.,* 222:581-597 (1991); Hoogenboom and Winter, *J. Mol. Biol.,* 227:381-388 (1992); Barbas et al., *Proc. Natl. Acad. Sci.*, USA, 89:4457-4461 (1992); Griffiths et al., *EMBO Journal,* 13:3245-3260 (1994); de Kruif et al., *J. Mol. Biol.,* 248:97-105 (1995); WO 98/05344; WO 98/15833; WO 97/47314; WO 97/44491; WO 97/35196; WO 95/34648; U.S. Pat. Nos. 5,712,089; 5,702,892; 5,427,908; 5,403,484; 5,432,018; 5,270,170; WO 92/06176; WO 99/06587; U.S. Pat. No. 5,514,548; WO97/08320; and U.S. Pat. No. 5,702,892. The antigen of interest is panned against the phage library using procedures known in the field for selecting phage-antibodies which bind to the target antigen (iv) Humanized Antibodies Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(v) Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571, 894; and 5,587,458. The antibody fragment may also be a "linear antibody", e.g., as described in U.S. Pat. No. 5,641, 870 for example. Such linear antibody fragments may be monospecific or bispecific.

(vi) Antibody Variant Sequences

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites. Such alterations may be made to the parent antibody and/or multivalent antibody and/or may be introduced in the multivalent antibody amino acid sequence at the time that sequence is made.

A useful method for identification of certain residues or regions of the antibody that are preferred locations for mutagenesis is called "alanine scanning mutagenesis" as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed multivalent antibodies are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability.

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The multivalent antibodies thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid modifications in an Fc region of the antibody, thereby generating a variant Fc region. The Fc region variant may comprise a human Fc region sequence (e.g., a human IgG1, IgG2, IgG3 or IgG4 Fc region) comprising an amino acid modification (e.g. a substitution) at one or more amino acid positions.

In one embodiment, the variant Fc region may mediate antibody-dependent cell-mediated cytotoxicity (ADCC) in the presence of human effector cells more effectively, or bind an Fc gamma receptor (Fc(R) with better affinity, than a native sequence Fc region. Such Fc region variants may comprise an amino acid modification at any one or more of positions 256, 290, 298, 312, 326, 330, 333, 334, 360, 378 or 430 of the Fc region, wherein the numbering of the residues in the Fc region is that of the EU index as in Kabat.

The Fc region variant with reduced binding to an Fc(R may comprise an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat.

For example, the Fc region variant may display reduced binding to an Fc(R1 and comprise an amino acid modification at any one or more of amino acid positions 238, 265, 269, 270, 327 or 329 of the Fc region, wherein the numbering of the residues in the Fc region is that of the EU index as in Kabat.

The Fc region variant may display reduced binding to an Fc(RII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

The Fc region variant of interest may display reduced binding to an Fc(RIII and comprise an amino acid modification at one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

In another embodiment, the Fc region variant displays improved binding to the Fc(R and comprises an amino acid modification at any one or more of amino acid positions 255, 256, 258, 267, 268, 272, 276, 280, 283, 285, 286, 290, 298, 301, 305, 307, 309, 312, 315, 320, 322, 326, 330, 331, 333, 334, 337, 340, 360, 378, 398 or 430 of the Fc region, wherein the numbering of the residues in the Fc region is that of the EU index as in Kabat.

For example, the Fc region variant may display increased binding to an Fc(RIII and, optionally, may further display decreased binding to an Fc(RII. An exemplary such variant comprises amino acid modification(s) at position(s) 298 and/or 333 of the Fc region, wherein the numbering of the residues in the Fc region is that of the EU index as in Kabat.

The Fc region variant may display increased binding to an Fc(RII and comprise an amino acid modification at any one or more of amino acid positions 255, 256, 258, 267, 268, 272, 276, 280, 283, 285, 286, 290, 301, 305, 307, 309, 312, 315, 320, 322, 326, 330, 331, 337, 340, 378, 398 or 430 of the Fc region, wherein the numbering of the residues in the Fc region is that of the EU index as in Kabat. Such Fc region variants with increased binding to an Fc(RII may optionally further display decreased binding to an Fc(RIII and may, for example, comprise an amino acid modification at any one or more of amino acid positions 268, 272, 298, 301, 322 or 340 of the Fc region, wherein the numbering of the residues in the Fc region is that of the EU index as in Kabat.

The variant Fc region may alternatively or additionally have altered neonatal Fc receptor (FcRn) binding affinity. Such variant Fc regions may comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Fc region variants with reduced binding to an FcRn may comprise an amino acid modification at any one or more of amino acid positions 252, 253, 254, 255, 288, 309, 386, 388, 400, 415, 433, 435, 436, 439 or 447 of the Fc region, wherein the numbering of the residues in the Fc region is that of the EU index as in Kabat. The above-mentioned Fc region variants may, alternatively, display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat.

Fc region variants with altered (i.e. improved or diminished) C1q binding and/or Complement Dependent Cytotoxicity (CDC) are described in WO99/51642. Such variants may comprise an amino acid substitution at one or more of amino acid positions 270, 322, 326, 327, 329, 331, 333 or 334 of the Fc region. See, also, Duncan & Winter Nature 322:738-40 (1988); U.S. Pat. Nos. 5,648,260;. 5,624,821; and WO94/29351 concerning Fc region variants.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, $IgG_2$, $IgG_3$, or $IgG_4$) that is responsible for increasing the in vivo serum half-life of the IgG molecule.

(vii) Immunoconjugates

The invention also pertains to immunoconjugates comprising an antibody conjugated to a cytotoxic agent such as a chemotherapeutic agent, toxin (e.g. a small molecule toxin or an enzymatically active toxin of bacterial, fungal, plant or animal origin, including fragments and/or variants thereof), or a radioactive isotope (i.e., a radioconjugate).

Chemotherapeutic agents useful in the generation of such immunoconjugates have been described above.

Conjugates of an antibody and one or more small molecule toxins, such as a calicheamicin, a maytansine (U.S. Pat. No. 5,208,020), a trichothene, and CC1065 are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. *Cancer Research* 52: 127-131 (1992)) to generate a maytansinoid-antibody immunoconjugate.

Another immunoconjugate of interest comprises an antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, $(_1^I, \forall_2^I, \forall_3^I,$ N-acetyl-$(_1^I,$ PSAG and $2^I_1$ (Hinman et al. *Cancer Research* 53: 3336-3342 (1993) and Lode et al. *Cancer Research* 58: 2925-2928 (1998)). See, also, U.S. Pat. Nos. 5,714,586; 5,712,374; 5,264,586; and 5,773,001 expressly incorporated herein by reference.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the antibody and cytotoxic agent may be made, e.g. by recombinant techniques or peptide synthesis.

In yet another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(viii) Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as beta-galactosidase and neuraminidase useful for converting glycosylated prodrugs into free drugs; beta-lactamase useful for converting drugs derivatized with beta-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature*, 312: 604-608 (1984).

(ix) Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

The antibodies disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

D. Vectors, Host Cells and Recombinant Methods

The invention also provides isolated nucleic acid encoding an antibody as disclosed herein, vectors and host cells comprising the nucleic acid, and recombinant techniques for the production of the antibody.

For recombinant production of the antibody, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The multivalent antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native multivalent antibody signal sequence, the signal sequence is substituted by a prokaryotic signal sequence selected, for example, from the group of the alkaline phosphatase, penicillinase, Ipp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the multivalent antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the multivalent antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding multivalent antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(iv) Promoter Component

Expression and cloning vectors usually contain a promoter that is recognized by the host organism and is operably linked to the multivalent antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the multivalent antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Multivalent antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the multivalent antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the multivalent antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the multivalent antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for multivalent antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated multivalent antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; a human hepatoma line (Hep G2); and myeloma or lymphoma cells (e.g. Y0, J558L, P3 and NS0 cells) (see U.S. Pat. No. 5,807,715).

Host cells are transformed with the above-described expression or cloning vectors for multivalent antibody production and cultured in conventional nutrient media modified as appropriate for inducing promoters, selecting transformants, or amplifying the genes encoding the desired sequences.

(viii) Culturing the Host Cells

The host cells used to produce the multivalent antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification

When using recombinant techniques, the multivalent antibody can be produced intracellularly, in the periplasmic space, or directly secreted into the medium. If the multivalent antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the multivalent antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The multivalent antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in the multivalent antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the multivalent antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the multivalent antibody to be recovered.

E. Pharmaceutical Formulations

Therapeutic formulations of the multivalent antibody are prepared for storage by mixing the multivalent antibody having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Examples of combinations of active compounds are provided in Section G below entitled "In Vivo Uses for the Multivalent Antibody". Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the multivalent antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3- hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

F. Non-Therapeutic Uses for the Multivalent Antibody

The multivalent antibody of the invention may be used as an affinity purification agent. In this process, the multivalent antibody is immobilized on a solid phase such a Sephadex resin or filter paper, using methods well known in the art. The immobilized multivalent antibody is contacted with a sample containing the antigen to be purified, and thereafter the support is washed with a suitable solvent that will remove substantially all the material in the sample except the antigen to be purified, which is bound to the immobilized multivalent antibody. Finally, the support is washed with another suitable solvent, such as glycine buffer, pH 5.0, that will release the antigen from the multivalent antibody.

The multivalent antibody may also be useful in diagnostic assays, e.g., for detecting expression of an antigen of interest in specific cells, tissues, or serum.

For diagnostic applications, the multivalent antibody typically will be labeled with a detectable moiety. Numerous labels are available which can be generally grouped into the following categories:

(a) Radioisotopes, such as $^{35}$S, $^{14}$C, $^{125}$I, $^{3}$H, and $^{131}$I. The multivalent antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the multivalent antibody using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the multivalent antibody. The skilled artisan will be aware of various techniques for achieving this. For example, the multivalent antibody can be conjugated with biotin and any of the three broad categories of labels mentioned above can be conjugated with avidin, or vice versa. Biotin binds selectively to avidin and thus, the label can be conjugated with the multivalent antibody in this indirect manner. Alternatively, to achieve indirect conjugation of the label with the multivalent antibody, the multivalent antibody is conjugated with a small hapten (e.g., digoxin) and one of the different types of labels mentioned above is conjugated with an anti-hapten multivalent antibody (e.g., anti-digoxin antibody). Thus, indirect conjugation of the label with the multivalent antibody can be achieved.

In another embodiment of the invention, the multivalent antibody need not be labeled, and the presence thereof can be detected using a labeled antibody which binds to the multivalent antibody.

The multivalent antibody of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc. 1987).

The multivalent antibody may also be used for in vivo diagnostic assays. Generally, the multivalent antibody is labeled with a radionuclide (such as $^{111}$In, $^{99}$Tc, $^{14}$C, $^{131}$I, $^{125}$I, $^{3}$H, $^{32}$P, or $^{35}$S) so that the antigen or cells expressing it can be localized using immunoscintiography.

G. In Vivo Uses for the Multivalent Antibody

It is contemplated that the multivalent antibody of the present invention may be used to treat a mammal e.g. a patient suffering from, or predisposed to, a disease or disorder who could benefit from administration of the multivalent antibody.

Where the antibody binds an ErbB receptor, such as HER2, conditions to be treated therewith include benign or malignant tumors; leukemias and lymphoid malignancies; other disorders such as neuronal, glial, astrocytal, hypothalamic, glandular, macrophagal, epithelial, stromal, blastocoelic, inflammatory, angiogenic and immunologic disorders. Generally, the disease or disorder to be treated with the antibody that binds an ErbB receptor is cancer.

Examples of cancer to be treated herein include, but are not limited to, carcinoma, lymphoma, blastoma, sarcoma, and leukemia or lymphoid malignancies. More particular examples of such cancers include squamous cell cancer, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma as well as head and neck cancer.

The cancer will generally comprise cells that express an antigen bound by the antibody, such that the antibody is able to bind to the cancer. In one embodiment, the cancer may be characterized by overexpression of the antigen (e.g. overexpression of an ErbB receptor). To determine expression of the antigen by the cancer, various diagnostic/prognostic assays are available. In one embodiment, antigen overexpression may be analyzed by IHC, e.g. using the HERCEPTEST® (Dako) where the antigen is HER2. In the HER2 IHC test, parrafin embedded tissue sections from a tumor biopsy may be subjected to the IHC assay and accorded a HER2 protein staining intensity criteria as follows:

| | |
|---|---|
| Score 0 | no staining is observed or membrane staining is observed in less than 10% of tumor cells. |
| Score 1+ | a faint/barely perceptible membrane staining is detected in more than 10% of the tumor cells. The cells are only stained in part of their membrane. |
| Score 2+ | a weak to moderate complete membrane staining is observed in more than 10% of the tumor cells. |
| Score 3+ | a moderate to strong complete membrane staining is observed in more than 10% of the tumor cells. |

Those tumors with 0 or 1+ scores for HER2 overexpression assessment may be characterized as not overexpressing HER2, whereas those tumors with 2+ or 3+ scores may be characterized as overexpressing HER2.

Alternatively, or additionally, FISH assays such as the INFORM™ (sold by Ventana, Arizona) or PATHVISION™ (Vysis, Illinois) may be carried out on formalin-fixed, paraffin-embedded tumor tissue to determine the extent (if any) of antigen overexpression by the tumor.

In one embodiment, the cancer will be one which expresses (and may overexpress) an ErbB receptor selected from the group consisting of EGFR, ErbB3 and ErbB4. Examples of cancers which may express/overexpress EGFR, ErbB3 or ErbB4 include squamous cell cancer, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma as well as head and neck cancer as well as glioblastomas.

The cancer to be treated herein may be one characterized by excessive activation of an ErbB receptor, e.g. EGFR. Such excessive activation may be attributable to overexpression or increased production of the ErbB receptor or an ErbB ligand. In one embodiment of the invention, a diagnostic or prognostic assay will be performed to determine whether the patient's cancer is characterized by excessive activation of an ErbB receptor. For example, ErbB gene amplification and/or overexpression of an ErbB receptor in the cancer may be determined. Various assays for determining such amplification/overexpression are available in the art and include the IHC, FISH and shed antigen assays described above. Alternatively, or additionally, levels of an ErbB ligand, such as TGF-alpha, in or associated with the tumor may be determined according to known procedures. Such assays may detect protein and/or nucleic acid encoding it in the sample to be tested. In one embodiment, ErbB ligand levels in the tumor may be determined using immunohistochemistry (INC); see, for example, Scher et al. *Clin. Cancer Research* 1:545-550 (1995). Alternatively, or additionally, one may evaluate levels of ErbB ligand-encoding nucleic acid in the sample to be tested; e.g. via fluorescent in situ hybridization or FISH, southern blotting, or polymerase chain reaction (PCR) techniques.

Moreover, ErbB receptor or ErbB ligand overexpression or amplification may be evaluated using an in vivo diagnostic assay, e.g. by administering a molecule (such as an antibody) which binds the molecule to be detected and is tagged with a detectable label (e.g. a radioactive isotope) and externally scanning the patient for localization of the label.

Where the antibody binds a B cell surface antigen, the antibody may be used to treat a B cell lymphoma (including low grade/follicular non-Hodkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; and chronic myeloblastic leukemia; and post-transplant lymphoproliferative disorder (PTLD).

The antibody, e.g. the anti-B cell surface antigen antibody, may also be used to treat an autoimmune disease. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitis); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc.

Antibodies directed against B cell surface antigens may also be used to block an immune response to a foreign antigen. By "foreign antigen" here is meant a molecule or molecules which is/are not endogenous or native to a mammal which is exposed to it. The foreign antigen may elicit an immune response, e.g. a humoral and/or T cell mediated response in the mammal. Generally, the foreign antigen will provoke the production of antibodies thereagainst. Examples of foreign antigens contemplated herein include immunogenic therapeutic agents, e.g. proteins such as antibodies, particularly antibodies comprising non-human amino acid residues (e.g. rodent, chimeric/humanized, and primatized antibodies); toxins (optionally conjugated to a targeting molecule such as an antibody, wherein the targeting molecule may also be immunogenic); gene therapy viral vectors, such as retroviruses and adenoviruses; grafts; infectious agents (e.g. bacteria and virus); alloantigens (i.e. an antigen that occurs in some, but not in other members of the same species) such as differences in blood types, human lymphocyte antigens (HLA), platelet antigens, antigens expressed on transplanted organs, blood components, pregnancy (Rh), and hemophilic factors (e.g. Factor VIII and Factor IX).

The anti-B cell surface antigen antibody may also be used to desenzitize a mammal awaiting transplantation.

Antibodies directed against a receptor in the TNF receptor superfamily may be employed to activate or stimulate apoptosis in cancer cells.

In certain embodiments, an immunoconjugate comprising the antibody conjugated with a cytotoxic agent is administered to the patient. Preferably, the immunoconjugate and/or antigen to which it is bound is/are internalized by the cell, resulting in increased therapeutic efficacy of the immunoconjugate in killing the cancer cell to which it binds. In a preferred embodiment, the cytotoxic agent targets or interferes with nucleic acid in the cancer cell. Examples of such cytotoxic agents include any of the chemotherapeutic agents noted herein (such as a maytansinoid or a calicheamicin), a radioactive isotope, or a ribonuclease or a DNA endonuclease. As noted above, the multivalent antibody may also be used for ADEPT.

The present application contemplates combining the multivalent antibody (or immunoconjugate thereof) with one or more other therapeutic agent(s), especially for treating cancer. For instance, the multivalent antibody may be co-administered with another multivalent antibody (or multivalent antibodies), a monovalent or bivalent antibody (or antibodies), chemotherapeutic agent(s) (including cocktails of chemotherapeutic agents), other cytotoxic agent(s), anti-angiogenic agent(s), cytokines, and/or growth inhibitory agent(s). Where the multivalent antibody induces apoptosis, it may be particularly desirable to combine the multivalent antibody with one or more other therapeutic agent(s) which also induce apoptosis. For instance, pro-apoptotic antibodies (e.g. bivalent or multivalent antibodies) directed against B cell surface antigens (e.g. RITUXAN®, ZEVALIN® or BEXXAR® anti-CD20 antibodies) may be combined with (1) pro-apoptotic antibodies (e.g. bivalent or multivalent antibodies directed against a receptor in the TNF receptor superfamily, such as anti-DR4 or anti-DR5 antibodies) or (2) with cytokines in the TNF family of cytokines (e.g. Apo2L). Likewise, anti-ErbB antibodies (e.g. HERCEPTIN® anti-HER2 antibody) may be combined with (1) and/or (2). Alternatively, or additionally, the patient may receive combined radiation therapy (e.g. external beam irradiation or therapy with a radioactive labelled agent, such as an antibody). Such combined therapies noted above include combined administration (where the two or more agents are included in the same or separate formulations), and separate administration, in which case, administration of the multivalent antibody can occur prior to, and/or following, administration of the adjunct therapy or therapies.

The multivalent antibody (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the multivalent antibody is suitably administered by pulse infusion, particularly with declining doses of the multivalent antibody. Preferably the dosing is given by injections, most preferably intravenous or subcutaneous injections, depending in part on whether the administration is brief or chronic.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus. The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:4429-4432 (1987); and Wagner et al., *Proc. Natl. Acad. Sci. USA* 87:3410-3414 (1990). For review of the currently known gene marking and gene therapy protocols see Anderson et al., *Science* 256:808-813 (1992). See also WO 93/25673 and the references cited therein.

For the prevention or treatment of disease, the appropriate dosage of multivalent antibody will depend on the type of disease to be treated, the severity and course of the disease, whether the multivalent antibody is administered for preventive or therapeutic purposes, previous therapy, the patient's clinical history and response to the multivalent antibody, and the discretion of the attending physician. The multivalent antibody is suitably administered to the patient at one time or over a series of treatments.

Depending on the type and severity of the disease, about 1 μg/kg to 15 mg/kg (e.g., 0.1-20 mg/kg) of multivalent antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The multivalent antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the multivalent antibody to be administered will be governed by such considerations, and is the minimum amount necessary to prevent, ameliorate, or treat a disease or disorder. The multivalent antibody need not be, but is optionally formulated with one or more agents currently used to prevent or treat the disorder in question. The effective amount of such other agents depends on the amount of multivalent antibody present in the formulation, the type of disorder or treatment, and other factors discussed above. These are generally used in the same dosages and with administration routes as used hereinbefore or about from 1 to 99% of the heretofore employed dosages.

H. Articles of Manufacture

In another embodiment of the invention, an article of manufacture containing materials useful for the treatment of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is a multivalent antibody. The label or package insert indicates that the composition is used for treating the condition of choice, such as cancer. Moreover, the article of manufacture may comprise (a) a first container with a composition contained therein, wherein the composition comprises a multivalent antibody; and (b) a second container with a composition contained therein, wherein the composition comprises a further cytotoxic agent. The article of manufacture in this embodiment of the invention may further comprises a package insert indicating that the first and second antibody compositions can be used to treat cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

I. Deposit of Materials

The following hybridoma cell lines have been deposited with the American Type Culture Collection, 10801 University Boulevard, Manassas, Va. 20110-2209, USA (ATCC):

| Antibody Designation | ATCC No. | Deposit Date |
|---|---|---|
| 7C2 (anti-HER2) | ATCC HB-12215 | Oct. 17, 1996 |
| 7F3 (anti-HER2) | ATCC HB-12216 | Oct. 17, 1996 |
| 4D5 (anti-HER2) | ATCC CRL 10463 | May 24, 1990 |
| 2C4 (anti-HER2) | ATCC HB-12697 | Apr. 8, 1999 |
| 3F11.39.7 (anti-DR5) | HB-12456 | Jan. 13, 1998 |
| 3H3.14.5 (anti-DR5) | HB-12534 | Jun. 2, 1998 |
| 3D5.1.10 (anti-DR5) | HB-12536 | Jun. 2, 1998 |
| 3H1.18.10 (anti-DR5) | HB-12535 | Jun. 2, 1998 |
| 4E7.24.3 (anti-DR4) | HB-12454 | Jan. 13, 1998 |
| 4H6.17.8 (anti-DR4) | HB-12455 | Jan. 13, 1998 |

The invention will be more fully understood by reference to the following examples. They should not, however, be construed as limiting the scope of this invention. All literature and patent citations mentioned herein are expressly incorporated by reference.

EXAMPLE 1

Construction of Multivalent Antibodies

Figures 4, 18A:
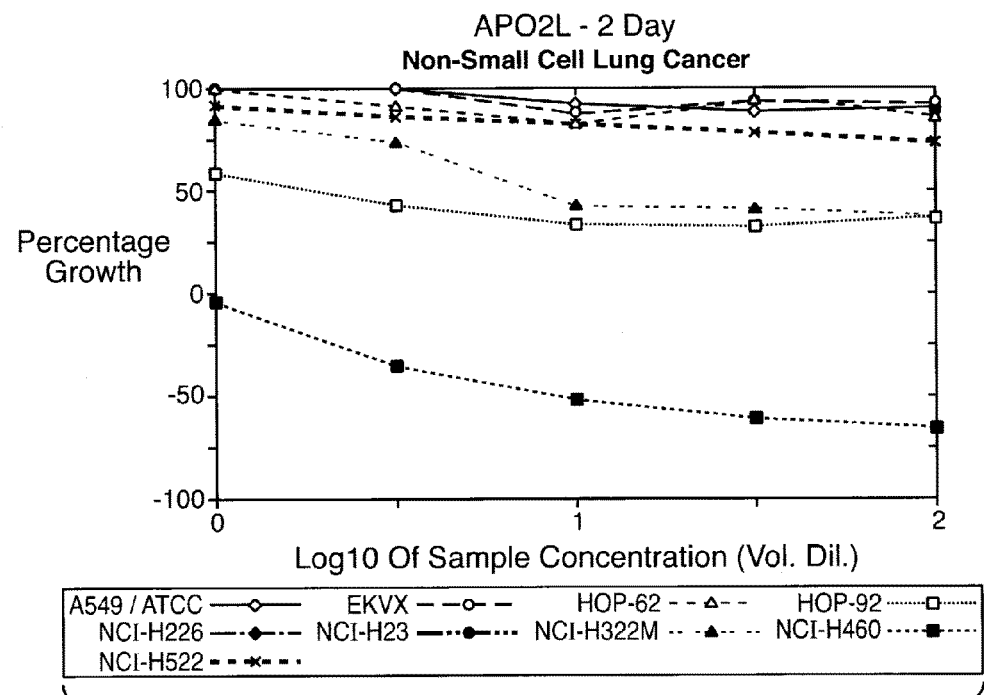
Figures 5, 18A:
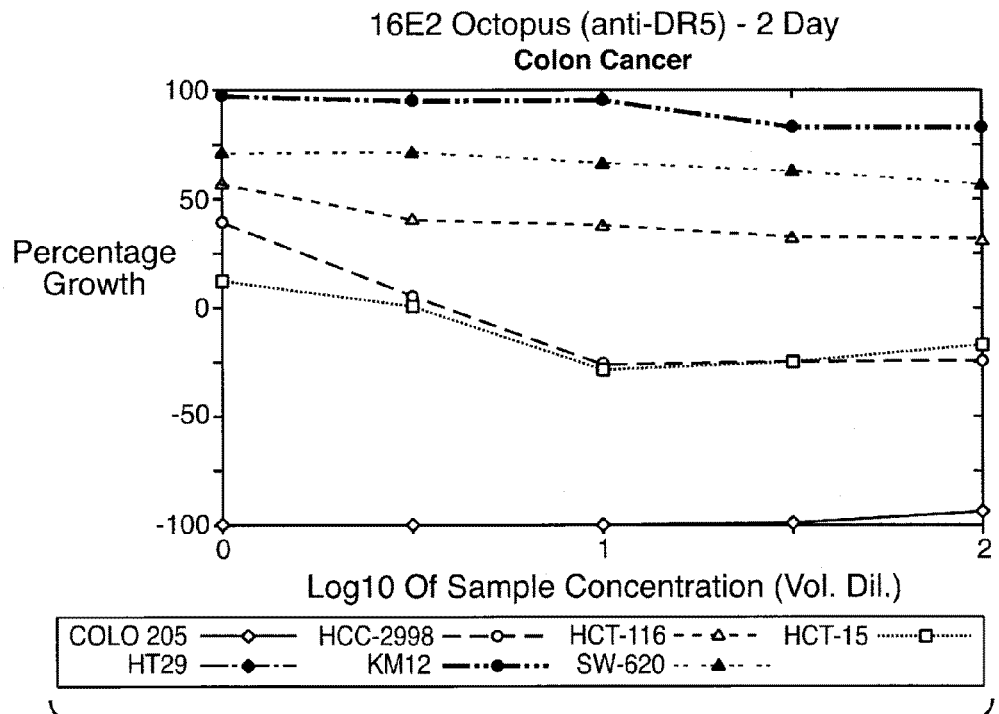
FIG. 5 shows the construct used in Example 1 for expression of a tetravalent anti-HER2 antibody (OctHER2) that includes amino acid sequences of EVQL (SEQ ID NO:12) and KTHT (SEQ ID NO:13).
Figures 6, 18A:
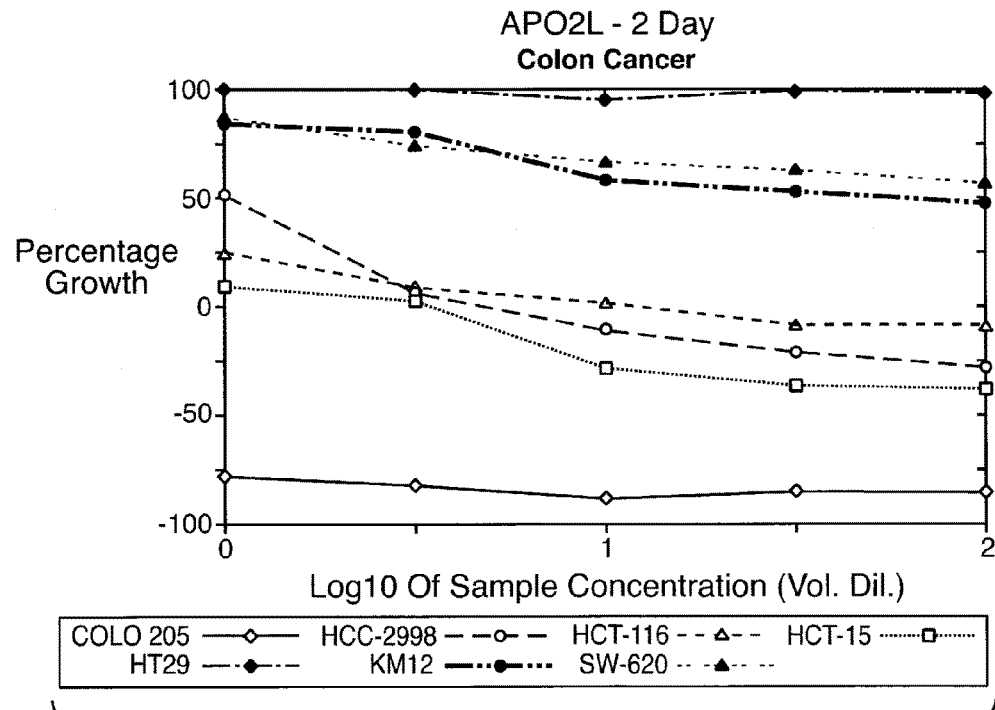

The construct used to generate a tetravalent anti-HER2 antibody, called an "Octopus antibody" (OctHER2), is illustrated in FIG. 5 herein. The backbone of this Octopus antibody is the recombinant, humanized monoclonal antibody 4D5 variant 8 (rhuMAb 4D5-8) (U.S. Pat. No. 5,821,337, Carter et al., expressly incorporated herein by reference). The heavy chain of rhuMAb 4D5-8 was subcloned into the pRK5 vector (EP 307,247, published Mar. 15, 1989). The VH-CH1 region of the heavy chain was removed by mutagenesis, and three unique restriction sites (BamHI; NheI; BspEI) were inserted. These sites were incorporated into PCR primers designed to amplify the VH-CH1 region from different antibodies. The resulting fragments were subcloned into the vector to create the Octopus heavy chain. Co-expression of the Octopus heavy chain with the appropriate light chain in a pRK5 vector in mammalian cell transfections results in the completed Octopus antibody (FIG. 4).

Octopus constructs containing flexible linkers inserted between the tandem Fd regions were are also engineered. Through mutagenesis, DNA encoding either "gly-ser" (flex 1 linker) or "gly-ser-gly-ser" (SEQ ID NO:10) (flex 2 linker) was inserted between the DNA encoding the VH-CH1 regions of the heavy chain.

EXAMPLE 2

Evaluation of Anti-HER2 Octopus Antibodies

OctHER2 was expressed in transiently transfected 293 cells (Graham et al. *J. Gen. Virol.* 36:59-72 (1977)) and purified over a Protein A sepharose column. The complete antibody is approximately 245 kDa, as compared to the 150 kDa molecular weight of the parent antibody. The Octopus heavy chain is 75 kDa (without carbohydrate), and the light chain is 30 kDa.

Antigen Binding

Binding of OCTHER2 to antigen, her2 extracellular domain (HER2ECD), was analyzed using a HER2ELISA assay (Sias et al. *J. Immunol. Methods* 132:73-80 (1990)). Ninety-six well plates were coated with the HER2 extracellular domain (ECD) (WO90/14357), and incubated with different dilutions of anti-HER2 antibodies. After washing to remove unbound antibody, a secondary peroxidase-conjugated antibody was then added to detect the anti-HER2 antibody bound to the ECD. The appropriate substrate was then added, and the wells were visualized and then quantitated on a plate reader at 562 nm.

Figure 6A:
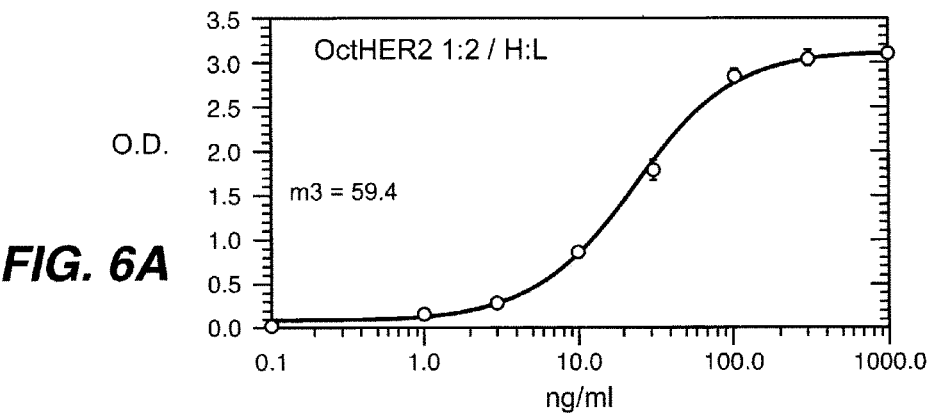
FIGS. 6A-C illustrate binding of OctHER2 (FIG. 6A); bivalent IgG1 rhuMAb 4D5-8 expressed by 293 cells (FIG. 6B); and vialed HERCEPTIN® (expressed by Chinese hamster ovary (CHO) cells) (FIG. 6C) to HER2 extracellular domain (ECD) as determined using an enzyme-linked immunosorbent assay (ELISA).
Figure 6B:
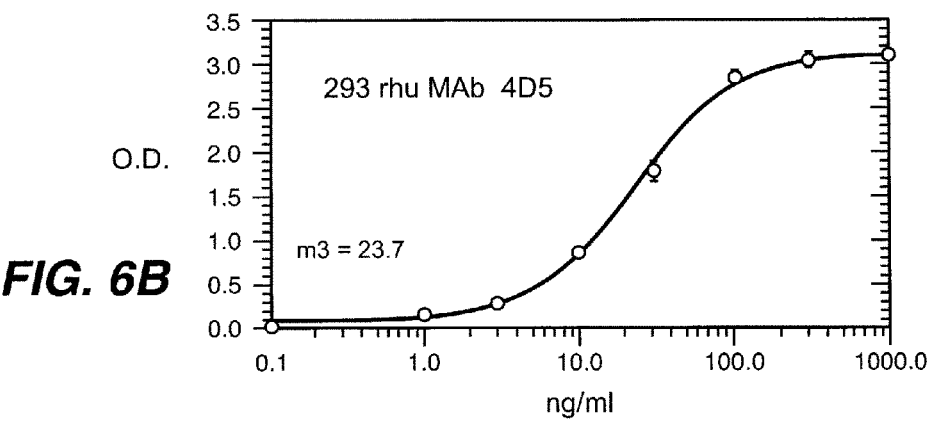
Figure 6C:
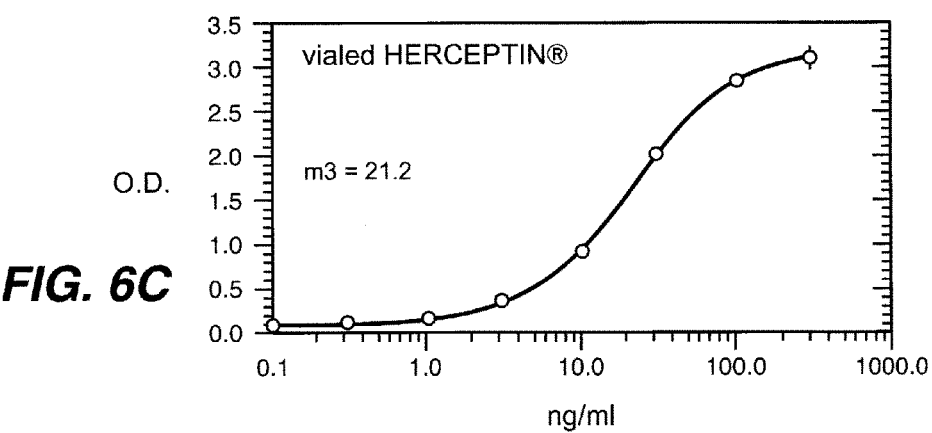

The ELISA results for OctHER2, bivalent human IgG1 anti-HER2 antibody rhuMAb 4D5-8 expressed by 293 cells, or bivalent anti-HER2 antibody HERCEPTIN® (commercially available from Genentech, Inc., South San Francisco, USA), are shown in FIGS. 6A-C. OctHER2 binds the HER2ECD similar to HERCEPTIN® when analyzed in an ELISA assay. The rhuMAb 4D5-8 expressed by 293 cells binds identically to the vialed HERCEPTIN® (produced by Chinese Hamster Ovary (CHO) cells), indicating that 293 cells do not substantially alter the antigen binding capability of the antibodies.

Figure 7:
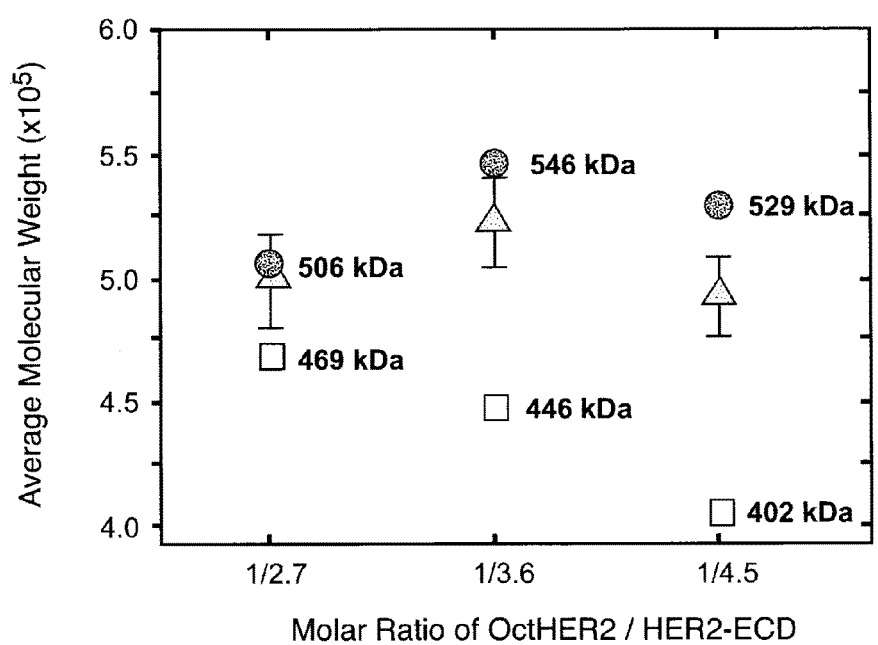
FIG. 7 depicts ultracentrifugation analysis of binding of OctHER2 to HER2 ECD. Average molecular weights (theoretical or experimentally determined) versus molar ratio of OctHER2 to HER2 ECD are shown. Theoretical calculated average molecular weights assuming tetravalent antibody has four fully functional binding sites are shown in circles; theoretical calculated average molecular weights assuming tetravalent antibody has three fully functional binding sites are shown in squares; and triangles represent experimentally determined molecular weights.

Ultracentrifugation analysis was used to determine whether OctHER2 was capable of binding target with all four antigen binding sites. Different amounts of the HER2 extracellular domain (ECD) (WO90/14357) were titrated in with the Octopus antibody, and based upon these ratios, the average molecular weight of the complexes was calculated assuming that the Octopus antibody either had four fully functional binding sites, or three functional binding sites. These theoretical values (circles, assuming OctHER2 has four functional binding sites; and squares, assuming OctHER2 has three functional binding sites) were compared to the actual experimental values obtained (triangles). The experimental values depicted in FIG. 7 more closely follow the curve representing four binding sites, however the drift observed is an indicator that all four sites probably do not bind with the same affinity.

Biological Function

Antiproliferation Assays: OctHER2 was compared to HERCEPTIN® in functional assays measuring growth inhibition of HER2 overexpressing tumor cell lines. The growth inhibition assay described in Lewis et al. *Cancer Immuno. Immunother.* 37:255-263 (1993) was used. Briefly, serial dilutions of OctHER2 and HERCEPTIN® were added to the media of plated cells which were then allowed to continue growing for five days. After this time, the media was removed and the cells were stained with crystal violet and quantitated by spectrophotometry. Crystal violet is a colorimetric dye that stains cells, thus allowing measurement of cell growth after treatment.

Figure 8A:
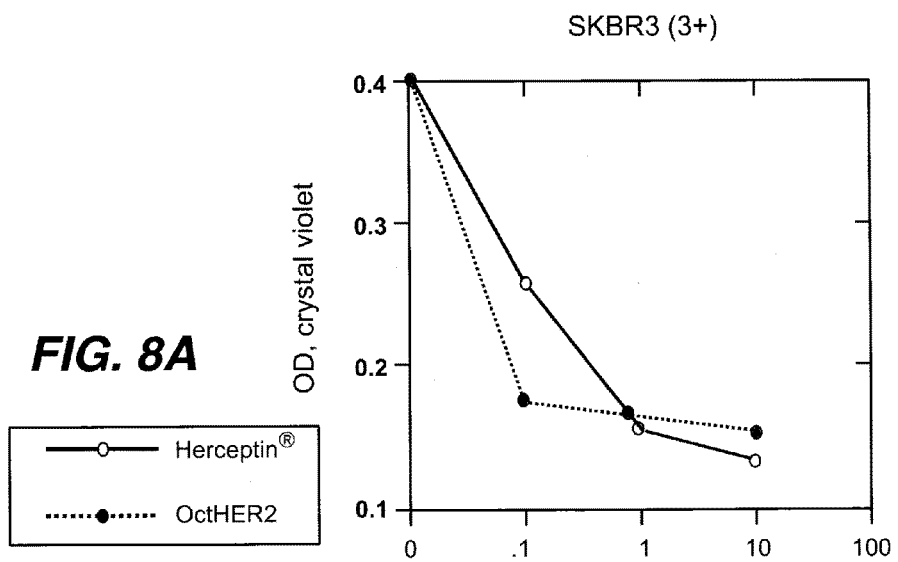
FIGS. 8A-D depict the growth inhibitory activity of HERCEPTIN® compared to OctHER2 using SKBR3 (3+ HER2 overexpressing) (FIG. 8A), MDA 361 (2+ HER2 overexpressing) (FIG. 8B), BT474 (3+HER2 overexpressing) (FIG. 8C) and MCF7 (0+ HER2 expressing) (FIG. 8D) cell lines.
Figure 8B:
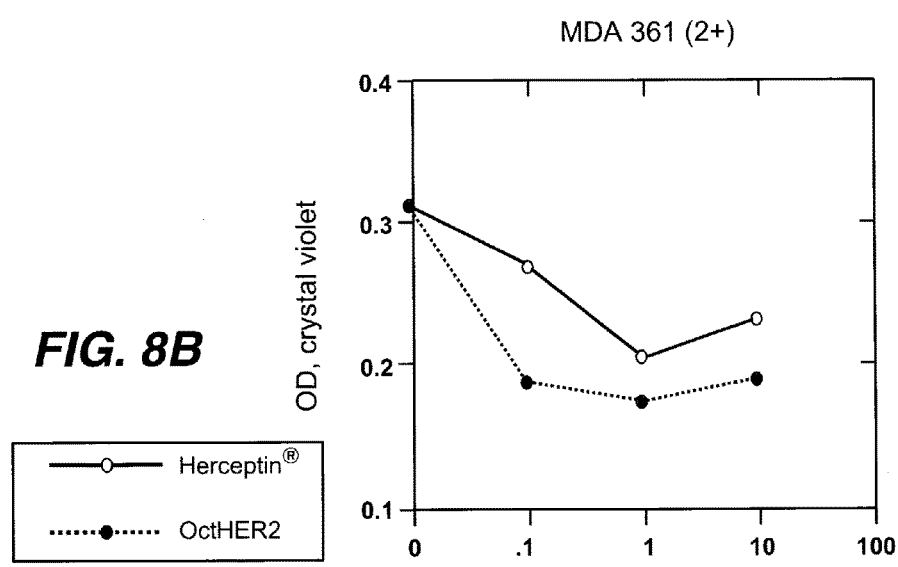
Figure 8C:
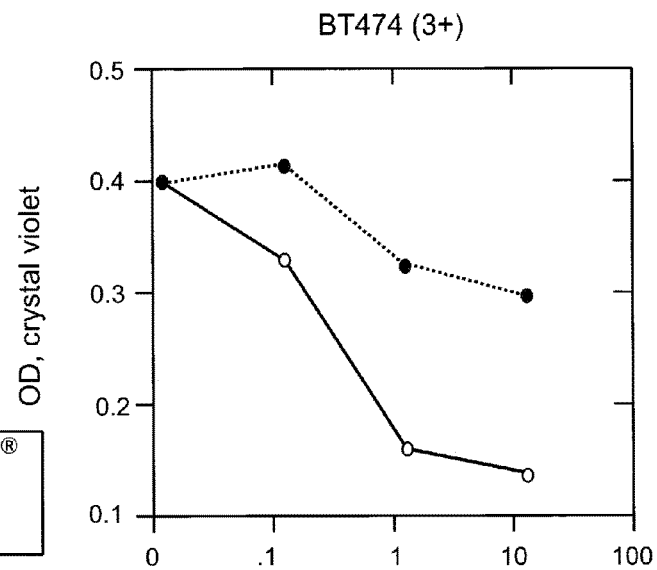
Figure 8D:
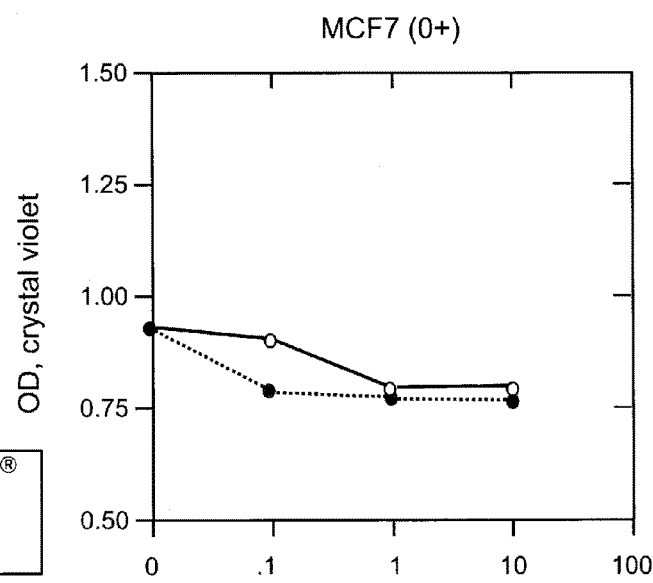

In 3+ HER2 overexpressing cells (on which HERCEPTIN® is very effective), OctHER2 was similar to slightly better at inhibiting growth of SKBR3 cells (FIG. 8A), however was not as effective on BT474 cells (FIG. 8B). Interestingly, OctHER2 inhibited more effectively than HERCEPTIN® a 2+ overexpressing cell line, MDA 361 (FIG. 8B).

Figure 9:
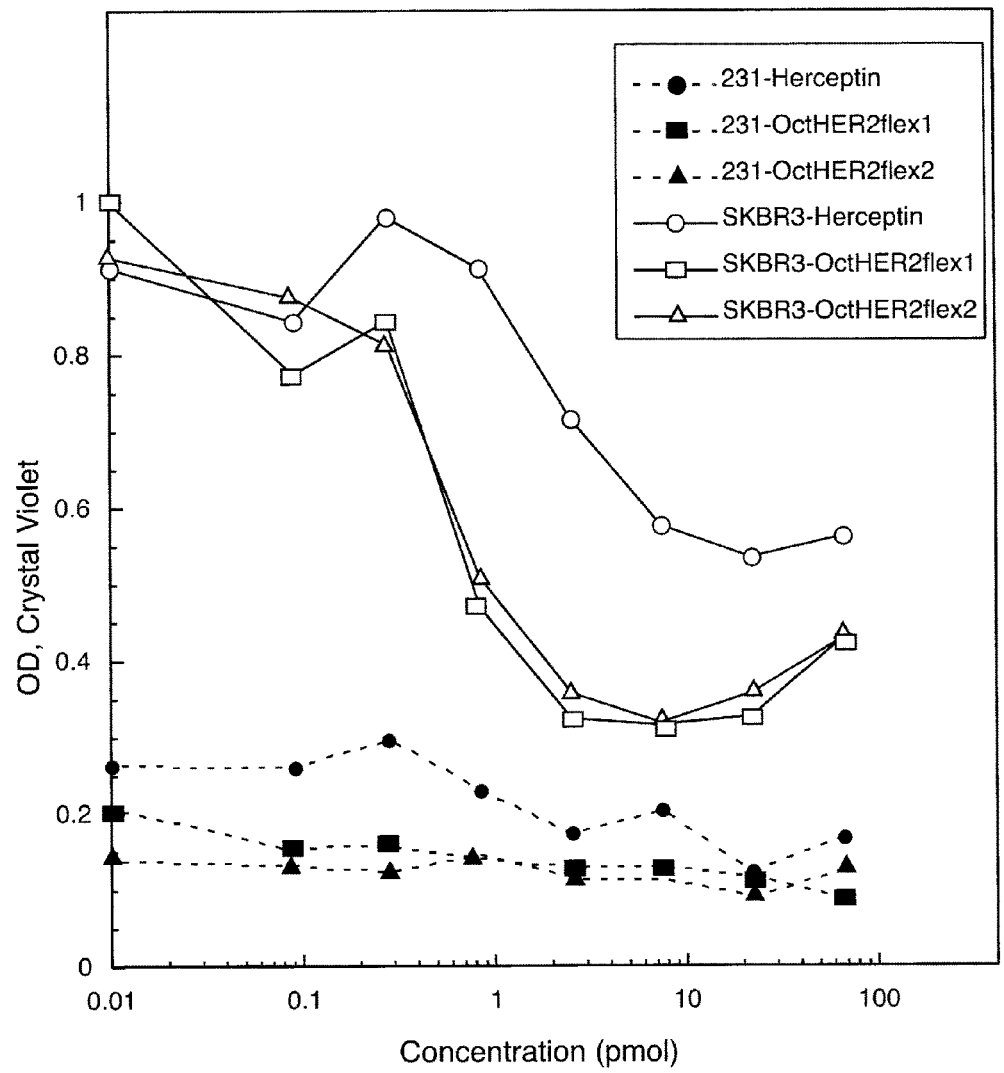
FIG. 9 depicts the effect of flexible linkers on the growth inhibitory activity of tetravalent anti-HER2 antibodies with respect to MDA 231 cells (1+ HER2 overexpressing) or SKBR3 cells (3+ HER2 overexpressing).

As shown in FIG. 9, the flexible linker Octopus constructs (OctHER2flex1, OctHER2flex2) inhibited cell growth more effectively than HERCEPTIN®.

Internalization Assays: In order to assess the application of the Octopus antibody for immunotoxin therapy, its internalization capabilities were evaluated. For antibody arming or immunotoxin therapy, a cytotoxic agent is conjuated with or fused to the antibody and the immunotoxin thus produced binds specifically to its cellular target; the thus-bound cell internalizes the antibody, and catabolizes or degrades the antibody releasing the toxin which kills the cell.

In the internalization assays performed herein, the antibody was radioiodinated, and incubated for varying times with the cells. This was followed by measurements of the amount of intact, unbound antibody in the supernatant, the amount bound to the cell surface, the amount internalized, and finally, the amount catabolized and degraded.

Figure 10A:
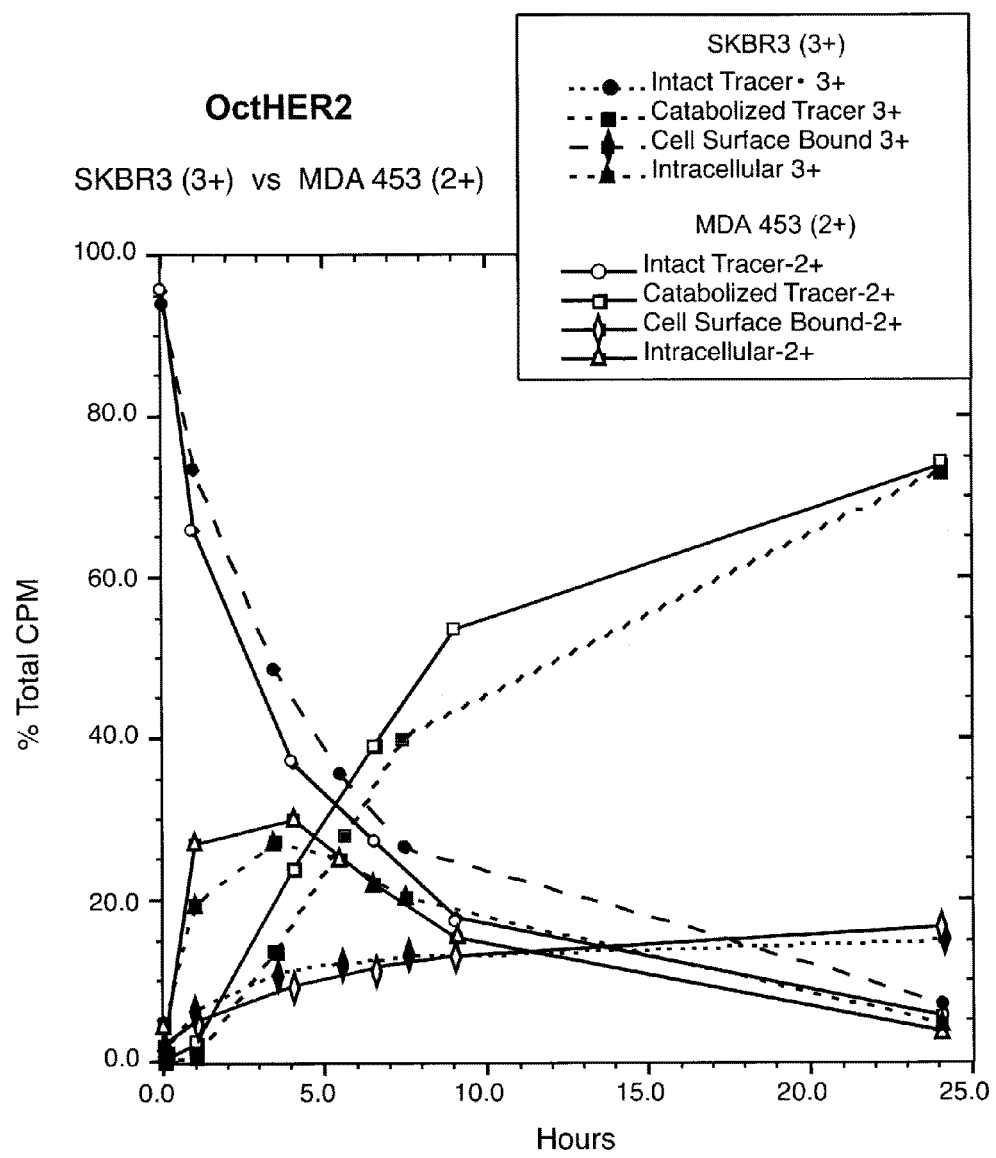
FIGS. 10A-B compare the rate of OctHER2 internalization/catabolism (FIG. 10A) to that of HERCEPTIN® (FIG. 10B), in relation to both MDA 453 (2+ HER2 overexpressing) and SKBR3 (3+ HER2 overexpressing) cell lines.
Figure 10B:
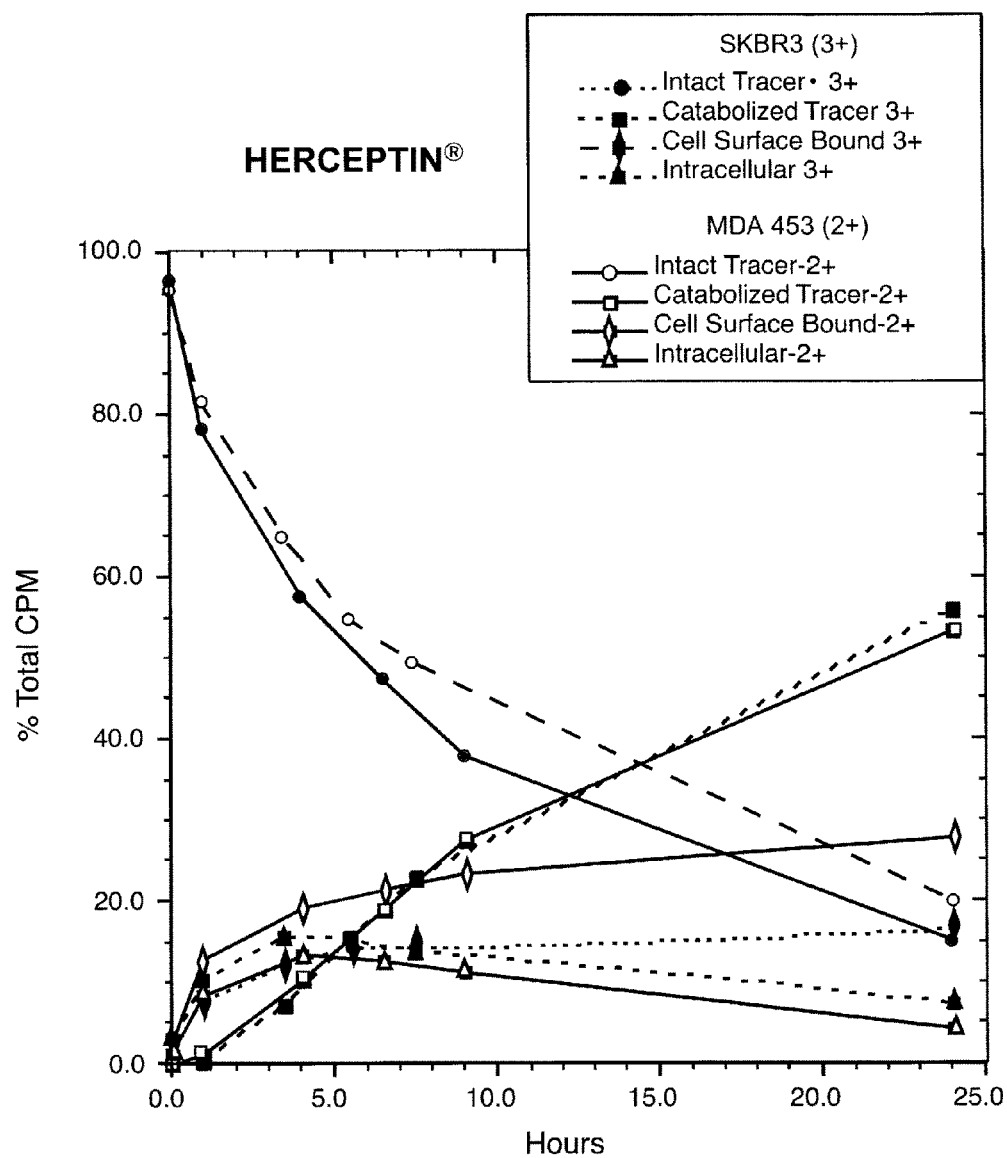

The results of internalization assays performed with respect to a 3+ overexpressing cell line (SKBR3) and a 2+ overexpressing cell line (MDA453) (the solid lines represent 2+ HER2 overexpressors, and the dashed lines, 3+ overexpressors) are depicted in FIGS. 10A-B. These results indicate that OctHER2, surprisingly, internalized and catabolized twice as fast as HERCEPTIN® in both cell lines. The rapid internalization and catabolism displayed by the Octopus antibody is ideal for an armed antibody. In comparison to unbound HERCEPTIN®, there is very little free Octopus antibody in a 2+ overexpressing cell. Once again, these results suggest that the Octopus antibody would be an excellent candidate for conjugating cytotoxic agents for tumor delivery.

Figures 11A, 11B:
FIGS. 11A-I are electron microscopy photographs showing internalization of OctHER2.
Figures 11C, 11D:
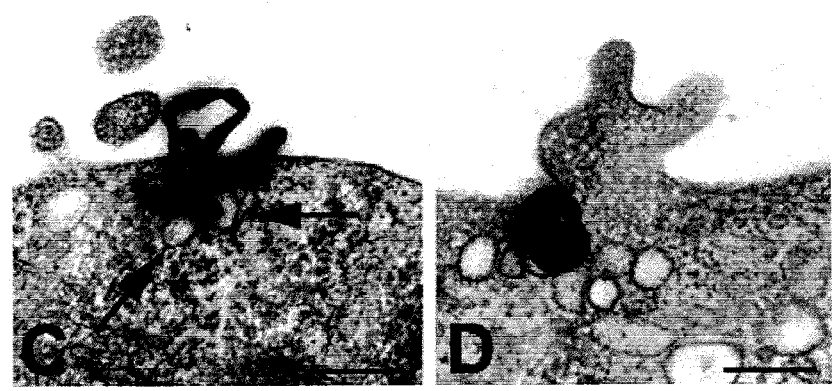
Figures 11E, 11F:
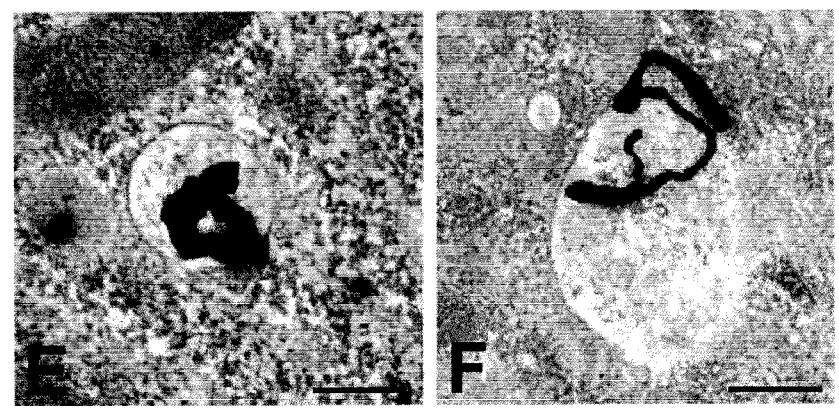
Figure 11G:
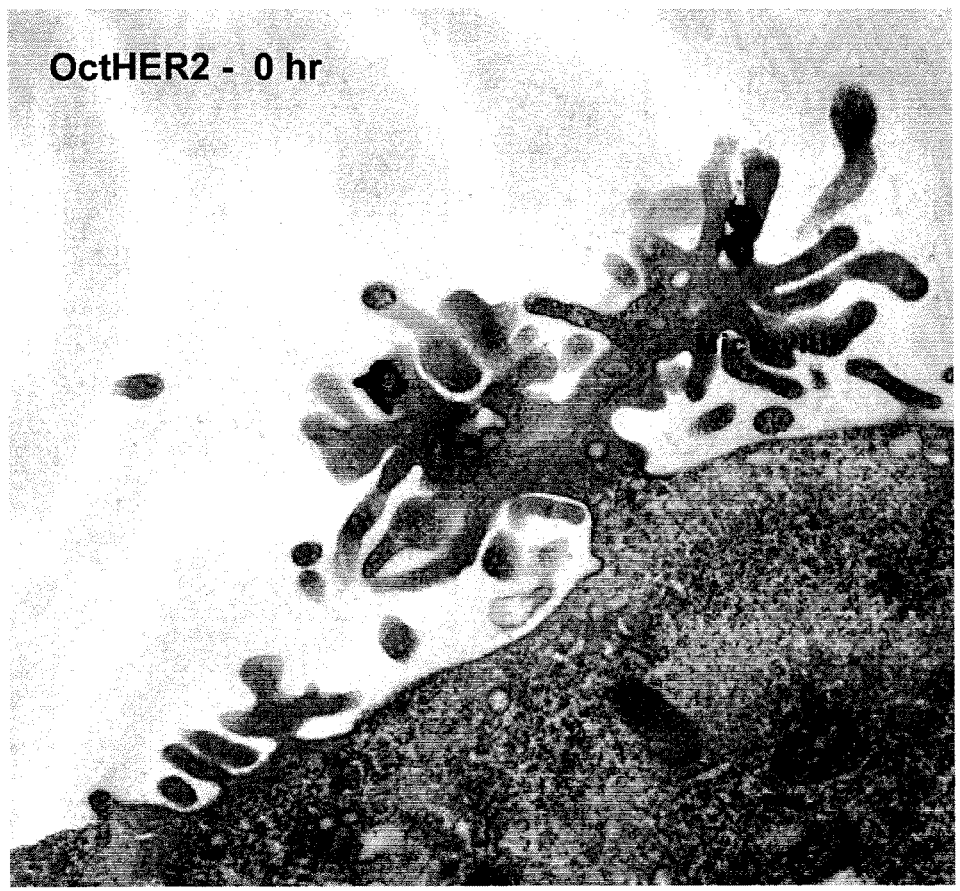
Figure 11H:
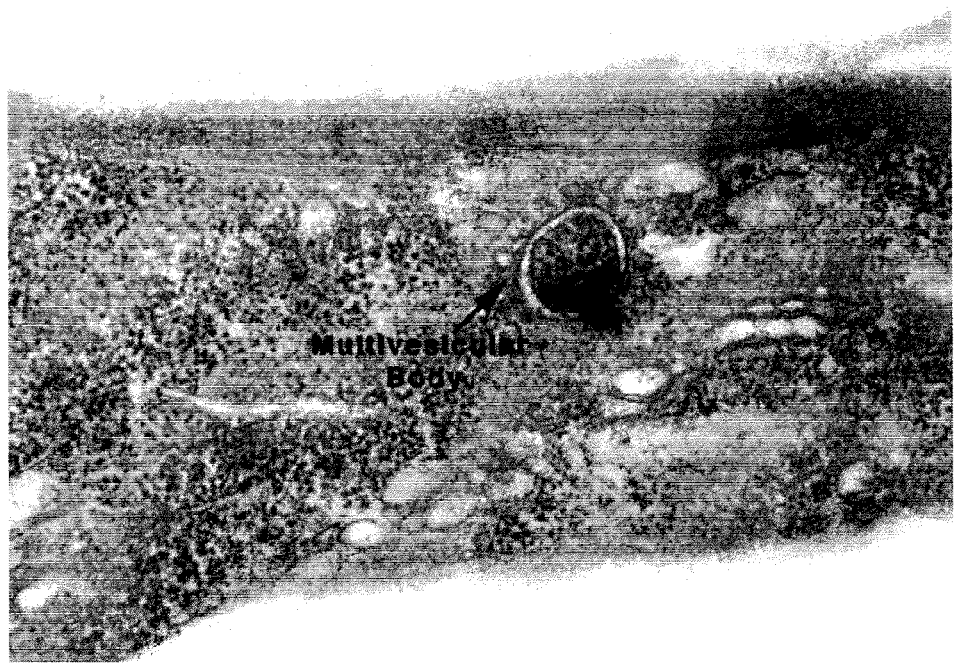
Figure 11I:
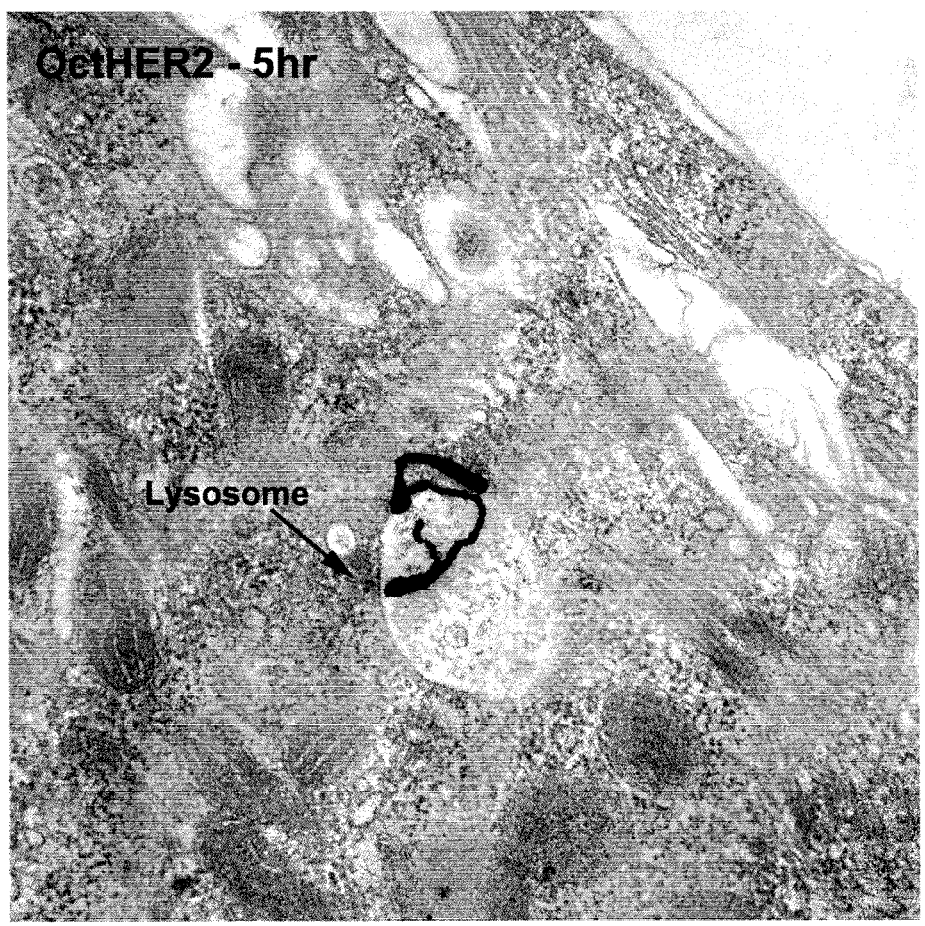
Figure 12A:
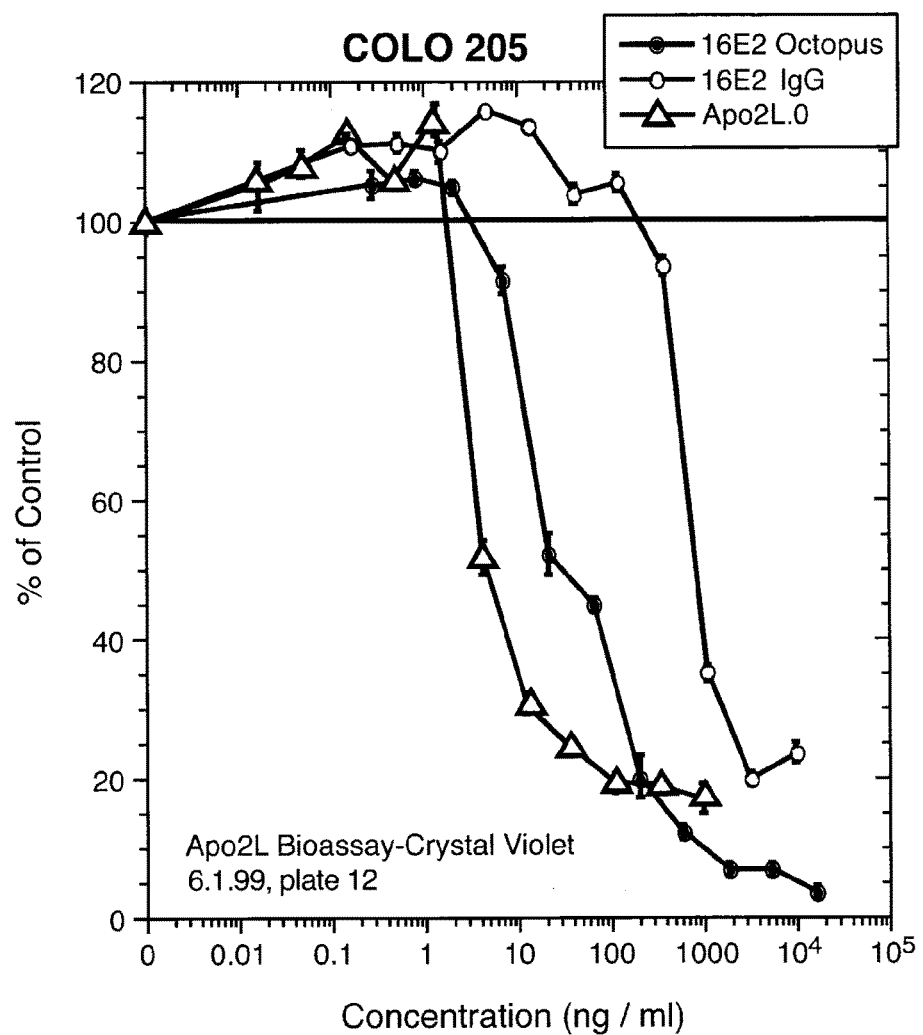
FIGS. 12A-E depict apoptosis induced by an anti-DR5 tetravalent antibody (16E2 Octopus), an anti-DR5 bivalent IgG antibody (16E2 IgG), and Apo2L/TRAIL (Apo2L) on cancer cell lines: COLO 205 (FIG. 12A), SK-MES-1 (FIG. 12B), HCT116 (FIG. 12C), and HOP 92 (FIG. 12D), compared to a non-cancer control cell line, HUMEC (FIG. 12E).
Figure 12B:
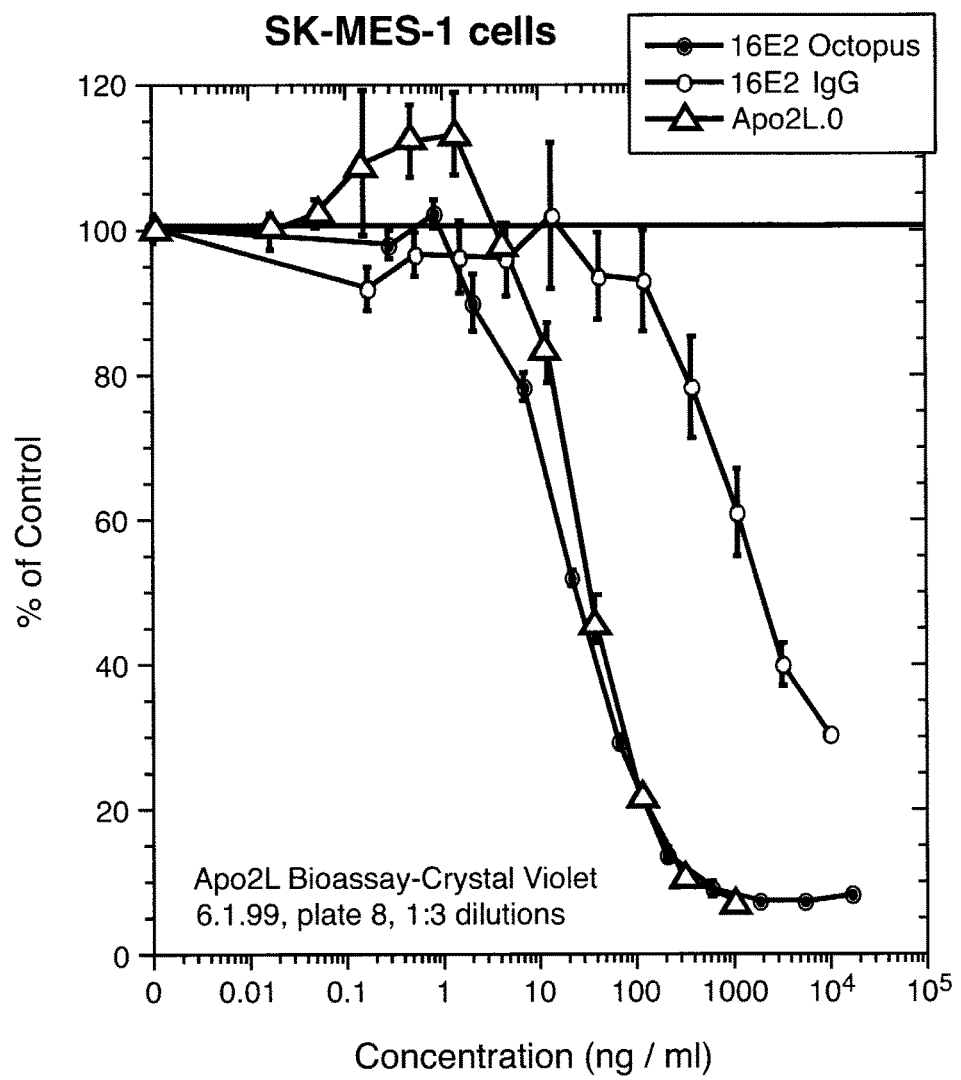
Figure 12C:
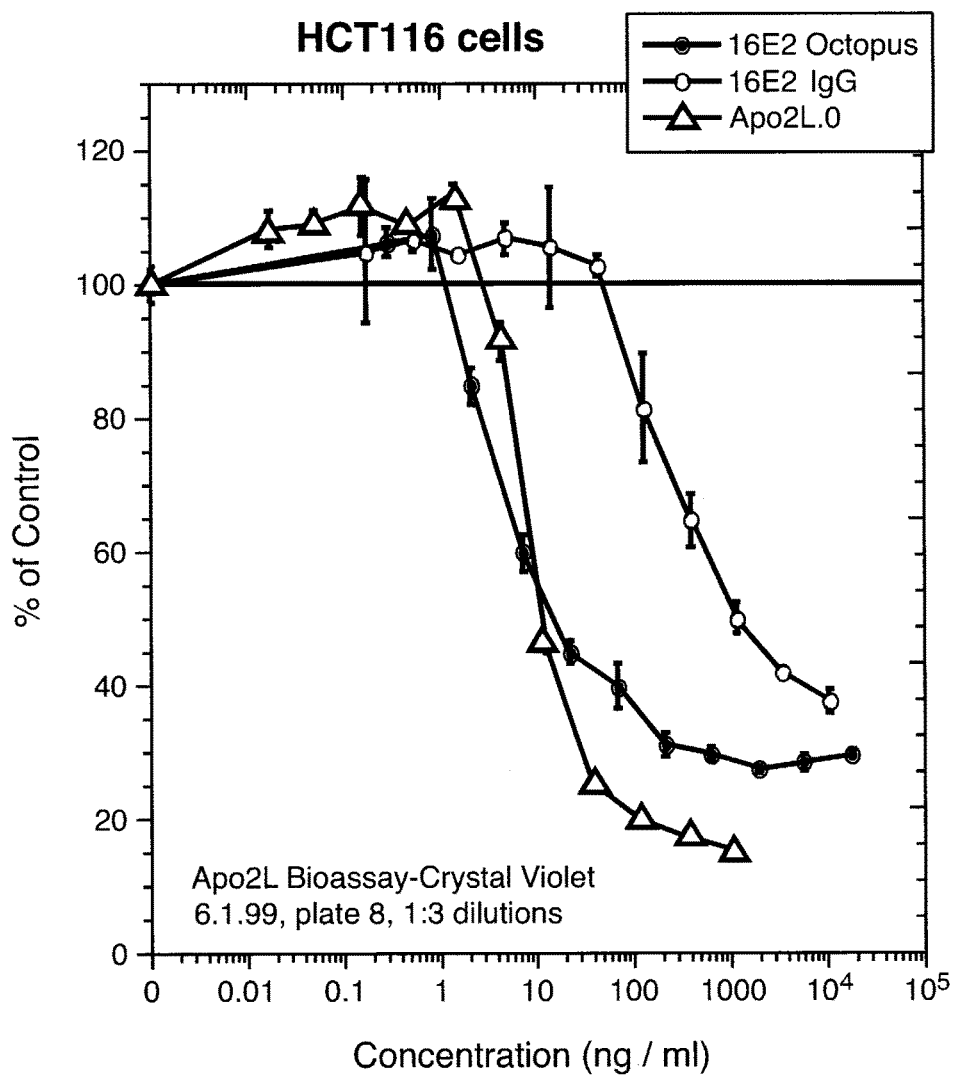
Figure 12D:
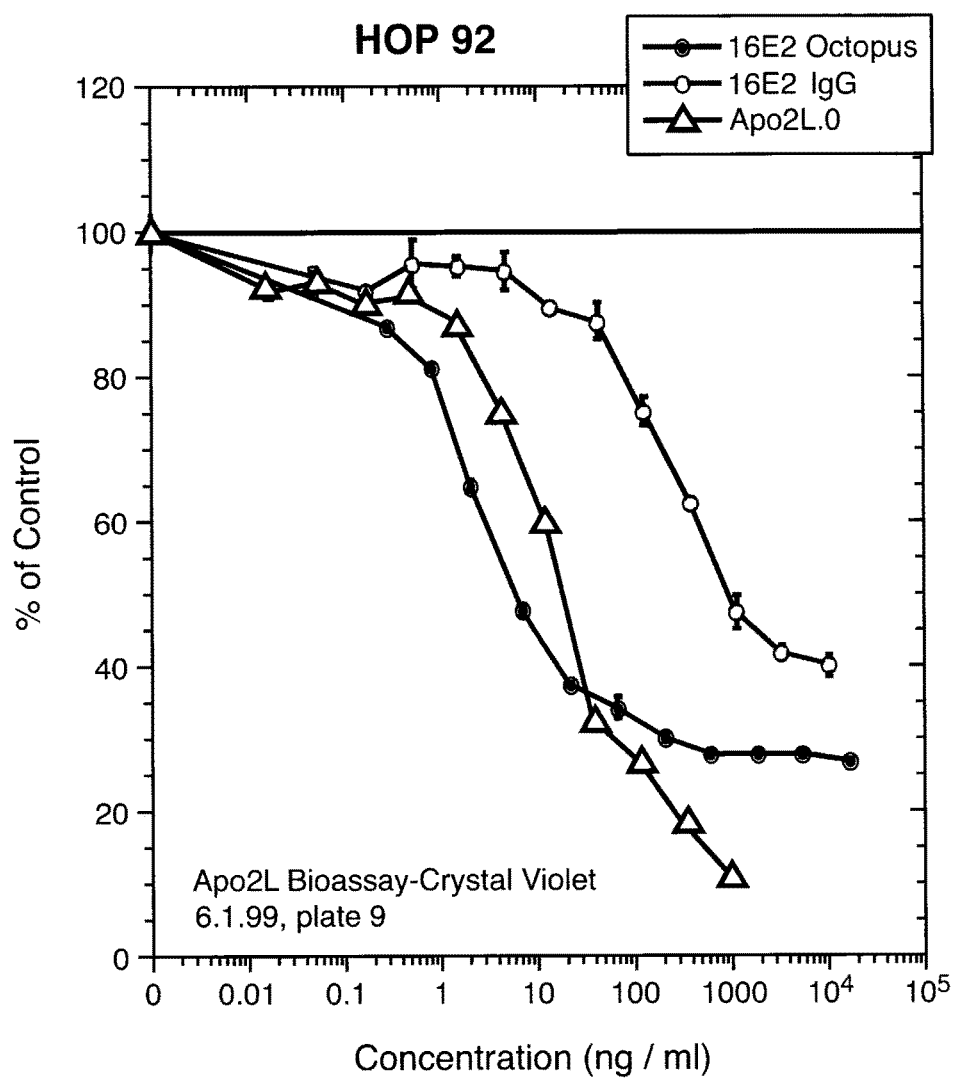
Figure 12E:
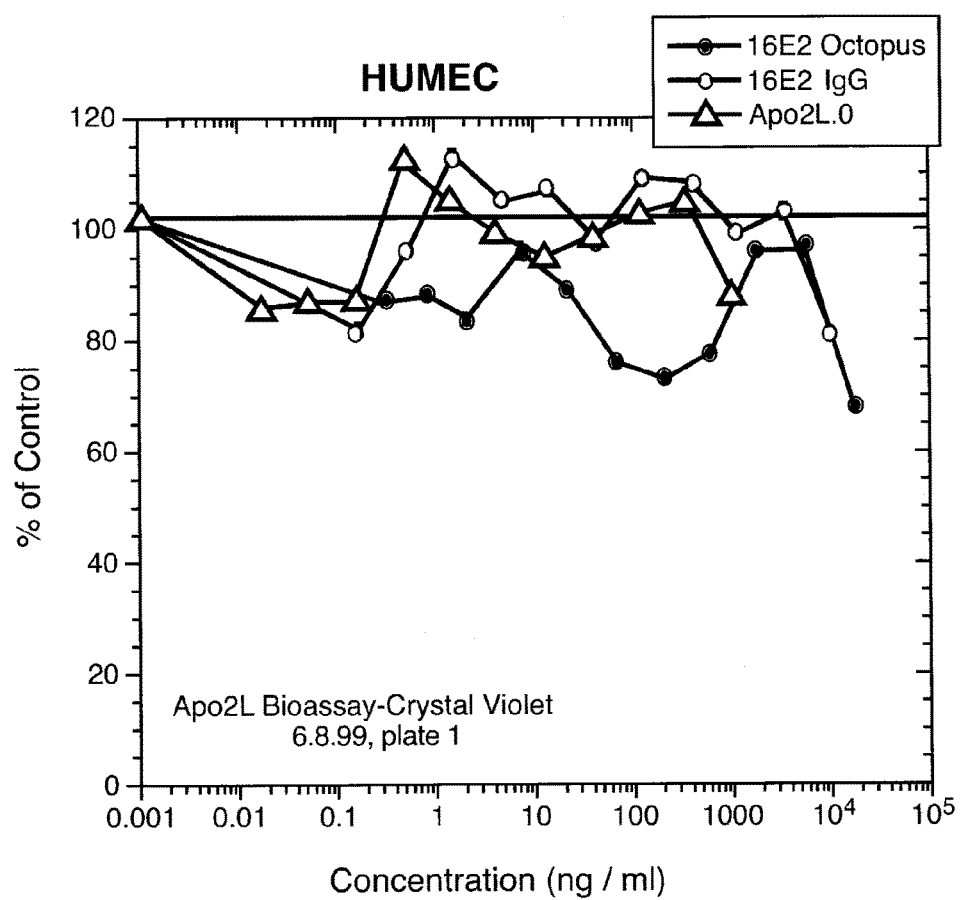
Figure 13C:
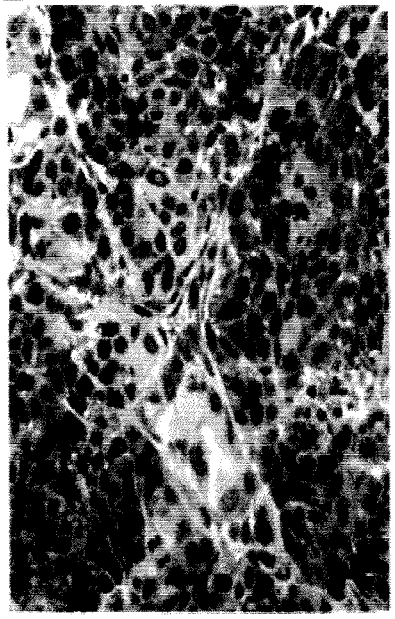
FIGS. 13A-D are histology slides stained to detect apoptotic cells. Tumor tissues from mice treated with 16E2 Octopus or Apo2L/TRAIL were fixed in 10% formalin and then embedded into parafilm and sectioned onto slides which were then stained with hematoxylin and eosin and visualized under a 400× magnification. The effect of 16E2 Octopus at 6 and 24 hours is shown in FIGS. 13A and B, respectively; control-treated cells are shown in FIG. 13C; and Apo2L/TRAIL-treated cells are shown in FIG. 13D.
Figure 13D:
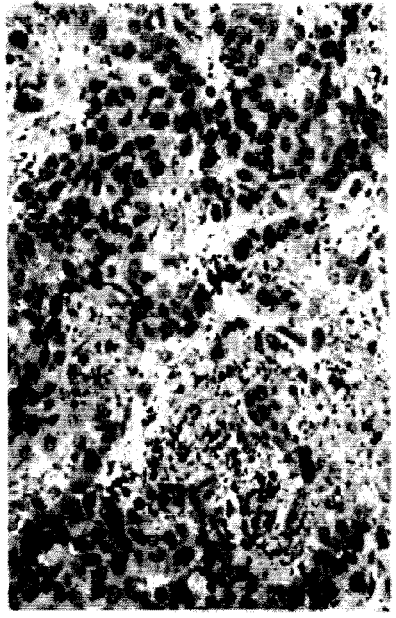
Figure 13A:
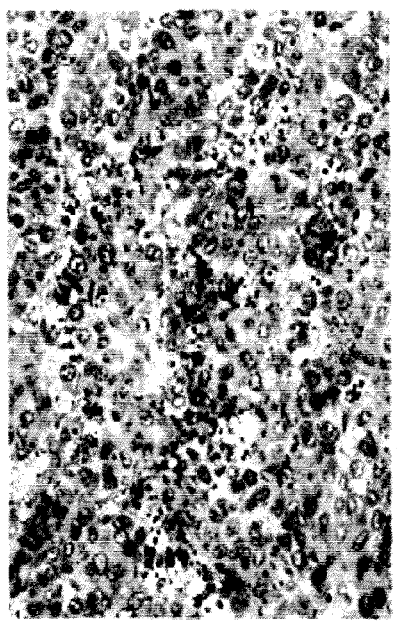
Figure 13B:
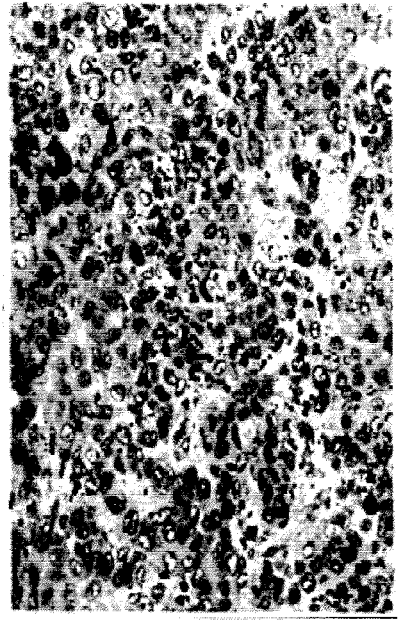

Electron Microscopy Autoradiography: To confirm that the Octopus antibody was being internalized and degraded in the appropriate vesicles, and not just nonspecifically, Electron Microscopy (EM) autoradiography was used. The Octopus antibody was iodinated and incubated with the cells in the same fashion as in the internalization assays. The results depicted in FIGS. 11A-C confirm that the Octopus antibody was being internalized into the correct vesicles (early endosome, FIG. 11B; and lysosome, FIG. 11C). Additionally, the percentage of internalization observed with OctHER2 and HERCEPTIN® in these assays matched with the measurements in the internalization assays.

EXAMPLE 3

Evaluation of Anti-DR5 Octopus Antibodies

DR5 a member of the TNF receptor superfamily that binds the trimeric Apo2L/TRAIL (Apo2L). After Apo2L receptors bind Apo2L and are clustered, death domains in the cytosolic region of the receptors induce caspases to trigger cellular apoptosis. Two versions of anti-DR5 Octopus constructs were made: one from 16E2, an anti-DR5 cloned from a single-chain human Fv phage library (see WO98/51793, expressly incorporated herein by reference); the second anti-DR5 Octopus antibody was made from Mab 3H3.14.5 (the "3H3" antibody; ATCC HB-12534, WO99/64461), a murine anti-DR5 MAb that induces apoptosis when it is crosslinked. Since anti-Death receptor monoclonal antibodies may require crosslinking to trigger apoptosis, they are candidates for the Octopus antibody construct. The anti-DR5 Octopus antibodies were prepared by replacing the variable domains of the OctHER2 construct described above with the VL and VH domains from 16E2 or 3H3.

The anti-DR5 Octopus antibodies were analyzed in apoptosis assays using either crystal violet or alamarBlue staining.

Briefly, serial dilutions of the Octopus antibody or Apo2L were added to the media of plated cells which were then allowed to continue growing for 24 hours. After this time, the media was either removed and the cells were stained with crystal violet, or alamarBlue was added to the media and incubated briefly with the cells. Crystal violet stains the cells, whereas alamarBlue detects metabolic activity in the culture media, thus these dyes allow for measurement of cells that survive treatment. Staining by both colorimetric dyes, crystal violet and alamarBlue, was quantitated by spectrophotometry.

As shown in FIGS. 12A-E, the 16E2 Octopus, surprisingly, induces apoptosis with comparable potency to Apo2L in lung (SK-MES-1; HOP 92) and colon (HCT116; COLO 205) tumor cell lines, however does not cause apoptosis on normal control cell line (HUMEC). The apoptosis induced by the 16E2 Octopus is caspase-dependent.

The anti-DR516E2 Octopus was also effective in vivo in inducing apoptosis and shrinking a colon tumor, human COL0205, in athymic nude mice. As shown in FIG. 13A-D, histology slides of tumor tissues stained with hematoxylin and eosin from mice treated with the 16E2 Octopus or Apo2L induced similar levels of apoptotic cells.

Figure 14:
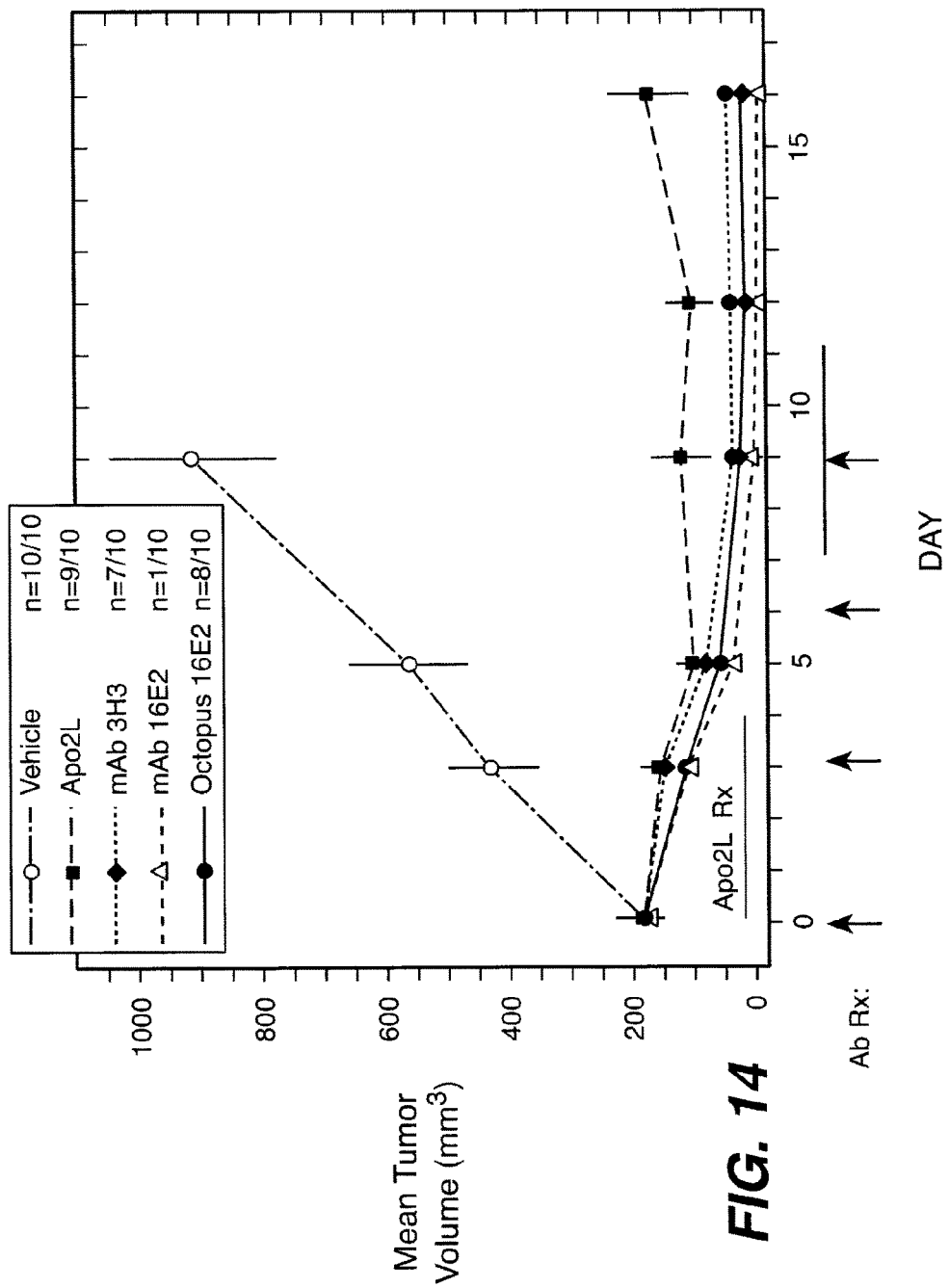
FIG. 14 represents the in vivo activity of Apo2L/TRAIL (60 mg/kg, 5×/week), 3H3 bivalent IgG (5 mg/kg given days 0, 3, 5 and 9), 16E2 bivalent IgG (16E2) (5 mg/kg given days 0, 3, 5 and 9), and 16E2 Octopus (5 mg/kg given days 0, 3, 5 and 9) with respect to COLO 205 tumors in athymic nude mice.

The 16E2 Octopus-treated mice also demonstrated significant decrease in tumor volume, similar to that measured for the Apo2L and two bivalent anti-DR5 mAbs, 16E2 and 3H3, as shown in FIG. 14. Mice that did not receive any anti-DR5 antibodies or Apo2L (Vehicle) showed dramatic increase in their tumor volume due to uncontrolled growth.

Figure 15:
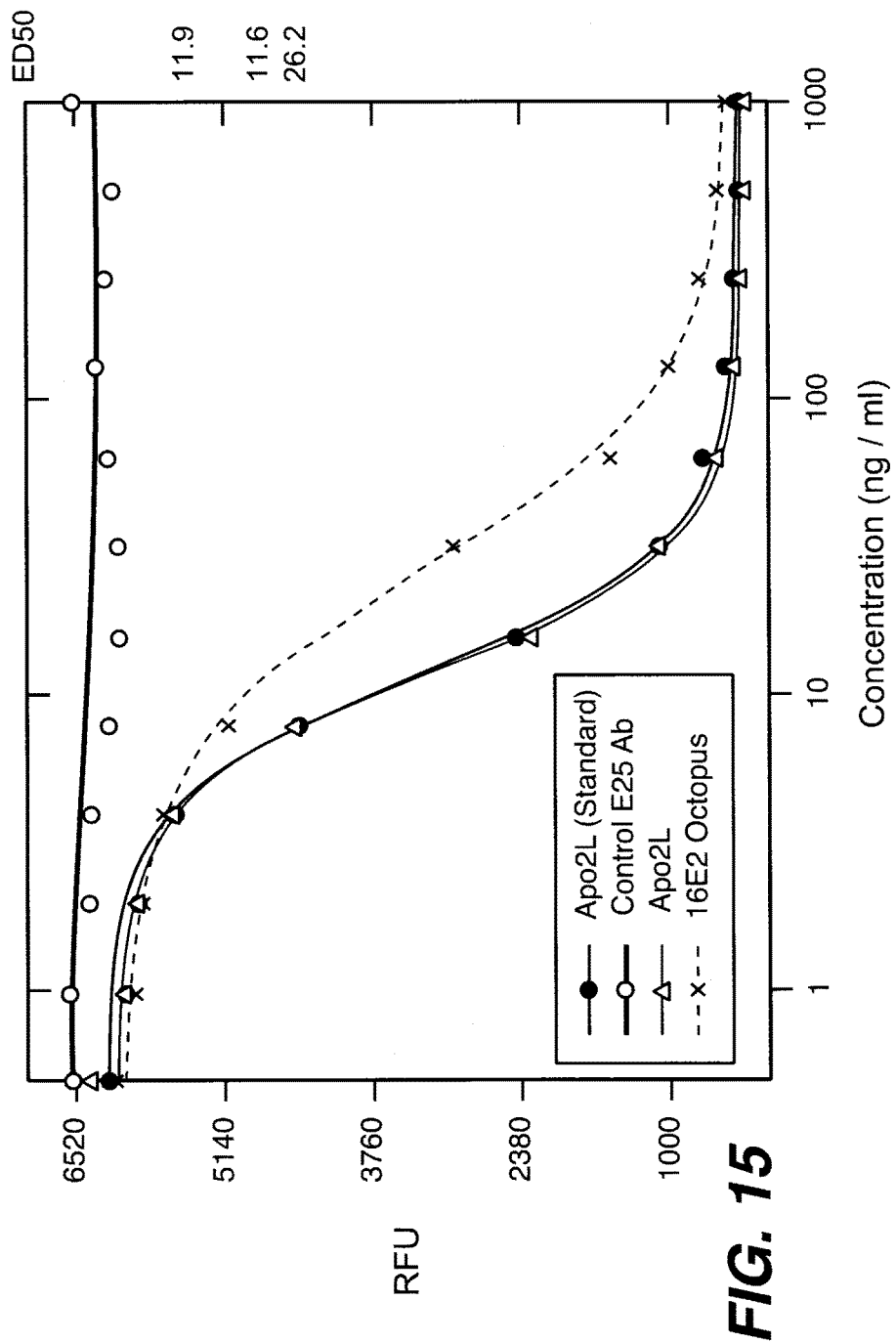
FIG. 15 represents an alamarBlue in vitro assay confirming the apoptotic activity of the material used in the mouse studies (Apo2L/TRAIL and 16E2 Octopus) as compared to an Apo2L standard positive control. The anti-IgE antibody (E25) used as a negative control in the mouse studies was confirmed to have no apoptotic activity.

The apoptotic activity of the material used in the mouse studies was confirmed in an in vitro apoptotic assay in FIG. 15. The anti-DR516E2 Octopus and the Apo2L used in the study were compared to an Apo2L standard positive control and an anti-IgE MAb (E25) negative control in an alamarBlue apoptosis assay.

Figure 16:
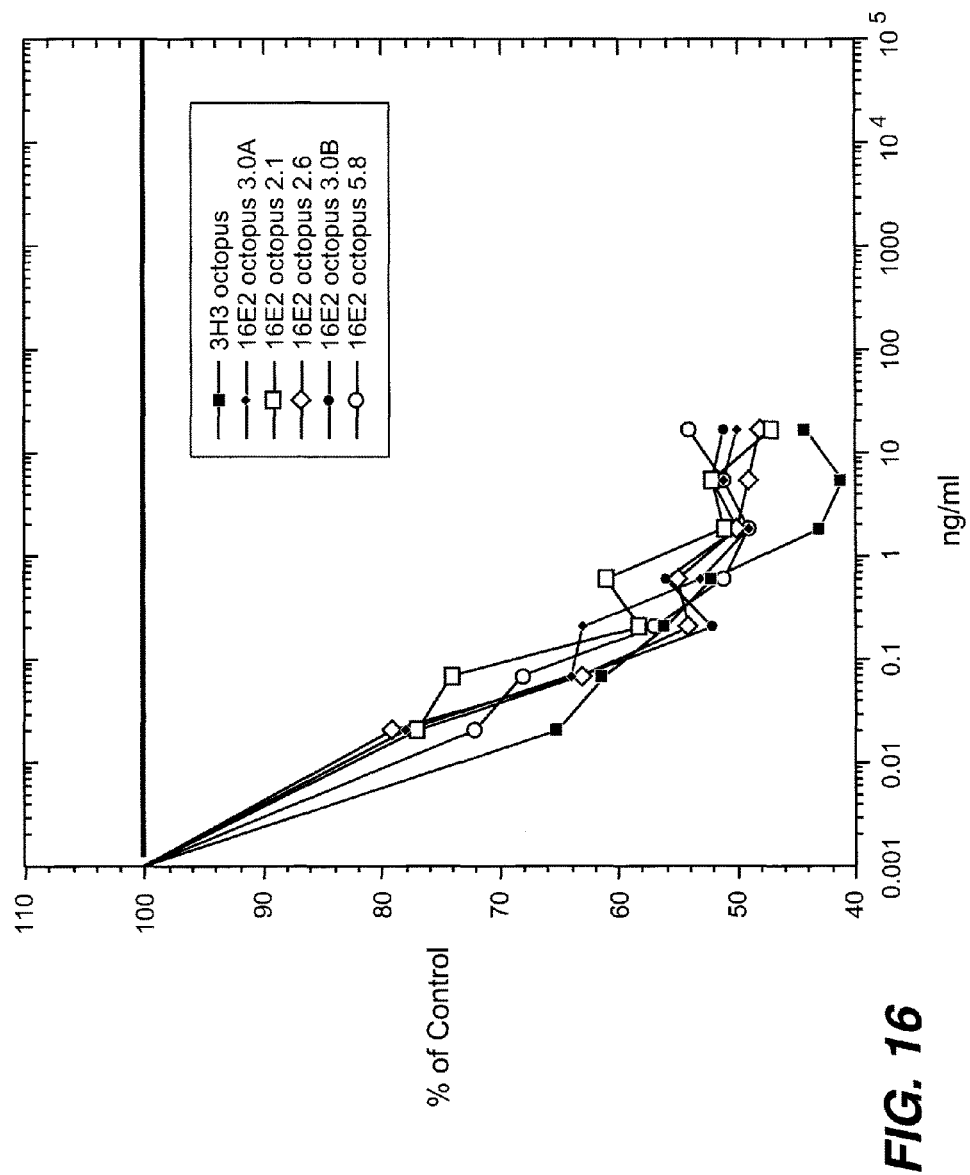
FIG. 16 represents the results of a crystal violet apoptosis assay comparing anti-DR5 3H3 Octopus to various batches of the anti-DR516E2 Octopus.

FIG. 16 demonstrates that another anti-DR5 Octopus, 3H3 Octopus, is capable of inducing apoptosis similar to the 16E2 Octopus. Additionally, FIG. 16 shows that the apoptotic activity of the Octopus antibody is not lot dependent, as several 16E2 Octopus antibodies prepared on different dates retain similar function.

Figure 17A:
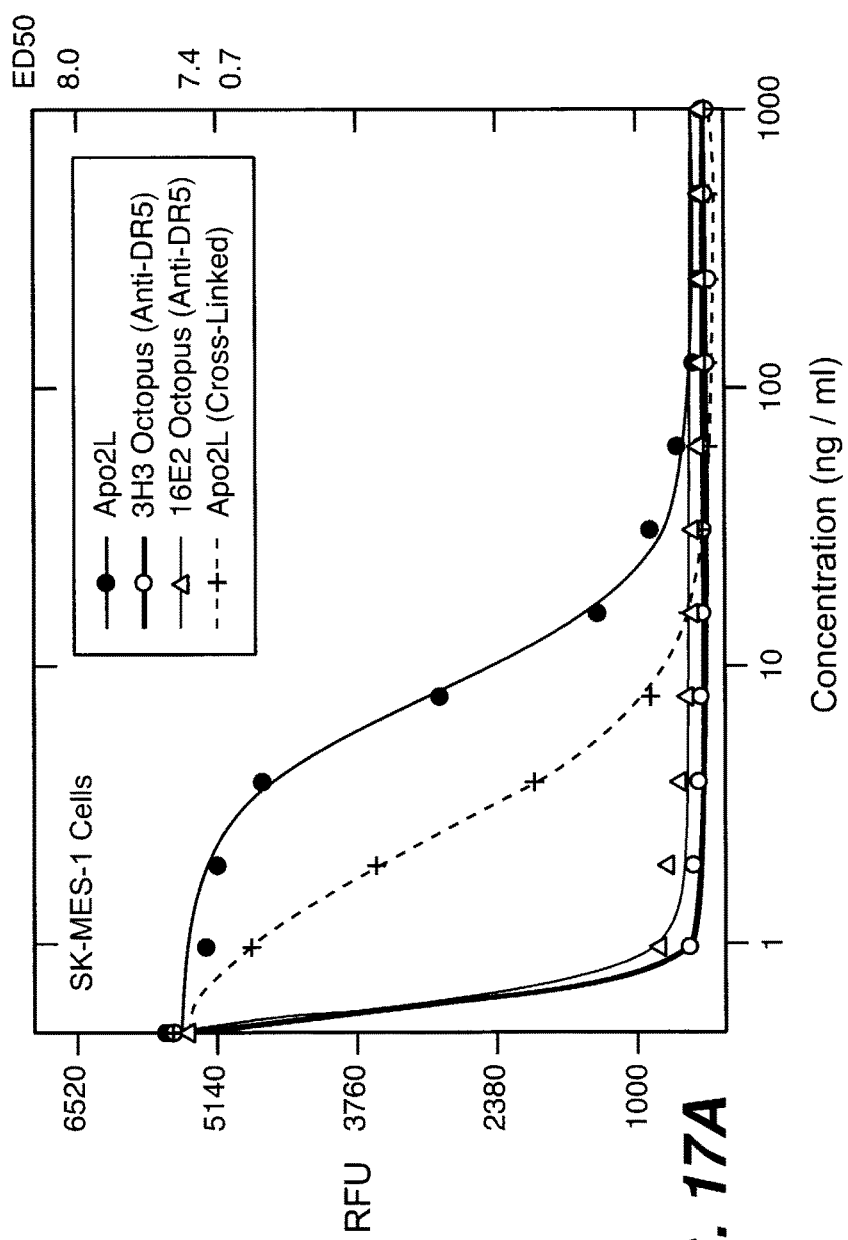
FIGS. 17A-B reveal the results of the alamarBlue apoptosis assay with respect to Apo2L/TRAIL (WO97/25428), anti-DR5 3H3 Octopus antibody, anti-DR516E2 Octopus antibody, and Apo2L/TRAIL with a FLAG epitope-tag cross linked by an anti-FLAG antibody (WO97/25428), with respect to SK-MES-1 (FIG. 17A) and Jurkat (FIG. 17B) cells in the presence of 5% fetal bovine serum (FBS).
Figure 17B:
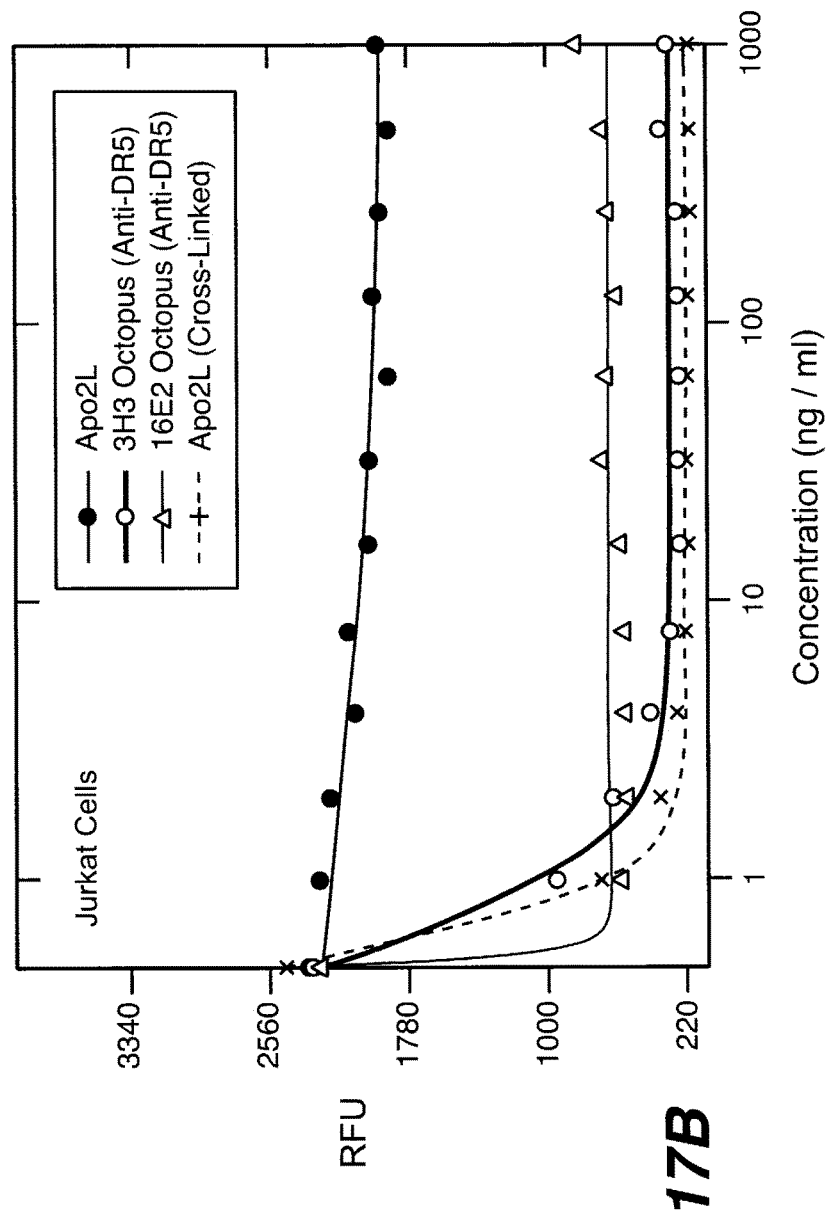

In FIGS. 17A and B, the apoptotic activity of both the 16E2 and 3H3 Octopus antibodies is better than Apo2L on a lung tumor cell line, SK-MES-1 (FIG. 17A), and a T cell tumor line, Jurkat (FIG. 17B). The anti-DR5 Octopus antibodies may be more effective at clustering DR5 on the tumor cell surface than Apo2L.

Figures 1, 18B:
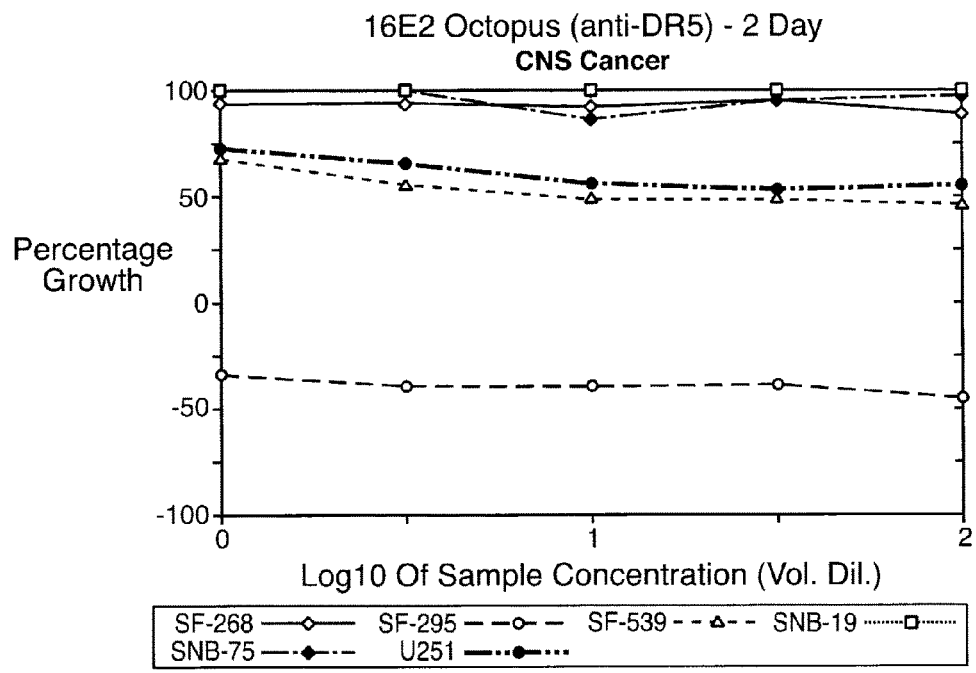
Figures 2, 18B:
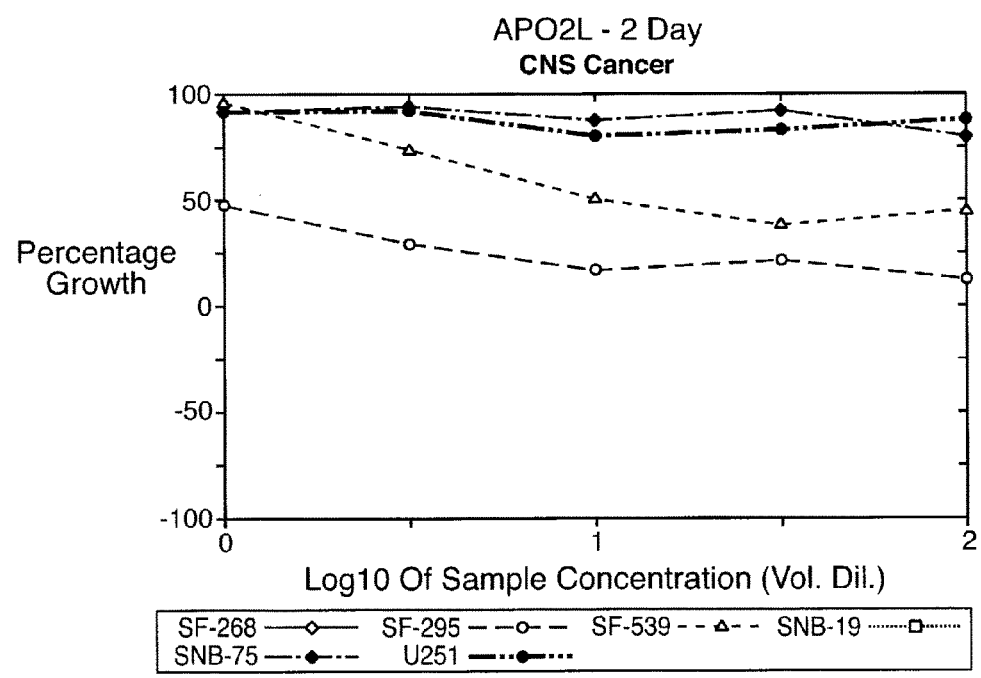
Figures 3, 18B:
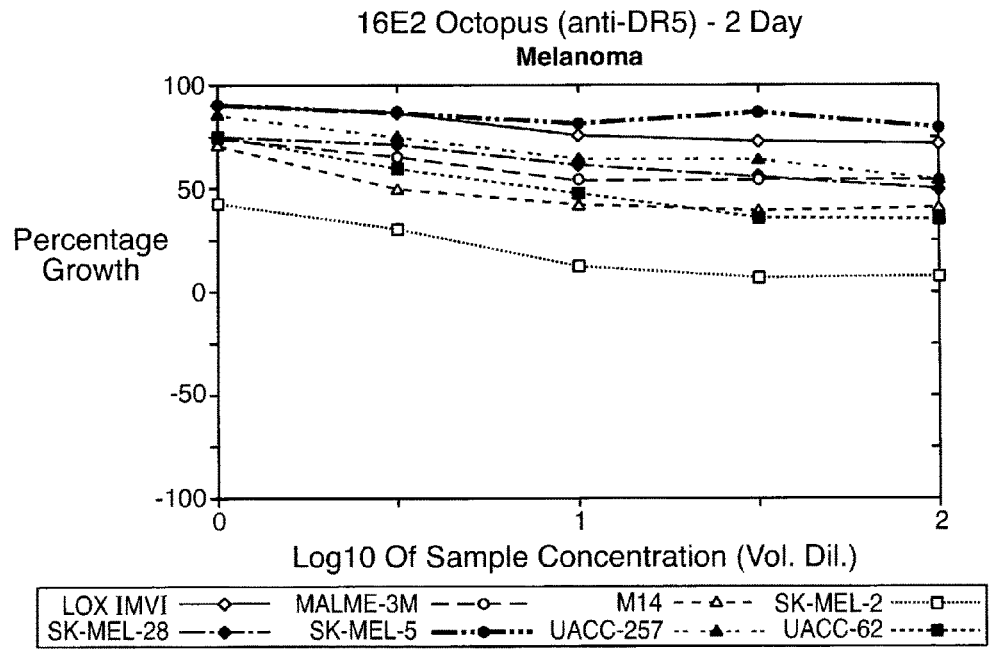
Figures 4, 18B:
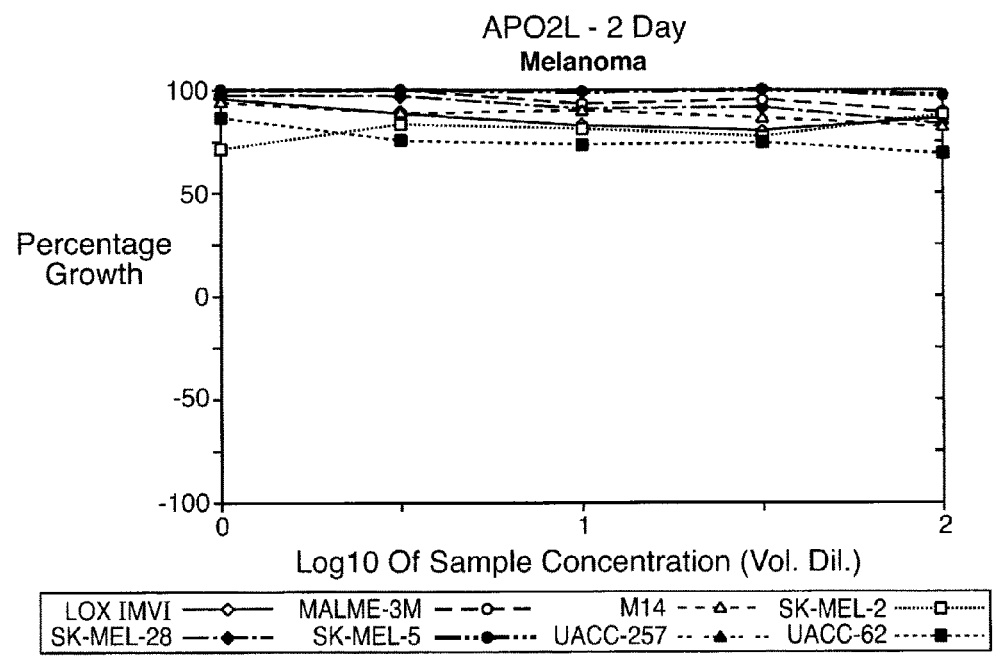
Figures 5, 18B:
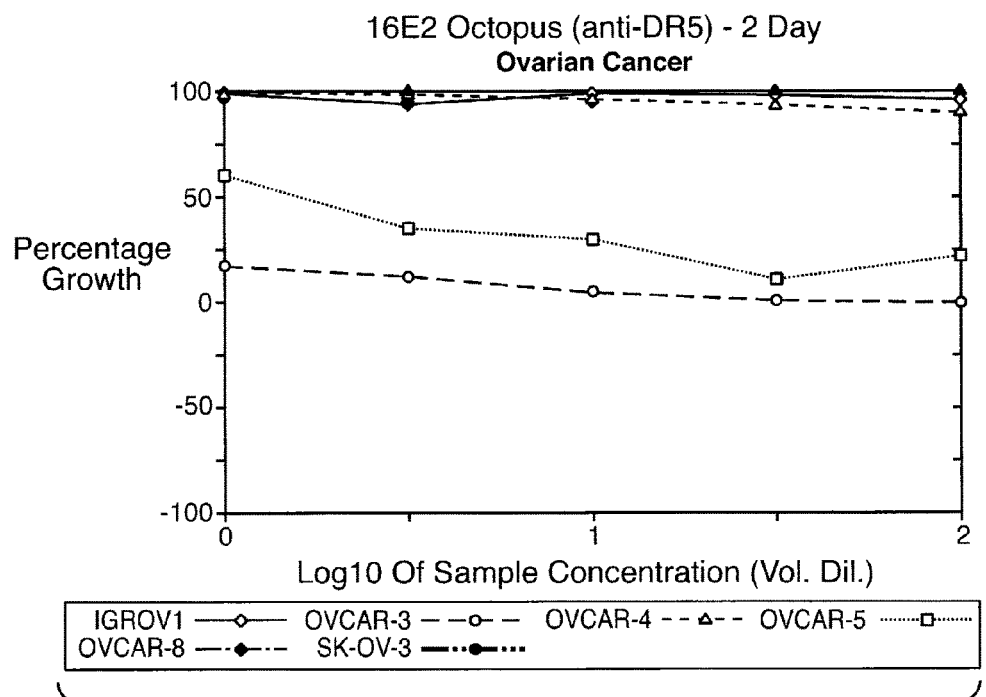
Figures 6, 18B:
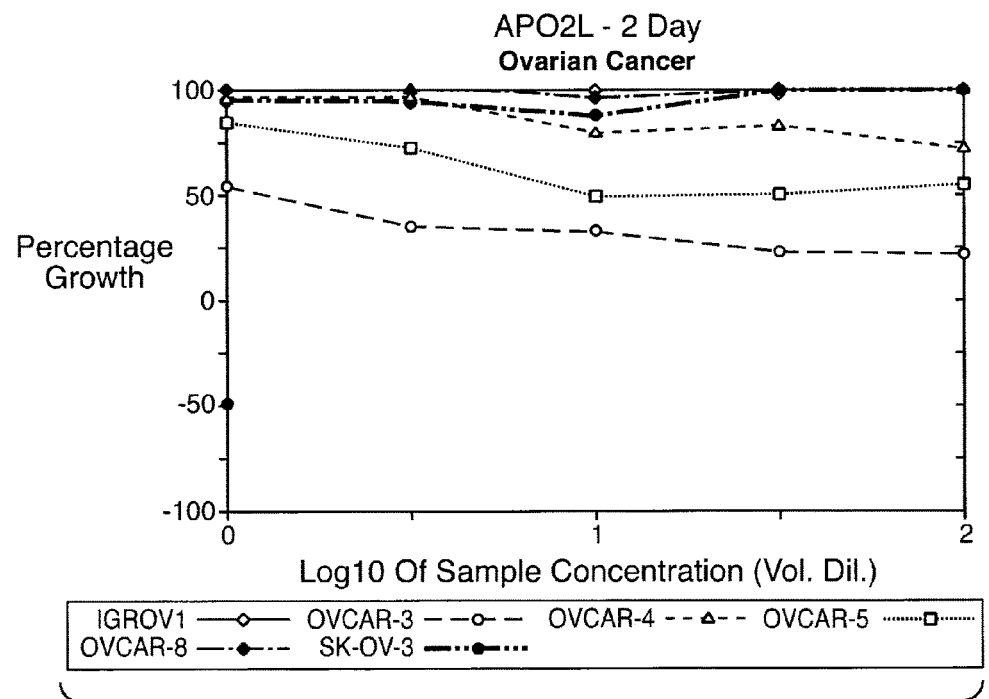
Figures 1, 18C:
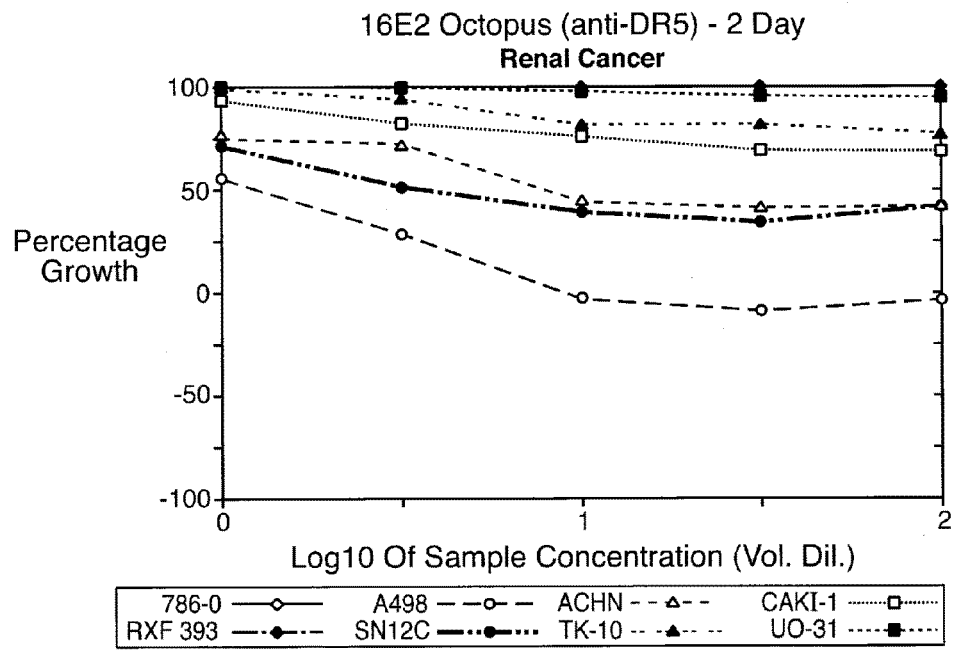
Figures 2, 18C:
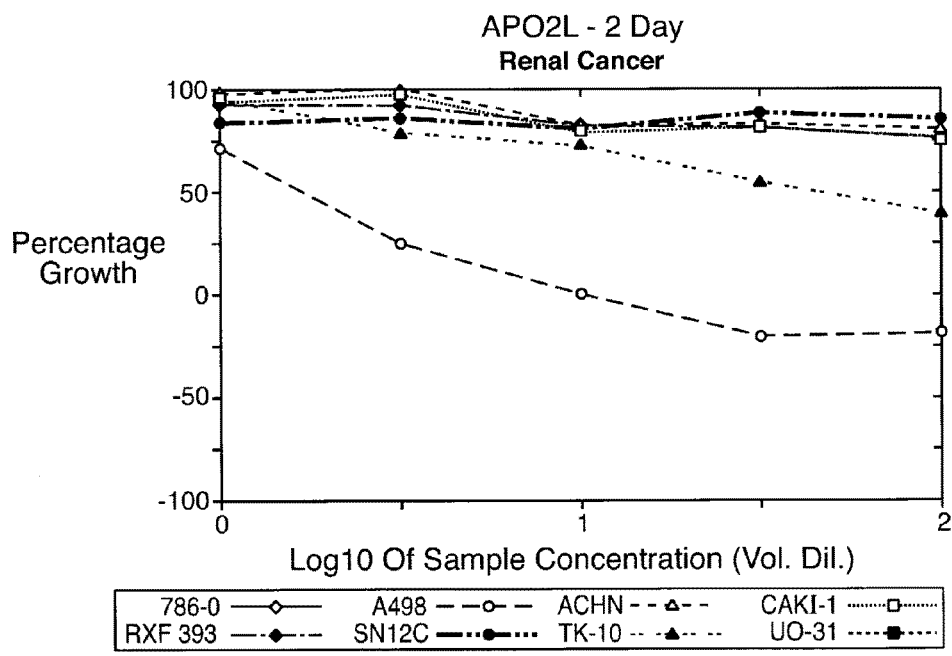
Figures 3, 18C:
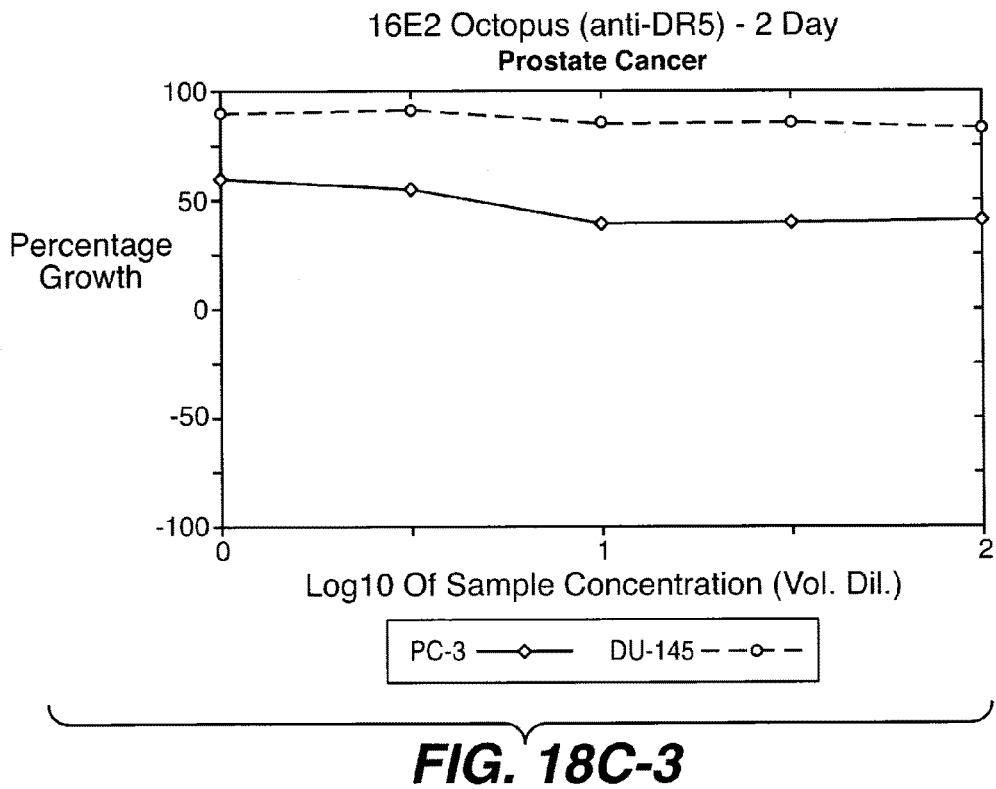
Figures 4, 18C:
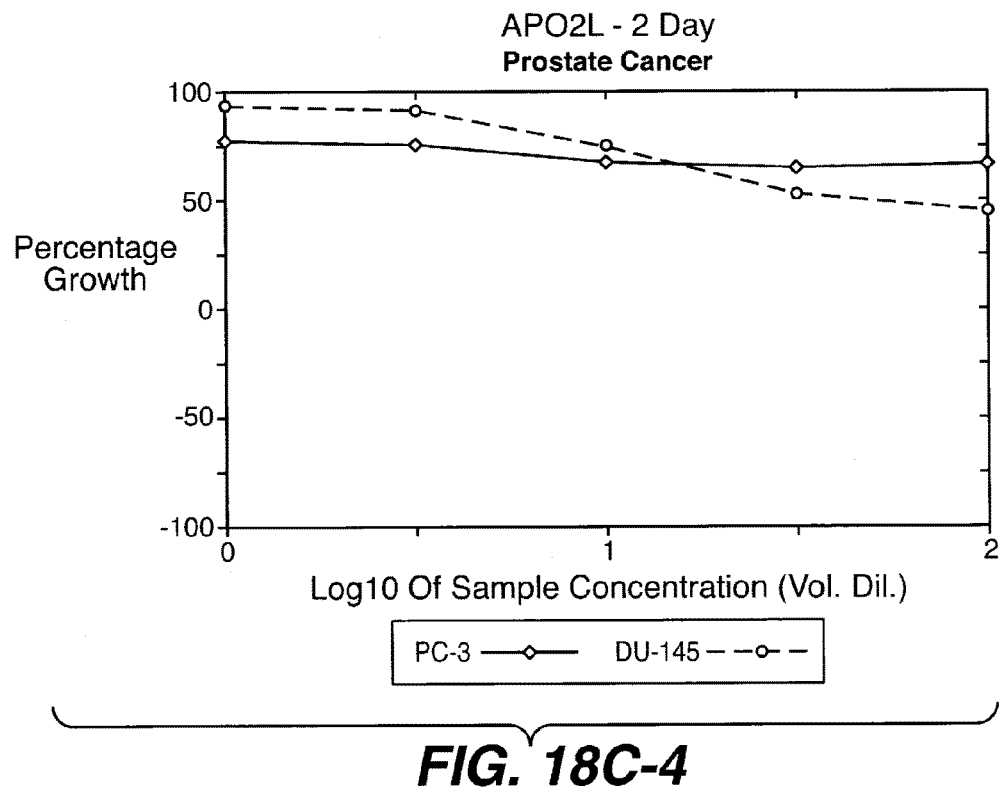
Figures 5, 18C:
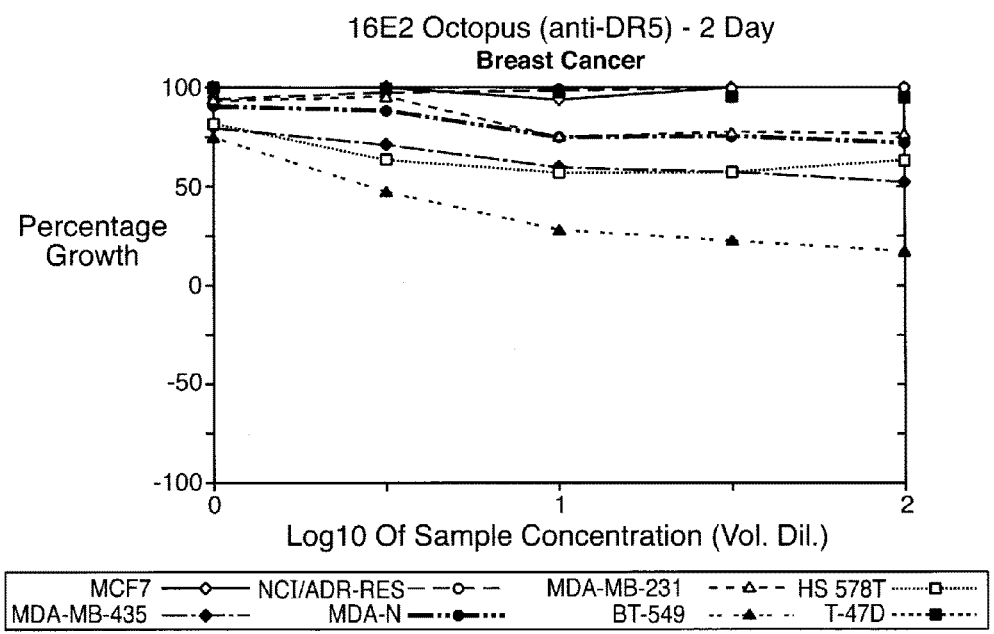
Figures 6, 18C:
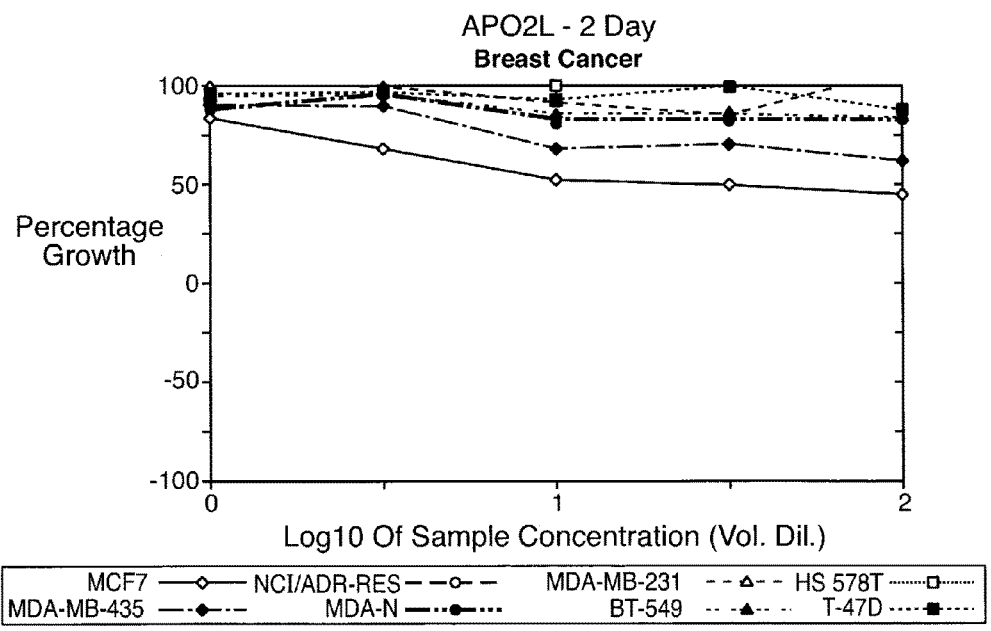
Figures 1, 19A:
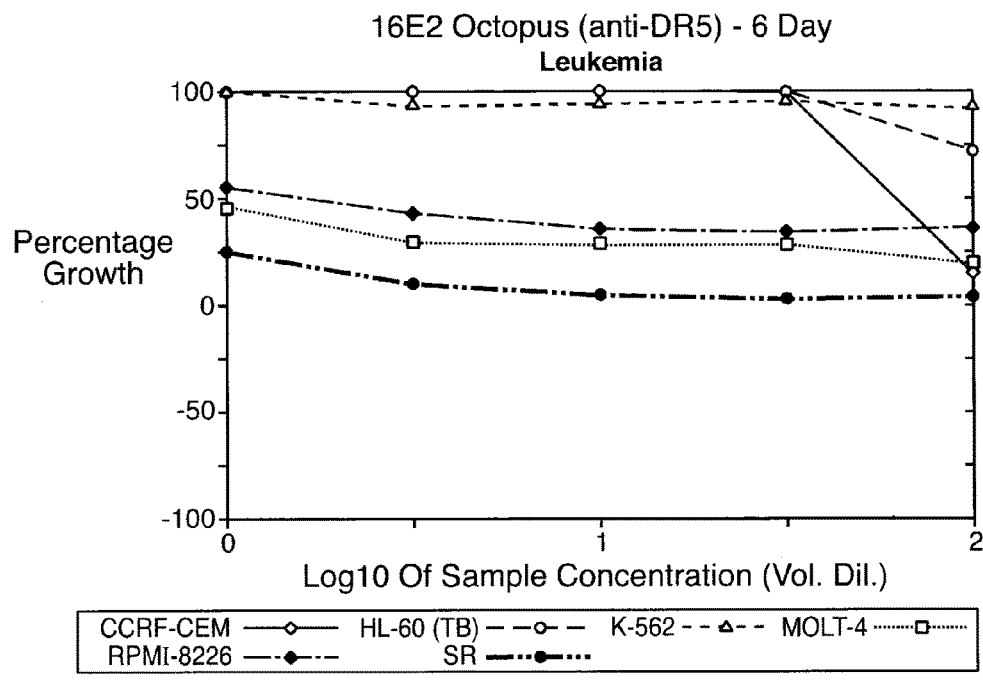
FIGS. 19A-C depict dose response curves that show the effect of the anti-DR516E2 Octopus (upper graphs) compared to Apo2L/TRAIL (lower graphs) on the growth of leukemia, non-small cell lung cancer, colon cancer, central nervous system (CNS) cancer, melanoma, ovarian cancer, renal cancer, prostate cancer and breast cancer human tumor cell lines at 6 days. Results are from the National Cancer Institute Developmental Therapeutics Program. All samples were tested at 5 concentrations, starting at 1% of the stock solution (16E2 Octopus stock 0.2 mg/ml) and 4×0.5 log dilutions.
Figures 2, 19A:
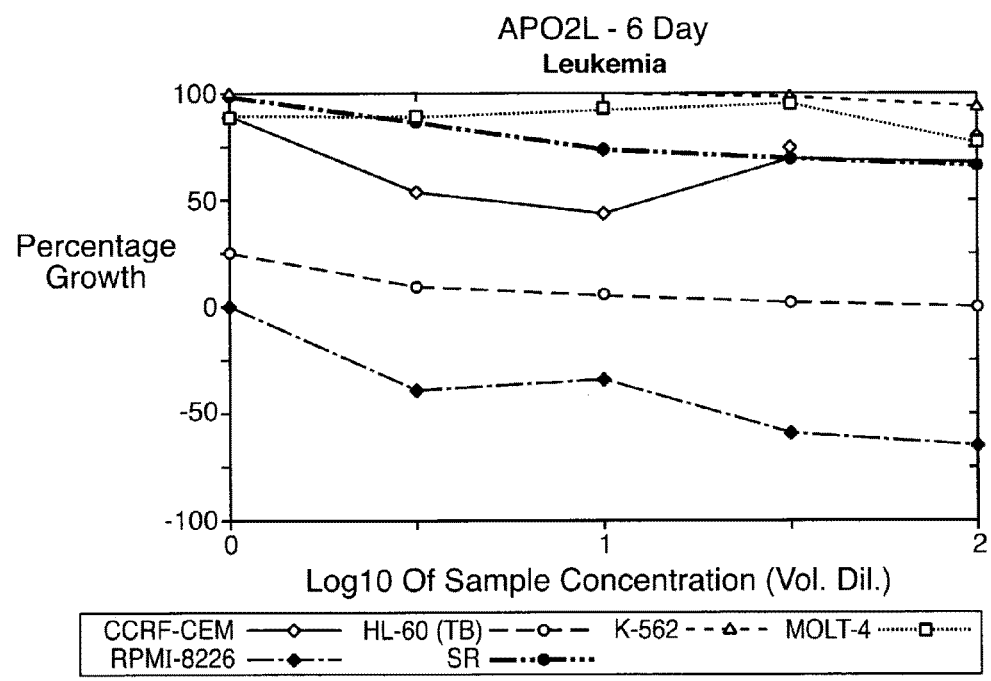
Figures 3, 19A:
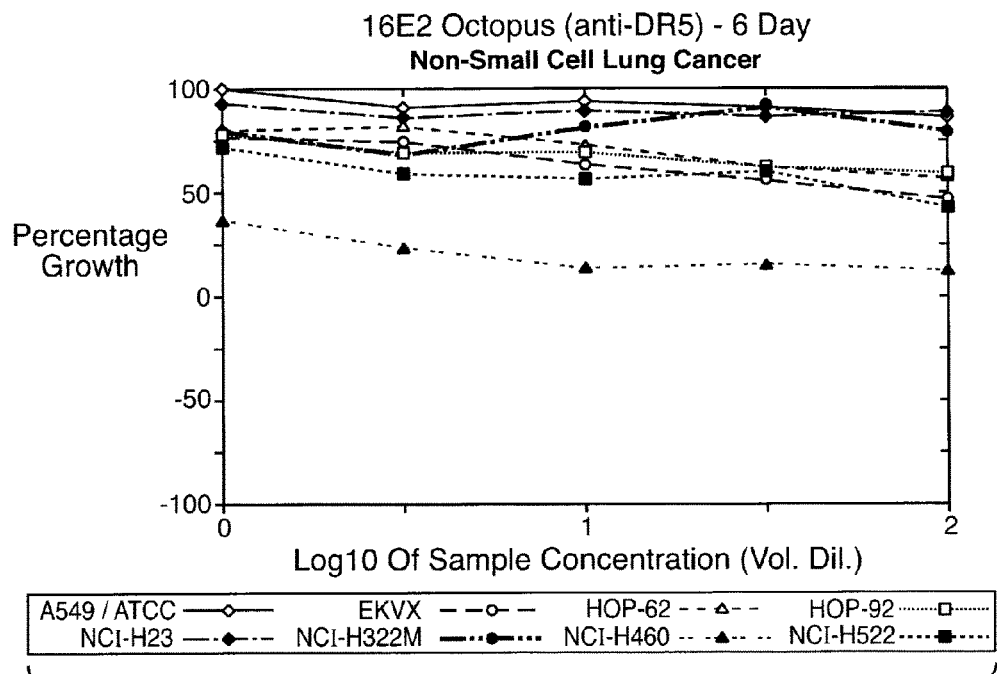
Figures 4, 19A:
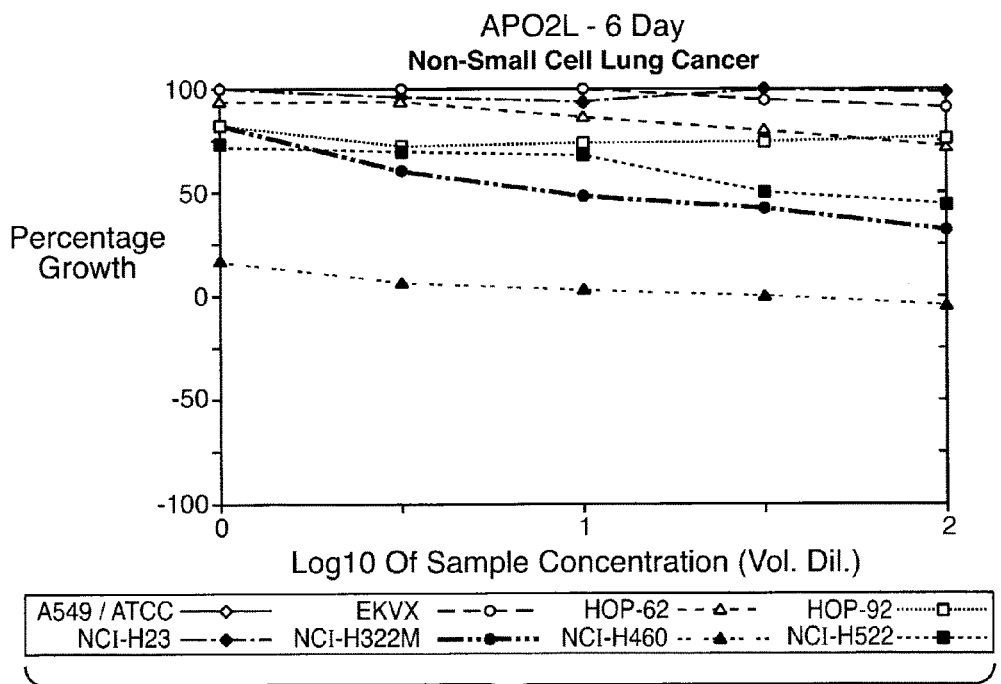
Figures 5, 19A:
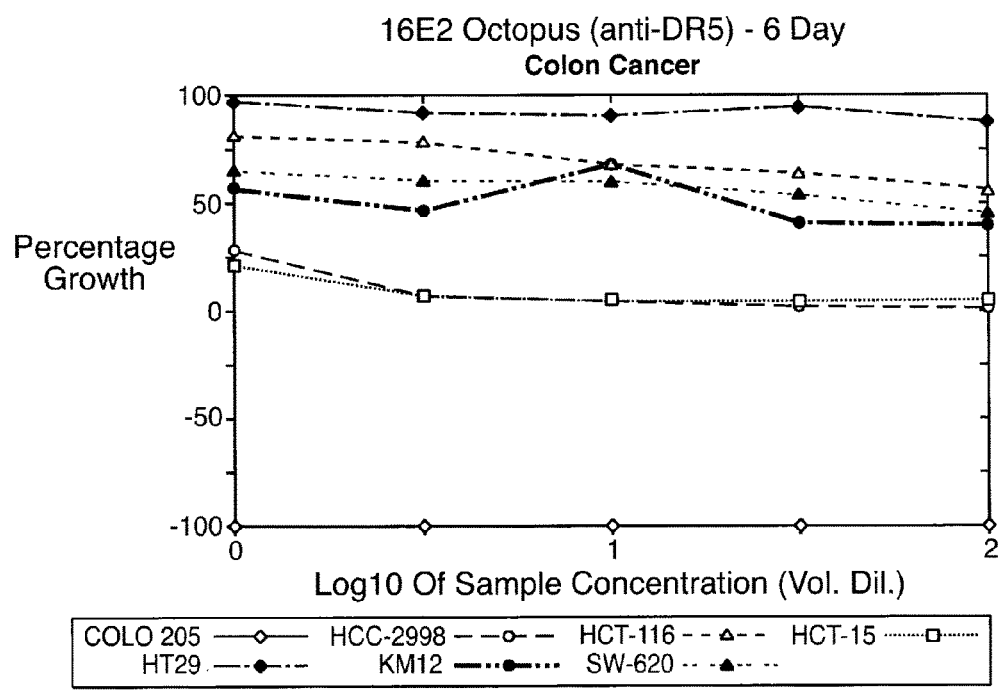
Figures 6, 19A:
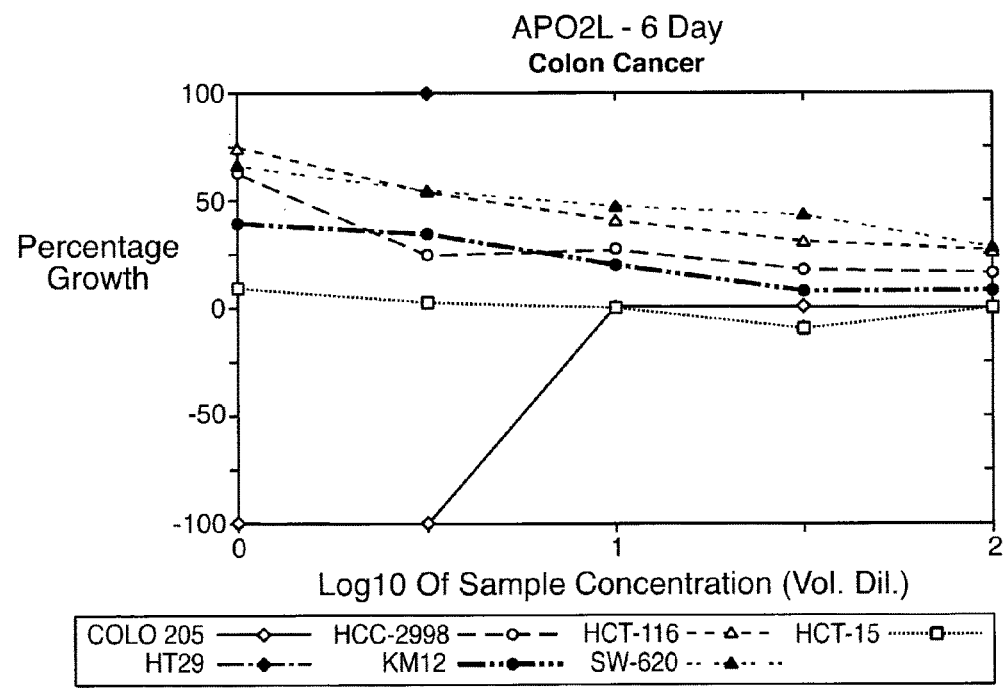
Figures 1, 19B:
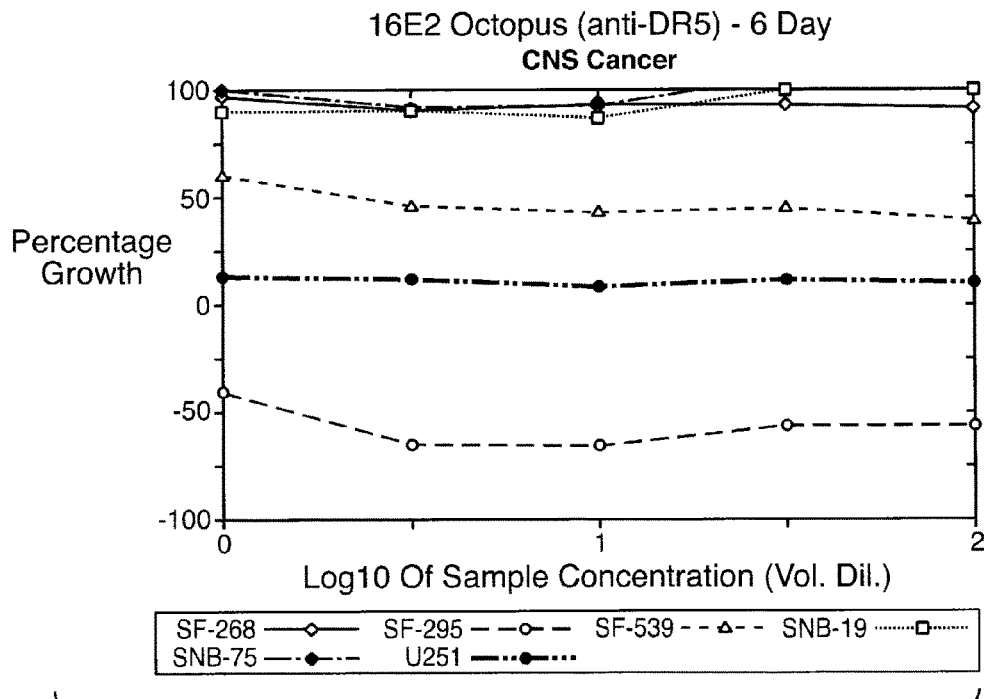
Figures 2, 19B:
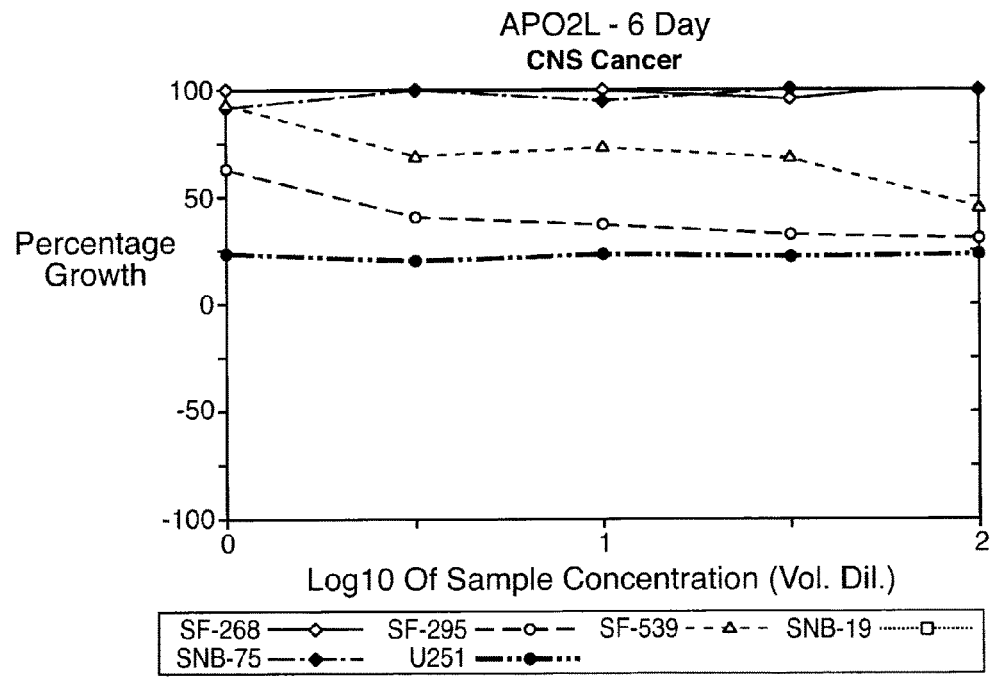
Figures 3, 19B:
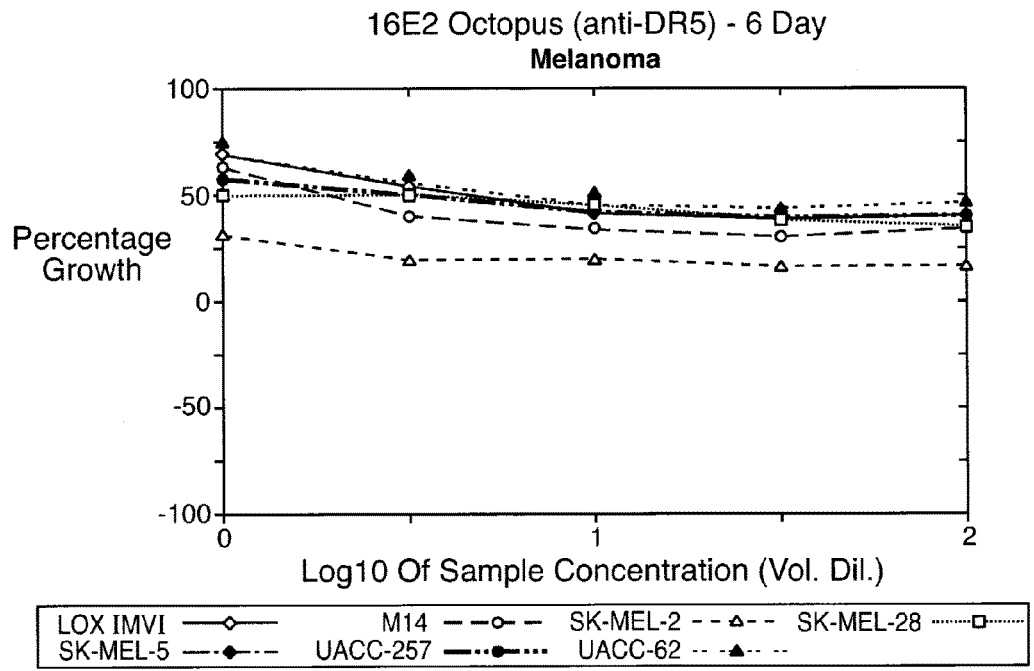
Figures 4, 19B:
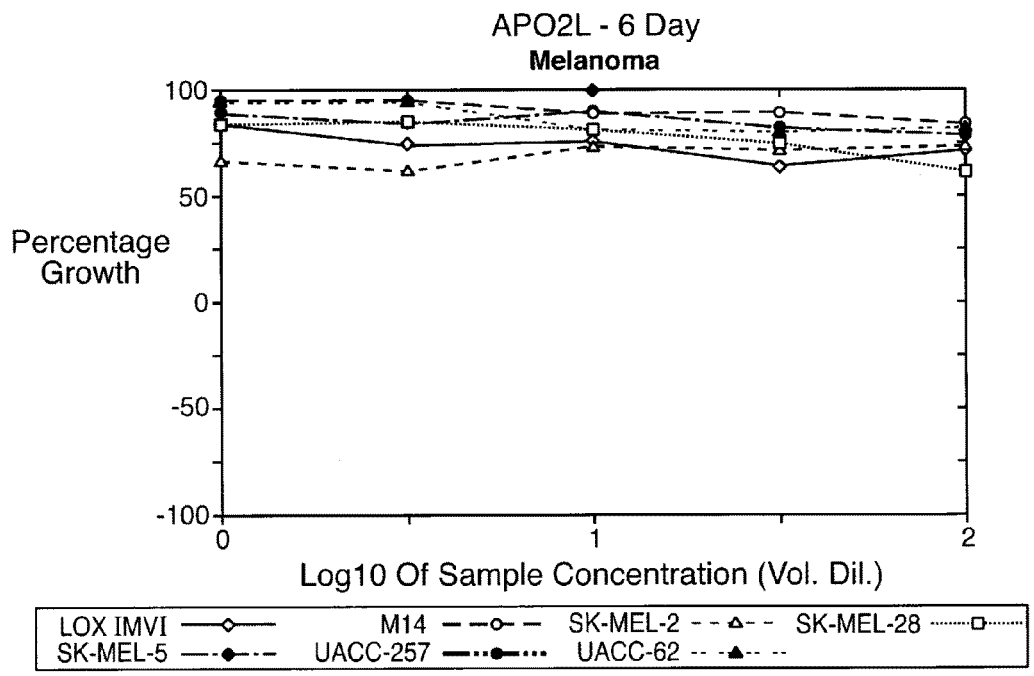
Figures 5, 19B:
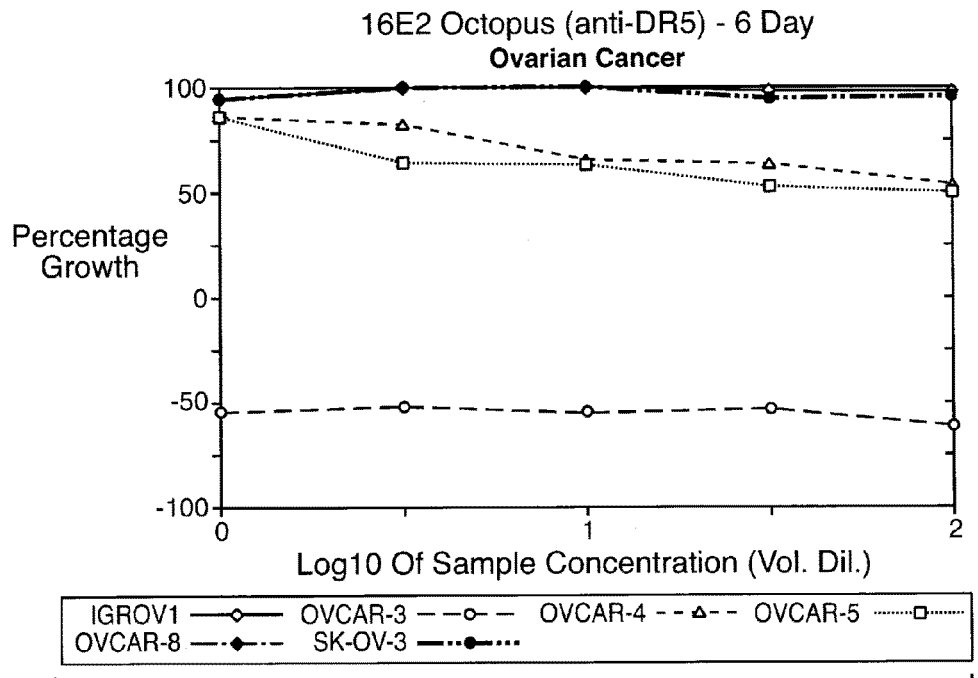
Figures 6, 19B:
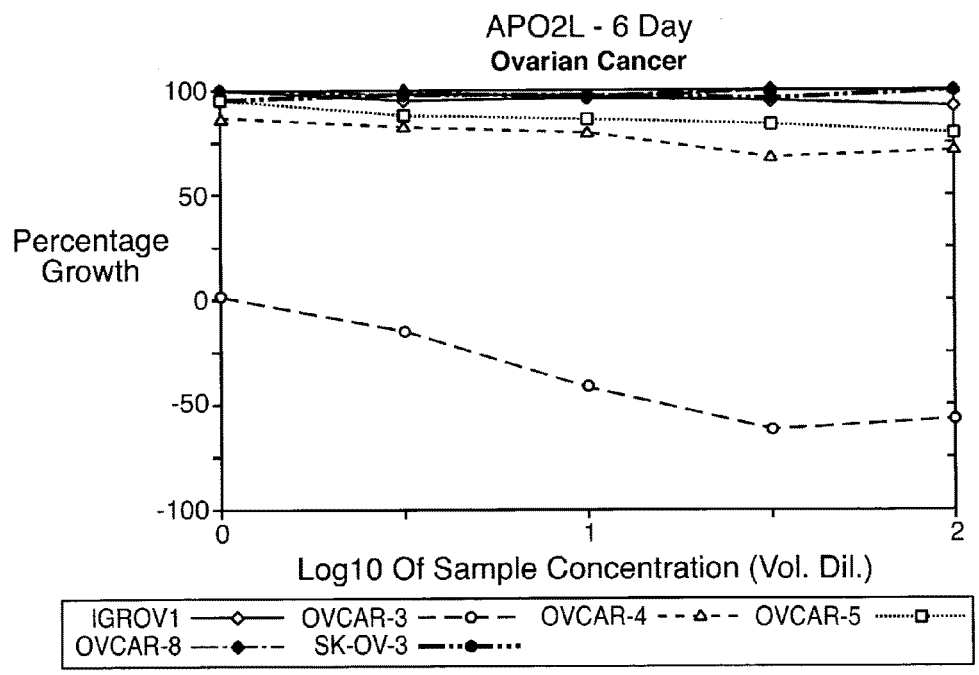
Figures 1, 19C:
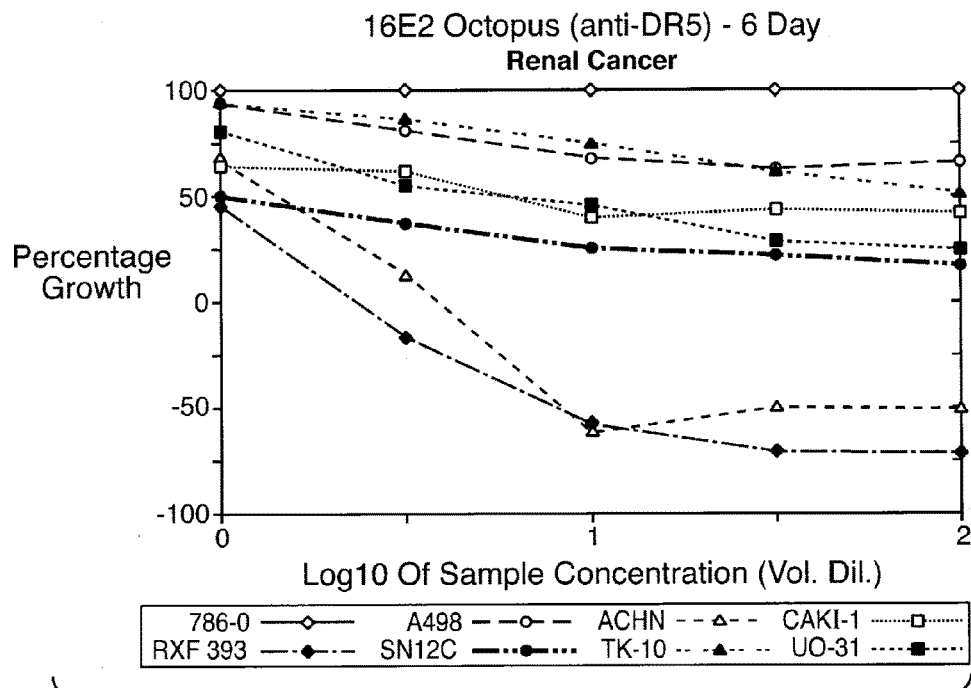
Figures 2, 19C:
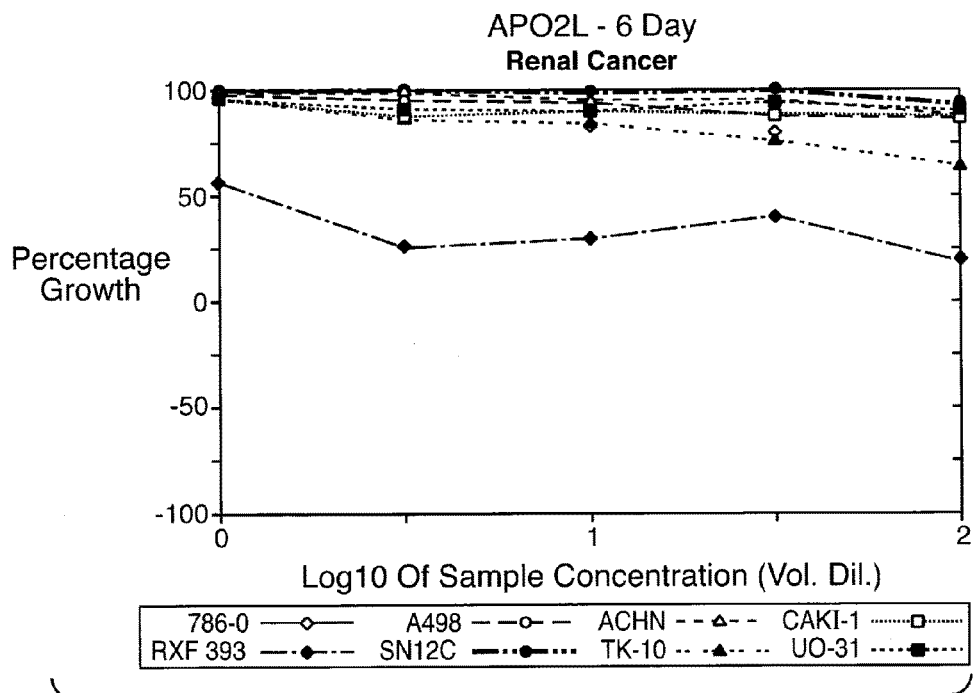
Figures 3, 19C:
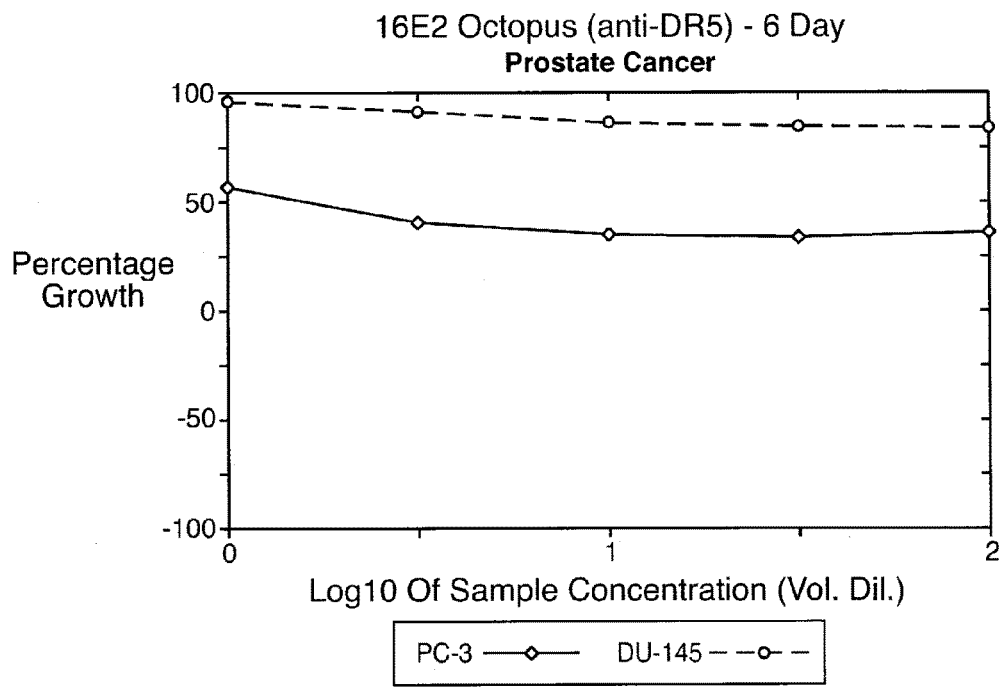
Figures 4, 19C:
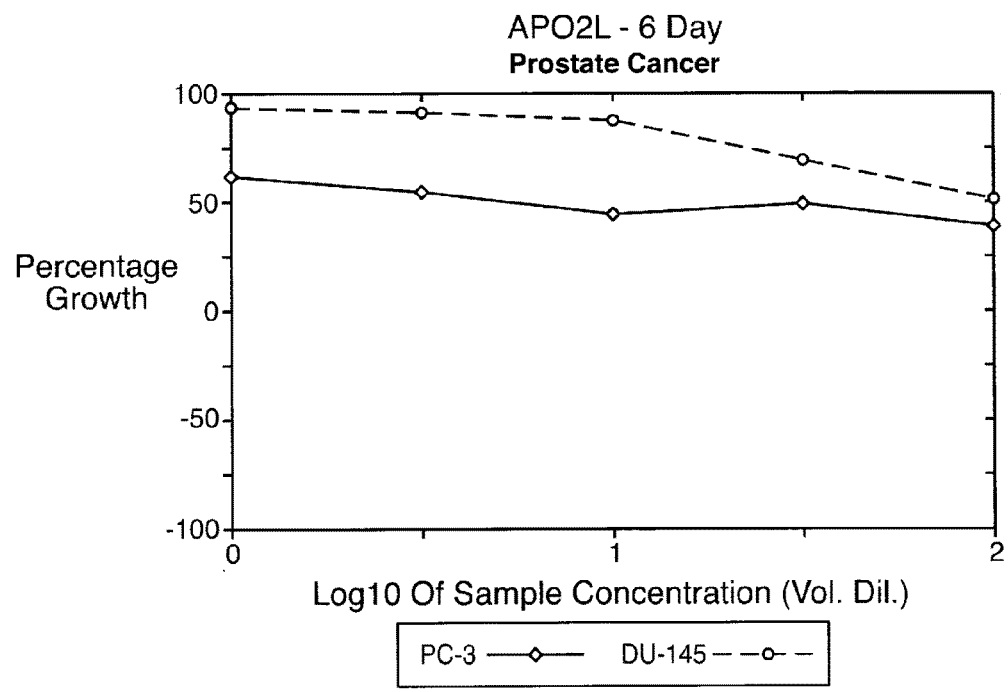
Figures 5, 19C:
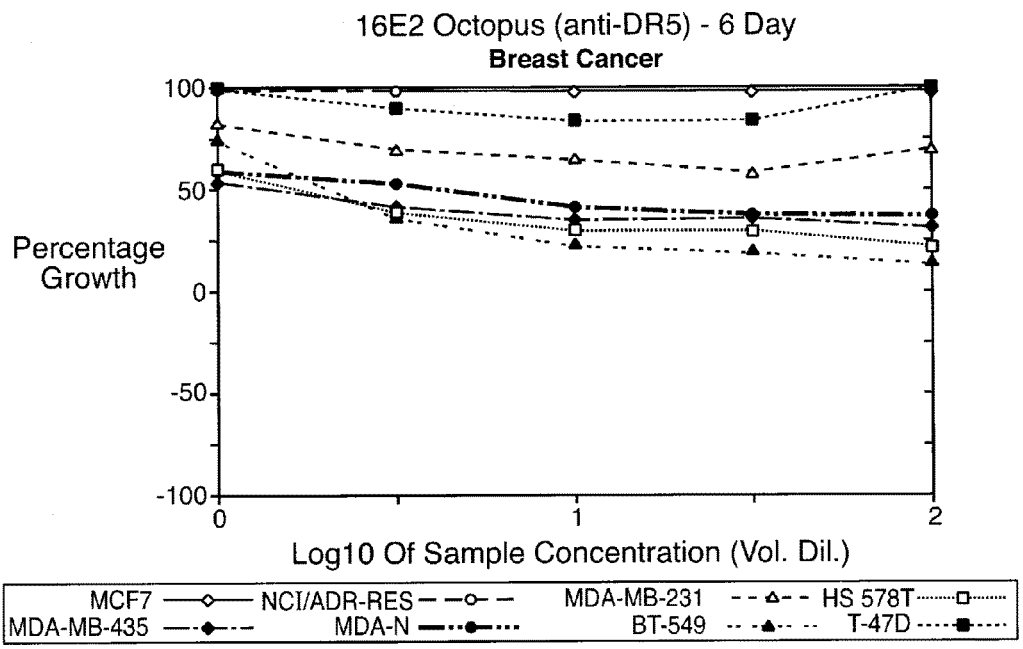
Figures 6, 19C:
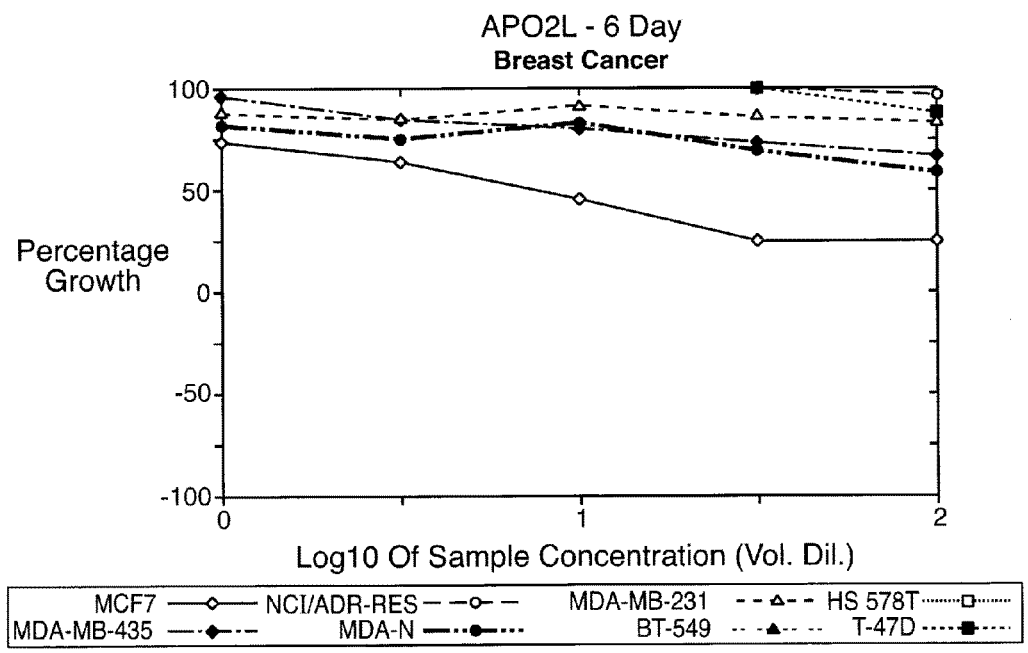

The 16E2 Octopus was analyzed in a 2-day and 6-day screen against the National Cancer Institute (NCI) panel of human tumor cell lines in comparison with the Apo2L. FIGS. 18A-C depict the 2-day dose response curves showing the effects of the 16E2 Octopus and Apo2L on the growth of several human leukemia, non-small cell lung cancer, colon cancer, central nervous system (CNS) cancer, melanoma, ovarian cancer, renal cancer, prostate cancer and breast cancer tumor cell lines, while FIGS. 19A-C show dose response curves from the 6 day screens. Comparable results were observed for 16E2 Octopus and Apo2L against most of the tumor cell lines, again indicating that the anti-DR5 Octopus functions similar to Apo2L. Similar inhibition of the lung and colon cancer cell lines confirmed the previous in vitro and in vivo results from apoptosis assays comparing 16E2 Octopus and Apo2L on cell lines of these cancers. The ability of 16E2 Octopus to kill certain tumor cell lines was unexpected; for example, a CNS cancer cell line, SF-295 (FIG. 19B), as well as two renal cancer cell lines, ACHN and RXF393 (FIG. 19C).

The results of the NCI tumor panel screens are depicted quantitatively in FIGS. 20 A and B (2-day results) and FIGS. 21A and B (6-day results) which summarize the effect of 16E2 Octopus compared to Apo2L on growth inhibition (GI50), stasis (TGI), and toxicity (LC50) of the treated tumor cell lines. Again, these results suggest that 16E2 Octopus may be effective against more types of cancer than previously observed.

EXAMPLE 4

Evaluation of anti-CD20 Octopus Antibody

In an effort to improve the potency of the chimeric anti-CD20 antibody C2B8 (RITUXAN®; U.S. Pat. No. 5,736,137, expressly incorporated herein by reference), one approach being investigated is the ability of the antibody to trigger apoptosis of tumor cells. The apoptosis assay in Koopman et al. *Blood* 84:1415-1420 (1994) was performed. An Octopus anti-CD20 antibody (OctCD20) was prepared by using the C2B8 VL and VH domains in the preparation of an anti-CD20 Octopus antibody. The OctCD20 antibody was expressed in 293 cells and purified via Protein A sepharose chromatograpy as described for the previous examples.

Figure 22:
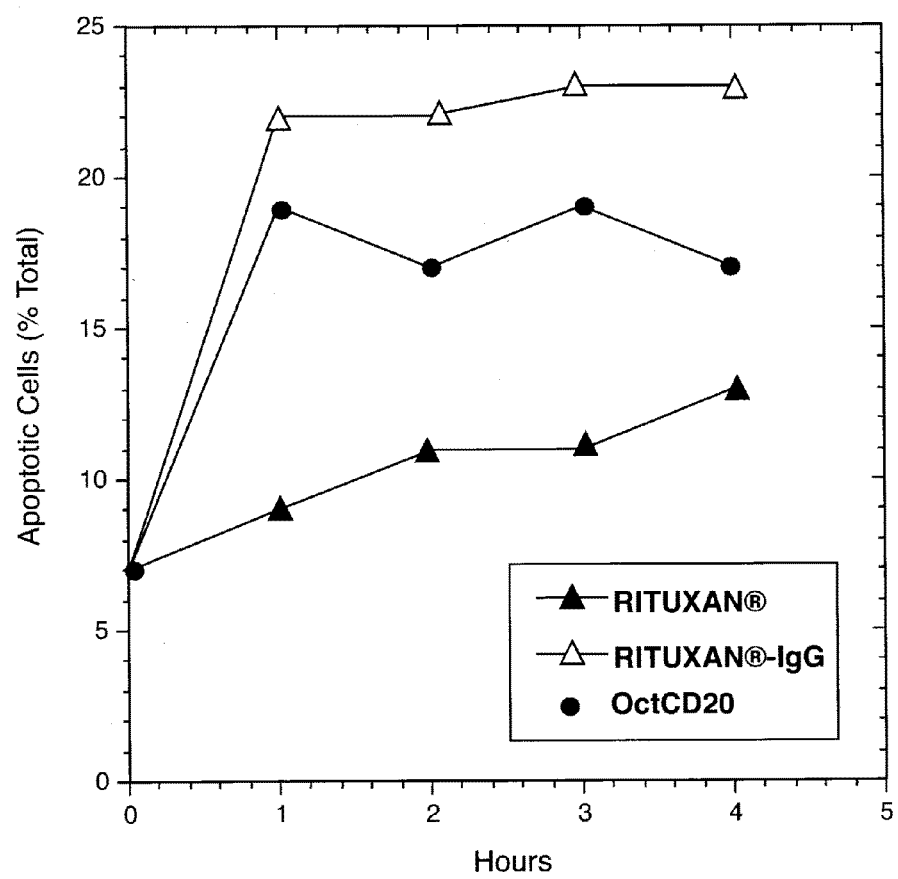
FIG. 22 depicts apoptosis of Wil-2 cells by the anti-CD20 antibody RITUXAN®, RITUXAN® cross-linked with anti-human IgG (RITUXAN®-IgG) and a tetravalent anti-CD20 antibody (OctCD20).

As shown in FIG. 22, RITUXAN® alone does not trigger much apoptosis of a non-Hodgkins lymphoma B cell line, Wil-2, unless it is crosslinked with anti-human IgG (RITUXAN®-IgG). OctCD20, however, is capable of inducing apoptosis in Wil-2 cells independent of crosslinking. The level of apoptosis observed with OctCD20 is lower than that of crosslinked RITUXAN®, however, suggesting that the apoptotic activity of OctCD20 could be improved, perhaps through the use of the flexible linkers.

EXAMPLE 5

Construction of Further Multivalent Antibodies

Figure 23A:
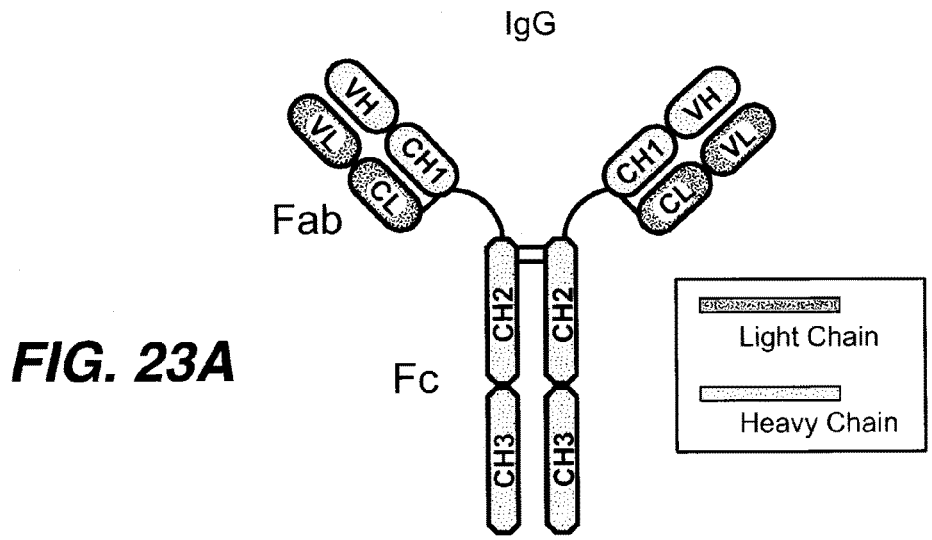
FIGS. 23A-E are cartoons depicting the full-length Octopus/tetravalent antibody (FIG. 23B), the Octopus F(ab')₂ (FIG. 23C), POPoct-3 Fab (FIG. 23D) and POPoct-4 Fab (FIG. 23E) in comparison to the native IgG (FIG. 23A). A representative coomassie stained Tris-Glycine gel of anti-CD20 (C2B8) Octopus proteins compares the sizes of the intact antibodies in non-reducing conditions (FIG. 23F), and of the heavy chains in reducing conditions, under which disulfide bonds are disrupted resulting in separation of the heavy and light chains (FIG. 23G).
Figure 23B:
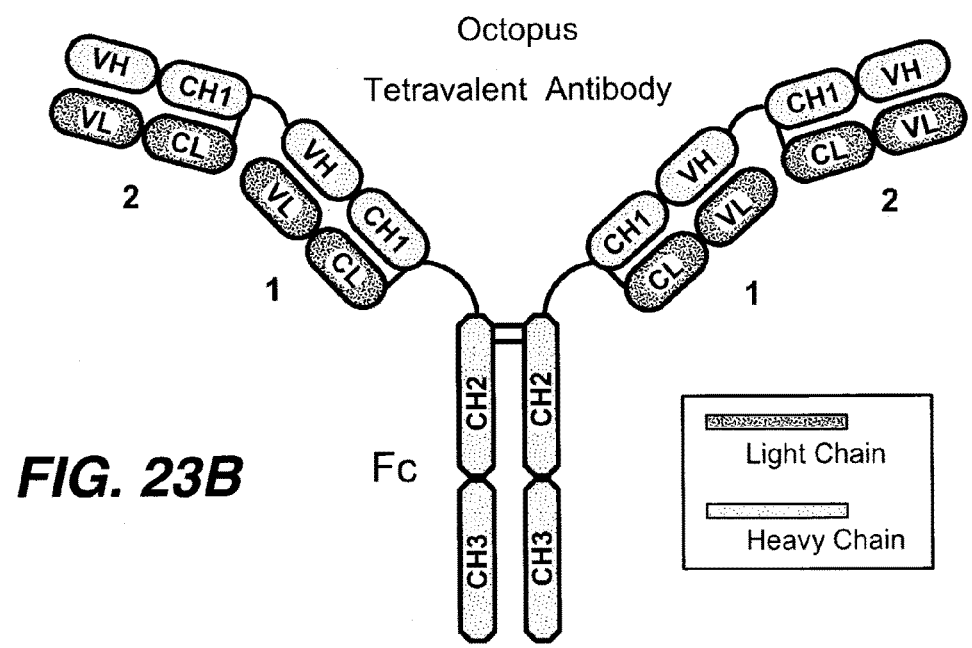
Figure 23C:
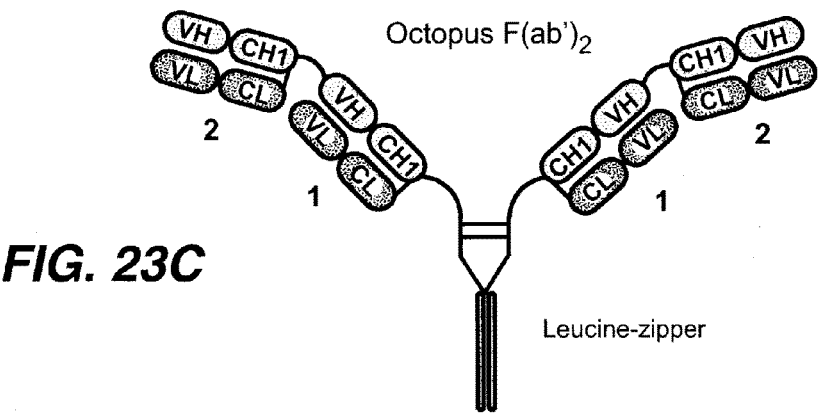
Figure 23D:
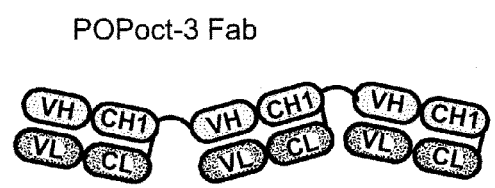
Figure 24:
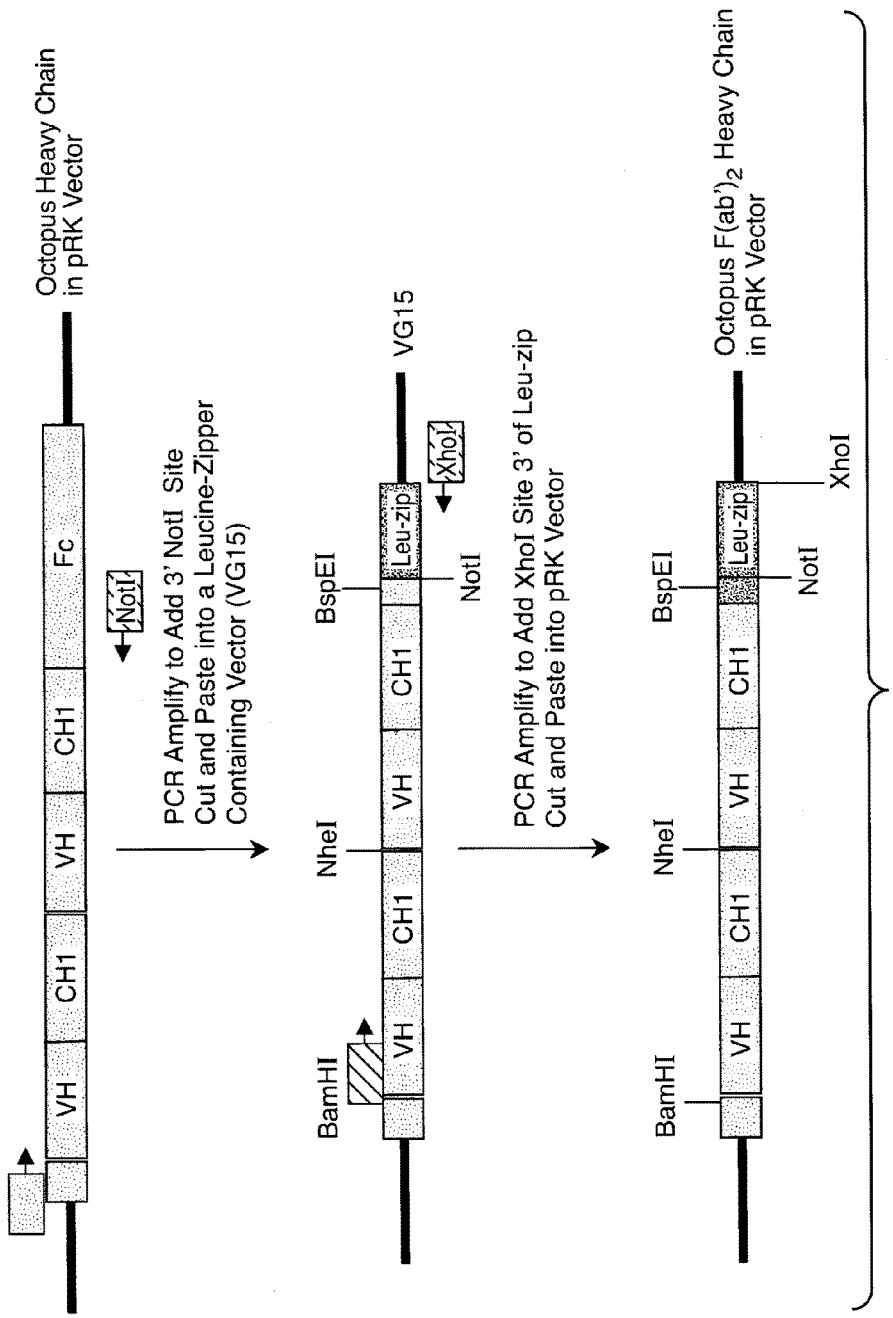
FIG. 24 depicts the construction of the Octopus F(ab')₂ backbone. Any VH/CH1 region can be substituted into the F(ab')₂ backbone via the BamHI, NheI and BspEI restriction enzyme sites.

Versions of the Octopus antibodies of Example 2 (anti-HER2), Example 3 (anti-DR5) and Example 4 (anti-CD20) with an antibody hing region dimerization domain (designated "Octopus F(ab')$_2$" herein) were engineered. The anti-HER2 Octopus F(ab')$_2$ construct was engineered by replacing the Fc region of the heavy chain cDNA with sequence encoding a leucine-zipper motif which, when expressed as protein, dimerizes to effectively join the Octopus Fab arms (FIG. 23C). The octopus F(ab')$_2$ can maintain the leucine zipper motif, or that motif can, e.g., be proteolytically removed as desired. As depicted in FIG. 24, PCR was used to amplify the duplicate VH/CH1 domains and to insert a restriction site onto the end of the Octopus heavy chain cDNA (NotI) to permit in-frame subcloning into a vector (VG15) containing a leucine-zipper motif. PCR was again utilized to add another restriction site downstream of the heavy chain termination codon (XhoI) to allow subcloning into the pRK vector for expression in mammalian cells. The VH/CH1 domains of anti-DR5 Mab16E2 and anti-CD20 Mab C2B8 were substituted into the Oct F(ab)'$_2$ heavy chain backbone using the unique restriction sites BamHI, NheI, and BspEI.

Figure 23E:
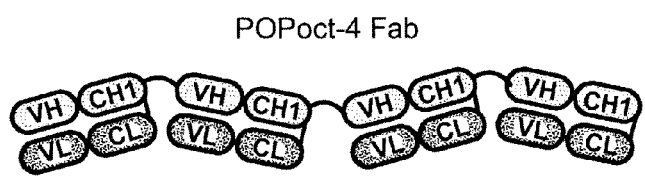

"POPoctopus" antibodies were created by linking together Fab domains in tandem repeats to form linear Fab multimers. "POPoct-3" contains three linked Fab domains (FIG. 23D), while "POPoct-4" has four Fab repeats (FIG. 23E). Anti-HER2 (rhuMab 4D5), anti-DR5 (16E2), and anti-CD20 (C2B8) POPoct-3 constructs were generated, as were anti- HER2 (rhuMab 4D5) and anti-DR5 (16E2) POPoct-4 constructs. POPoct-3 antibodies were engineered both with and without flex 1 linkers.

Figure 25:
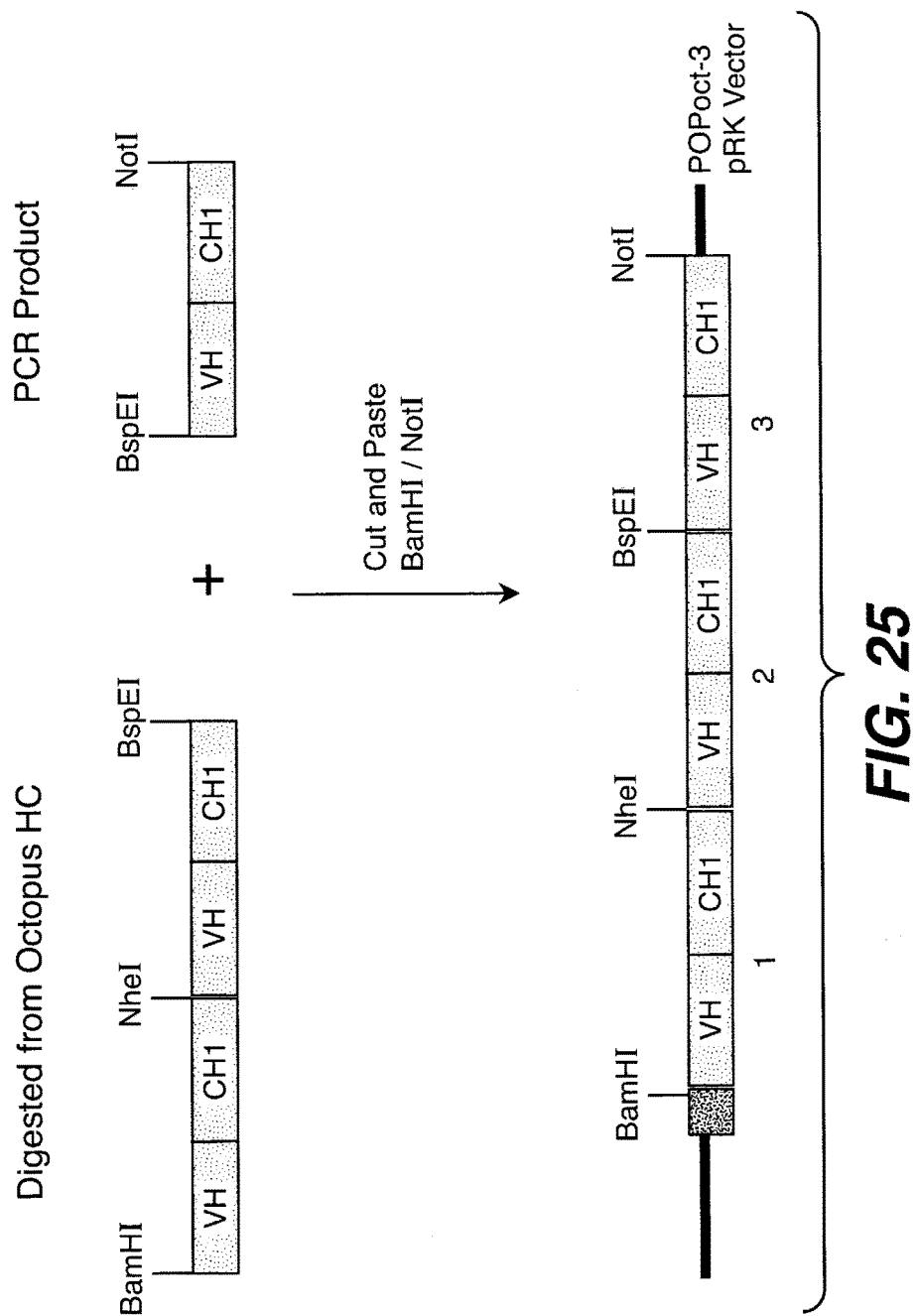
FIG. 25 depicts the construction of the POPoct-3 heavy chain.

FIG. 25 depicts the construction of the POPoct-3 heavy chain cDNA. PCR was used to amplify the VH/CH1 domain adding a 5'-BspEI site and a 3'-NotI site. This sequence was digested and along with BamHI/BspEI digested Octopus heavy chain, ligated into a pRK vector to yield an Octopus heavy chain containing sequence for three VH/CH1 domains. The BspEI site encodes for a serine and a glycine residue.

Figure 26:
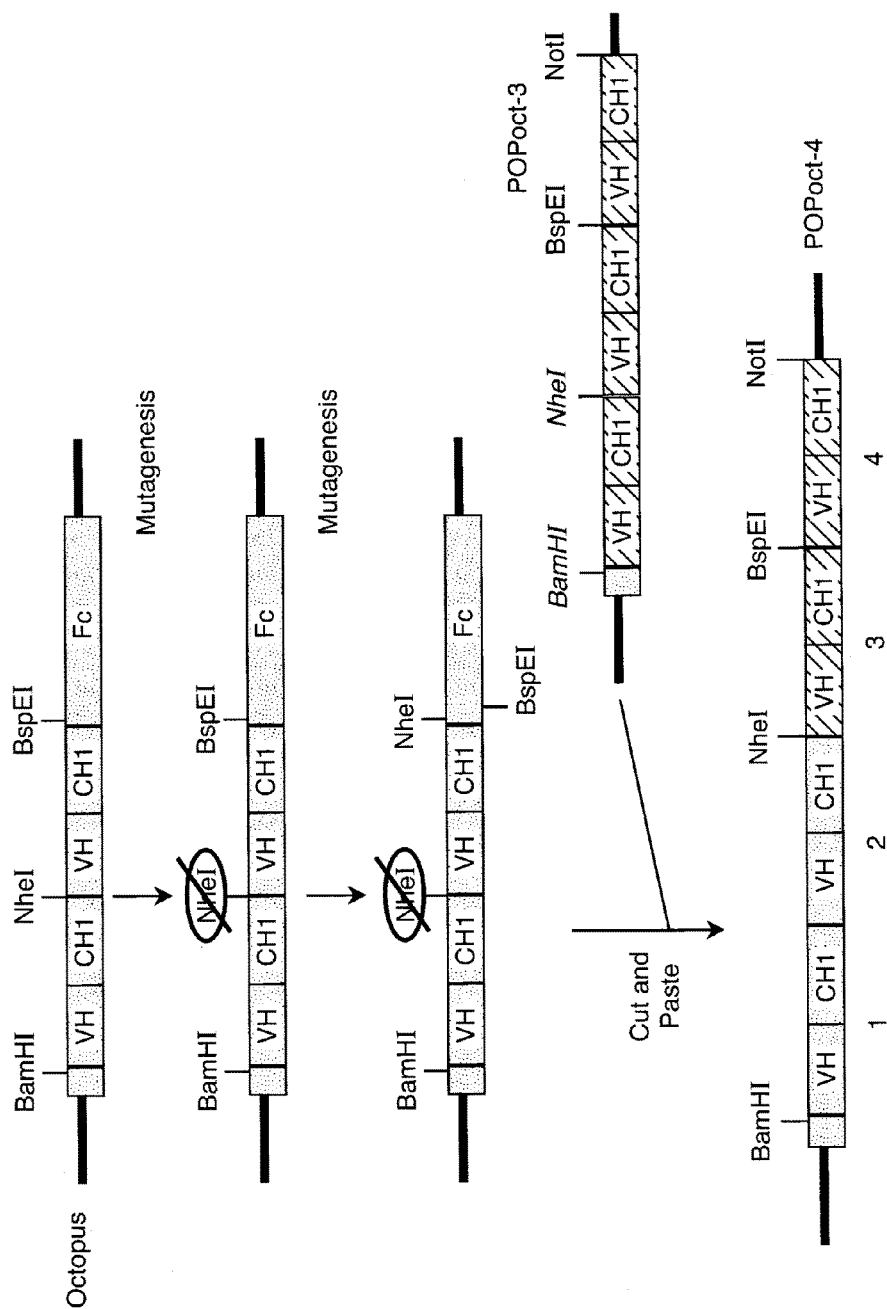
FIG. 26 depicts the construction of the POPoct-4 heavy chain.

To engineer the POPoct-4 antibody (FIG. 26), site-directed oligomutagenesis was used to introduce a silent mutation, resulting in the elimination of the NheI restriction site in-between the duplicate VH/CH1 domains on the Octopus heavy chain cDNA. Oligomutagenesis was again employed to add a NheI restriction site immediately downstream of the second VH/CH1 sequence. This cDNA along with the POPoct-3 construct were digested with BamHI/NheI restriction endonucleases, and ligated together with the pRK vector to produce a heavy chain cDNA containing sequence for four VH/CH1 domains.

The different Octopus heavy chains were transiently cotransfected with the appropriate light chain cDNAs into 293 mammalian cells to express antibodies containing either three Fab domains (POPoct-3 Fab) or four Fab domains (full-length Octopus; Octopus F(ab)'$_2$; POPoct-4 Fab). While native IgG Mabs and full-length Octopus antibodies were purified over Protein A sepharose, Octopus F(ab)'$_2$ and POPoct-3 and -4 were purified over Protein G sepharose columns.

Figures 23F, 23G:
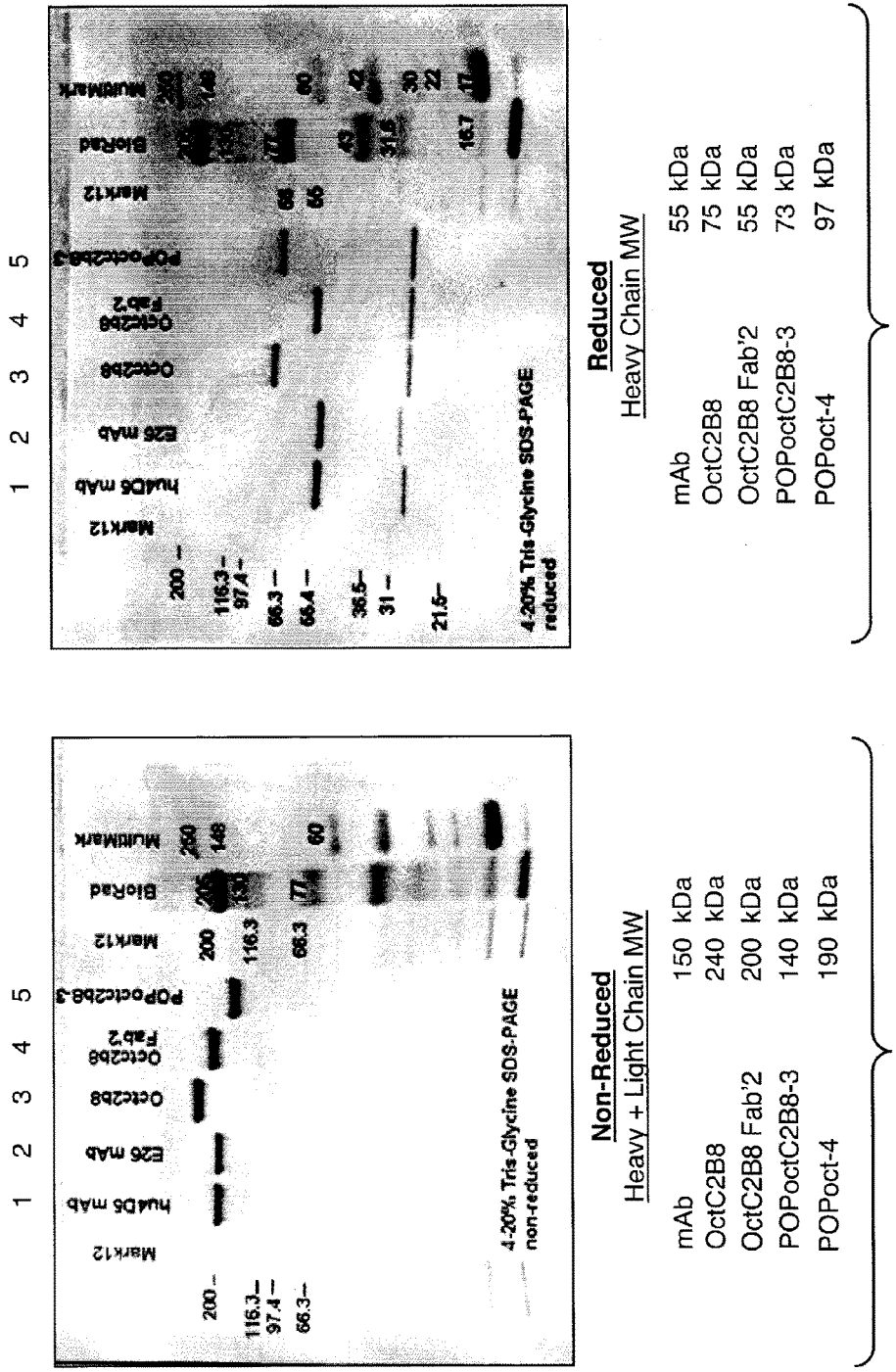

The Octopus F(ab)'$_2$ is approximately 200 kDa (FIG. 23F, lane 4), smaller than the 240 kDa of the full-length Octopus antibody (FIG. 23F, lane 3), but larger than the 150 kDa native IgG Mab (FIG. 23F, lanes 1 and 2). At approximately 140 kDa (FIG. 23F, lane 5), POPoct-3 is slightly smaller than native IgG Mab, while POPoct-4 is slightly larger at 190 kDa. The heavy chain of the Octopus F(ab)'$_2$ (FIG. 23G, lane 4) is approximately the same size as the native IgG Mab heavy chain (FIG. 23G, lanes 1 and 2) at 55 kDa. The POPoct-3 heavy chain (FIG. 23G, lane 5) is similar in size to the full-length Octopus heavy chain (FIG. 23G, lane 3), while at approximately 97 kDa the POPoct-4 has the largest heavy chain

EXAMPLE 6

Evaluation of Anti-HER2 Multivalent Antibodies

Figure 27:
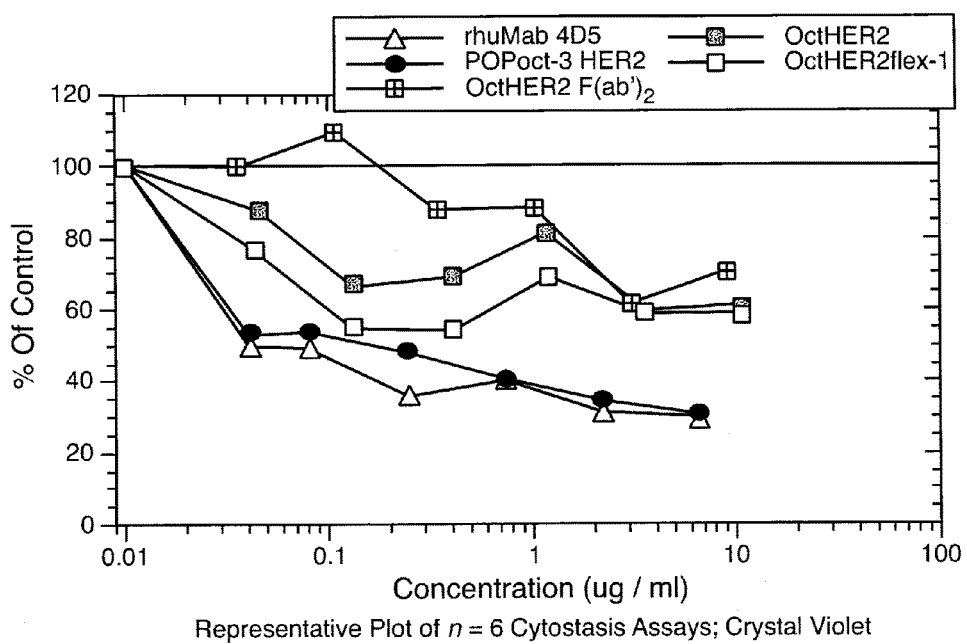
FIG. 27 depicts the activity of multivalent anti-HER2 antibodies in cytostasis assays using BT474 cells.

Antiproliferation Assays: OctHER F(ab)'$_2$, POPoct-3 HER2, OctHER2, OctHER2 flex 1, and rhuMAb 4D5 (HERCEPTIN®) were added to the 3+ HER2 over-expressing tumor cell line, BT474, at equimolar concentrations and evaluated for their ability to inhibit cell growth as measured by crystal violet staining. The results of these assays are shown in FIG. 27. Although all of the antibodies induced some cytostasis of the BT474 cells, POPoct-3HER2 and rhuMAb 4D5 showed the most efficacy and inhibited growth equivalently, while OctHER2 F(ab)'$_2$ lost potency rapidly as its concentration decreased. OctHER2 flex1 demonstrated a slight but consistent improvement over OctHER2 (n=6), suggesting that improved flexibility may result in better access of the Fab to the HER2 target.

Figure 28A:
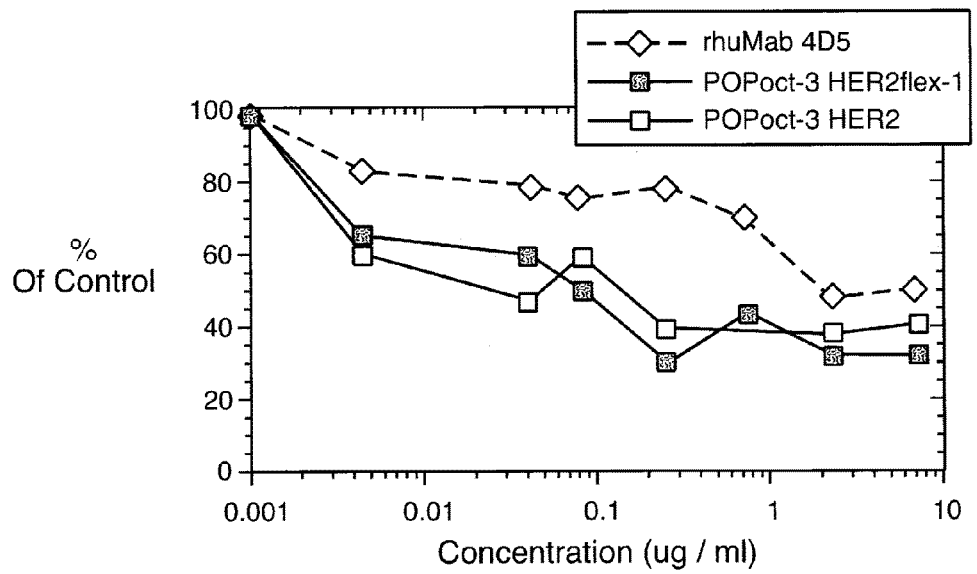
FIGS. 28A-B depict the activity of multivalent anti-HER2 antibodies in cytostasis assays using SKBR3 cells. The figures are representative plots of n=4 cytostasis assays.
Figure 28B:
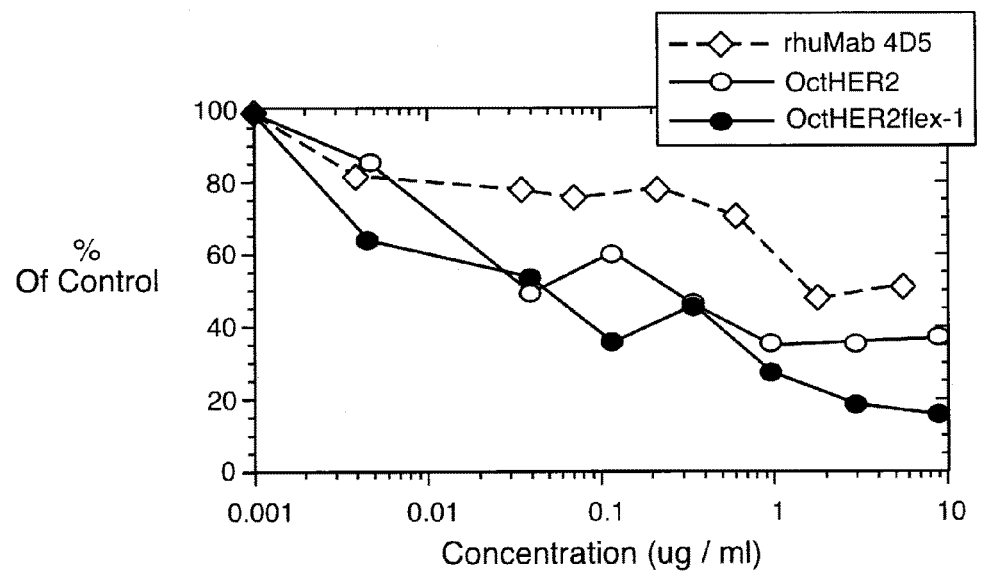

OctHER2, OctHER2 flex-1, POPoct-3HER2, POPoct-3HER2 flex-1 and rhuMAb 4D5 (HERCEPTIN®) were also evaluated at equimolar concentrations on another 3+ HER2 over-expressing cell line, SKBR3, in crystal violet cytostasis assays. The results of this assay are depicted in FIG. 28. On this cell line, all Octopus constructs tested inhibited cell growth equivalently, and better than rhuMab 4D5 (n=4). Any improvement in efficacy due to the flexible-linker in between the Fab arms of OctHER2 or POPoct-3 was less evident on this cell line.

Figure 29A:
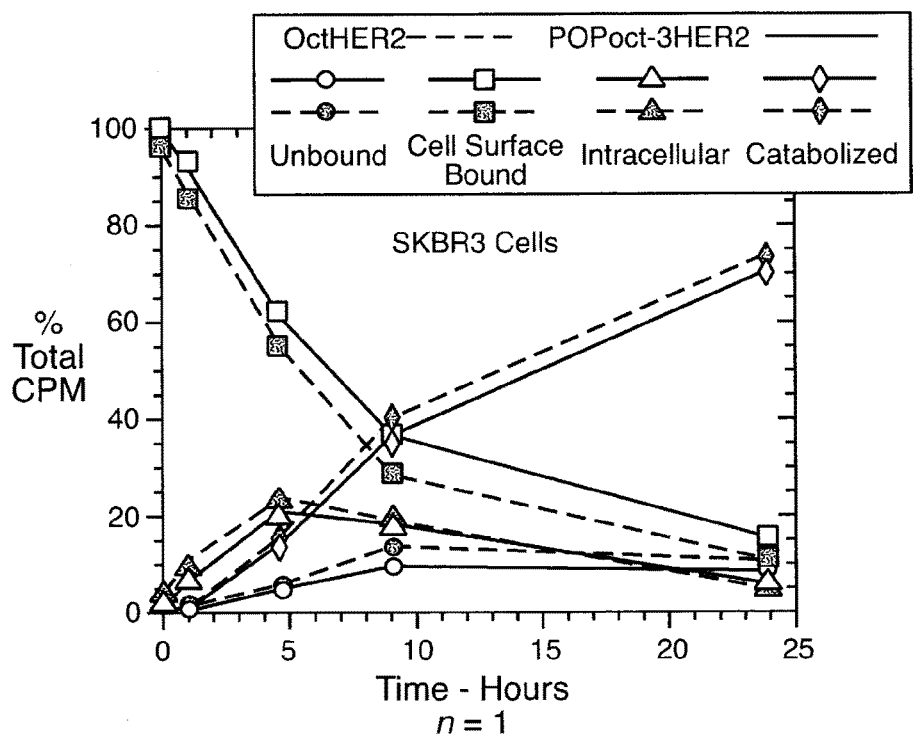
FIGS. 29A-B show internalization capability of multivalent anti-HER2 antibodies in SKBR3 cells (FIG. 29A) and BT474 cells (FIG. 29B).
Figure 29B:
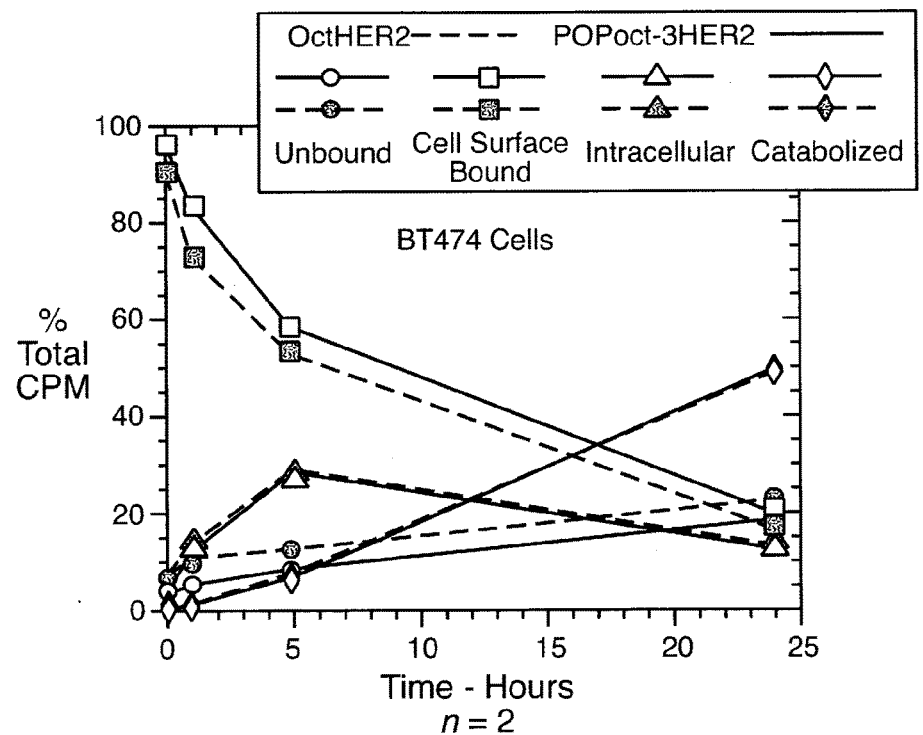

Internalization Assays: POPoct-3HER2 was compared to OctHER and HERCEPTIN® in internalization assays on two 3+ HER2 over-expressing tumor cell lines, SKBR3 and BT474, to assess its candidacy for applications in immunotoxin therapies. Although structurally different than the full-length OctHER2 antibody, POPoct-3HER2 was internalized and catabolized identically to OctHER2 by both cell lines (FIGS. 29A and B) and at twice the rate of HERCEPTIN®.

EXAMPLE 7

Evaluation of Anti-DR5 Multivalent Antibodies

Figure 30A:
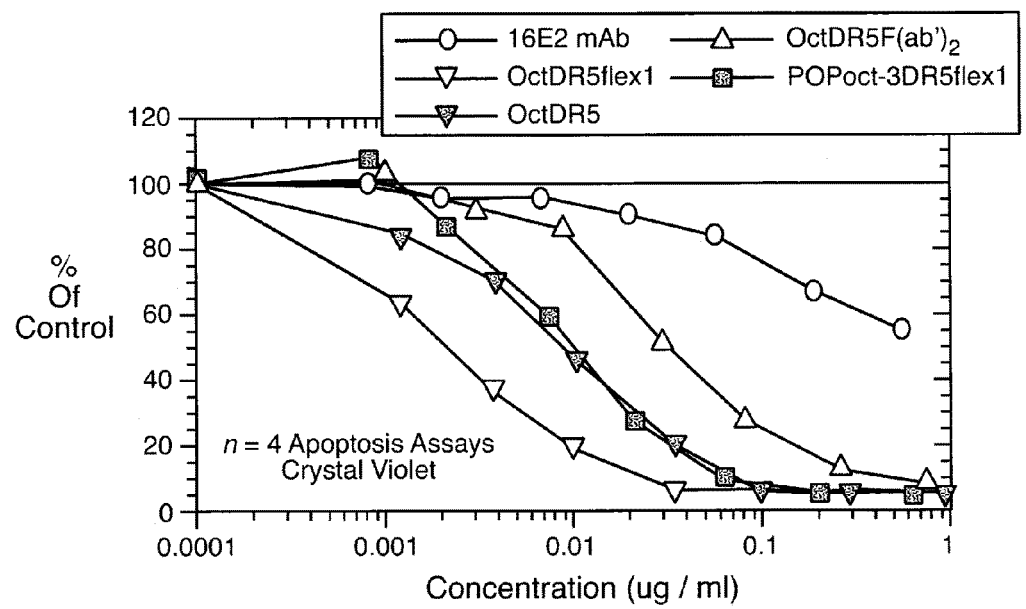
FIGS. 30A-B reveal apoptosis of COL0205 cells by multivalent anti-DR5 antibodies FIGS. 31A-B demonstrate signalling of multivalent anti-DR5 antibodies through the caspase pathway.
Figure 30B:
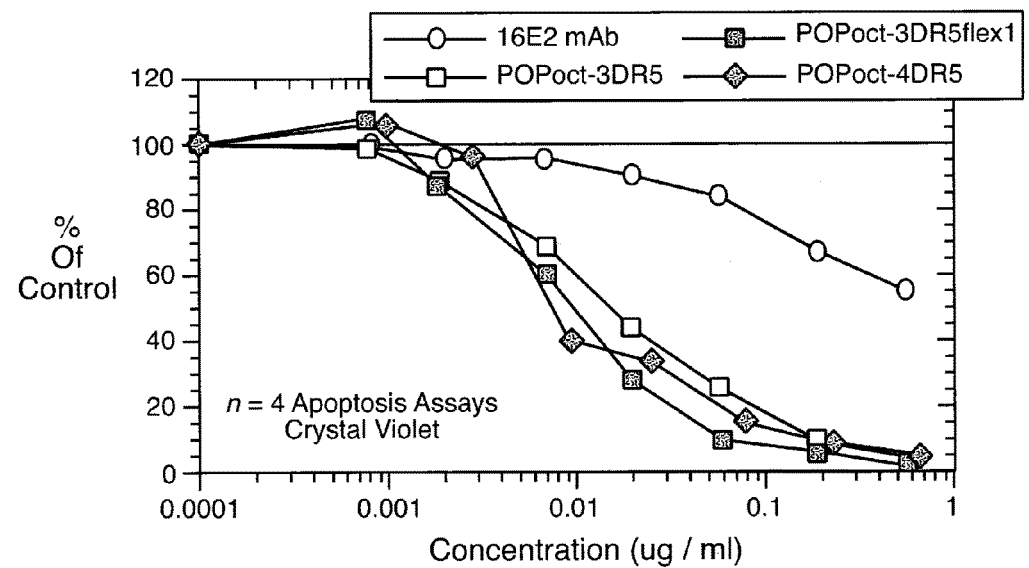

Apoptosis Assays: Multivalent versions of the anti-DR5 16E2 MAb were evaluated in this example. Oct1DR5, OctDR5flex-1, OctDR5F(ab)'$_2$, POPoct-3DR5, POPoct-3DR5flex-1 and POPoct-4 DR5 were added at equimolar concentrations to the colon tumor cell line COL0205 and analyzed in crystal violet apoptosis assays in comparison to the 16E2 MAb (n=4). The results are shown in FIGS. 30A and B. All Octopus antibodies induced more apoptosis than the 16E2 MAb, with the order of efficacy from most potent to least: OctDR5flex-1>OctDR5=POPoct-4 DR5=POPoct-3flex-1 DR5=POPoct-3DR5>OctDR5F(ab)'$_2$>16E2 MAb. OctDR5flex-1 showed increased potency compared to OctDR5, especially at lower concentrations (FIG. 30A), indicating that flexibility between the Fab arms improves efficacy. POPoct-3flex-1 DR5 induced equivalent levels of apoptosis as OctHER (FIG. 30A) and showed similar efficacy to POPoct16-3 and POPoct16-4 (FIG. 30B).

Figure 31A:
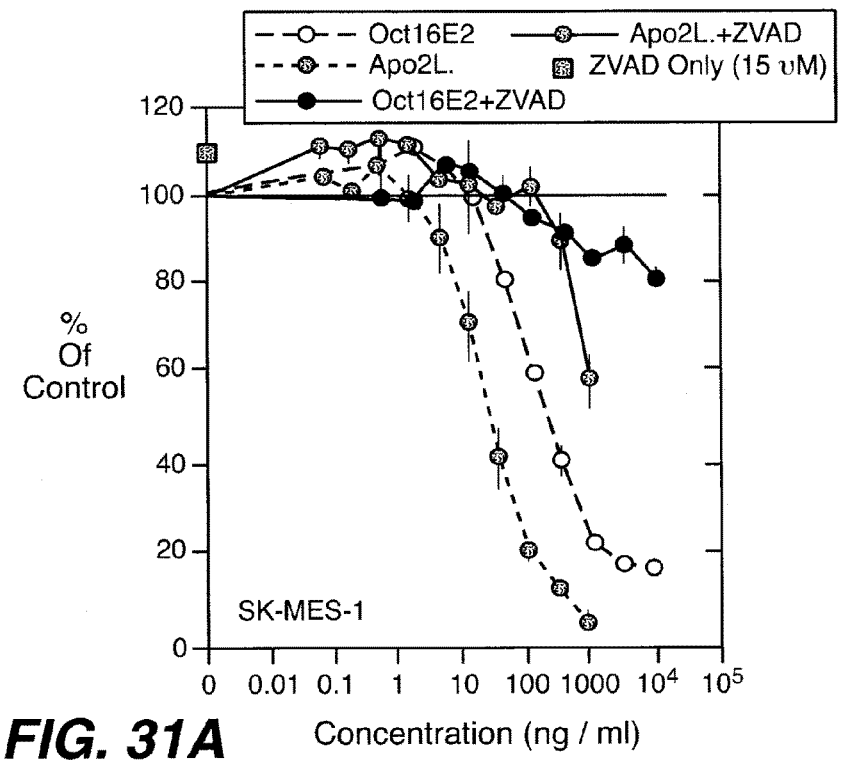
Figure 31B:
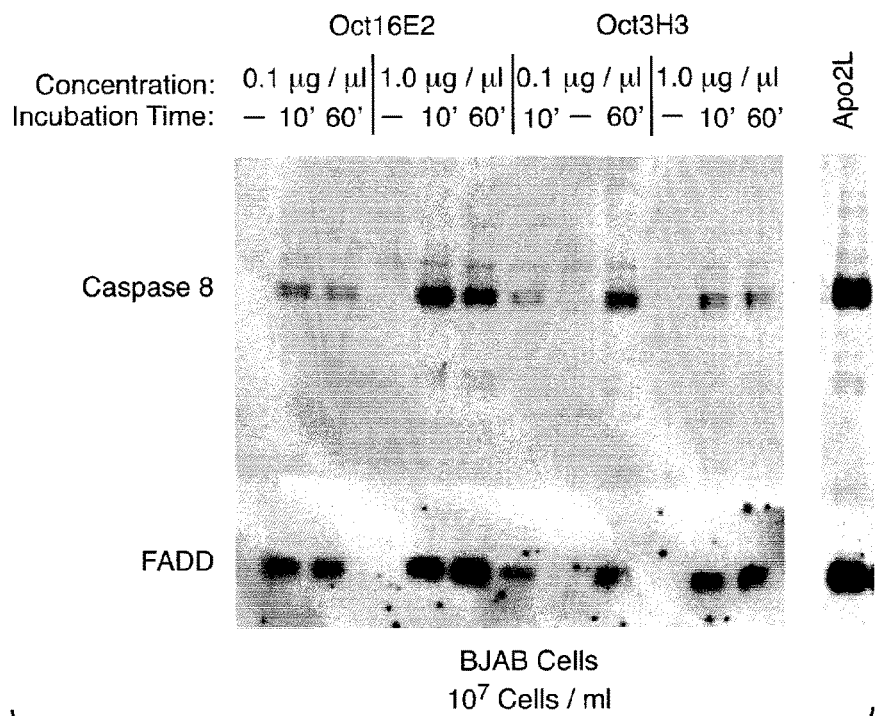

Cell Signaling: Apo2L binds to the death receptors and triggers cellular apoptosis through the caspase signaling pathway. As shown in FIGS. 31A and B, the anti-DR5 Octopus antibodies were shown to induce apoptosis through the same signaling pathway as Apo2L. Oct16E2 triggered similar levels of apoptosis as APO2L on the lung tumor cell line SK-MES-1 (FIG. 31A, dashed lines), but after the addition of ZVAD, an inhibitor of caspase 3 and 9, cellular apoptosis triggered by both Apo2L and Oct16E2 was inhibited (FIG. 31B solid lines). Further evidence that the anti-DR5 Octopus antibodies signaled through the same pathway as Apo2L was obtained by DISC (Death Induced Signaling Complex) analyses (FIG. 31B). BJAB cells, a B-cell lymphoma line that expresses DR5, was incubated at two different concentrations of two anti-DR5 Octopus antibodies, Oct16E2 and Oct3H3, for varying times. Purification of the antibody-DR5 complexes was followed Western blot analysis to identify the signaling molecules that copurified with the complexes. As with Apo2L, the signaling molecules caspase 8 and FADD associated with DR5 after the receptor was bound by both Oct16E2 and Oct3H3 (FIG. 31B).

EXAMPLE 8

Evaluation of anti-CD20 Octopus Antibody

Figure 32:
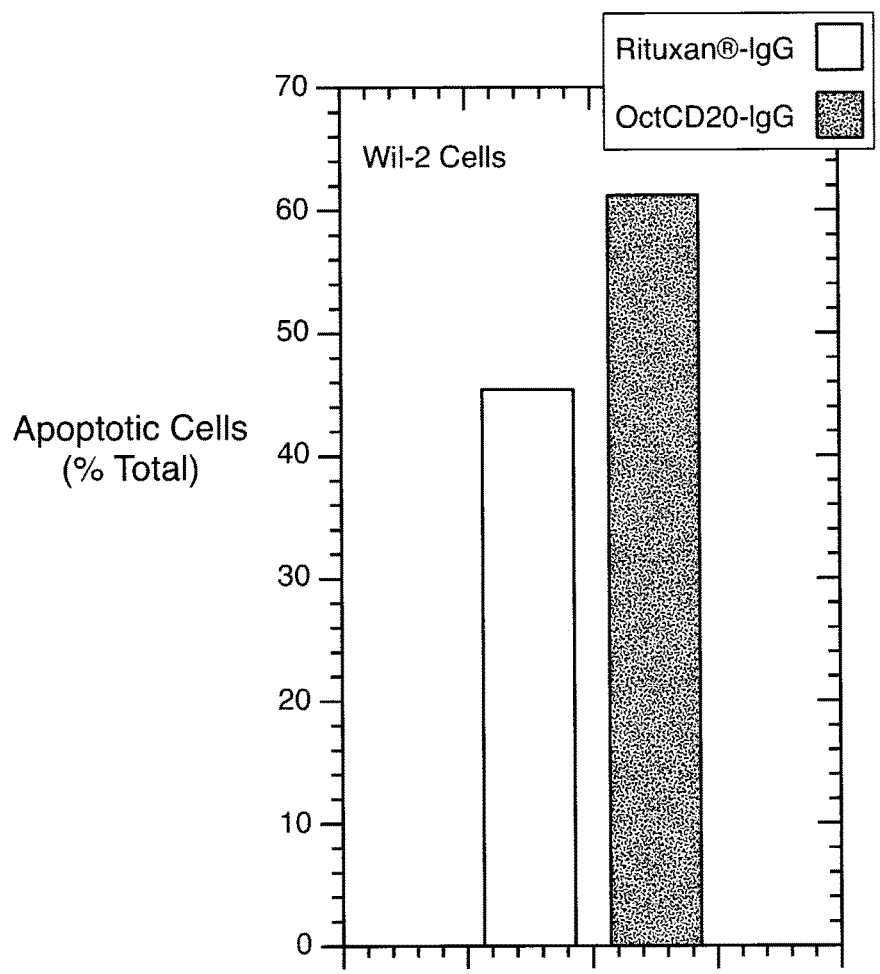
FIG. 32 compares apoptosis induced by IgG cross-linked RITUXAN® (RITUXAN-IgG) and IgG cross-linked OctCD20 (OctCD20-IgG).

Apoptosis Assays: As shown in FIG. 22, RITUXAN® did not efficiently trigger apoptosis in vitro on the B-cell lymphoma cell line WIL-2 unless first crosslinked by anti-IgG antibody. OctCD20 was capable of inducing apoptosis of WIL-2 cells independent of crosslinking, at levels higher than RITUXAN® alone, yet slightly lower than anti-IgGcrosslinked RITUXAN®. When crosslinked with anti-IgG antibody, OctCD20 induced more apoptosis of the WIL-2 cells than crosslinked RITUXAN® (FIG. 32). Since one potential explanation for the efficacy of RITUXAN® in vivo is that the antibody is being crosslinked by either complement or FcγR bearing cells, this observation suggests that OctCD20 will be even more efficacious in vivo.

Figure 33:
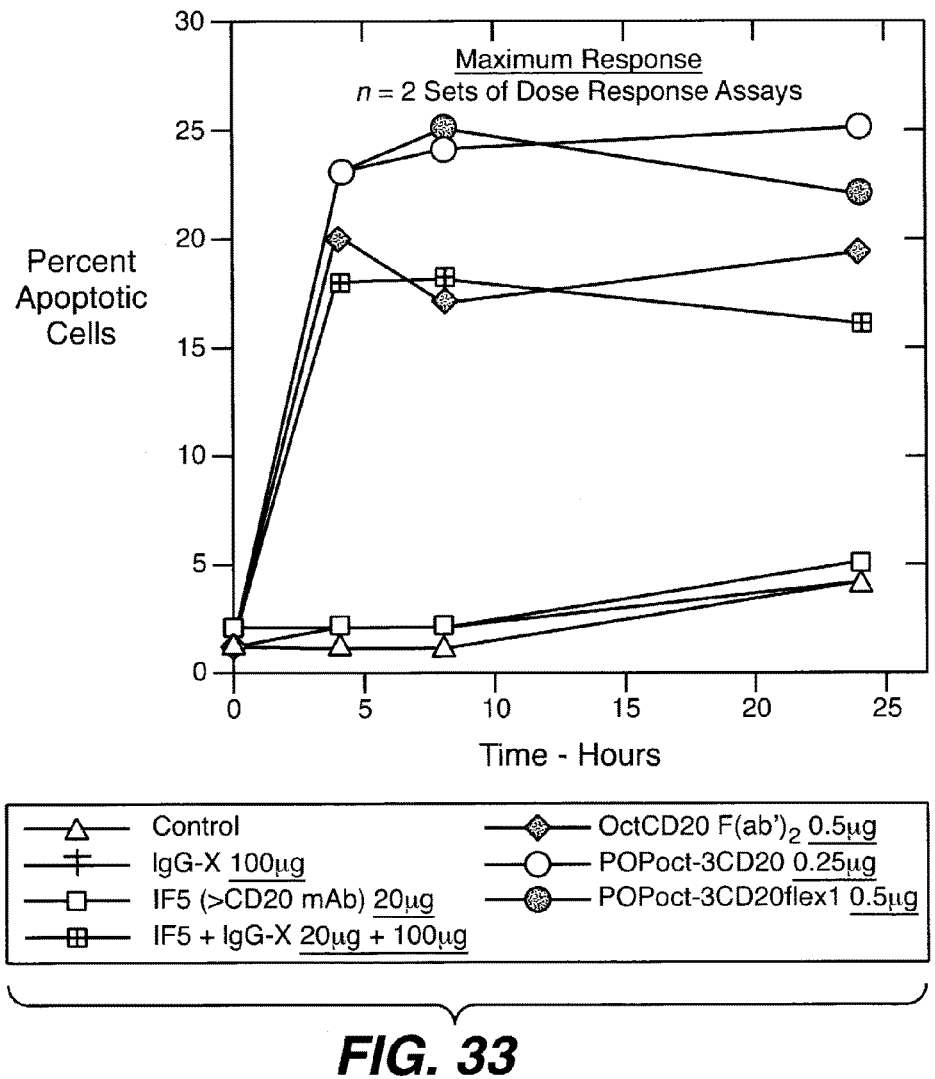
FIG. 33 shows apoptosis of WIL2 cells by multivalent anti-CD20 antibodies, the IFS anti-CD20 antibody (Clark et al. *PNAS (USA)* 82: 1766-1770 (1985)) and IgG cross-linked IFS antibody (IF5+IgG-X).
Figure 35A:
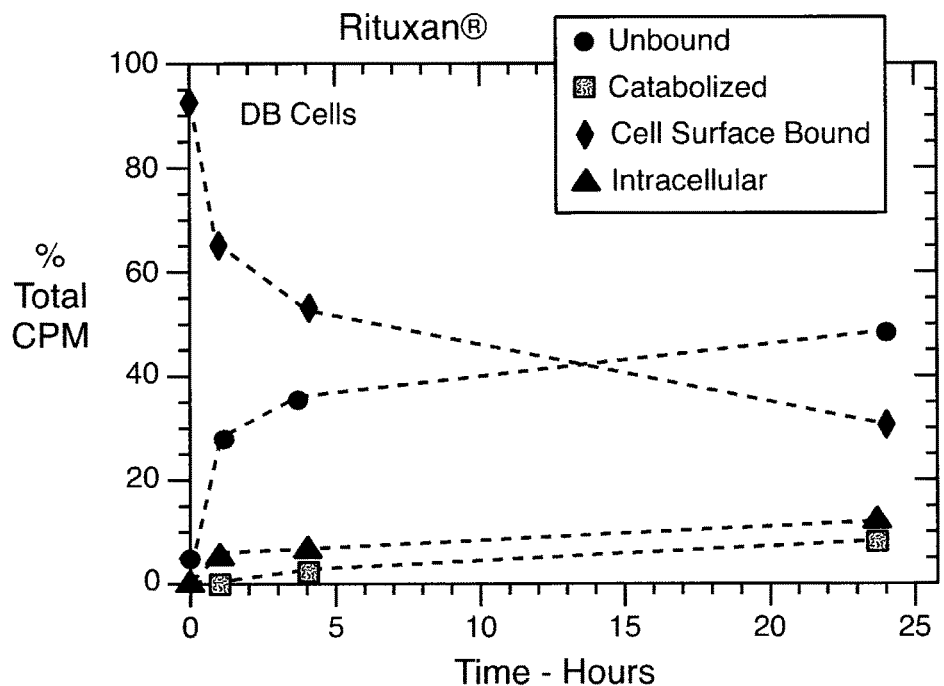
FIG. 35 reflects RITUXAN® or OctCD20 internalization/catabolism on DB, WIL2 and Ramos B-cell lymphoma lines.
Figure 35B:
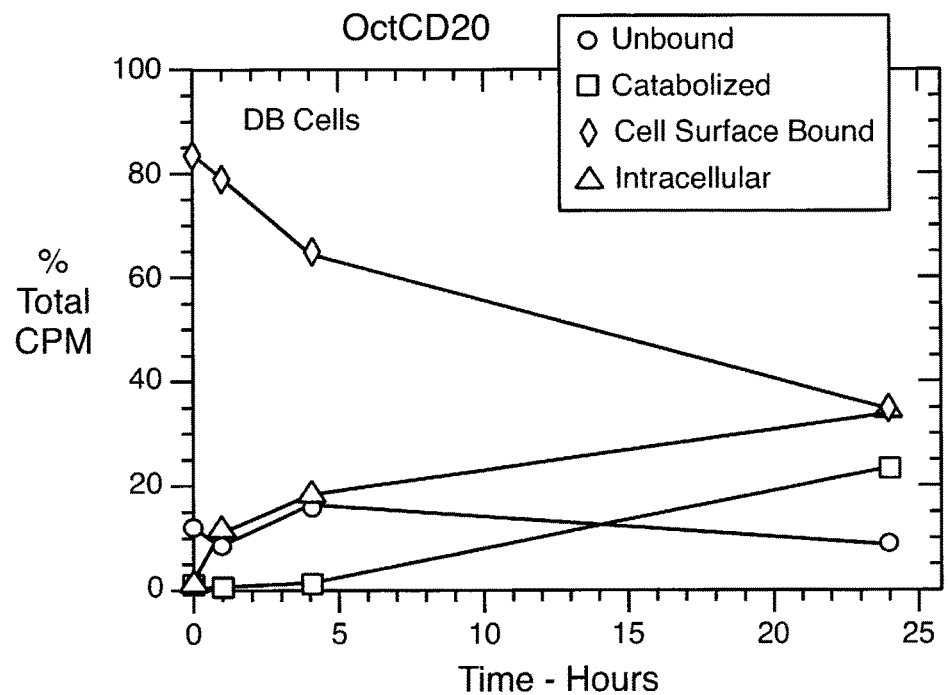
Figure 35C:
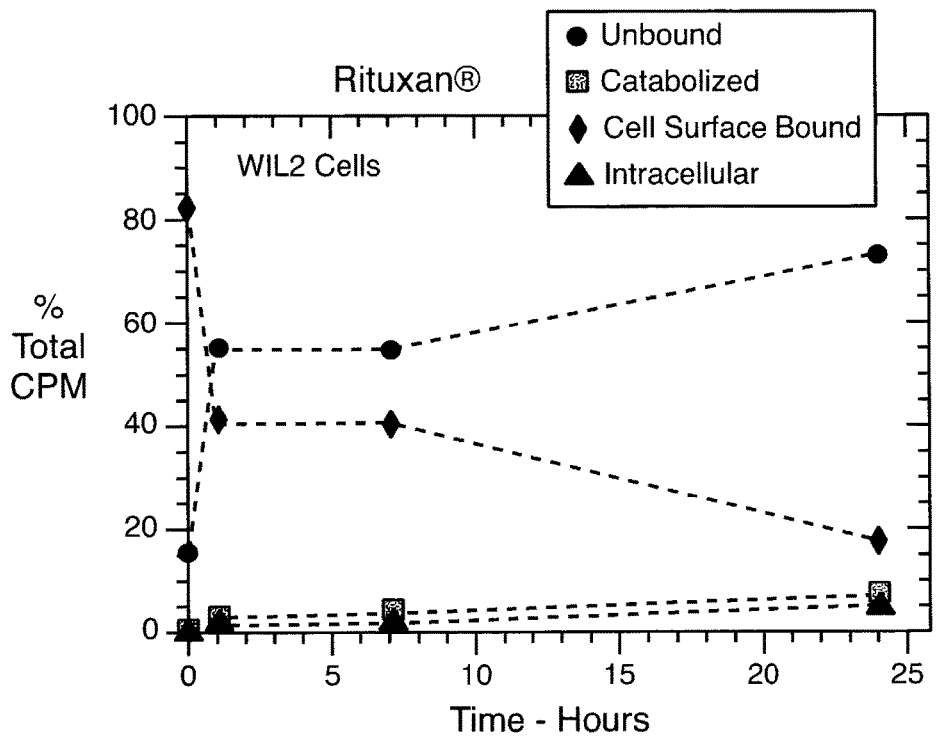
Figure 35D:
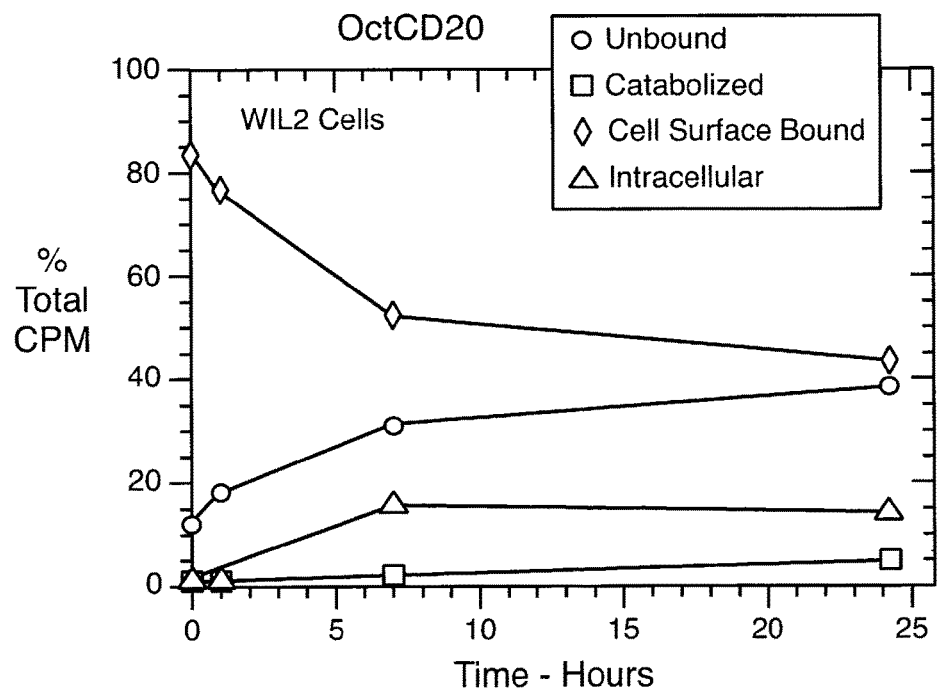
Figure 35E:
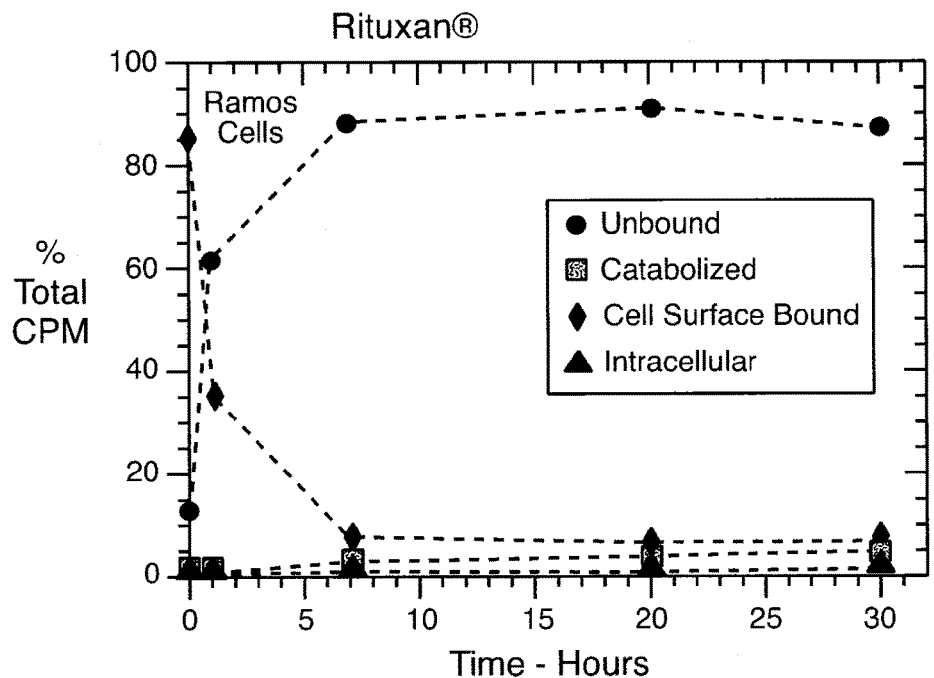
Figure 35F:
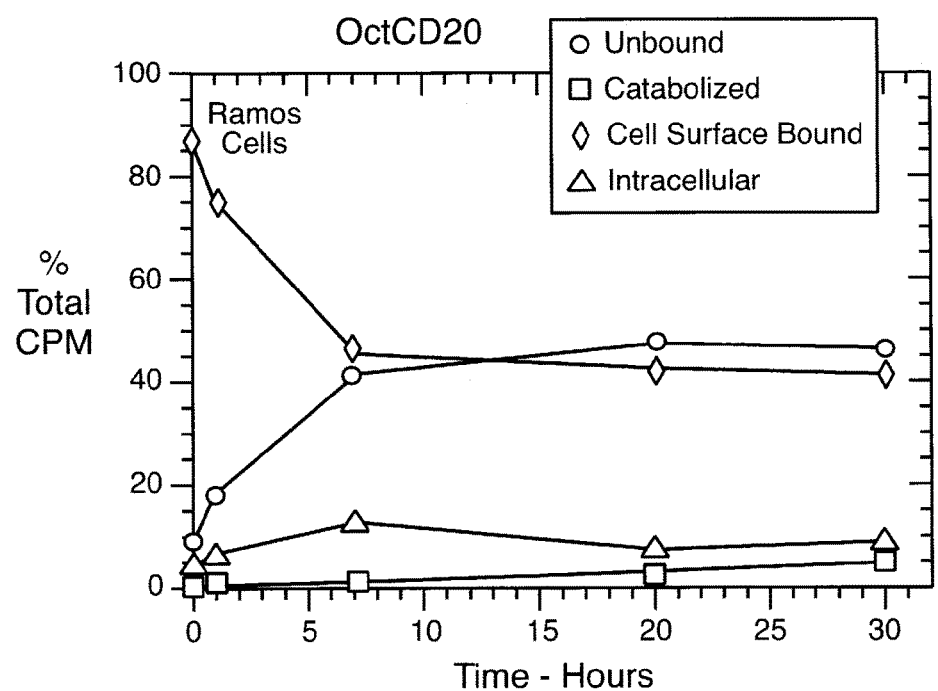

OctCD20 F(ab')$_2$, POPoct-3CD20 and POPoct-3CD20flex-1 were tested at various concentrations in apoptosis assays with WIL-2 cells, and the optimal doses are shown in the maximum response curves in FIG. 33. The Octopus antibodies were compared to the anti-CD20 antibody 1F5 (Clark et al. supra), which functions similar to RITUXAN® in that it does not induce apoptosis unless crosslinked with anti-IgG antibody. Both Octopus antibodies tested induced either similar (OctCD20 F(ab')$_2$) or higher (POPoct-3CD20, POPoct-3CD20flex-1) levels of apoptosis than crosslinked IF5 anti-CD20. Additionally, the Octopus antibodies were efficacious at considerably lower concentrations than the crosslinked anti-CD20.

When crosslinked anti-CD20 antibodies are added to the B cell lymphoma line WIL-2S, a homotypic adhesion of the cells is observed. This cell clumping is one indication that the cells have been activated through CD20. The Octopus anti-CD20 antibodies induce this same homotypic adhesion phenomenon independent of crosslinker, and as shown in FIG. 34 with POPoct-3CD20, at much lower concentrations than crosslinked IF5 anti-CD20.

Apoptosis induction by the various anti-CD20 antibodies was further assessed using blood from a patient with chronic lymphocytic leukemia (CLL). PBL's were separated out using dextran sedimentation, washed and plated in serum-free lymphocyte medium treated overnight with no sample, 1F5 (20:g/ml), 1F5+cross-linking mouse anti-IgG (100:g/ml), OctCD20 F(ab')$_2$ at approx 0.5 or 1.0:g/ml and POPoct-3 CD20 at 0.5:g/ml.

An apoptosis assay was performed using annexin and PI staining. The percentage of apoptotic cells were:

| | |
|---|---|
| Untreated | 38.5% |
| 1F5 | 37.1% |
| 1F5 X-linked with anti-IgG | 25.1% |
| POPoct-3 CD20 (0.5:g) | 50.2% |
| OctCD20 F(ab')$_2$ (0.5:g) | 37.7% |
| OctCD20 F(ab')$_2$ (1.0:g) | 48.6% |

The data indicate that multivalent anti-CD20 antibodies (especially POPoct-3 CD20) enhance apoptosis in a dose-dependent manner.

Internalization Assays: OctCD20 was also evaluated as a candidate for immunotoxin therapy in internalization assays on three B-cell lymphoma lines, DB, WIL-2, and Ramos, and compared to RITUXAN®. As shown in FIG. 35, twice as much OctCD20 was internalized by the cells as compared to RITUXAN®, which was not internalized by the cells at appreciable levels. The higher avidity that would be expected for the multivalent antibodies due to the increased number of binding sites is evident in the fact that more OctCD20 remains bound to the cell surface of the cells over time as compared to RITUXAN®.

---

What is claimed is:

1. An isolated antibody comprising two heavy chain polypeptides, four light chain polypeptides and four antigen binding sites,
   wherein each of the two heavy chain polypeptides comprises
      VD1-(X1)n-VD2-(X2)n-Fc,
   wherein VD1 is a first VH domain, VD2 is a second VH domain, Fc is an Fc region, X1 and X2 each represents an optional intervening amino acid or polypeptide, and n is 0 or 1; and
      each of the four light chain polypeptides comprises a VL domain that forms one of the four antigen binding sites with one of the VH domains from one of the two heavy chain polypeptides.

2. The isolated antibody of claim 1, wherein the antibody binds to an antigen selected from the group consisting of HER2, DR5 and CD20.

3. The isolated antibody of claim 1, wherein VD1-(X1)n-VD2-(X2)n-Fc of each of the two heavy chain polypeptides comprises VH-CH1-VH-CH1-Fc wherein CH1 is a heavy chain constant domain and each of the four light chain polypeptides further comprises a light chain constant (CL) domain.

4. The isolated antibody of claim 1, wherein VD1-(X1)n-D2-(X2)n-Fc of each of the two heavy chain polypeptides comprises
   VH-CH1-flexible linker-VH-CH1-Fc, wherein CH1 is a heavy chain constant domain, flexible linker is the amino acid sequence of glycine-serine or glycine-serine-glycine-serine (SEQ ID NO:10) and each of the four light chain polypeptides further comprises a CL domain.

* * * * *

SEQUENCE LISTING

```
<160> NUMBER OF SEQ ID NOS: 13

<210> SEQ ID NO 1
<211> LENGTH: 218
<212> TYPE: PRT
<213> ORGANISM: Homo sapiens

<400> SEQUENCE: 1

Pro Ala Pro Glu Leu Leu Gly Gly Pro Ser Val Phe Leu Phe Pro
 1               5                  10                  15

Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys
                35                  40                  45

Phe Asn Trp Tyr Val Asp Gly Val Glu Val His Asn Ala Lys Thr
                50                  55                  60

Lys Pro Arg Glu Glu Gln Tyr Asn Ser Thr Tyr Arg Val Val Ser
                65                  70                  75

Val Leu Thr Val Leu His Gln Asp Trp Leu Asn Gly Lys Glu Tyr
                80                  85                  90

Lys Cys Lys Val Ser Asn Lys Ala Leu Pro Ala Pro Ile Glu Lys
                95                 100                 105

Thr Ile Ser Lys Ala Lys Gly Gln Pro Arg Glu Pro Gln Val Tyr
               110                 115                 120

Thr Leu Pro Pro Ser Arg Glu Glu Met Thr Lys Asn Gln Val Ser
               125                 130                 135

Leu Thr Cys Leu Val Lys Gly Phe Tyr Pro Ser Asp Ile Ala Val
               140                 145                 150
```

Glu Trp Glu Ser Asn Gly Gln Pro Glu Asn Asn Tyr Lys Thr Thr
                155                 160                 165

Pro Pro Val Leu Asp Ser Asp Gly Ser Phe Phe Leu Tyr Ser Lys
                170                 175                 180

Leu Thr Val Asp Lys Ser Arg Trp Gln Gln Gly Asn Val Phe Ser
                185                 190                 195

Cys Ser Val Met His Glu Ala Leu His Asn His Tyr Thr Gln Lys
                200                 205                 210

Ser Leu Ser Leu Ser Pro Gly Lys
                215

<210> SEQ ID NO 2
<211> LENGTH: 218
<212> TYPE: PRT
<213> ORGANISM: Homo sapiens

<400> SEQUENCE: 2

Pro Ala Pro Glu Leu Leu Gly Gly Pro Ser Val Phe Leu Phe Pro
  1               5                  10                  15

Pro Lys Pro Lys Asp Thr Leu Met Ile Ser Arg Thr Pro Glu Val
                 20                  25                  30

Thr Cys Val Val Val Asp Val Ser His Glu Asp Pro Glu Val Lys
                 35                  40                  45

Phe Asn Trp Tyr Val Asp Gly Val Glu Val His Asn Ala Lys Thr
                 50                  55                  60

Lys Pro Arg Glu Glu Gln Tyr Asn Ser Thr Tyr Arg Val Val Ser
                 65                  70                  75

Val Leu Thr Val Leu His Gln Asp Trp Leu Asn Gly Lys Glu Tyr
                 80                  85                  90

Lys Cys Lys Val Ser Asn Lys Ala Leu Pro Ala Pro Ile Glu Lys
                 95                 100                 105

Thr Ile Ser Lys Ala Lys Gly Gln Pro Arg Glu Pro Gln Val Tyr
                110                 115                 120

Thr Leu Pro Pro Ser Arg Asp Glu Leu Thr Lys Asn Gln Val Ser
                125                 130                 135

Leu Thr Cys Leu Val Lys Gly Phe Tyr Pro Ser Asp Ile Ala Val
                140                 145                 150

Glu Trp Glu Ser Asn Gly Gln Pro Glu Asn Asn Tyr Lys Thr Thr
                155                 160                 165

Pro Pro Val Leu Asp Ser Asp Gly Ser Phe Phe Leu Tyr Ser Lys
                170                 175                 180

Leu Thr Val Asp Lys Ser Arg Trp Gln Gln Gly Asn Val Phe Ser
                185                 190                 195

Cys Ser Val Met His Glu Ala Leu His Asn His Tyr Thr Gln Lys
                200                 205                 210

Ser Leu Ser Leu Ser Pro Gly Lys
                215

<210> SEQ ID NO 3
<211> LENGTH: 217
<212> TYPE: PRT
<213> ORGANISM: Homo sapiens

<400> SEQUENCE: 3

Pro Ala Pro Pro Val Ala Gly Pro Ser Val Phe Leu Phe Pro Pro
  1               5                  10                  15

```
Lys Pro Lys Asp Thr Leu Met Ile Ser Arg Thr Pro Glu Val Thr
                20                  25                  30

Cys Val Val Asp Val Ser His Glu Asp Pro Glu Val Gln Phe
            35                  40                  45

Asn Trp Tyr Val Asp Gly Val Glu Val His Asn Ala Lys Thr Lys
            50                  55                  60

Pro Arg Glu Glu Gln Phe Asn Ser Thr Phe Arg Val Val Ser Val
            65                  70                  75

Leu Thr Val Val His Gln Asp Trp Leu Asn Gly Lys Glu Tyr Lys
            80                  85                  90

Cys Lys Val Ser Asn Lys Gly Leu Pro Ala Pro Ile Glu Lys Thr
            95                  100                 105

Ile Ser Lys Thr Lys Gly Gln Pro Arg Glu Pro Gln Val Tyr Thr
            110                 115                 120

Leu Pro Pro Ser Arg Glu Glu Met Thr Lys Asn Gln Val Ser Leu
            125                 130                 135

Thr Cys Leu Val Lys Gly Phe Tyr Pro Ser Asp Ile Ala Val Glu
            140                 145                 150

Trp Glu Ser Asn Gly Gln Pro Glu Asn Asn Tyr Lys Thr Thr Pro
            155                 160                 165

Pro Met Leu Asp Ser Asp Gly Ser Phe Phe Leu Tyr Ser Lys Leu
            170                 175                 180

Thr Val Asp Lys Ser Arg Trp Gln Gln Gly Asn Val Phe Ser Cys
            185                 190                 195

Ser Val Met His Glu Ala Leu His Asn His Tyr Thr Gln Lys Ser
            200                 205                 210

Leu Ser Leu Ser Pro Gly Lys
            215

<210> SEQ ID NO 4
<211> LENGTH: 218
<212> TYPE: PRT
<213> ORGANISM: Homo sapiens

<400> SEQUENCE: 4

Pro Ala Pro Glu Leu Leu Gly Gly Pro Ser Val Phe Leu Phe Pro
 1               5                   10                  15

Pro Lys Pro Lys Asp Thr Leu Met Ile Ser Arg Thr Pro Glu Val
                20                  25                  30

Thr Cys Val Val Val Asp Val Ser His Glu Asp Pro Glu Val Gln
            35                  40                  45

Phe Lys Trp Tyr Val Asp Gly Val Glu Val His Asn Ala Lys Thr
            50                  55                  60

Lys Pro Arg Glu Glu Gln Phe Asn Ser Thr Phe Arg Val Val Ser
            65                  70                  75

Val Leu Thr Val Leu His Gln Asp Trp Leu Asn Gly Lys Glu Tyr
            80                  85                  90

Lys Cys Lys Val Ser Asn Lys Ala Leu Pro Ala Pro Ile Glu Lys
            95                  100                 105

Thr Ile Ser Lys Thr Lys Gly Gln Pro Arg Glu Pro Gln Val Tyr
            110                 115                 120

Thr Leu Pro Pro Ser Arg Glu Glu Met Thr Lys Asn Gln Val Ser
            125                 130                 135

Leu Thr Cys Leu Val Lys Gly Phe Tyr Pro Ser Asp Ile Ala Val
            140                 145                 150
```

```
Glu Trp Glu Ser Ser Gly Gln Pro Glu Asn Asn Tyr Asn Thr Thr
            155                 160                 165

Pro Pro Met Leu Asp Ser Asp Gly Ser Phe Phe Leu Tyr Ser Lys
            170                 175                 180

Leu Thr Val Asp Lys Ser Arg Trp Gln Gln Gly Asn Ile Phe Ser
            185                 190                 195

Cys Ser Val Met His Glu Ala Leu His Asn Arg Phe Thr Gln Lys
            200                 205                 210

Ser Leu Ser Leu Ser Pro Gly Lys
            215

<210> SEQ ID NO 5
<211> LENGTH: 218
<212> TYPE: PRT
<213> ORGANISM: Homo sapiens

<400> SEQUENCE: 5

Pro Ala Pro Glu Phe Leu Gly Gly Pro Ser Val Phe Leu Phe Pro
  1               5                  10                  15

Pro Lys Pro Lys Asp Thr Leu Met Ile Ser Arg Thr Pro Glu Val
                 20                  25                  30

Thr Cys Val Val Val Asp Val Ser Gln Glu Asp Pro Glu Val Gln
                 35                  40                  45

Phe Asn Trp Tyr Val Asp Gly Val Glu Val His Asn Ala Lys Thr
                 50                  55                  60

Lys Pro Arg Glu Glu Gln Phe Asn Ser Thr Tyr Arg Val Val Ser
                 65                  70                  75

Val Leu Thr Val Leu His Gln Asp Trp Leu Asn Gly Lys Glu Tyr
                 80                  85                  90

Lys Cys Lys Val Ser Asn Lys Gly Leu Pro Ser Ser Ile Glu Lys
                 95                 100                 105

Thr Ile Ser Lys Ala Lys Gly Gln Pro Arg Glu Pro Gln Val Tyr
                110                 115                 120

Thr Leu Pro Pro Ser Gln Glu Glu Met Thr Lys Asn Gln Val Ser
                125                 130                 135

Leu Thr Cys Leu Val Lys Gly Phe Tyr Pro Ser Asp Ile Ala Val
                140                 145                 150

Glu Trp Glx Ser Asn Gly Gln Pro Glu Asn Asn Tyr Lys Thr Thr
                155                 160                 165

Pro Pro Val Leu Asp Ser Asp Gly Ser Phe Phe Leu Tyr Ser Arg
                170                 175                 180

Leu Thr Val Asp Lys Ser Arg Trp Gln Glu Gly Asn Val Phe Ser
                185                 190                 195

Cys Ser Val Met His Glu Ala Leu His Asn His Tyr Thr Gln Lys
                200                 205                 210

Ser Leu Ser Leu Ser Leu Gly Lys
                215

<210> SEQ ID NO 6
<211> LENGTH: 215
<212> TYPE: PRT
<213> ORGANISM: Mus musculus

<400> SEQUENCE: 6

Thr Val Pro Glu Val Ser Ser Val Phe Ile Phe Pro Pro Lys Pro
  1               5                  10                  15

Lys Asp Val Leu Thr Ile Thr Leu Thr Pro Lys Val Thr Cys Val
```

-continued

```
                20                  25                  30
Val Val Asp Ile Ser Lys Asp Pro Glu Val Gln Phe Ser Trp
                35                  40                  45
Phe Val Asp Asp Val Glu Val His Thr Ala Gln Thr Gln Pro Arg
                50                  55                  60
Glu Glu Gln Phe Asn Ser Thr Phe Arg Ser Val Ser Glu Leu Pro
                65                  70                  75
Ile Met His Gln Asp Cys Leu Asn Gly Lys Glu Phe Lys Cys Arg
                80                  85                  90
Val Asn Ser Ala Ala Phe Pro Ala Pro Ile Glu Lys Thr Ile Ser
                95                  100                 105
Lys Thr Lys Gly Arg Pro Lys Ala Pro Gln Val Tyr Thr Ile Pro
                110                 115                 120
Pro Pro Lys Glu Gln Met Ala Lys Asp Lys Val Ser Leu Thr Cys
                125                 130                 135
Met Ile Thr Asp Phe Phe Pro Glu Asp Ile Thr Val Glu Trp Gln
                140                 145                 150
Trp Asn Gly Gln Pro Ala Glu Asn Tyr Lys Asn Thr Gln Pro Ile
                155                 160                 165
Met Asp Thr Asp Gly Ser Tyr Phe Val Tyr Ser Lys Leu Asn Val
                170                 175                 180
Gln Lys Ser Asn Trp Glu Ala Gly Asn Thr Phe Thr Cys Ser Val
                185                 190                 195
Leu His Glu Gly Leu His Asn His His Thr Glu Lys Ser Leu Ser
                200                 205                 210
His Ser Pro Gly Lys
                215

<210> SEQ ID NO 7
<211> LENGTH: 218
<212> TYPE: PRT
<213> ORGANISM: Mus musculus

<400> SEQUENCE: 7

Pro Ala Pro Asn Leu Leu Gly Gly Pro Ser Val Phe Ile Phe Pro
 1              5                   10                  15
Pro Lys Ile Lys Asp Val Leu Met Ile Ser Leu Ser Pro Ile Val
                20                  25                  30
Thr Cys Val Val Asp Val Ser Glu Asp Asp Pro Asp Val Gln
                35                  40                  45
Ile Ser Trp Phe Val Asn Asn Val Glu Val His Thr Ala Gln Thr
                50                  55                  60
Gln Thr His Arg Glu Asp Tyr Asn Ser Thr Leu Arg Val Val Ser
                65                  70                  75
Ala Leu Pro Ile Gln His Gln Asp Trp Met Ser Gly Lys Glu Phe
                80                  85                  90
Lys Cys Lys Val Asn Asn Lys Asp Leu Pro Ala Pro Ile Glu Arg
                95                  100                 105
Thr Ile Ser Lys Pro Lys Gly Ser Val Arg Ala Pro Gln Val Tyr
                110                 115                 120
Val Leu Pro Pro Glu Glu Glu Met Thr Lys Lys Gln Val Thr
                125                 130                 135
Leu Thr Cys Met Val Thr Asp Phe Met Pro Glu Asp Ile Tyr Val
                140                 145                 150
Glu Trp Thr Asn Asn Gly Lys Thr Glu Leu Asn Tyr Lys Asn Thr
```

```
                 155                 160                 165

Glu Pro Val Leu Asp Ser Asp Gly Ser Tyr Phe Met Tyr Ser Lys
                170                 175                 180

Leu Arg Val Glu Lys Lys Asn Trp Val Glu Arg Asn Ser Tyr Ser
                185                 190                 195

Cys Ser Val Val His Glu Gly Leu His Asn His His Thr Thr Lys
                200                 205                 210

Ser Phe Ser Arg Thr Pro Gly Lys
                215

<210> SEQ ID NO 8
<211> LENGTH: 218
<212> TYPE: PRT
<213> ORGANISM: Mus musculus

<400> SEQUENCE: 8

Pro Ala Pro Asn Leu Glu Gly Gly Pro Ser Val Phe Ile Phe Pro
  1               5                  10                  15

Pro Asn Ile Lys Asp Val Leu Met Ile Ser Leu Thr Pro Lys Val
                 20                  25                  30

Thr Cys Val Val Val Asp Val Ser Glu Asp Asp Pro Asp Val Gln
                 35                  40                  45

Ile Ser Trp Phe Val Asn Asn Val Glu Val His Thr Ala Gln Thr
                 50                  55                  60

Gln Thr His Arg Glu Asp Tyr Asn Ser Thr Ile Arg Val Val Ser
                 65                  70                  75

His Leu Pro Ile Gln His Gln Asp Trp Met Ser Gly Lys Glu Phe
                 80                  85                  90

Lys Cys Lys Val Asn Asn Lys Asp Leu Pro Ser Pro Ile Glu Arg
                 95                 100                 105

Thr Ile Ser Lys Pro Lys Gly Leu Val Arg Ala Pro Gln Val Tyr
                110                 115                 120

Thr Leu Pro Pro Pro Ala Glu Gln Leu Ser Arg Lys Asp Val Ser
                125                 130                 135

Leu Thr Cys Leu Val Val Gly Phe Asn Pro Gly Asp Ile Ser Val
                140                 145                 150

Glu Trp Thr Ser Asn Gly His Thr Glu Glu Asn Tyr Lys Asp Thr
                155                 160                 165

Ala Pro Val Leu Asp Ser Asp Gly Ser Tyr Phe Ile Tyr Ser Lys
                170                 175                 180

Leu Asn Met Lys Thr Ser Lys Trp Glu Lys Thr Asp Ser Phe Ser
                185                 190                 195

Cys Asn Val Arg His Glu Gly Leu Lys Asn Tyr Tyr Leu Lys Lys
                200                 205                 210

Thr Ile Ser Arg Ser Pro Gly Lys
                215

<210> SEQ ID NO 9
<211> LENGTH: 218
<212> TYPE: PRT
<213> ORGANISM: Mus musculus

<400> SEQUENCE: 9

Pro Pro Gly Asn Ile Leu Gly Gly Pro Ser Val Phe Ile Phe Pro
  1               5                  10                  15

Pro Lys Pro Lys Asp Ala Leu Met Ile Ser Leu Thr Pro Lys Val
                 20                  25                  30
```

-continued

```
Thr Cys Val Val Asp Val Ser Glu Asp Pro Asp Val His
                35                  40                  45

Val Ser Trp Phe Val Asp Asn Lys Glu Val His Thr Ala Trp Thr
                50                  55                  60

Gln Pro Arg Glu Ala Gln Tyr Asn Ser Thr Phe Arg Val Val Ser
                65                  70                  75

Ala Leu Pro Ile Gln His Gln Asp Trp Met Arg Gly Lys Glu Phe
                80                  85                  90

Lys Cys Lys Val Asn Asn Lys Ala Leu Pro Ala Pro Ile Glu Arg
                95                  100                 105

Thr Ile Ser Lys Pro Lys Gly Arg Ala Gln Thr Pro Gln Val Tyr
                110                 115                 120

Thr Ile Pro Pro Arg Glu Gln Met Ser Lys Lys Val Ser
                125                 130                 135

Leu Thr Cys Leu Val Thr Asn Phe Phe Ser Glu Ala Ile Ser Val
                140                 145                 150

Glu Trp Glu Arg Asn Gly Glu Leu Glu Gln Asp Tyr Lys Asn Thr
                155                 160                 165

Pro Pro Ile Leu Asp Ser Asp Gly Thr Tyr Phe Leu Tyr Ser Lys
                170                 175                 180

Leu Thr Val Asp Thr Asp Ser Trp Leu Gln Gly Glu Ile Phe Thr
                185                 190                 195

Cys Ser Val Val His Glu Ala Leu His Asn His His Thr Gln Lys
                200                 205                 210

Asn Leu Ser Arg Ser Pro Gly Lys
                215

<210> SEQ ID NO 10
<211> LENGTH: 4
<212> TYPE: PRT
<213> ORGANISM: Artificial Sequence
<220> FEATURE:
<223> OTHER INFORMATION: Sequence is synthesized

<400> SEQUENCE: 10

Gly Ser Gly Ser
 1

<210> SEQ ID NO 11
<211> LENGTH: 4
<212> TYPE: PRT
<213> ORGANISM: Artificial Sequence
<220> FEATURE:
<223> OTHER INFORMATION: Sequence is synthesized

<400> SEQUENCE: 11

Gly Gly Gly Ser
 1

<210> SEQ ID NO 12
<211> LENGTH: 4
<212> TYPE: PRT
<213> ORGANISM: Artificial Sequence
<220> FEATURE:
<221> NAME/KEY: SITE
<222> LOCATION: 1-4
<223> OTHER INFORMATION: Amino acids in antibody heavy chain variable
      (VH) domain

<400> SEQUENCE: 12

Glu Val Gln Leu
```

```
<210> SEQ ID NO 13
<211> LENGTH: 4
<212> TYPE: PRT
<213> ORGANISM: Artificial Sequence
<220> FEATURE:
<221> NAME/KEY: SITE
<222> LOCATION: 1-4
<223> OTHER INFORMATION: Amino acids in antibody heavy chain constant
      (CH1) domain

<400> SEQUENCE: 13

Lys Thr His Thr
  1
```